(12) United States Patent
de Juan et al.

(10) Patent No.: US 10,835,416 B2
(45) Date of Patent: Nov. 17, 2020

(54) OCULAR INSERT APPARATUS AND METHODS

(71) Applicant: ForSight Vision5, Inc., Parsippany, NJ (US)

(72) Inventors: Eugene de Juan, Parsippany, NJ (US); Yair Alster, Parsippany, NJ (US); Cary J. Reich, Parsippany, NJ (US); K. Angela Macfarlane, Parsippany, NJ (US); Janelle Chang, Parsippany, NJ (US); Stephen Boyd, Parsippany, NJ (US); David Sierra, Parsippany, NJ (US); Jose D. Alejandro, Parsippany, NJ (US); Douglas Sutton, Parsippany, NJ (US); Alexander J. Gould, Parsippany, NJ (US)

(73) Assignee: ForSight Vision5, Inc., Madison, NJ (US)

( * ) Notice: Subject to any disclaimer, the term of this patent is extended or adjusted under 35 U.S.C. 154(b) by 447 days.

(21) Appl. No.: 15/905,525

(22) Filed: Feb. 26, 2018

(65) Prior Publication Data

US 2018/0177634 A1 Jun. 28, 2018

Related U.S. Application Data

(63) Continuation of application No. 14/600,505, filed on Jan. 20, 2015, now Pat. No. 9,937,073, which is a
(Continued)

(51) Int. Cl.
*A61F 9/00* (2006.01)
*A61K 9/00* (2006.01)
(Continued)

(52) U.S. Cl.
CPC ...... *A61F 9/0017* (2013.01); *A61B 17/00234* (2013.01); *A61K 9/0051* (2013.01);
(Continued)

(58) Field of Classification Search
CPC ........ A61F 9/00; A61F 9/0017; A61F 9/0008; A61F 9/0026; A61K 9/0051
See application file for complete search history.

(56) References Cited

U.S. PATENT DOCUMENTS

| 3,113,076 A | 12/1963 | Jacobs |
| 3,312,215 A | 4/1967 | Silber et al. |

(Continued)

FOREIGN PATENT DOCUMENTS

| CN | 1630494 A | 6/2005 |
| CN | 100339058 C | 9/2007 |

(Continued)

OTHER PUBLICATIONS

International Search Report and Written Opinion of PCT Application No. PCT/US2010/037268 dated Jul. 21, 2010. 7 pages.
(Continued)

*Primary Examiner* — Susan S Su

(74) *Attorney, Agent, or Firm* — Mintz Levin Cohn Ferris Glovsky and Popeo, P.C.

(57) ABSTRACT

A comfortable insert comprises a retention structure sized for placement under the eyelids and along at least a portion of conjunctival sac of the upper and lower lids of the eye. The retention structure resists deflection when placed in the conjunctival sac of the eye and to guide the insert along the sac when the eye moves. The retention structure can be configured in many ways to provide the resistance to deflection and may comprise a hoop strength so as to urge the retention structure outward and inhibit movement of the retention structure toward the cornea. The insert may move
(Continued)

rotationally with deflection along the conjunctival sac, and may comprise a retention structure having a cross sectional dimension sized to fit within folds of the conjunctiva. The insert may comprise a release mechanism and therapeutic agent to release therapeutic amounts of the therapeutic agent for an extended time.

46 Claims, 73 Drawing Sheets

Related U.S. Application Data continuation of application No. 13/618,052, filed on Sep. 14, 2012, now Pat. No. 8,939,948.

(60) Provisional application No. 61/568,624, filed on Dec. 8, 2011, provisional application No. 61/534,845, filed on Sep. 14, 2011.

(51) Int. Cl.
*A61B 17/00* (2006.01)
*A61L 27/02* (2006.01)
*A61L 27/16* (2006.01)
*A61K 47/34* (2017.01)

(52) U.S. Cl.
CPC ............ *A61L 27/025* (2013.01); *A61L 27/16* (2013.01); *A61K 47/34* (2013.01)

(56) References Cited

U.S. PATENT DOCUMENTS

| | | | |
|---|---|---|---|
| 3,416,530 A | 12/1968 | Ness |
| 3,545,439 A | 12/1970 | Kalamazoo et al. |
| 3,566,874 A | 3/1971 | Shepherd et al. |
| 3,618,604 A | 11/1971 | Ness |
| 3,626,940 A | 12/1971 | Zaffaroni |
| 3,710,796 A | 1/1973 | Neefe |
| 3,760,805 A | 9/1973 | Higuchi |
| 3,811,444 A | 5/1974 | Heller et al. |
| 3,826,258 A | 7/1974 | Abraham |
| 3,828,777 A | 8/1974 | Ness |
| 3,845,201 A | 10/1974 | Haddad et al. |
| 3,867,519 A | 2/1975 | Michaels |
| 3,903,880 A | 9/1975 | Higuchi et al. |
| 3,916,899 A | 11/1975 | Theeuwes et al. |
| 3,920,805 A | 11/1975 | Roseman |
| 3,926,188 A | 12/1975 | Baker et al. |
| 3,960,150 A | 6/1976 | Hussain et al. |
| 3,961,628 A | 6/1976 | Arnold |
| 3,962,414 A | 6/1976 | Michaels |
| 3,963,025 A | 6/1976 | Whitaker et al. |
| 3,991,760 A | 11/1976 | Drobish et al. |
| 3,993,073 A | 11/1976 | Zaffaroni |
| 3,995,633 A | 12/1976 | Gougeon |
| 3,995,634 A | 12/1976 | Drobish |
| 3,995,635 A | 12/1976 | Higuchi et al. |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,335 A | 3/1977 | Arnold |
| 4,016,251 A | 4/1977 | Higuchi et al. |
| 4,052,505 A | 10/1977 | Higuchi et al. |
| 4,057,619 A | 11/1977 | Higuchi et al. |
| 4,067,961 A | 1/1978 | Laughlin |
| 4,093,709 A | 6/1978 | Choi et al. |
| 4,131,648 A | 12/1978 | Choi et al. |
| 4,155,991 A | 5/1979 | Schopflin et al. |
| 4,157,864 A | 6/1979 | Koller et al. |
| 4,160,452 A | 7/1979 | Theeuwes |
| 4,164,560 A | 8/1979 | Folkman et al. |
| 4,177,256 A | 12/1979 | Michaels et al. |
| 4,179,497 A | 12/1979 | Cohen et al. |
| 4,190,642 A | 2/1980 | Gale et al. |
| 4,201,210 A | 5/1980 | Hughes et al. |
| 4,215,691 A | 8/1980 | Wong |
| 4,249,531 A | 2/1981 | Heller et al. |
| 4,281,654 A | 8/1981 | Shell et al. |
| 4,285,987 A | 8/1981 | Ayer et al. |
| 4,292,965 A | 10/1981 | Nash et al. |
| 4,303,637 A | 12/1981 | Shell et al. |
| 4,304,765 A | 12/1981 | Shell et al. |
| 4,322,323 A | 3/1982 | Capozza |
| 4,343,787 A | 8/1982 | Katz |
| 4,432,964 A | 2/1984 | Shell et al. |
| 4,439,198 A | 3/1984 | Brightman, II et al. |
| 4,469,671 A | 9/1984 | Zimmerman et al. |
| 4,484,922 A | 11/1984 | Rosenwald |
| 4,524,776 A | 6/1985 | Withers et al. |
| 4,540,417 A | 9/1985 | Poler |
| 4,652,099 A | 3/1987 | Lichtman |
| 4,678,466 A | 7/1987 | Rosenwald |
| 4,822,616 A | 4/1989 | Zimmermann et al. |
| 4,888,074 A | 12/1989 | Pocknell |
| 4,961,931 A | 10/1990 | Wong |
| 4,973,304 A | 11/1990 | Graham et al. |
| 5,071,657 A | 12/1991 | Oloff et al. |
| 5,098,443 A | 3/1992 | Parel et al. |
| 5,137,728 A | 8/1992 | Bawa |
| 5,147,647 A | 9/1992 | Darougar |
| 5,178,635 A | 1/1993 | Gwon et al. |
| 5,205,611 A | 4/1993 | Stephens |
| 5,248,700 A | 9/1993 | Lance |
| 5,300,114 A | 4/1994 | Gwon et al. |
| 5,314,419 A | 5/1994 | Pelling |
| 5,322,691 A | 6/1994 | Darougar et al. |
| 5,370,607 A | 12/1994 | Memmen |
| 5,378,475 A | 1/1995 | Smith et al. |
| 5,395,618 A | 3/1995 | Darougar et al. |
| 5,443,505 A | 8/1995 | Wong et al. |
| 5,472,436 A | 12/1995 | Fremstad |
| 5,474,780 A | 12/1995 | Chang |
| 5,476,511 A | 12/1995 | Gwon et al. |
| 5,496,811 A | 3/1996 | Aviv et al. |
| 5,605,696 A | 2/1997 | Eury et al. |
| 5,618,274 A | 4/1997 | Rosenthal |
| 5,694,947 A | 12/1997 | Lehtinen et al. |
| 5,773,019 A | 6/1998 | Ashton et al. |
| 5,773,021 A | 6/1998 | Gurtler et al. |
| 5,788,977 A | 8/1998 | Aguadisch et al. |
| 5,824,086 A | 10/1998 | Silvestrini |
| 5,851,547 A | 12/1998 | Fujioka et al. |
| 5,855,906 A | 1/1999 | McClay |
| 5,902,598 A | 5/1999 | Chen et al. |
| 5,972,372 A | 10/1999 | Saleh et al. |
| 5,989,579 A | 11/1999 | Darougar et al. |
| 6,001,386 A | 12/1999 | Ashton et al. |
| 6,015,213 A | 1/2000 | Nakada et al. |
| 6,096,076 A | 8/2000 | Silvestrini |
| 6,109,537 A | 8/2000 | Heath |
| 6,120,460 A | 9/2000 | Abreu |
| 6,146,366 A | 11/2000 | Schachar |
| 6,149,685 A | 11/2000 | Sigoloff |
| 6,217,896 B1 | 4/2001 | Benjamin |
| 6,264,971 B1 | 7/2001 | Darougar et al. |
| 6,361,780 B1 | 3/2002 | Ley et al. |
| 6,375,642 B1 | 4/2002 | Grieshaber et al. |
| 6,375,972 B1 | 4/2002 | Guo et al. |
| 6,394,094 B1 | 5/2002 | McKenna et al. |
| 6,485,735 B1 | 11/2002 | Steen et al. |
| 6,547,714 B1 | 4/2003 | Dailey |
| 6,634,576 B2 | 10/2003 | Verhoff et al. |
| 6,669,950 B2 | 12/2003 | Yaacobi |
| 6,719,750 B2 | 4/2004 | Varner et al. |
| 6,746,686 B2 | 6/2004 | Hughes et al. |
| 6,841,574 B2 | 1/2005 | Mo et al. |
| 6,939,569 B1 | 9/2005 | Green et al. |
| 6,964,781 B2 | 11/2005 | Brubaker |
| 6,966,927 B1 | 11/2005 | Silverstrini |
| 6,986,900 B2 | 1/2006 | Yaacobi |
| 6,991,808 B2 | 1/2006 | Brubaker et al. |
| 7,094,226 B2 | 8/2006 | Yaacobi |

(56) References Cited

U.S. PATENT DOCUMENTS

| | | |
|---|---|---|
| 7,195,774 B2 | 3/2007 | Carvalho et al. |
| 7,488,343 B2 | 2/2009 | O'Brien et al. |
| 7,544,371 B2 | 6/2009 | Kunzler et al. |
| 7,762,662 B1 | 7/2010 | Eno |
| 7,785,578 B2 | 8/2010 | Miller et al. |
| 7,799,336 B2 | 9/2010 | Hughes |
| 7,833,545 B2 | 11/2010 | Ron et al. |
| 7,862,552 B2 | 1/2011 | McIntyre et al. |
| 7,910,126 B2 | 3/2011 | Ahmed et al. |
| 7,985,208 B2 | 7/2011 | Christensen |
| 7,998,497 B2 | 8/2011 | de Juan, Jr. et al. |
| 8,021,680 B2 | 9/2011 | Anderson et al. |
| 8,469,934 B2 | 6/2013 | Weiner et al. |
| 8,663,194 B2 * | 3/2014 | Ambati .................. A61P 37/06 604/521 |
| 8,715,712 B2 | 5/2014 | de Juan, Jr. et al. |
| 2002/0026176 A1 | 2/2002 | Varner et al. |
| 2002/0047058 A1 | 4/2002 | Verhoff et al. |
| 2002/0115985 A1 | 8/2002 | Larson et al. |
| 2003/0088307 A1 | 5/2003 | Shulze et al. |
| 2003/0149479 A1 | 8/2003 | Snyder et al. |
| 2003/0176854 A1 | 9/2003 | Rodstrom |
| 2004/0042073 A1 | 3/2004 | Pynson |
| 2004/0115234 A1 | 6/2004 | Gewirtz |
| 2004/0121014 A1 | 6/2004 | Guo et al. |
| 2004/0133155 A1 | 7/2004 | Varner et al. |
| 2004/0170685 A1 | 9/2004 | Carpenter et al. |
| 2004/0220660 A1 | 11/2004 | Shanley et al. |
| 2004/0241243 A1 | 12/2004 | Lin et al. |
| 2004/0249364 A1 | 12/2004 | Kaploun |
| 2004/0265355 A1 | 12/2004 | Shalaby |
| 2005/0019371 A1 | 1/2005 | Anderson et al. |
| 2005/0042292 A1 | 2/2005 | Muldoon et al. |
| 2005/0048099 A1 | 3/2005 | Shiah et al. |
| 2005/0053639 A1 | 3/2005 | Shalaby |
| 2005/0060021 A1 | 3/2005 | O'Brien et al. |
| 2005/0125059 A1 | 6/2005 | Pinchuk et al. |
| 2005/0163844 A1 | 7/2005 | Ashton |
| 2005/0196424 A1 | 9/2005 | Chappa |
| 2005/0197651 A1 | 9/2005 | Chen et al. |
| 2005/0228473 A1 | 10/2005 | Brown |
| 2005/0228482 A1 | 10/2005 | Herzog et al. |
| 2005/0244461 A1 | 11/2005 | Nivaggioli et al. |
| 2005/0244464 A1 | 11/2005 | Hughes |
| 2005/0276841 A1 | 12/2005 | Davis et al. |
| 2005/0288197 A1 | 12/2005 | Horn |
| 2006/0024350 A1 | 2/2006 | Varner et al. |
| 2006/0034891 A1 | 2/2006 | Lawin et al. |
| 2006/0140867 A1 | 6/2006 | Helfer et al. |
| 2006/0185678 A1 | 8/2006 | Bronnenkant et al. |
| 2006/0212115 A1 | 9/2006 | Maldonado Bas |
| 2006/0216328 A1 | 9/2006 | Kis et al. |
| 2006/0235513 A1 | 10/2006 | Price |
| 2006/0246112 A1 | 11/2006 | Snyder et al. |
| 2006/0264912 A1 | 11/2006 | McIntyre et al. |
| 2006/0292222 A1 | 12/2006 | Jonasse |
| 2007/0112318 A1 | 5/2007 | Leahy et al. |
| 2007/0134305 A1 | 6/2007 | Zilberman |
| 2007/0196433 A1 | 8/2007 | Ron et al. |
| 2007/0202150 A1 | 8/2007 | Dave |
| 2007/0212387 A1 | 9/2007 | Patravale et al. |
| 2007/0243230 A1 | 10/2007 | de Juan et al. |
| 2007/0269487 A1 | 11/2007 | de Juan et al. |
| 2008/0090911 A1 | 4/2008 | Frank et al. |
| 2008/0097591 A1 | 4/2008 | Savage et al. |
| 2008/0103584 A1 | 5/2008 | Su et al. |
| 2008/0145406 A1 | 6/2008 | Asgharian et al. |
| 2008/0181930 A1 | 7/2008 | Rodstrom et al. |
| 2008/0243095 A1 | 10/2008 | Kaiser et al. |
| 2009/0005864 A1 | 1/2009 | Eggleston |
| 2009/0081278 A1 | 3/2009 | De Graaff et al. |
| 2009/0082863 A1 | 3/2009 | Schieber et al. |
| 2009/0092654 A1 | 4/2009 | de Juan, Jr. et al. |
| 2009/0104243 A1 | 4/2009 | Utkhede et al. |
| 2009/0104248 A1 | 4/2009 | Rapacki et al. |
| 2009/0110756 A1 | 4/2009 | McCray, Jr. et al. |
| 2009/0143752 A1 | 6/2009 | Higuchi et al. |
| 2009/0148485 A1 | 6/2009 | Whitehead |
| 2009/0155326 A1 | 6/2009 | Mack et al. |
| 2009/0155338 A1 | 6/2009 | Conway et al. |
| 2009/0162417 A1 | 6/2009 | Eells |
| 2009/0196903 A1 | 8/2009 | Kliman |
| 2009/0220573 A1 | 9/2009 | Kaufman |
| 2009/0234005 A1 | 9/2009 | Ishida et al. |
| 2009/0252807 A1 | 10/2009 | Jenkins et al. |
| 2009/0280158 A1 | 11/2009 | Butuner |
| 2009/0287300 A1 | 11/2009 | Dave et al. |
| 2009/0291120 A1 | 11/2009 | Tuominen et al. |
| 2009/0312724 A1 | 12/2009 | Pipkin et al. |
| 2009/0312836 A1 | 12/2009 | Pinchuk et al. |
| 2009/0318549 A1 | 12/2009 | Butuner |
| 2010/0040671 A1 | 2/2010 | Ahmed et al. |
| 2010/0055139 A1 | 3/2010 | Lee |
| 2010/0069857 A1 | 3/2010 | Christensen |
| 2010/0074942 A1 | 3/2010 | Ratner et al. |
| 2010/0114309 A1 | 5/2010 | de Juan, Jr. et al. |
| 2010/0124565 A1 | 5/2010 | Spada et al. |
| 2010/0166841 A1 | 7/2010 | Roth et al. |
| 2010/0178316 A1 | 7/2010 | Chauhan et al. |
| 2010/0209477 A1 | 8/2010 | Butuner et al. |
| 2010/0209478 A1 | 8/2010 | Sawhney et al. |
| 2010/0226962 A1 | 9/2010 | Rodstrom et al. |
| 2010/0233241 A1 | 9/2010 | Leahy et al. |
| 2010/0266664 A1 | 10/2010 | Asgharian et al. |
| 2010/0278898 A1 | 11/2010 | Hughes et al. |
| 2010/0331796 A1 | 12/2010 | Leahy et al. |
| 2011/0009958 A1 | 1/2011 | Wardle et al. |
| 2011/0105986 A1 | 5/2011 | Bronstein et al. |
| 2011/0184358 A1 | 7/2011 | Weiner et al. |
| 2011/0195123 A1 | 8/2011 | Shemi |
| 2011/0268783 A1 | 11/2011 | Shalaby et al. |
| 2011/0280909 A1 | 11/2011 | Moazed |
| 2011/0282328 A1 | 11/2011 | Ambati et al. |
| 2012/0022473 A1 | 1/2012 | Shikamura et al. |
| 2012/0089072 A1 | 4/2012 | Cunningham, Jr. |
| 2012/0109054 A1 | 5/2012 | Thompson et al. |
| 2012/0136322 A1 | 5/2012 | Alster et al. |
| 2012/0177716 A1 | 7/2012 | Ho et al. |
| 2012/0187594 A1 | 7/2012 | Utkhede et al. |
| 2012/0218184 A1 | 8/2012 | Wissmar |
| 2012/0245505 A1 | 9/2012 | Robinson et al. |
| 2012/0269893 A1 | 10/2012 | Lee |
| 2013/0062809 A1 | 3/2013 | Ellis et al. |
| 2013/0090612 A1 | 4/2013 | de Juan, Jr. et al. |
| 2013/0142858 A1 | 6/2013 | Kopczynski et al. |
| 2013/0144128 A1 | 6/2013 | de Juan, Jr. et al. |
| 2013/0156752 A1 | 6/2013 | Jarrett et al. |
| 2013/0156840 A1 | 6/2013 | Basinger et al. |
| 2013/0177615 A1 | 7/2013 | Lee |
| 2013/0209538 A1 | 8/2013 | Venkatraman et al. |
| 2013/0261569 A1 | 10/2013 | Weiner et al. |
| 2014/0121612 A1 | 5/2014 | Rubin et al. |
| 2014/0135716 A1 | 5/2014 | Clarke et al. |
| 2016/0243291 A1 | 8/2016 | Reich et al. |

FOREIGN PATENT DOCUMENTS

| | | |
|---|---|---|
| CN | 201012180 Y | 1/2008 |
| CN | 102026599 A | 4/2011 |
| CN | 102239431 A | 11/2011 |
| EP | 1473003 A2 | 11/2004 |
| GB | 1372944 | 11/1974 |
| GB | 1529143 A | 10/1978 |
| JP | S48-036993 | 5/1973 |
| JP | S5560452 | 5/1980 |
| JP | S629561 B2 | 2/1987 |
| JP | H07067910 A | 3/1995 |
| JP | 2007167358 | 7/2007 |
| JP | 2008523917 A | 7/2008 |
| JP | 2010513555 A | 4/2010 |
| JP | 2010538696 A | 12/2010 |
| JP | 2011520805 A | 7/2011 |
| JP | 2012512904 A | 6/2012 |
| JP | 2012528695 A | 11/2012 |

(56) References Cited

FOREIGN PATENT DOCUMENTS

| | | |
|---|---|---|
| RU | 2357709 C1 | 6/2009 |
| SU | 404474 A1 | 10/1973 |
| WO | WO-92/014450 A1 | 9/1992 |
| WO | WO-95/01764 A2 | 1/1995 |
| WO | WO-97/11655 A1 | 4/1997 |
| WO | WO-97/43984 A1 | 11/1997 |
| WO | WO-02/076426 A2 | 10/2002 |
| WO | WO-02/096868 A2 | 12/2002 |
| WO | WO-2005/020907 A3 | 3/2005 |
| WO | WO-2006/066103 A2 | 6/2006 |
| WO | WO-2007/083293 A1 | 7/2007 |
| WO | WO-2009/035562 A2 | 3/2009 |
| WO | WO-2009/153206 A2 | 12/2009 |
| WO | WO-2010/141729 | 12/2010 |
| WO | WO-2013/040426 A2 | 3/2013 |

OTHER PUBLICATIONS

International Search Report and Written Opinion of PCT Application No. PCT/US2012/055532. dated Feb. 26, 2013. 10 pages.

Kawakita et al.,"Measurement of fornix depth and area: a novel method of determining the severity of fornix shortening", Eye (2009) 23, 1115-1119.

Kumari A. et al. "Ocular inserts—Advancement in therapy of eye diseases." J. Adv. Pharm. Technol. Res. Jun.-Sep. 2010, 1(3): 291-296. Web. Downloaded from Internet Jan. 4, 2018.

Zeus Technical Newsletter. "Strength and Stiffness of Plastics". (Obtained from http://www.zeusinc.com/UserFiles/zeusinc/Documents/technical_newsletters/Zeus_StrengthStiffnessPlastics.pdf on Oct. 18, 2013). 11 pages.

\* cited by examiner

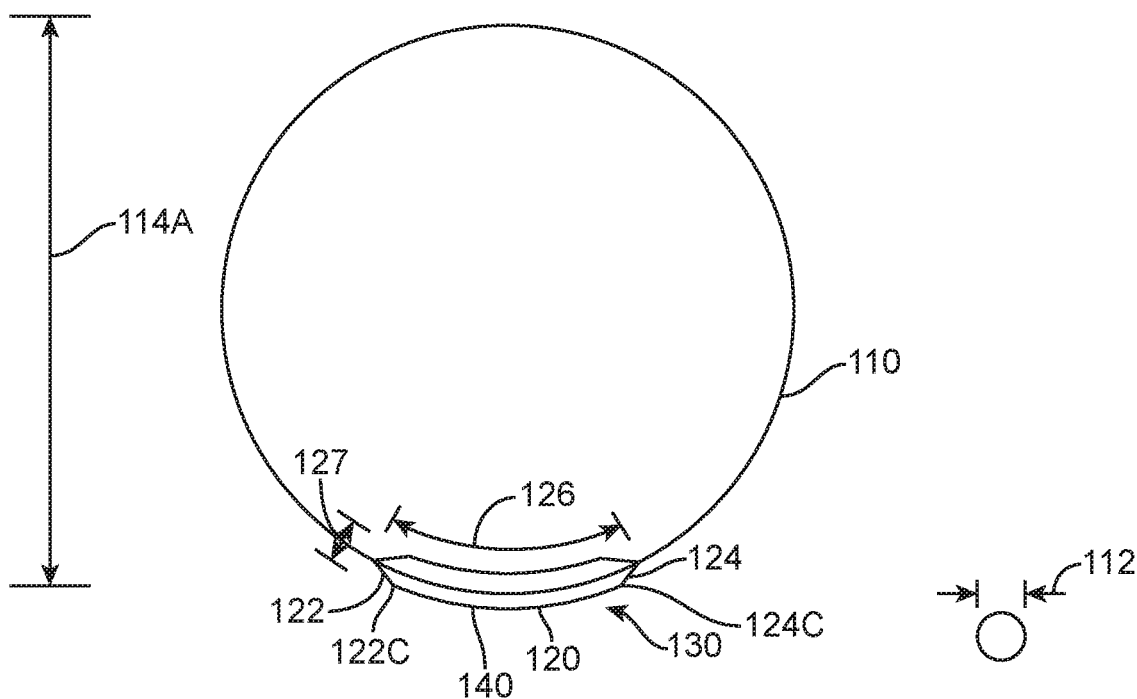
FIG. 2A
FIG. 2B
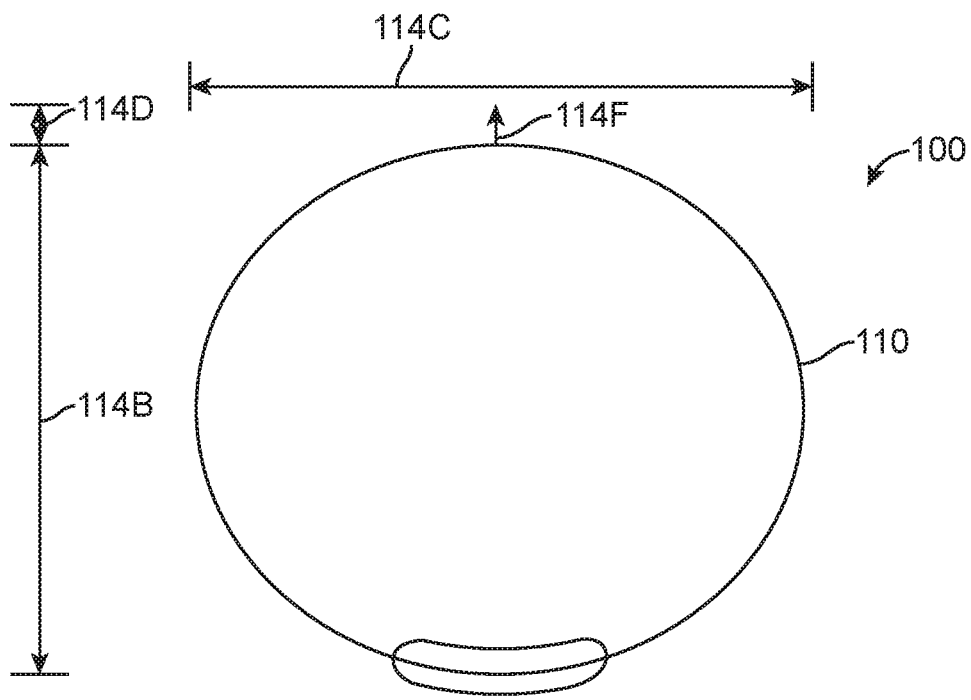
FIG. 2C

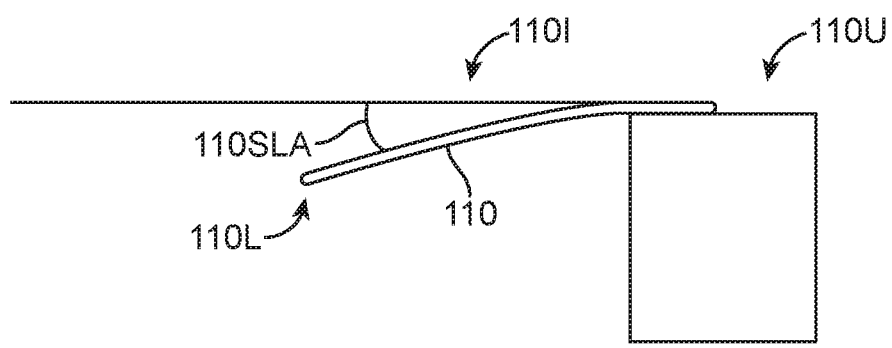
FIG. 2C1
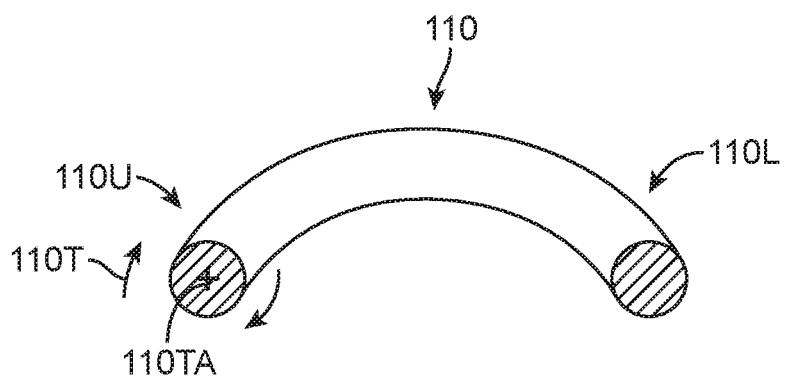
FIG. 2C2

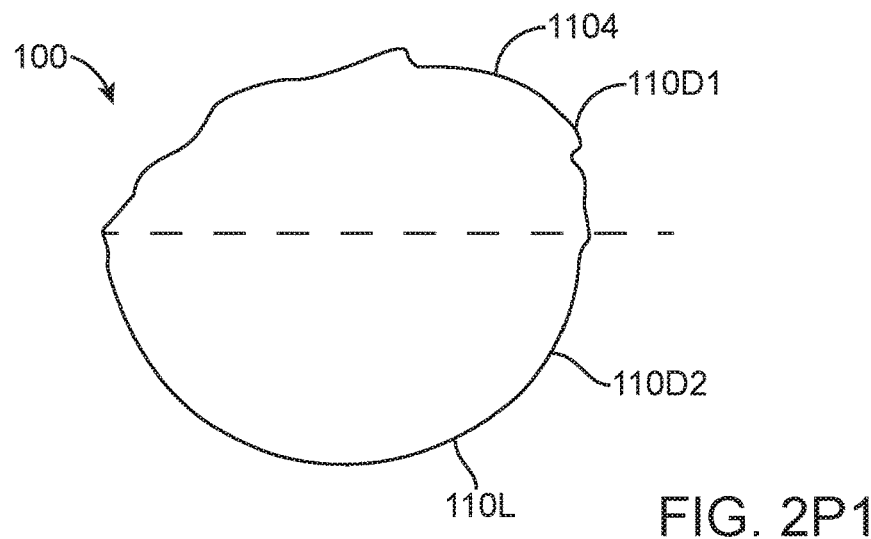
FIG. 2P1
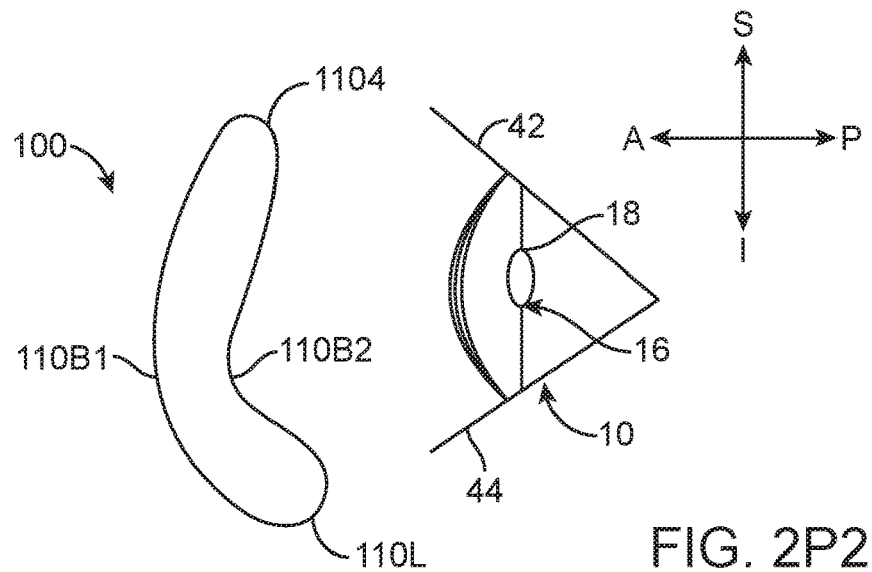
FIG. 2P2
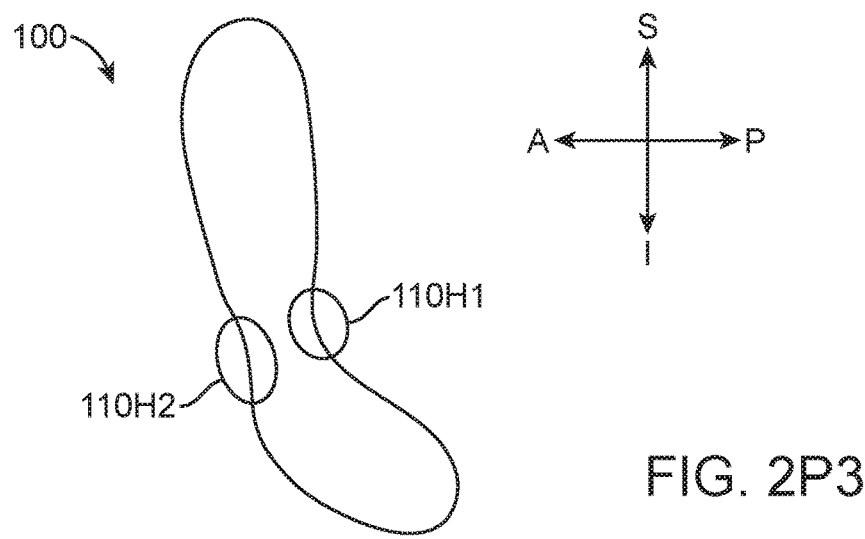
FIG. 2P3

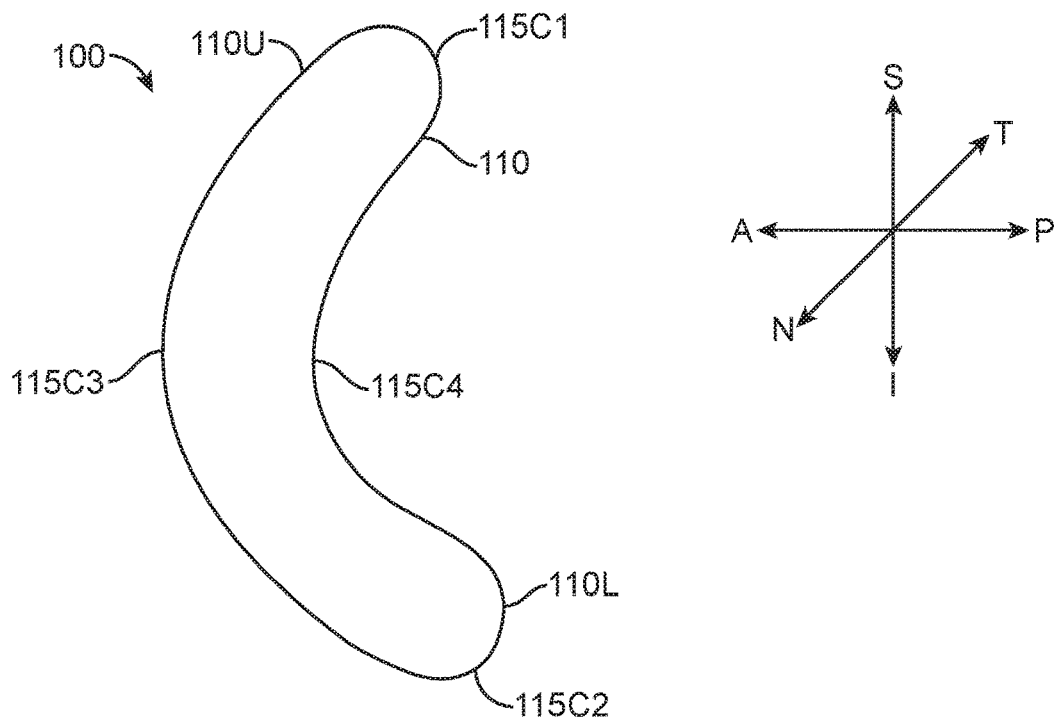
FIG. 2P4
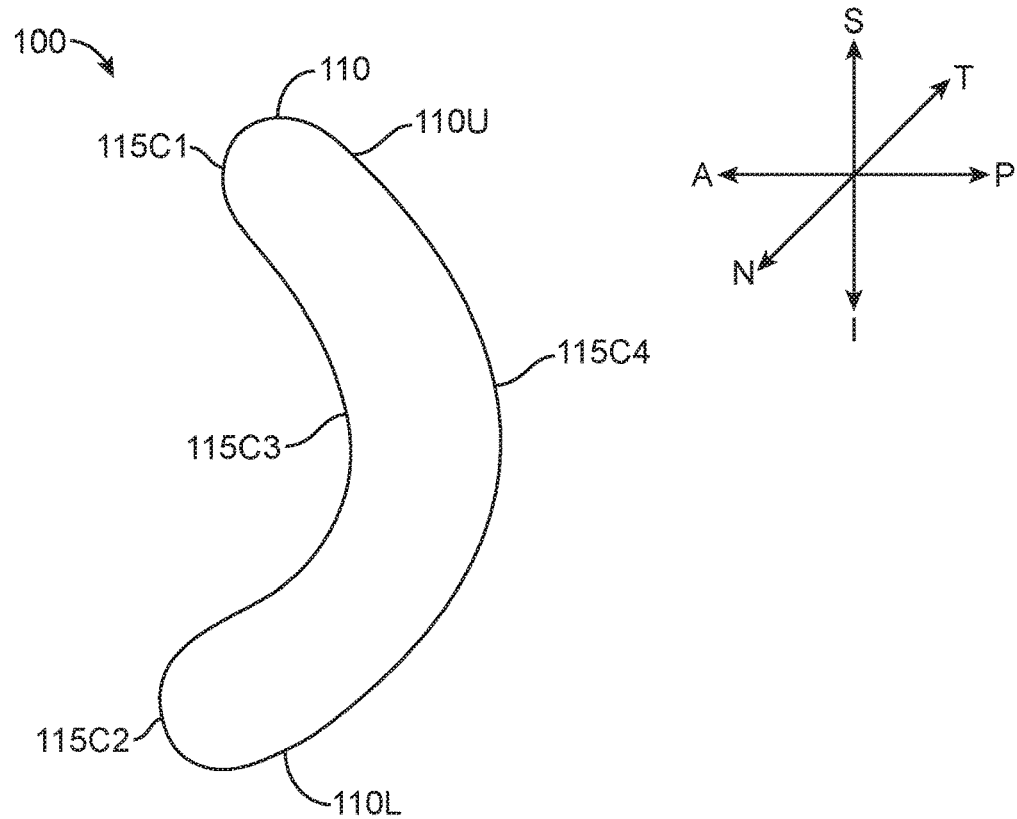
FIG. 2P5

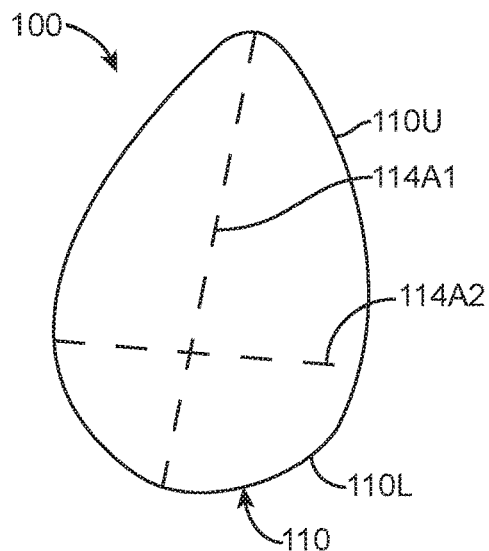
FIG. 2P6
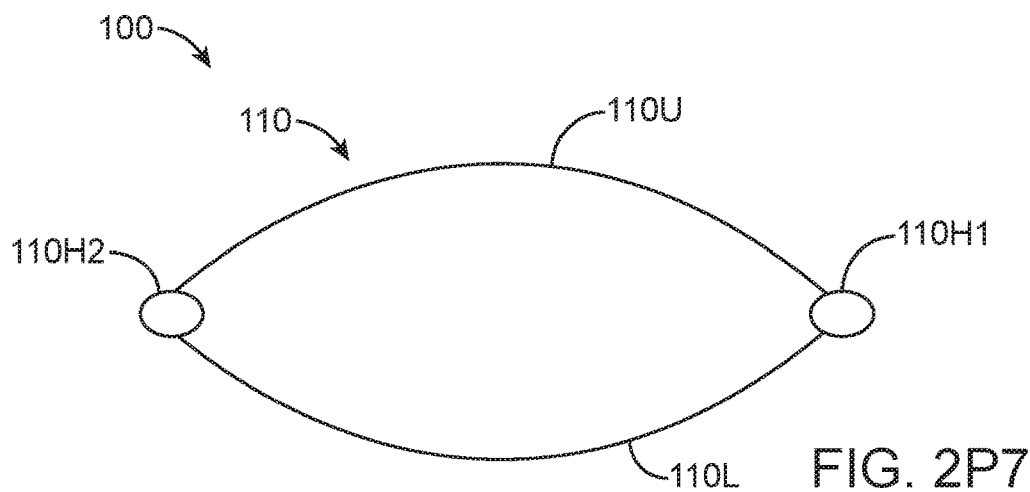
FIG. 2P7
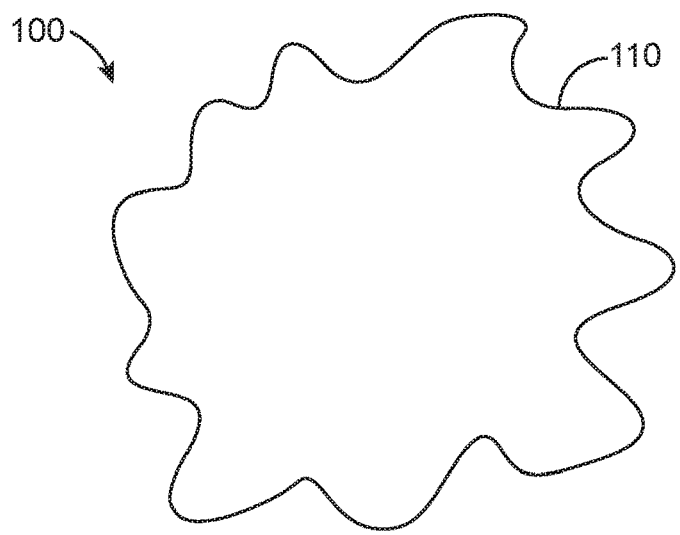
FIG. 2P8

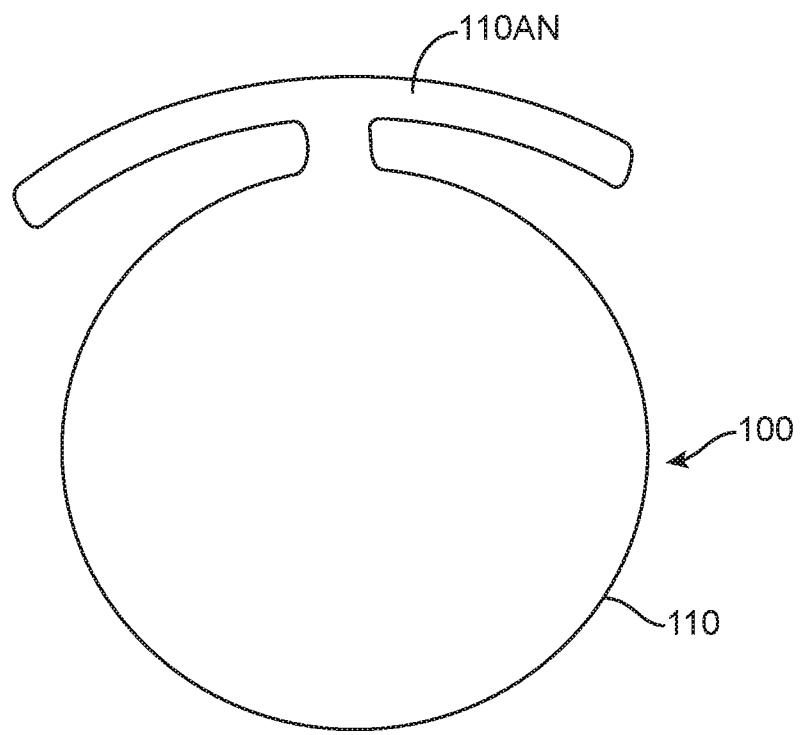
FIG. 2P9
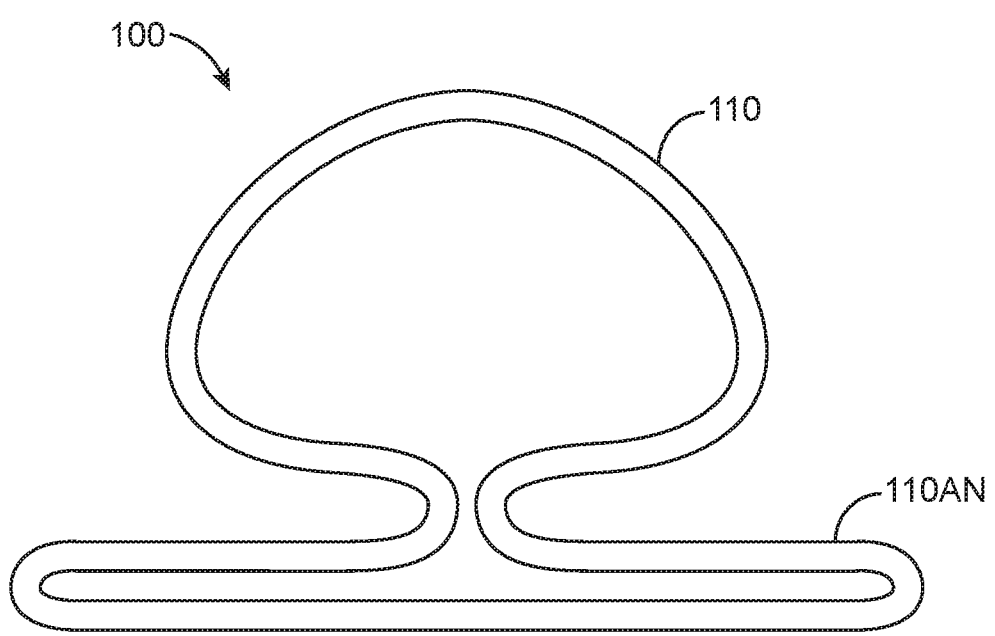
FIG. 2P10

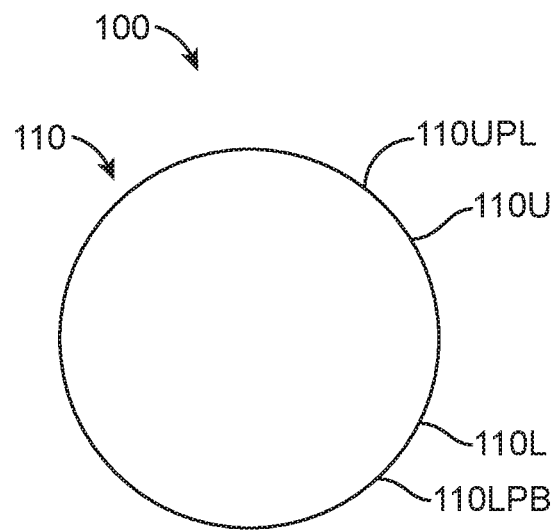
FIG. 2W
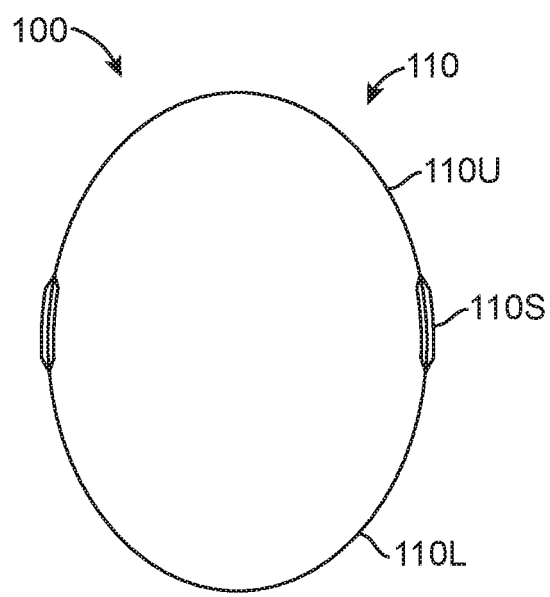
FIG. 2X1
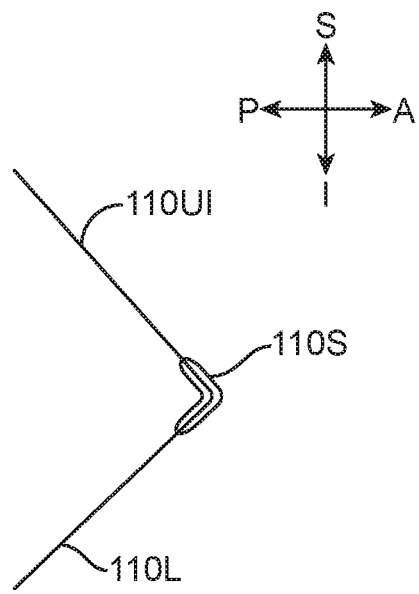
FIG. 2X2

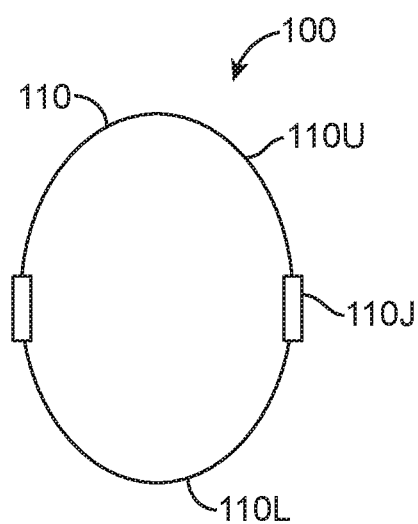
FIG. 2Z1
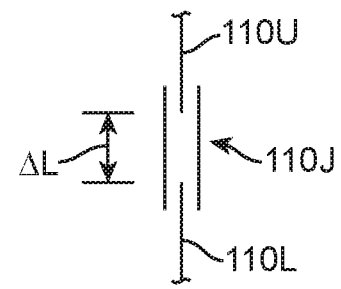
FIG. 2Z2
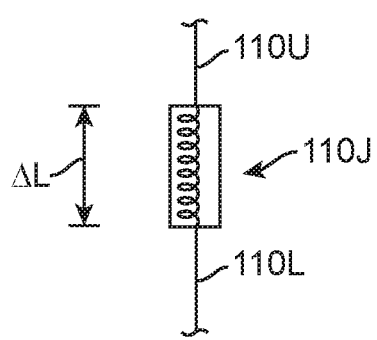
FIG. 2Z3
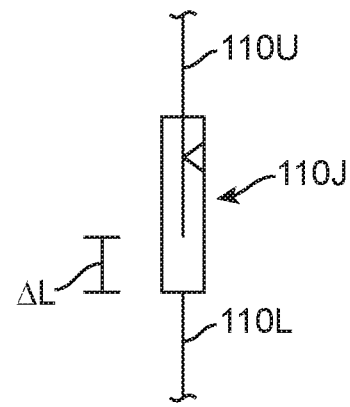
FIG. 2Z4

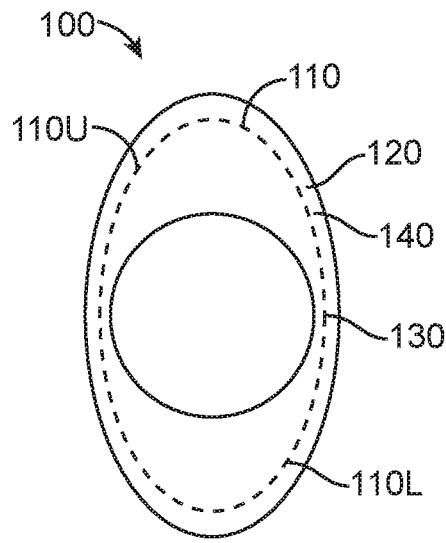
FIG. 2Z5
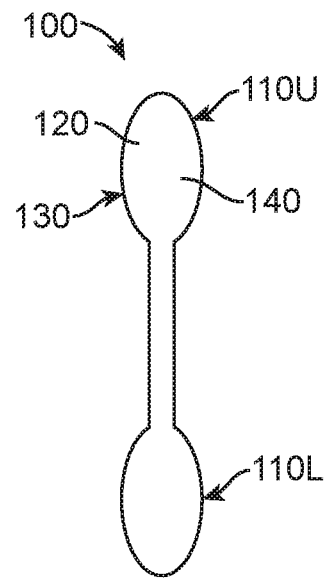
FIG. 2Z6
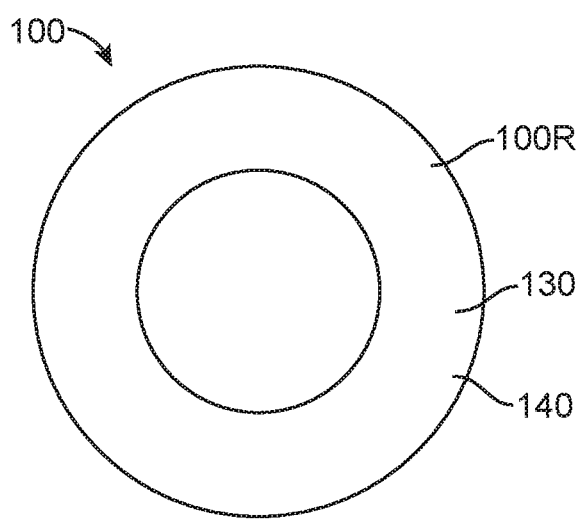
FIG. 2Z7
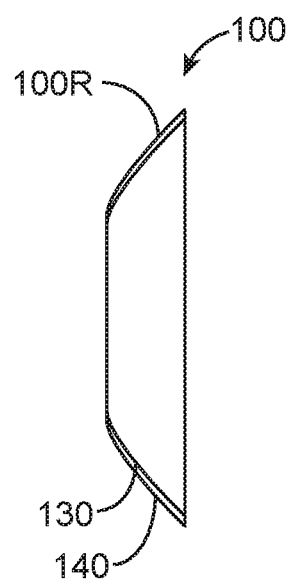
FIG. 2Z8

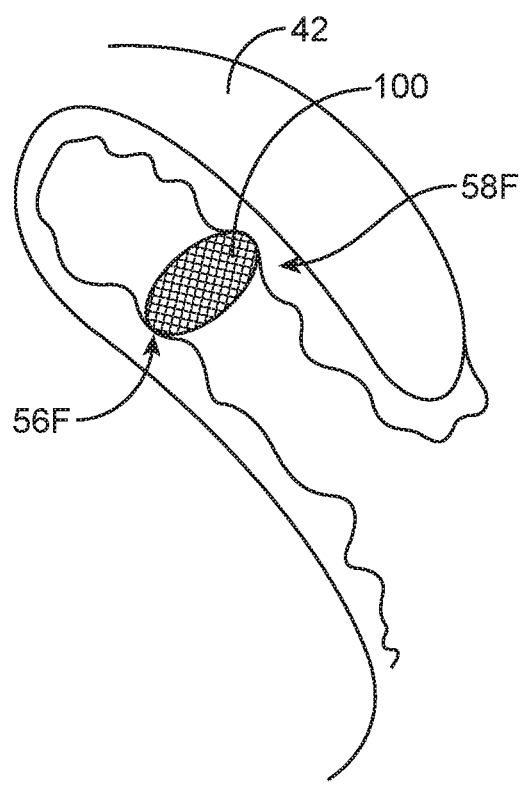
FIG. 3A1
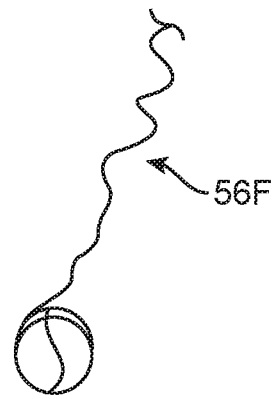
FIG. 3A2
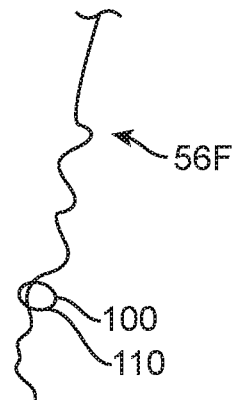
FIG. 3A3

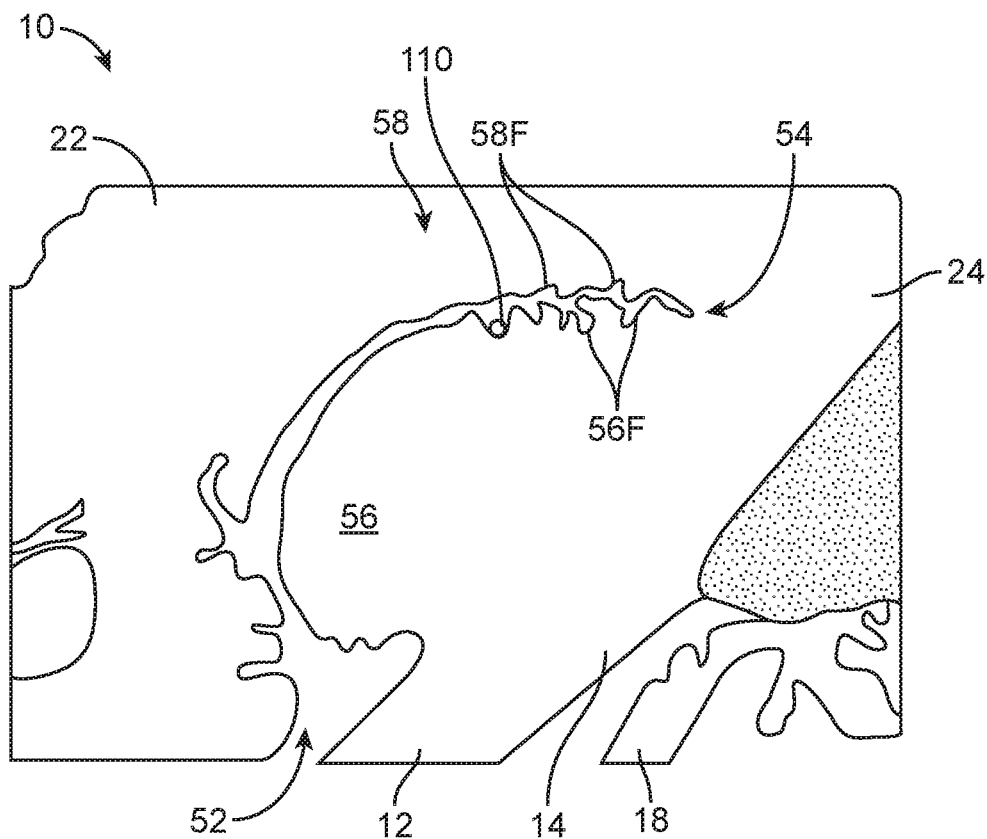
FIG. 3A4
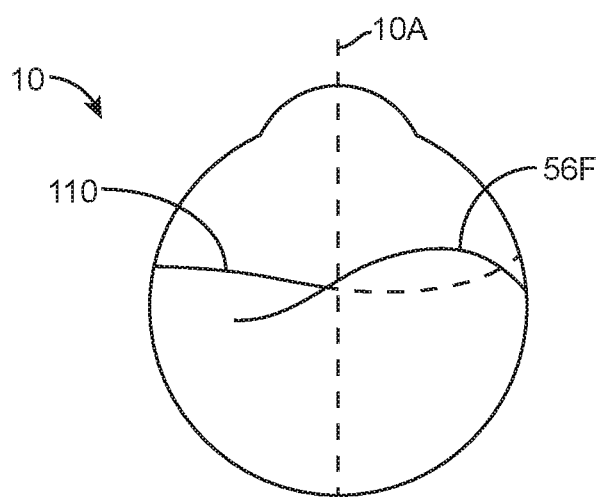
FIG. 3B

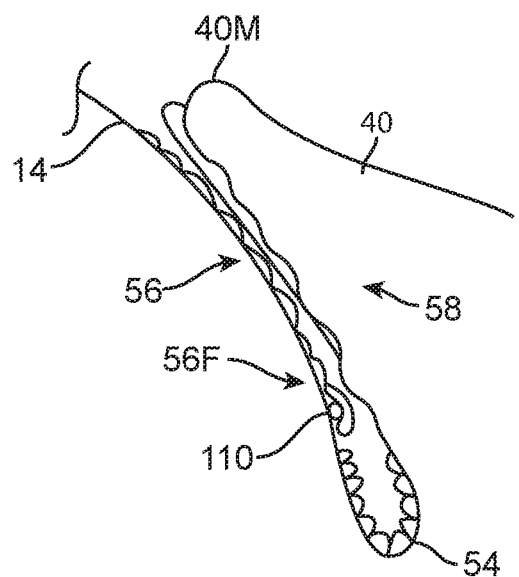
FIG. 3C1
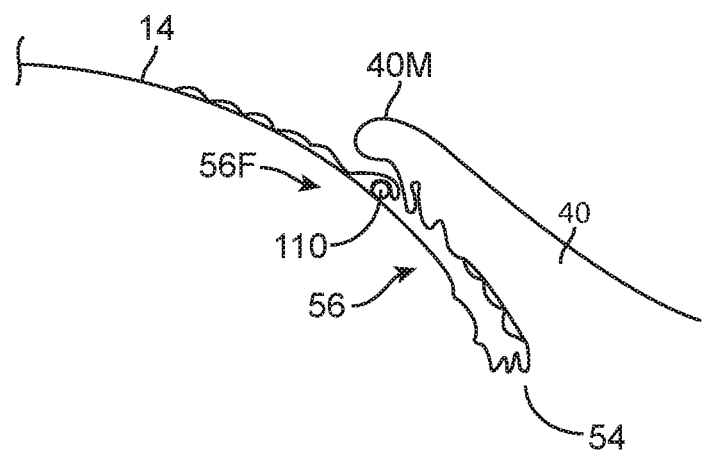
FIG. 3C2
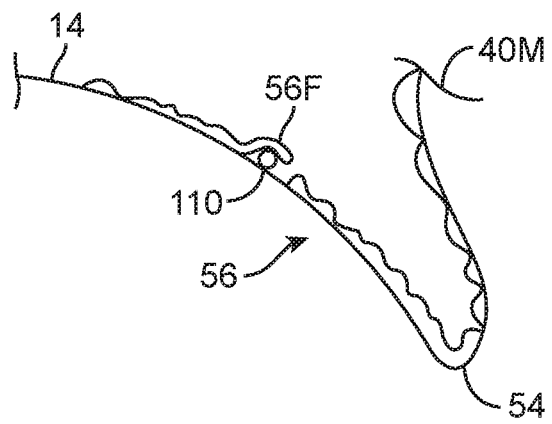
FIG. 3C3

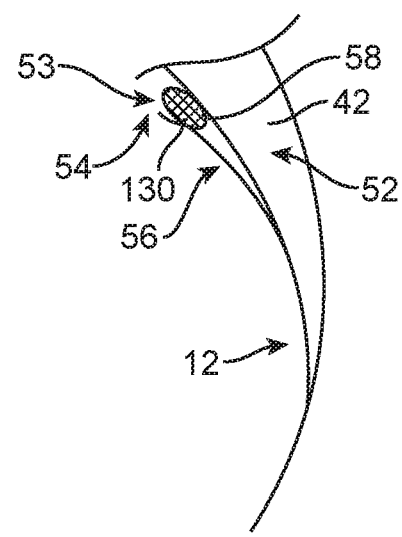
FIG. 3G2
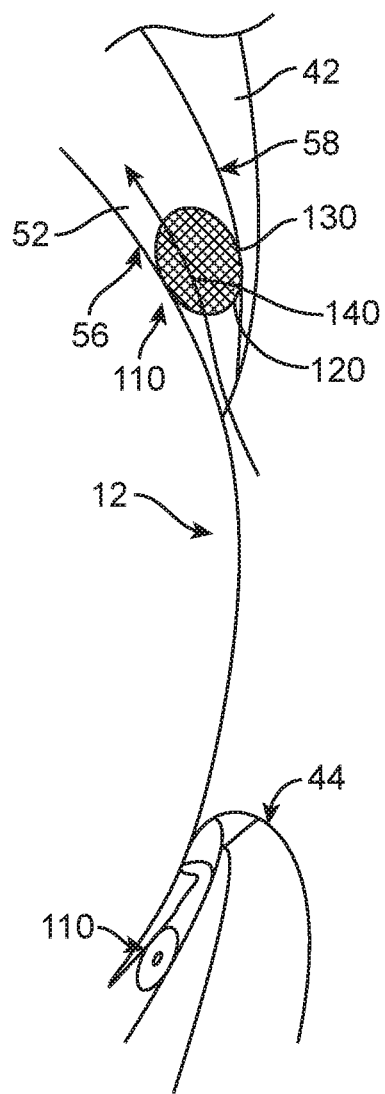
FIG. 3G1

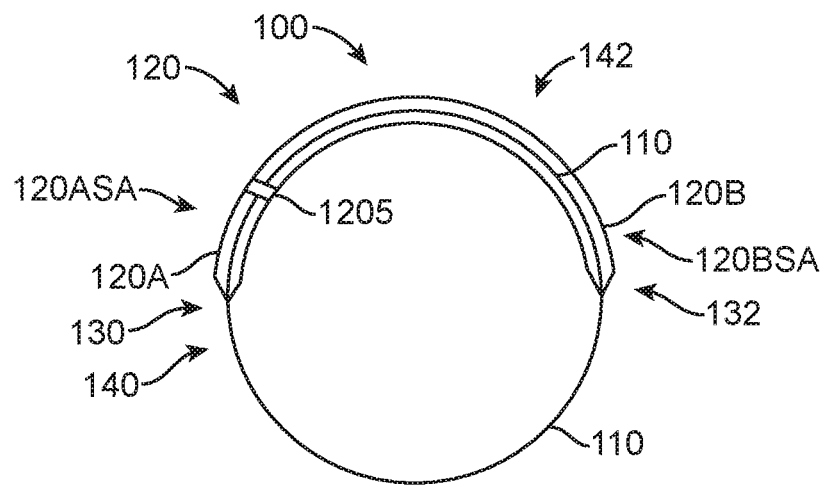
FIG. 4G1
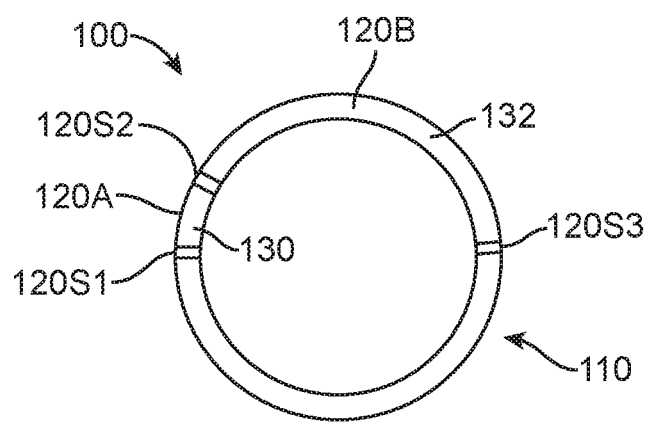
FIG. 4G2

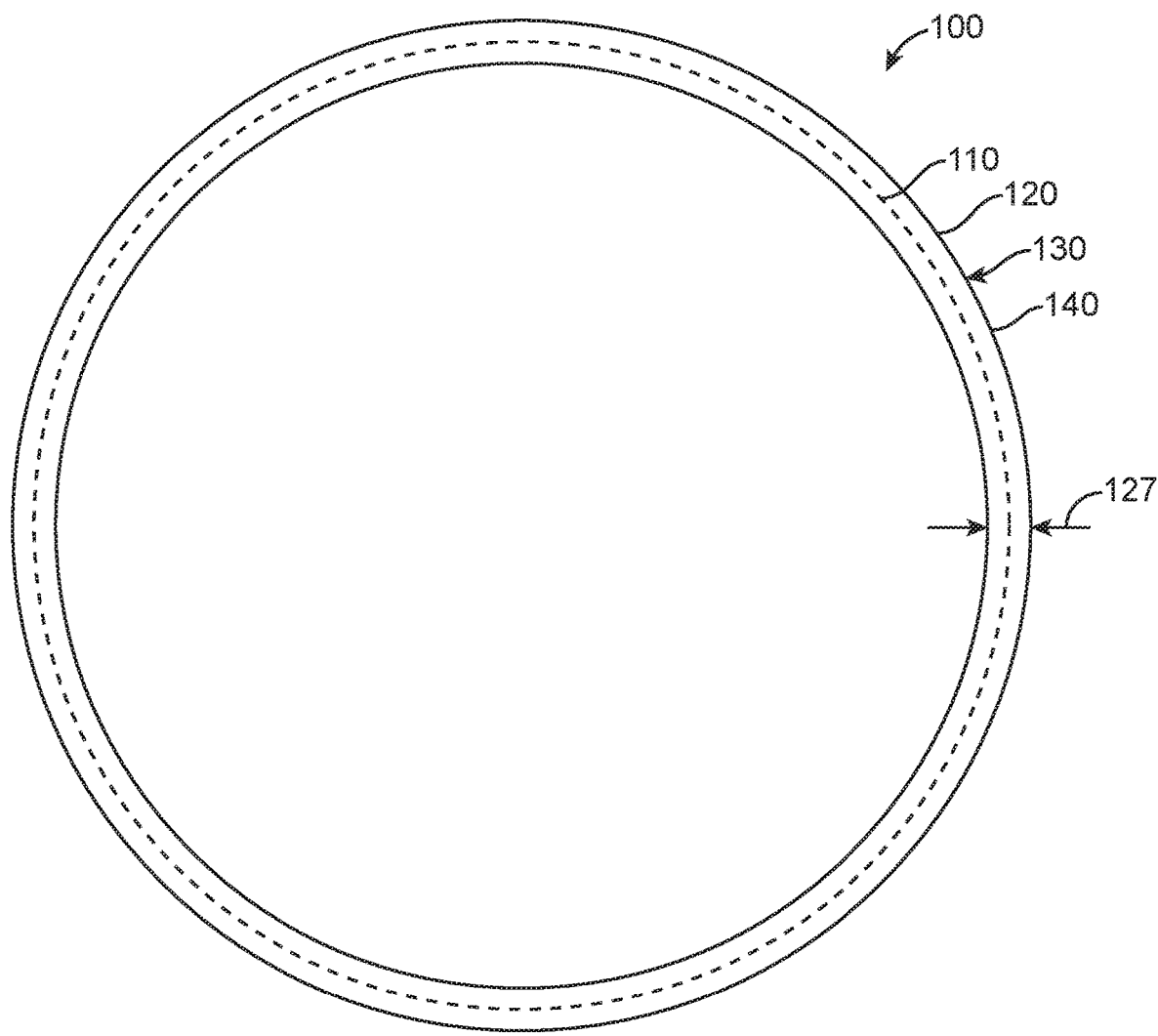
FIG. 4G3
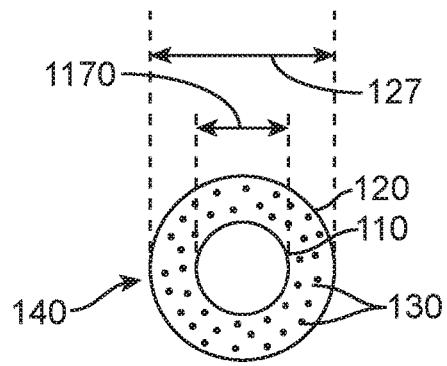
FIG. 4G4

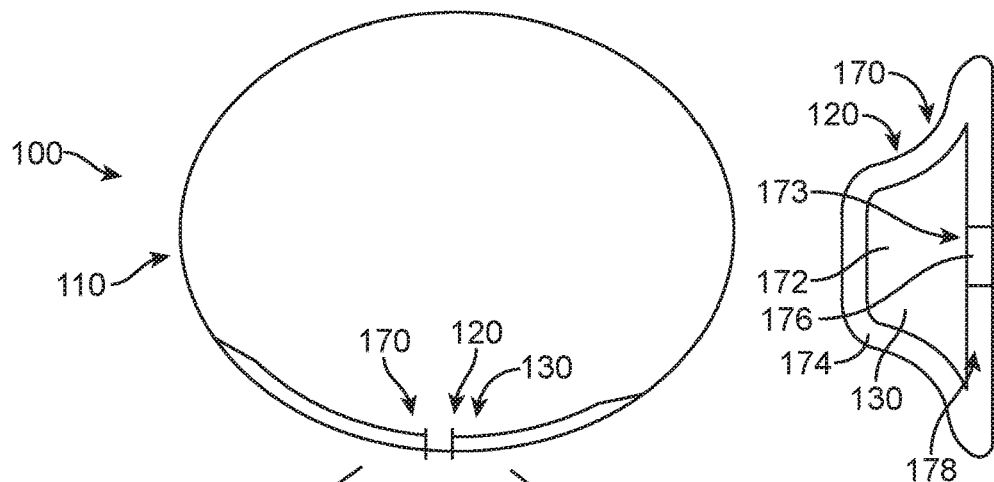
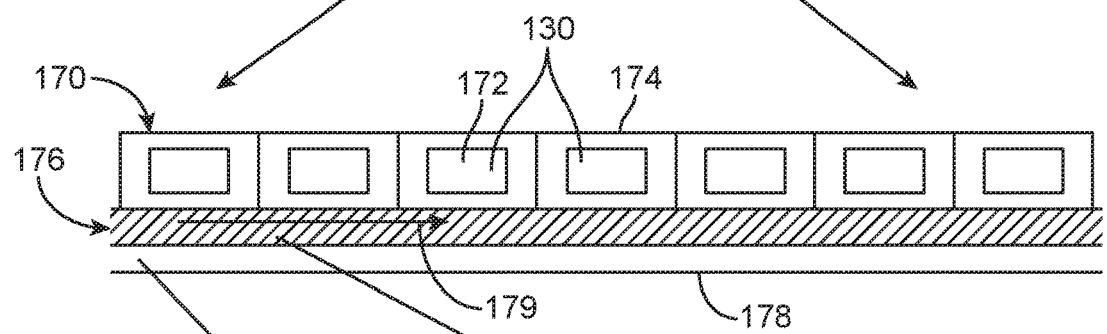
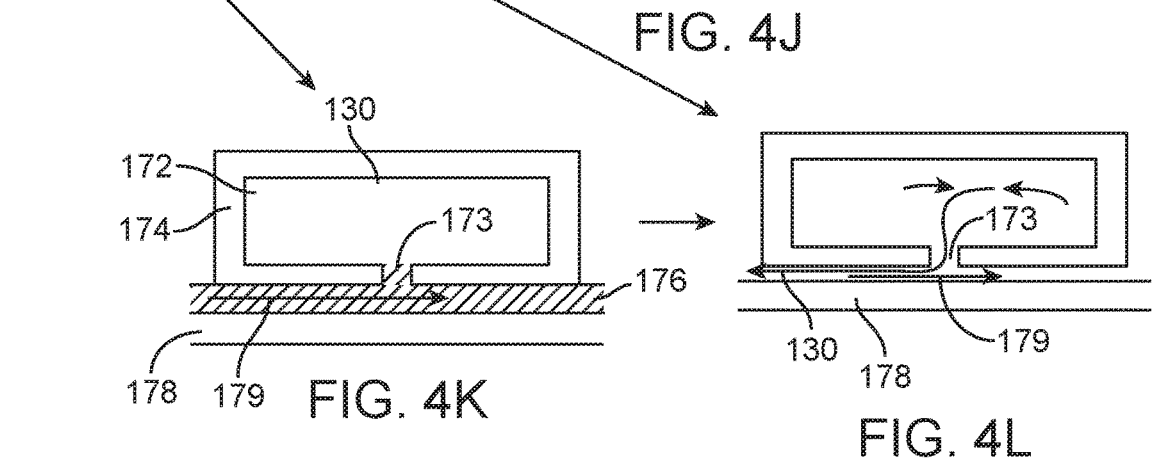
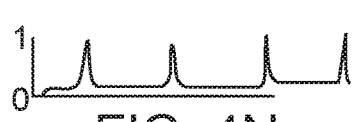
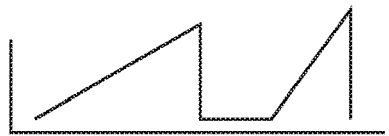

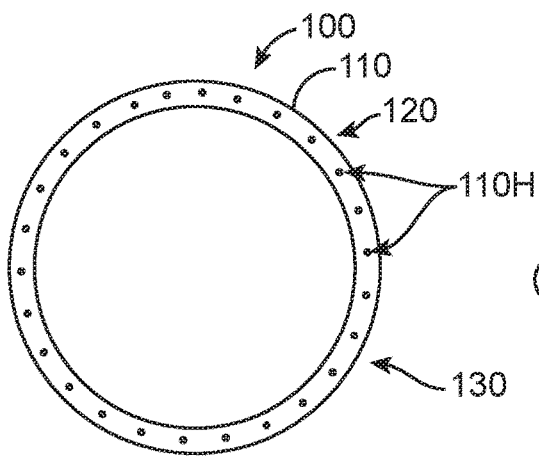
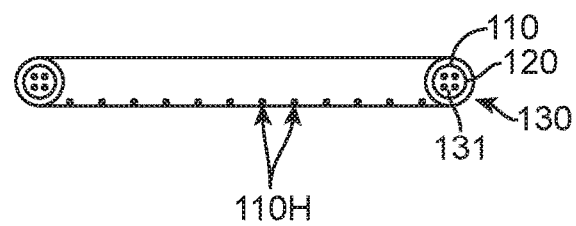
FIG. 7A
FIG. 7B
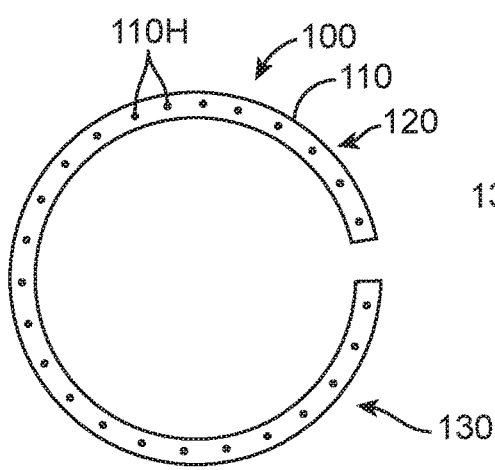
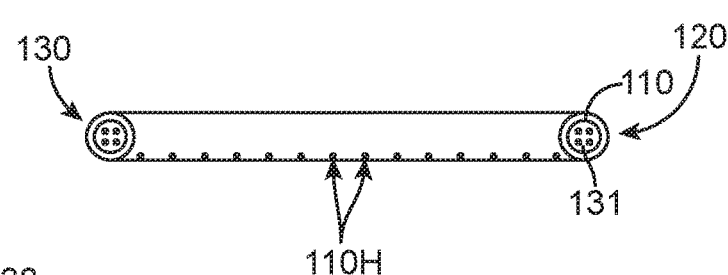
FIG. 7C
FIG. 7D

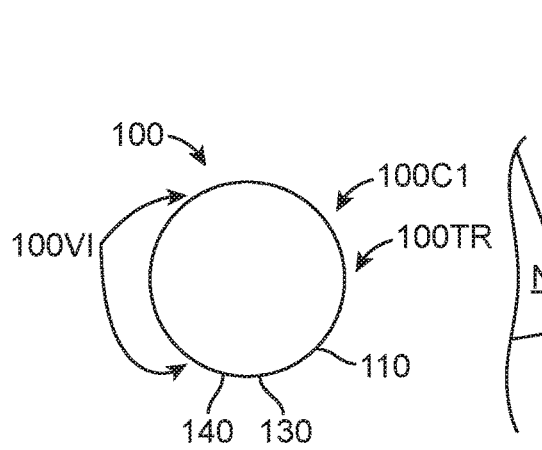
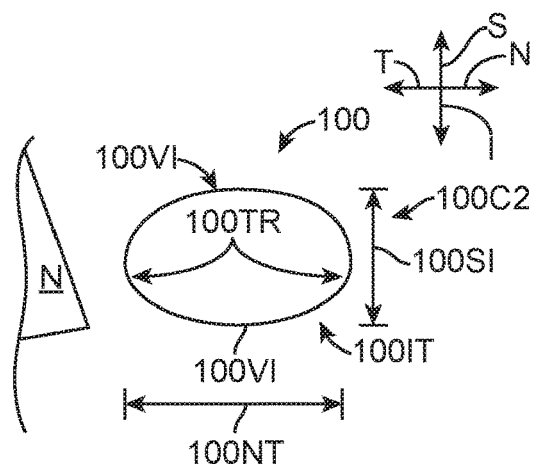
FIG. 12A1  FIG. 12B1
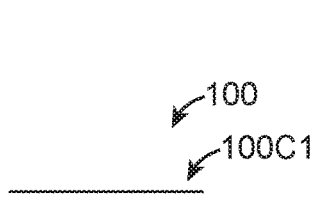
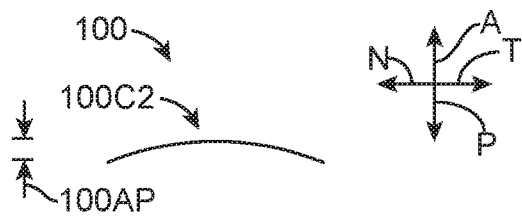
FIG. 12A2  FIG. 12B2
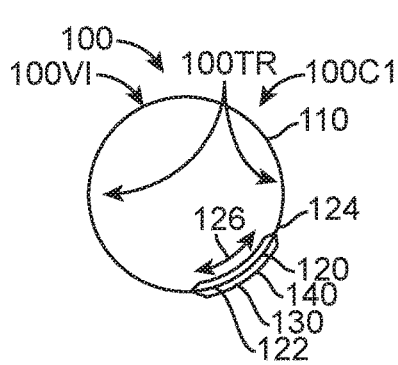
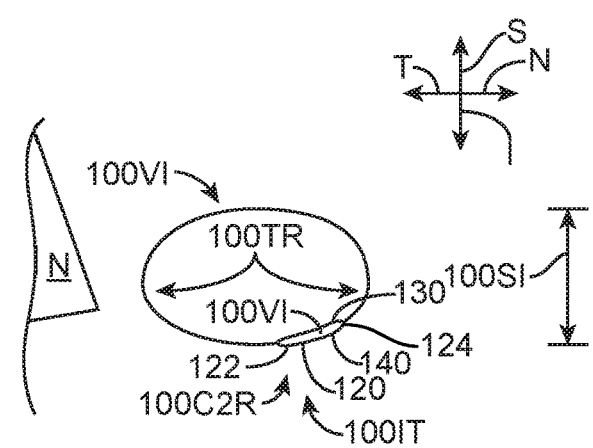
FIG. 13A1  FIG. 13B1
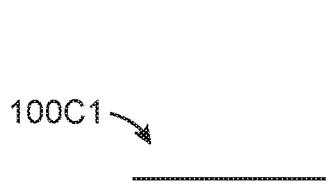
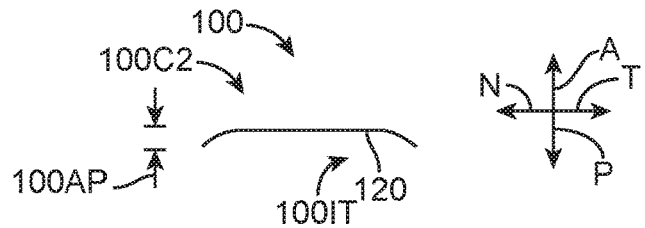
FIG. 13A2  FIG. 13B2

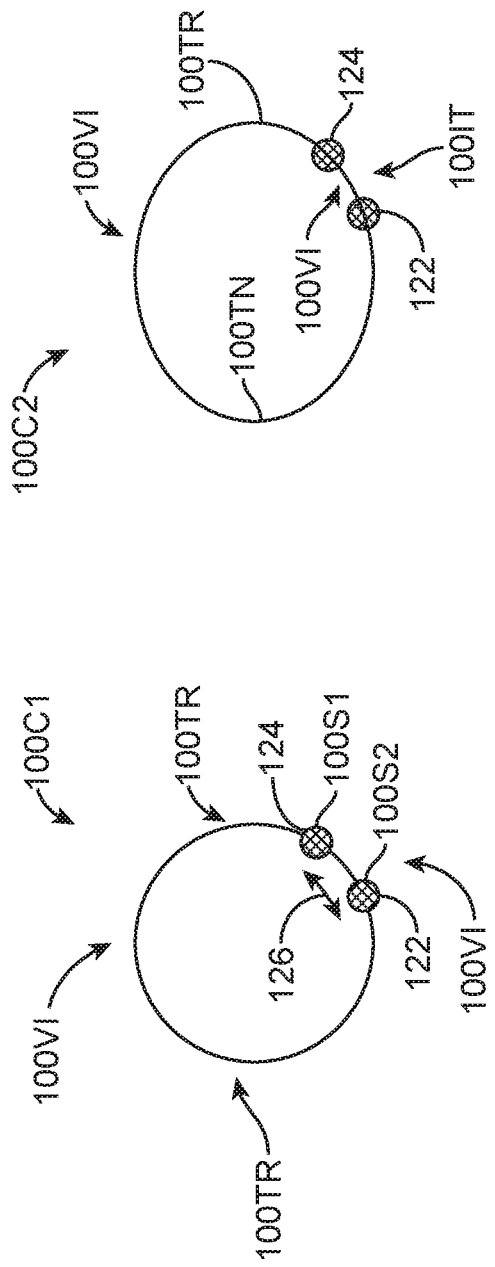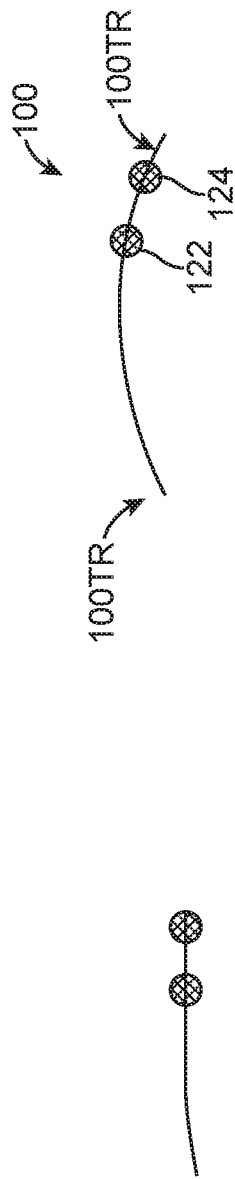

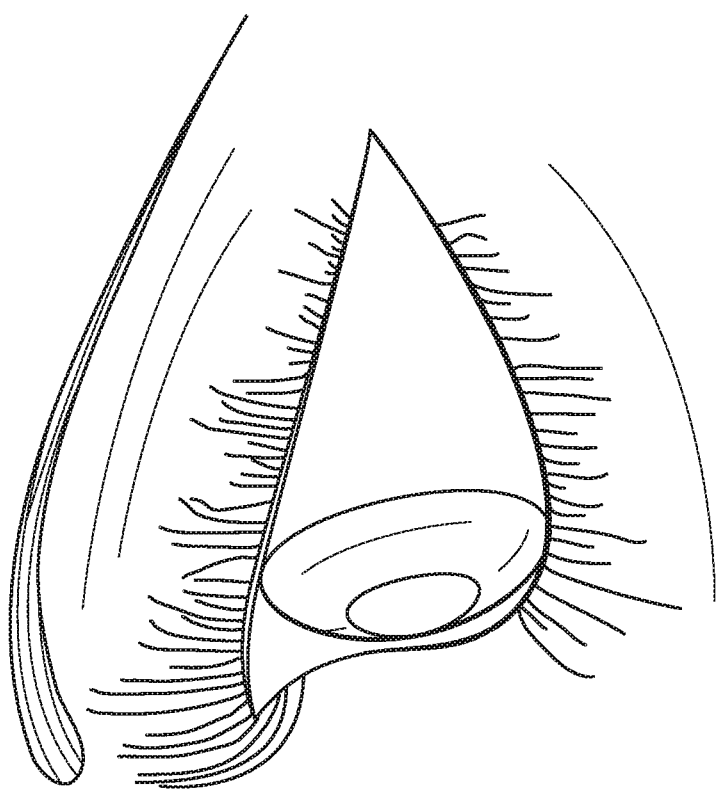
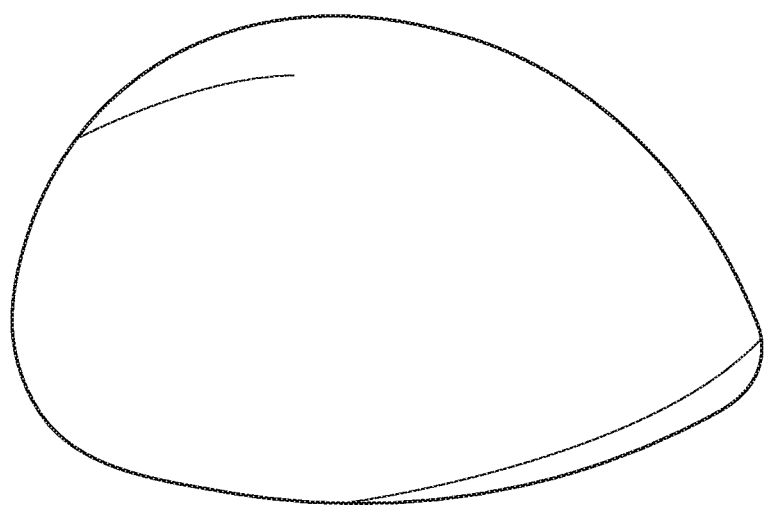
FIG. 25

OCULAR INSERT APPARATUS AND METHODS

CROSS-REFERENCES TO RELATED APPLICATIONS

This application is a continuation of co-pending U.S. application Ser. No. 14/600,505, filed Jan. 20, 2015, which is a continuation of U.S. application Ser. No. 13/618,052, titled "Ocular Insert Apparatus and Methods," filed on Sep. 14, 2012, now U.S. Pat. No. 8,939,948, which claims priority of the following U.S. Provisional Patent Applications: (1) U.S. Provisional Application Ser. No. 61/534,845, titled "Ocular Insert Apparatus And Methods," filed on Sep. 14, 2011; and (2) U.S. Provisional Application Ser. No. 61/568,624, titled "Ocular Insert Apparatus And Methods," filed on Dec. 8, 2011. The disclosures of the Patent Applications are hereby incorporated by reference in their entirety.

The subject matter of the present application is related to the following co-assigned patent applications: PCT App. No. PCT/US2010/037268, published as WO2010/141729 on Dec. 9, 2010, entitled "Anterior Segment Drug Delivery"; U.S. patent application Ser. No. 13/151,001, filed on Jun. 1, 2010, now U.S. Pat. No. 9,421,126, entitled "Anterior Segment Drug Delivery"; and U.S. Prov. Pat. App. Ser. No. 61/534,845, filed on Sep. 14, 2011, entitled "Ocular Insert Apparatus and Methods", the full disclosures of which are incorporated herein by reference.

BACKGROUND

1. Field

Described herein are structures, systems, and methods for placement of an insert on an eye that may be used to treat the eye. Exemplary embodiments provide ocular inserts used for drug delivery, along with methods for using ocular inserts positioned on or near the anterior surface of the eye. The exemplary inserts may be worn along an anterior surface of the eye outside the optical zone, and can deliver therapeutically efficacious amounts of one or more therapeutic agents.

2. Background

A variety of ophthalmic and non-ophthalmic conditions necessitate administration of various drugs to the eye. Eye drops and gels can be effective drug delivery vehicles, but can also have significant disadvantages. Specifically, eye drops mix with fluid in the tear film, but may have a residence time of only 2-5 minutes in the tear film. As little as 5% of the drug may be absorbed locally; some or all of the rest being carried from the lacrimal sac into the lacrimal duct, which can have potentially undesirable effects. Consequently, most of the drug may be wasted with less than ideal amounts delivered to the targeted tissue. Also, the presence of the drug in the bloodstream may have potentially harmful side effects. Gels may adhere more effectively to the eye, but can also blur the patient's vision. Both eye drops and gels may need to be reapplied frequently for some therapies, and patients may not administer the eye drops or gels as frequently as directed in at least some instances, such that the amount of drug delivered can be less than ideal. For example, in at least some instances a substantial number of patients may not refill their prescription after one year, and the substantial number of patients can be up to fifty percent in some instances. Thus, a need remains for improved drug delivery to the eye having less frequent user application and providing improved regularity of the amount of drug delivered to the eye. Another potential disadvantage of topically applied drops and gels can be that such bolus dosing may result in hyperemia and irritation of ocular tissue in at least some instances.

In light of the disadvantages of eye drops, it is understandable that a variety of alternatives have been proposed. Among the known prior alternatives to drops include treatments in which insert structures containing or impregnated with drugs have been placed under an eyelid, in a punctum, or on the cornea with drug-impregnated contact lenses, and the like.

Although such prior insert structures appear to present significant potential advantages over drop-administered drug treatment of the eye, the prior approaches with insert structures can provide less than ideal results in at least some instances. Although intravitreal and intraocular implants have been proposed, such implants can be more invasive that would be ideal in at least some instances. While punctual plugs can be less invasive, the amount of therapeutic agent available for sustained release can be less than ideal in at least some instances. The clinical acceptance of the prior insert structures has been less than ideal, and many drugs continue to be delivered to the front of the eye with drops. Clinical studies with prior insert structures appear to have shown that in at least some instances the prior insert structures may not work as well as would be ideal for at least some patients of a patient population. Factors that may have contributed to the limited acceptance of prior ocular inserts include: a lack of efficacy, a lack of comfort, propensity for displacement or movement from a desired position on the eye, incidents of inadvertent expulsion during sleep or rubbing of the eye, interference with vision, and difficulty with placement and removal. For example, in at least some instances the prior insert structures may not be retained in the eye as long as would be ideal, resulting in less than ideal amounts of the drug delivered to the eye. In at least some instances, the force of the eyelids, eye movement, change in insert position, or eye rubbing may not keep the prior inserts in the eye and the force of the eyelid may expel the insert from the eye. The prior insert devices can be less comfortable than would be ideal, and in at least some instances blinking of the eye may cause the insert to touch the cornea, or rub against the palpebral or bulbar conjunctiva, resulting in discomfort for the patient in at least some instances. Further, assuming the prior insert structure can be retained in the eye for the extended time, the amount of drug released and the release rate profile of the amount released for the extended time can be less than ideal for at least some of the prior insert structures in at least some instances.

In light of the above, new drug delivery devices, systems, and methods would be beneficial, particularly for delivering therapeutic agents to the anterior segment of the eye. It would be particularly advantageous to provide improved ocular inserts which are configured as to gain greater acceptance from both physicians and users, with such inserts ideally being easier to insert and remove, providing greater retention and compliance with a population of patients, providing greater patient comfort while remaining on the eye for an extended time, being non-toxic and not interfering with vision, and the like. It would also be desirable to provide improved ocular inserts which would provide improved amounts of release, release profiles and pharmacokinetics throughout long term use, including providing safe, efficient and reproducible local therapeutic agent release from the device with limited systemic or localized side effects and effective transportation to and absorption by tissues that provide therapeutic benefits, ideally while being relatively easy to manufacture at a reasonable price.

SUMMARY

Embodiments are generally provided for improved inserts and methods for placement on the conjunctiva of the eye, such that the inserts can be retained on the eyes of many patients for an extended time. Although, specific reference is made to drug-delivery devices and associated methods, embodiments can be used with many applications where it would be helpful to retain a structure on the eye. Many embodiments provide an ocular insert to deliver a therapeutic agent that can be comfortably placed at many locations of the conjunctiva, including along at least a portion of the conjunctival sac. The insert can move when placed on the conjunctiva and can be retained with the eye so as to provide improved comfort for the patient. The insert may comprise a resistance to deflection to retain the insert comfortably within the eye. The insert can be configured in many ways to provide the resistance to deflection. The insert may comprise a matrix comprising a therapeutic agent and the resistance to deflection, and the matrix may comprise a material providing the resistance to deflection. Alternatively or in combination, the insert may comprise a retention structure and a support structure coupled to the retention structure, in which the support structure may contain the therapeutic agent. The retention structure may comprise an inner structure with the support structure comprising the therapeutic agent covering at least a portion of the retention structure, or the retention structure may comprise an outer structure covering at least a portion of the support structure comprising the therapeutic agent.

The insert may be configured such that the insert can be deflected during insertion and removal and may comprise the resistance to deflection for comfort and retention. The insert comprising the resistance to deflection can be comfortably placed at one or more of many locations of the conjunctiva, such that many patients can be treated comfortably and the placement can be adjusted based on the anatomy of the patient and physician preference. The insert may comprise the resistance to deflection such that the conjunctiva can be shaped with the insert so as to receive the insert, and in many embodiments the insert may comprise an amount of resistance to form one or more of a fold, a pocket, or deformation of the conjunctiva so as to receive and retain the insert. The one or more locations where the insert can be placed include the inferior conjunctival sac, an inferior temporal location of the conjunctival sac, an inferior nasal location of the conjunctival sac, the superior conjunctival sac, portions of the upper and lower conjunctival sacs near lateral canthus of the palpebral fissure, portions of the upper and lower conjunctival sacs near the medial canthus and caruncle. These areas are well suited to receive structures having relatively large volumes for extended release of one or more therapeutic agents.

The insert can be configured in many ways to treat a patient with a therapeutic agent for an extended time, and may comprise one or more of a high dose of therapeutic agent, a substantial surface area to release the therapeutic agent, a hoop strength to resist deflection, a bending strength to resist deflection, a shape profile to fit the eye, or a biasing curve to retain the insert, and combinations thereof. The insert may comprise biasing shape so as to retain the insert, for example with a curve, bend, or other deflected shape to retain the insert. The biasing shape may comprise a resiliently curved biasing spring structure shaped to provide force in response to deflection so as to urge one or more of the first portion or the second portion toward the eye to retain the insert.

The insert can be sized and shaped for placement under the eyelids and along at least a portion of a conjunctival sac of the upper and lower lids of the eye, or combinations thereof. The insert can be sized and shaped so as to move within the conjunctival sac of the eye and be held on the eye without attachment to the eye so as to provide improved comfort. The insert may comprise a preformed shape profile corresponding to a curved shape profile of the eye extending away from a plane, such that the insert can resist deflection away from bulbar conjunctiva toward the plane when placed. The insert can be configured to deflect when placed in the conjunctival sac of the eye and guide the insert along the sac when the eye moves with one or more of rotation or cyclotorsion. The insert may also comprise resistance to deflection so as to urge the insert outward and inhibit movement of the retention structure toward the cornea. The insert may comprise a first portion having a first resistance to deflection and a second portion having a second resistance to deflection less than the first portion, such that first portion can resist deflection of the upper lid and the second portion can fit within the one or more folds of the lower lid. The first portion and the second portion may comprise a similar material, and the first portion may have a cross sectional size greater than the second portion to provide the increased resistance to deflection, and the increased cross sectional size of the first portion may help to retain the first portion with the upper lid. Alternatively or in combination, the increased cross-sectional size of the first portion may provide anchoring under the upper lid. The insert may move rotationally with deflection along the conjunctival sac such that the retention structure can slide along the conjunctival sac about an axis of rotation passing through the iris and the pupil of the eye. In many embodiments the insert can allow sliding movement along the conjunctiva in response to torsional or other movement of the eye so as to improve comfort for the patient.

The insert can be configured in many ways to provide the resistance to deflection. The insert may comprise a retention structure providing a majority of the resistance to deflection. Alternatively, the insert can be configured to provide the resistance to deflection without a retention structure, and in many embodiments may comprise with a drug delivery matrix configured to provide the resistance to deflection such that the insert can be provided without the retention structure.

The eye comprises upper and lower conjunctival sacs corresponding to the upper eyelid and the lower eyelid, and each of the upper and lower conjunctival sacs comprises a bulbar portion of conjunctiva and a palpebral portion of conjunctiva. The bulbar portion and the palpebral portion of each sac may comprise a plurality of folds, and the insert may comprise a resistance to deflection so as to shape the conjunctiva and form one or more of an indentation, a deformation, a fold or a pocket of the conjunctiva. The insert can be elongate and sized to extend a substantial distance along the shaped conjunctiva, such that the retention structure can be held with the one or more of the indentation, the deformation, the fold or the pocket of the conjunctiva. The palpebral and bulbar conjunctiva may each be shaped with the retention structure so as to comprise one or more folds or pockets, and the insert can extend substantially along the one or more folds or pockets such that the retention structure can move with the eye. The shaped conjunctival tissue may comprise tissue of the fornix, or conjunctival tissue located away from the fornix, or combinations thereof. The movement of the insert along the conjunctival sac, resistance to inward deflection, resistance to deflection to shape the conjunctiva can provide improved comfort for the patient.

The insert may comprise an amount of therapeutic agent sufficient to release therapeutic amounts of the therapeutic agent for an extended time, and the insert can be configured in many ways so as to release the therapeutic amounts for the extended time. The therapeutic agent may be contained in a matrix having inclusions of the therapeutic agent, and a surface area of the matrix can be sized to release the therapeutic amounts for the extended time. The insert may comprise a lubricous coating on one or more of the retention structure or the support structure, and the therapeutic agent may be released from the surface through the lubricous coating. The therapeutic amounts of the therapeutic agent may be substantially released at intervals with one or more of an erodible material or a pump, which may provide increased efficacy of at least some therapeutic agents such as prostaglandins. The therapeutic agent can be released at intervals with pulsatile flow from a pump such as an osmotic pump, and the pump may be coupled to a container comprising inclusions of the therapeutic agent so as to release solubilized therapeutic agent with pulsatile flow and inhibit release of the inclusions. Alternatively, an inner drug delivery matrix having a therapeutic agent loaded thereon may comprise the retention structure, and an outer structure provided over the inner drug delivery matrix, in which the outer structure comprises a rate limiting structure, a structure to provide comfort, or combinations thereof.

The retention structure can be configured in many ways to provide increased comfort for the patient, and can be placed in many ways. The retention structure may comprise soft material at locations corresponding to one or more of the lacrimal gland or the caruncle, and can be shaped to inhibit contact with tissue near one or more of the lacrimal gland or the caruncle. Although the retention structure may comprise one or more of many shapes such as circular, oval, serpentine, saddle shaped, cylindrical or toric, the retention structure may comprise one or more portions shaped to inhibit irritation to the lacrimal gland and the caruncle. The retention structure can be shaped to inhibit contact with the conjunctiva covering the lacrimal gland, and the retention structure may comprise an extension shaped to extend around the lacrimal gland. The extension can extend inward toward the pupil around the lacrimal gland, or outward away from the pupil around the lacrimal gland. The retention structure may comprise a portion shaped to extend away from the caruncle when placed, such as an inward extension.

Additional aspects are recited in the claims below, and can provide additional summary in accordance with embodiments described herein. It is contemplated that the embodiments as described herein and recited in the claims may be combined in many ways, and any one or more of the elements recited in the claims can be combined together in accordance with embodiments and teachings as described herein.

BRIEF DESCRIPTION OF THE DRAWINGS

FIG. 1-2-1 shows an embodiment of a therapeutic system comprising an ocular insert, that may also include an insertion device, a configuration altering material that dissolves (or swells, weakens, tightens, or effects some other activation mechanism) to reconfigure the implant from an insertion configuration to a deployed configuration, or the like;

FIGS. 1-2-2 and 1-2-3 show a top view and cross-sectional view of the therapeutic system shown in FIG. 1-2-1;

FIG. 1-2-4 shows an embodiment of the therapeutic system where the ring comprises two radially outwardly and/or anteriorly extending protrusions or bumps on opposed portions of its surface;

FIG. 1-2-5 shows an alternative embodiment of the ring-shaped therapeutic device system. In this embodiment, a crescent or banana-shaped reservoir is attached to the inferior portion of the ocular insert;

FIGS. 1-3-1 to 1-3-3 show another embodiment of the therapeutic system including a ring-shaped structure with a diameter of at least 8 mm, sized to fit outside the optical zone of the cornea, and also having two or more haptics;

FIGS. 1-4-1 to 1-4-2 show an alternate embodiment of the therapeutic system in which two or more concentric ring-shaped structures are held together by four or more haptics;

FIG. 1-4-3 shows an embodiment that employs an eccentric design such that the one or more ring portions or arc segments are present in the inferior area of the ring to target delivery to the area of the eye where tears may more readily pool, as in the cul-de-sac;

FIGS. 1-5-1 through 1-5-3 show a serpentine embodiment of therapeutic system which shows an expandable ocular insert;

FIGS. 1-6-1 and 1-6-2 show another embodiment where the second cushioning structure comprises two hydrogel scleral contact lenses attached to each other, so as to sandwich the first rigid structure between them;

FIG. 1-7-1 shows a close-up of an exemplary ocular insert of the therapeutic device system in which the second structure is disposed throughout the circumferential length of the first structure;

FIG. 1-7-2 shows a cross-section of a therapeutic device system comprising a second structure with a tapered outer and/or inner edge;

FIG. 1-7-3 shows a cross-section of a therapeutic device system comprising a second structure with a beveled edge;

FIG. 1-7-4 shows a cross-section of a therapeutic device system comprising a second structure with a rounded edge;

FIG. 1-8-1 shows a therapeutic device system with a second structure that may have an anterior and/or posterior surface that can be shaped as well to the radius of curvature of the eye;

FIG. 1-9-1 shows the second, cushioning structure disposed over discrete portions of the length of the first supporting structure;

FIG. 2A shows an insert for insertion into an eye, in accordance with an embodiment;

FIG. 2B shows a cross sectional view of a retention structure, in accordance with an embodiment;

FIG. 2C shows an insert as in FIGS. 2A and 2B deflected in response to placement in an eye and corresponding force to urge the retention structure outward, in accordance with an embodiment;

FIG. 2C1 shows a retention structure self-loaded and deflected at an angle, in accordance with an embodiment;

FIG. 2C2 shows torsion of a retention structure at a first location at resistance to twisting, in accordance with an embodiment;

FIG. 2P1 shows an insert comprising a retention structure having an upper portion comprising a first durometer and a lower portion comprising a second durometer, in accordance with an embodiment;

FIG. 2P2 shows an insert comprising a retention structure having an upper portion and a lower portion in which the lower portion is curved inward toward the eye, for example with a lower bend, in accordance with an embodiment;

FIG. 2P3 shows an insert comprising a retention structure having a hinges to couple an upper portion to a lower portion and allow the upper portion to swing toward the lower portion, in accordance with an embodiment;

FIG. 2P4 shows an insert comprising a retention structure having a first upper portion and a second lower portion with bias curve such that the upper and lower portions extend posteriorly to the nasal and temporal portions prior to placement, in accordance with an embodiment;

FIG. 2P5 shows an insert comprising a retention structure having a first upper portion and a second lower portion with bias curve such that the upper and lower portions extend anteriorly to the nasal and temporal portions prior to placement, in accordance with an embodiment;

FIG. 2P6 shows an insert comprising a retention structure having an oblong shape and having first upper portion and a second lower portion in which the upper portion comprises an elongate oval shape portion to extend into the upper fornix and the lower portion comprises a shorter wider oval shape to extend into the lower fornix, in accordance with an embodiment;

FIG. 2P7 shows an insert comprising a retention structure comprising an upper portion and a lower portion coupled with hinges so as to define an elliptical shape, in accordance with an embodiment;

FIG. 2P8 shows an insert comprising a flexible redundant retention structure to seat the retention structure in the eye, in accordance with an embodiment;

FIG. 2P9 shows an insert comprising an upper anchor, in accordance with an embodiment;

FIG. 2P10 shows an insert comprising a lower anchor to resist pull of the round structure, in accordance with an embodiment;

FIG. 2W shows an insert comprising an upper portion comprising a hydrophilic surface and a lower portion comprising a hydrophobic surface, in accordance with an embodiment;

FIGS. 2X1 and 2X2 show front and side views, respectively, of an insert comprising an upper portion and a lower portion and a stiff portions to angularly bias the upper portion and the lower portion toward each other, in accordance with an embodiment;

FIG. 2Z1 shows an insert comprising a retention structure having an upper portion and a lower portion coupled with a variable joint to as to vary a size of the retention structure and insert, in accordance with an embodiment;

FIG. 2Z2 shows a telescopic joint of an insert as in FIG. 2Z1, in accordance with an embodiment;

FIG. 2Z3 shows a shock absorbing spring joint of an insert as in FIG. 2Z1, in accordance with an embodiment;

FIG. 2Z4 shows a ratcheting joint of an insert as in FIG. 2Z1, in accordance with an embodiment;

FIGS. 2Z5 and 2Z6 show front and side views, respectively, of an insert comprising an elongate shape having upper and lower portions sized to extend into upper and lower fornices, respectively, so as to provide substantially greater amounts of therapeutic agent than the intermediate portions locatable near the lateral and medial canthus, in accordance with an embodiment;

FIGS. 2Z7 and 2Z8 show front and side views, respectively, of a rigid insert having a curved shape sized to fit the eye of the patient such that the insert can be worn comfortably for an extended time, in accordance with an embodiment;

FIG. 3A1 shows an insert placed between folds of conjunctiva, in accordance with an embodiment;

FIG. 3A2 shows a fold of conjunctiva receiving an insert, in accordance with an embodiment;

FIG. 3A3 shows an insert sized to fit between folds of conjunctiva, in accordance with an embodiment;

FIG. 3A4 shows a retention structure of an insert as in FIGS. 2A to 2G placed on an eye such that the retention structure has fit into one or more of a plurality of folds of the bulbar conjunctiva, in accordance with an embodiment;

FIG. 3B shows a retention structure under a fold of bulbar conjunctiva, in accordance with an embodiment;

FIGS. 3C1 to 3C3 show a retention structure under a fold of bulbar conjunctiva moving with rotation of the eye, in accordance with an embodiment;

FIG. 3G-1 shows the support structure placed superiorly at an initial location of the superior conjunctival sac, in accordance with an embodiment;

FIG. 3G-2 shows the support structure seated in the cul-de-sac of the superior conjunctival sac following placement as in FIG. 3G-1, in accordance with an embodiment;

FIG. 3J-1 shows a side cross sectional view of the retention structure as in FIG. 3J, in accordance with an embodiment;

FIG. 3L-1 shows a layer of the lubricous coating on the surface of the matrix containing the therapeutic agent as in FIG. 3L, in accordance with an embodiment;

FIG. 4G-1 shows a plurality of support structures comprising a first therapeutic agent contained within a first matrix and a second therapeutic agent contained within a second matrix, in accordance with an embodiment;

FIG. 4G-2 shows a retention structure comprising a ring, the ring comprising a plurality of ring segments, in accordance with an embodiment;

FIG. 4G-3 shows an annular insert comprising a retention structure comprising an annular ring and an annular support comprising a matrix of therapeutic agent covering the retention structure, in accordance with an embodiment;

FIG. 4G-4 shows a cross-sectional view of the retention structure and support structure of FIG. 4G-3, in accordance with an embodiment;

FIG. 4H shows an insert comprising a structure having an erodible material to release a therapeutic agent for an extended time, in accordance with an embodiment;

FIG. 4I shows a transverse cross sectional view of the structure comprising the erodible material as in FIG. 4H, in accordance with an embodiment;

FIG. 4J shows a side cross sectional view of the structure comprising the erodible material as in FIGS. 4H and 4I, in accordance with an embodiment;

FIG. 4K shows a container having a channel occluded with an erodible material as in FIGS. 4H to 4J, in accordance with an embodiment;

FIG. 4L shows the container as in FIG. 4K having the material eroded away from the channel to release the therapeutic agent, in accordance with an embodiment;

FIG. 4M shows a pump to release a therapeutic agent with pulsatile flow, in accordance with an embodiment;

FIG. 4N shows a release profile of therapeutic agent of the pump as in FIG. 4M, in accordance with an embodiment;

FIG. 4O shows a pressure profile of a chamber of the pump as in FIGS. 4M and 4N, in accordance with an embodiment;

FIGS. 7A and 7B show plan and side cross-sectional views, respectively, of an insert comprising an outer retention structure having a resistance to deflection to remain within the eye for an extended time, in accordance with an embodiment;

FIGS. 7C and 7D show plan and side cross-sectional views, respectively, of an arcuate C-shaped insert comprising an outer retention structure having a resistance to deflection to remain within the eye for an extended time, in accordance with an embodiment;

FIG. 8B shows in situ forming of a retention structure of an insert, in accordance with an embodiment;

FIG. 8C shows a flowable material placed on the eye to form at least a portion of the insert, in accordance with an embodiment;

Figure 1A:
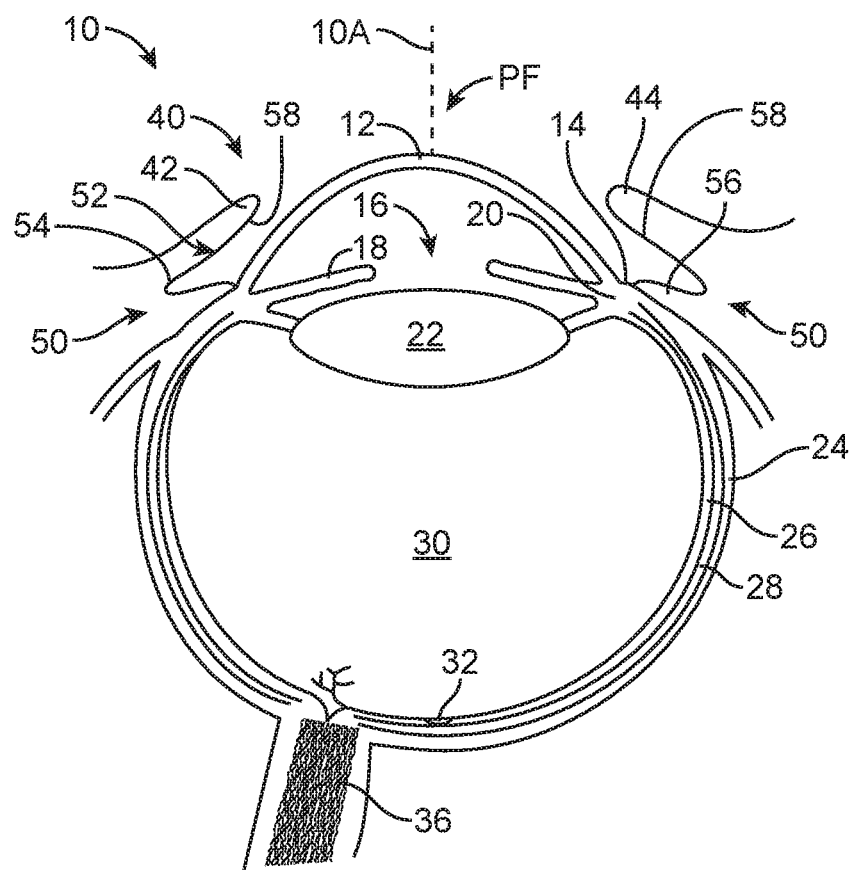
FIG. 1A shows a side sectional view of an eye suitable for combination with an insert, in accordance with an embodiment.
Figure 1B:
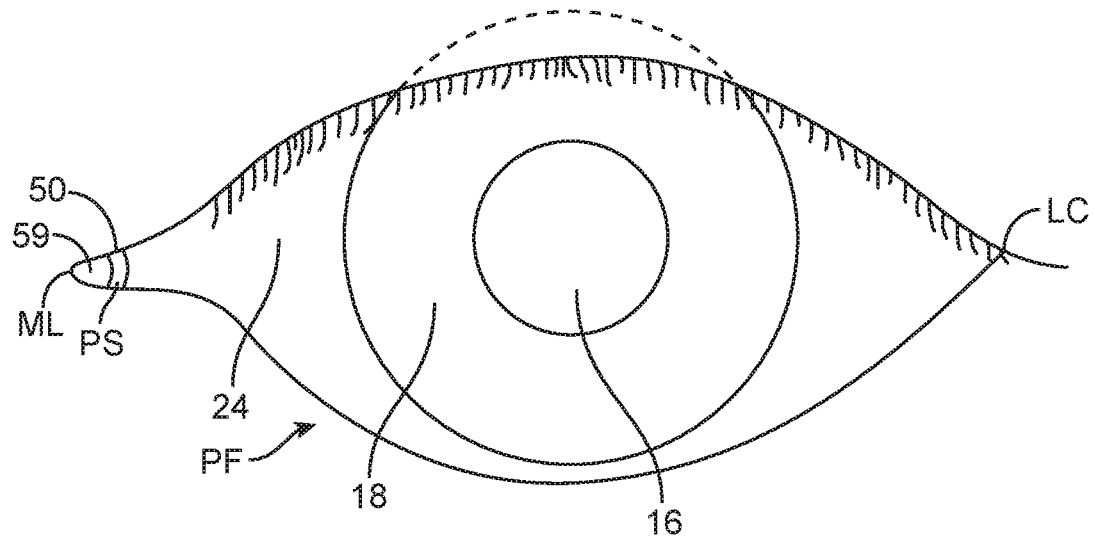
FIG. 1B shows front view of the eye as in FIG. 1A, in accordance with an embodiment.
Figure 1C:
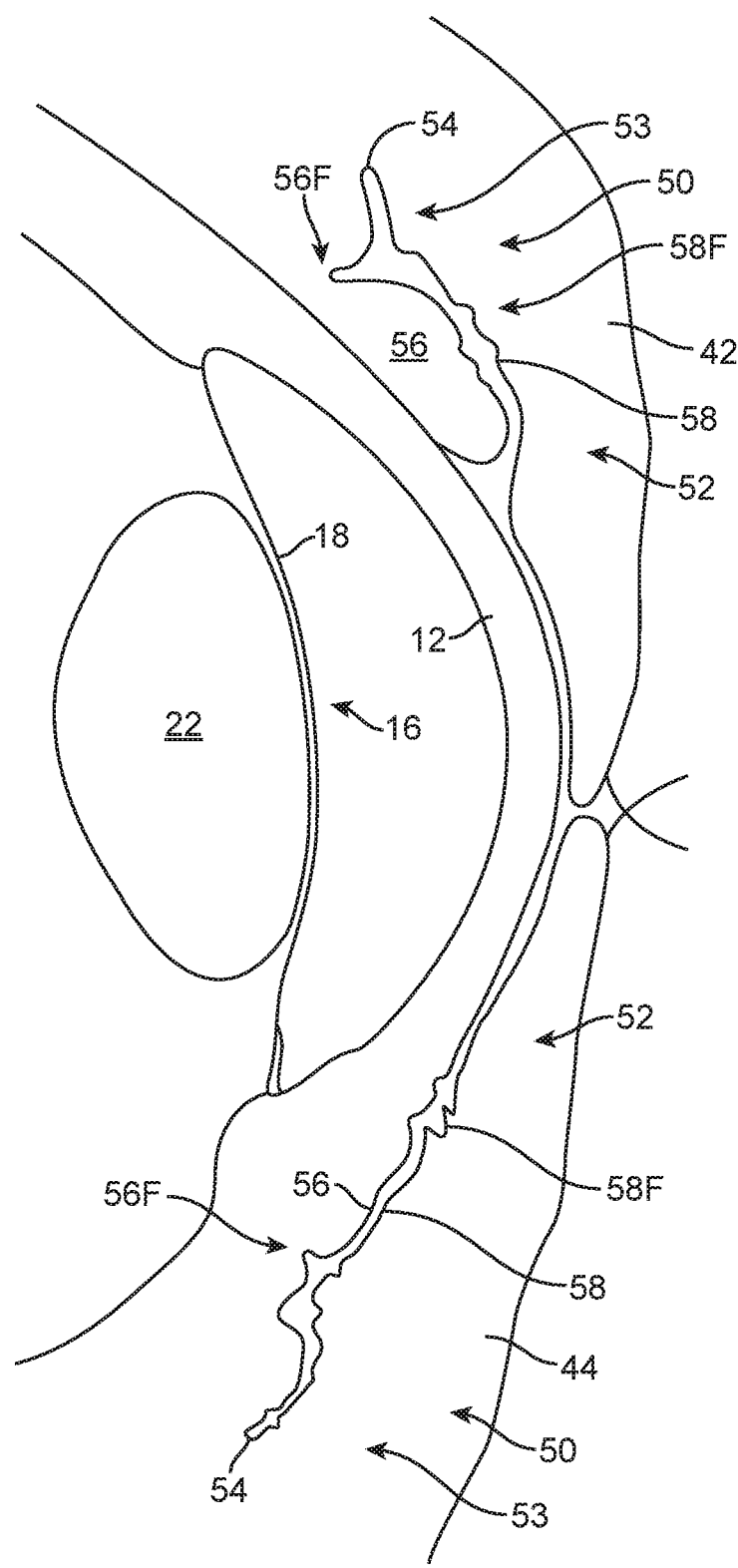
FIG. 1C side sectional view of the conjunctiva of the upper and lower lids of the eye as in FIGS. 1A and 1B, in accordance with an embodiment.
Figure 1D:
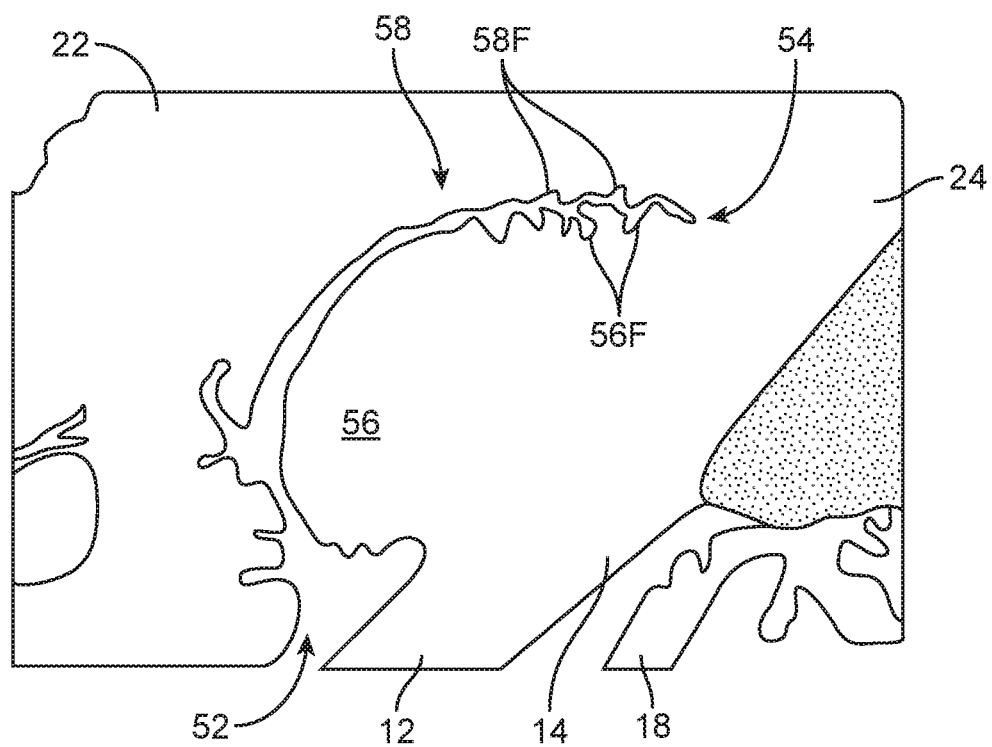
FIG. 1D shows a side sectional view of the upper lid of the eye as in FIGS. 1A to 1C and the folds of the conjunctiva, in accordance with an embodiment.
Figure 1E:
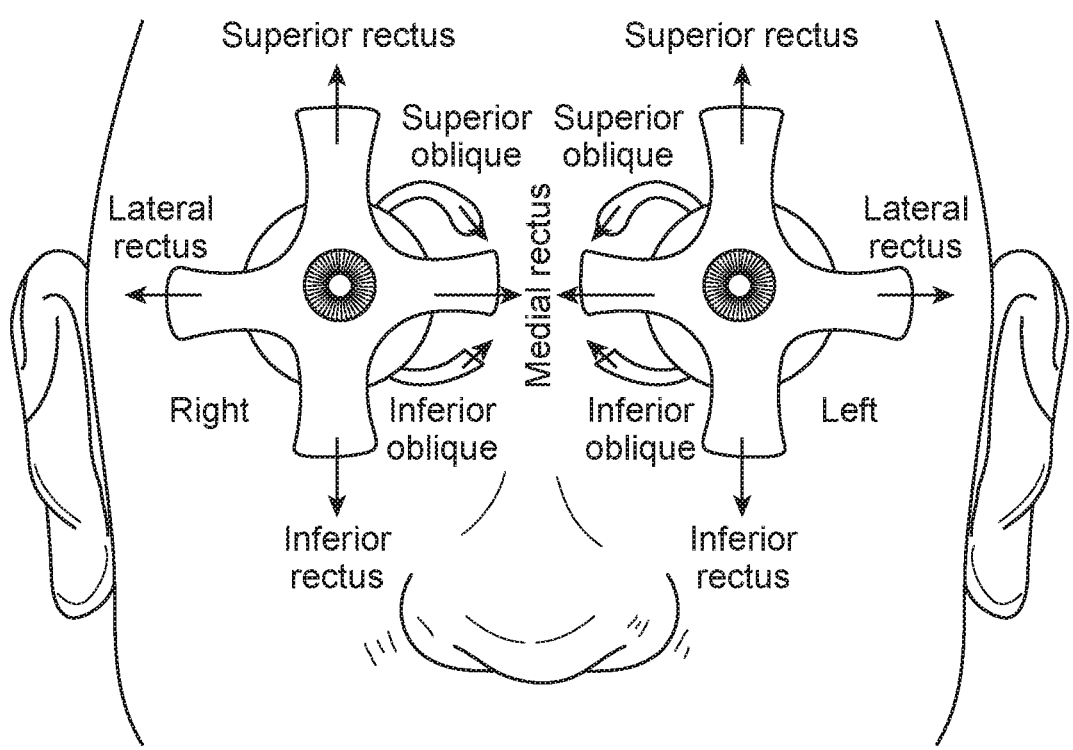
FIG. 1E shows muscles of a pair of eyes that provide cyclotorsion of the eye suitable for combination with an ocular insert, in accordance with an embodiment.
Figures 1, 2:
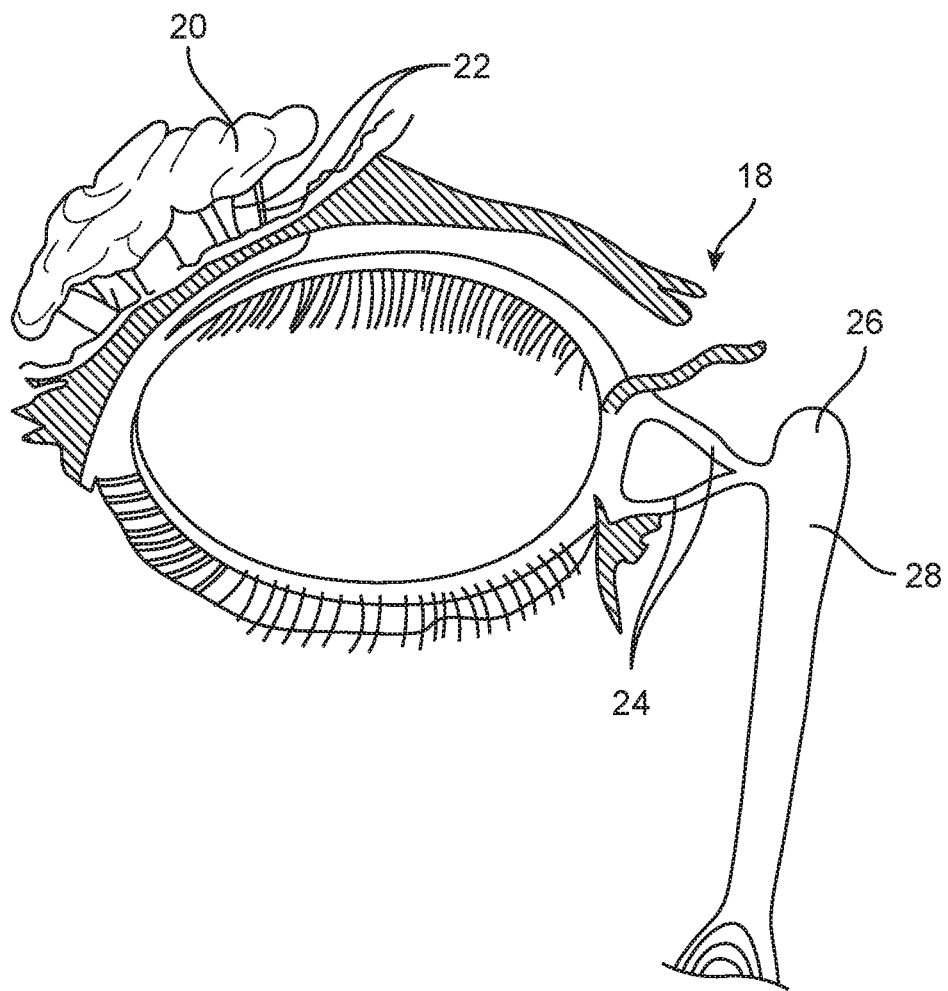
FIG. 1-1-2 shows an anatomical tissue structure of an eye suitable for treatment with ocular inserts.
Figures 1, 2:
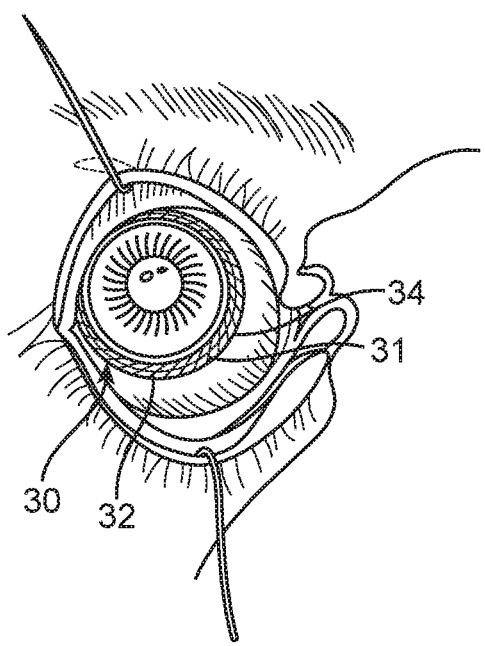
Figures 1, 2:
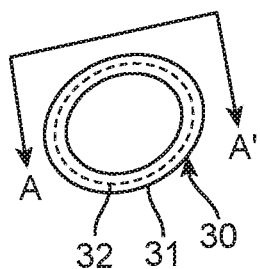
Figures 1, 2, 3:
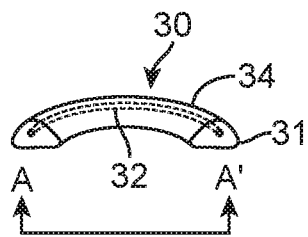
Figures 1, 2, 4:
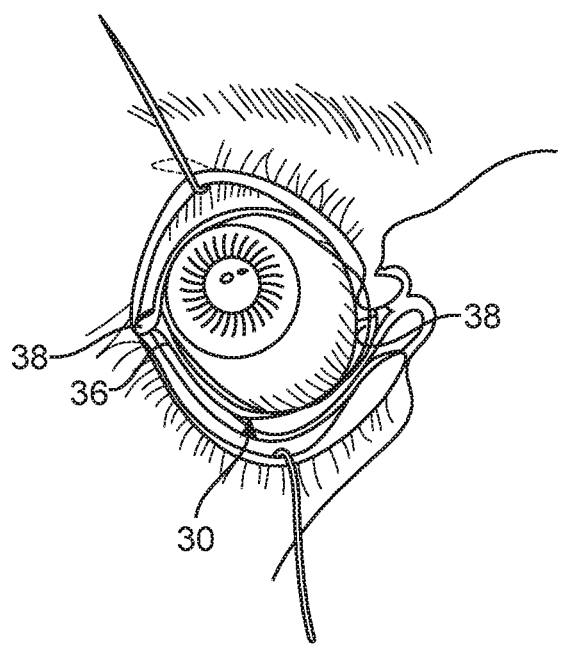
Figures 1, 2, 5:
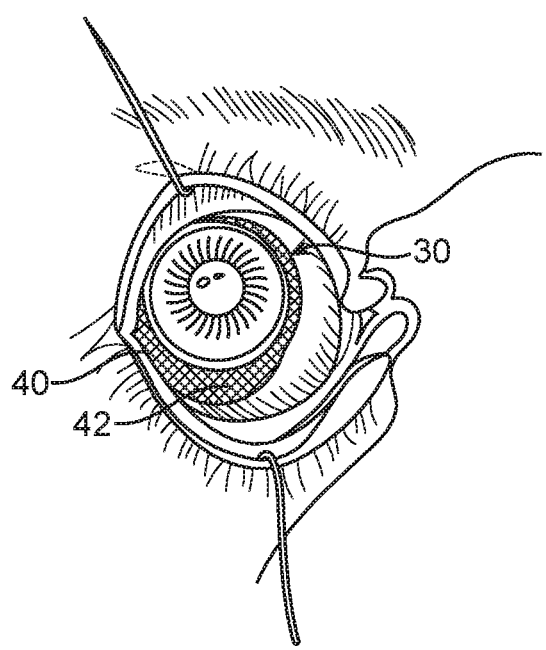
Figures 1, 2, 3:
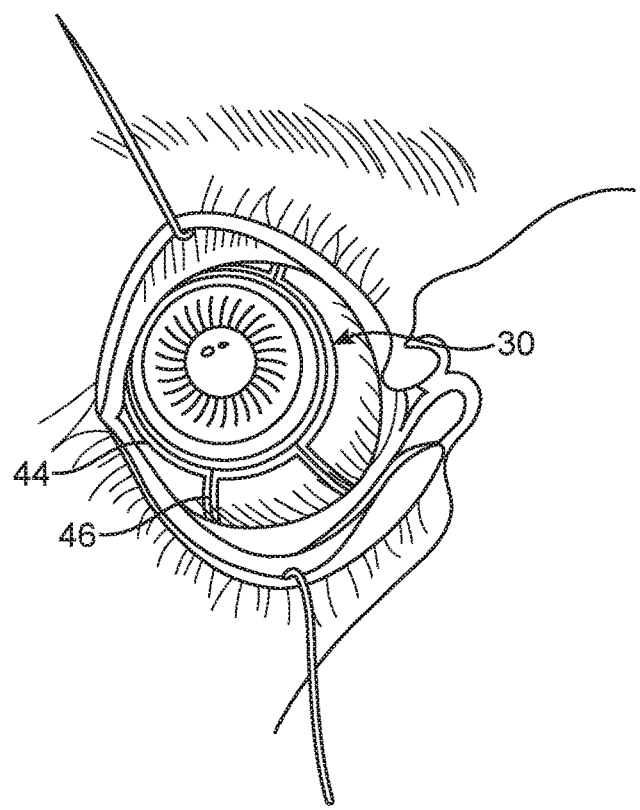
Figures 1, 2, 3:
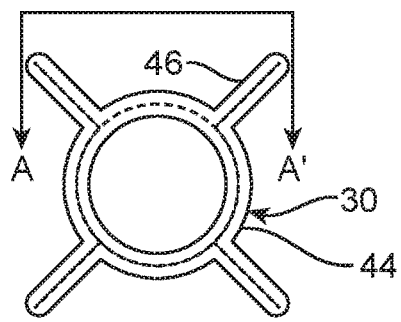
Figures 1, 2, 3:
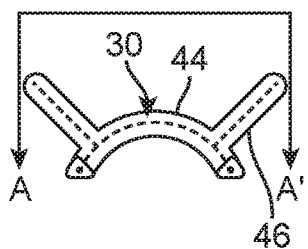
Figures 1, 2, 3, 4:
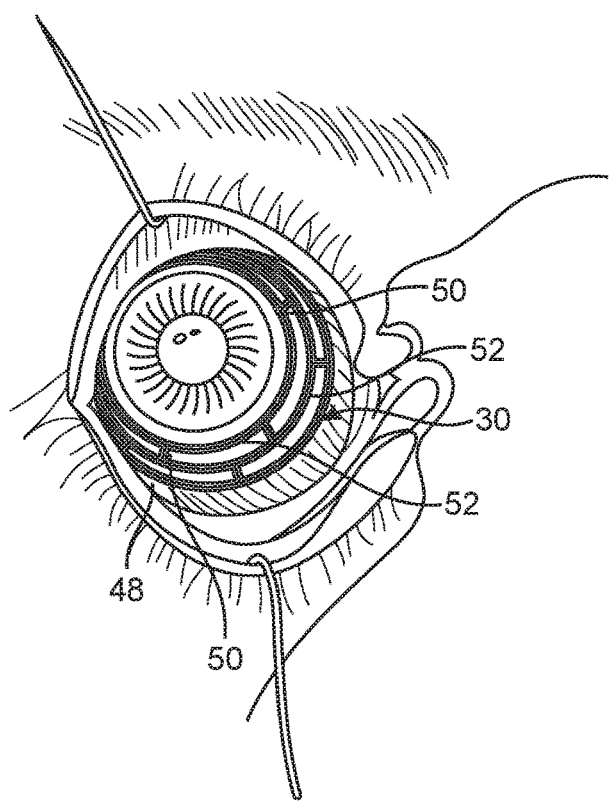
Figures 1, 2, 3, 4:
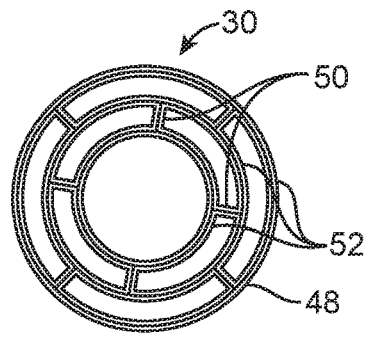
Figures 1, 2, 3, 4:
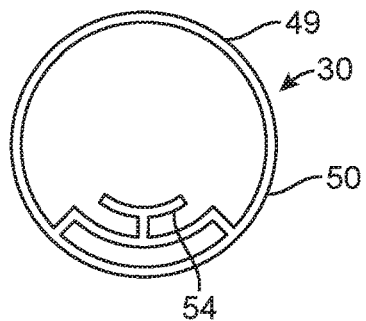
Figures 1, 2, 3, 4, 5:
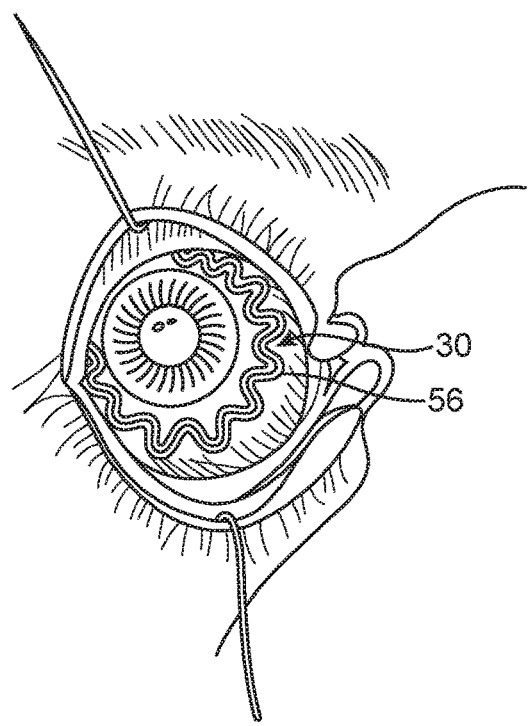
Figures 1, 2, 3, 4, 5:
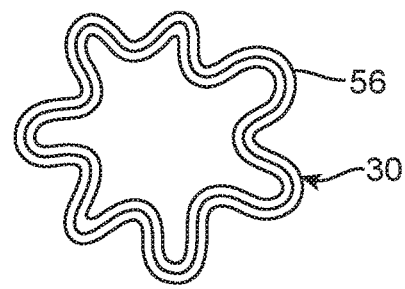
Figures 1, 2, 3, 4, 5:
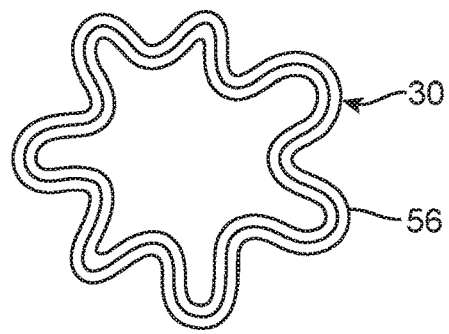
Figures 1, 2, 3, 4, 5, 6:
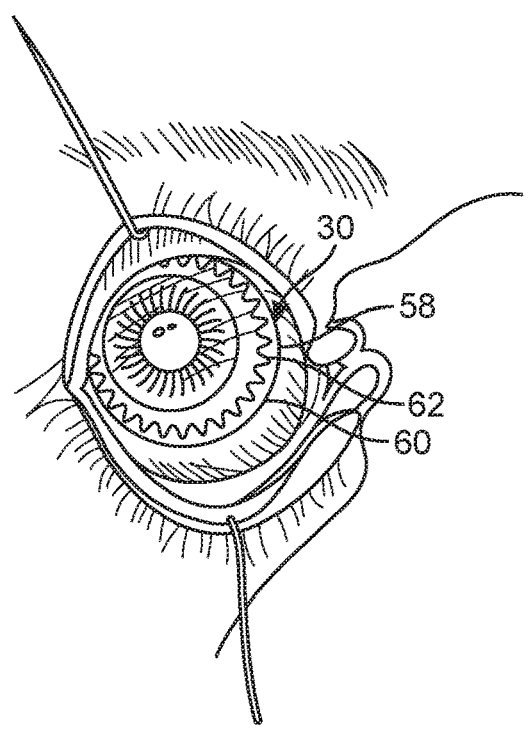
Figures 1, 2, 3, 4, 5, 6:
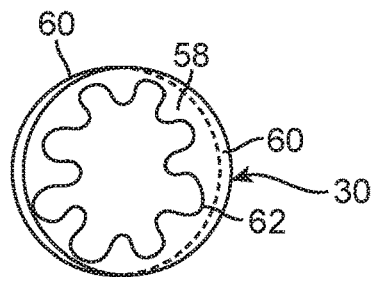
Figures 1, 2, 3, 4, 5, 6, 7:
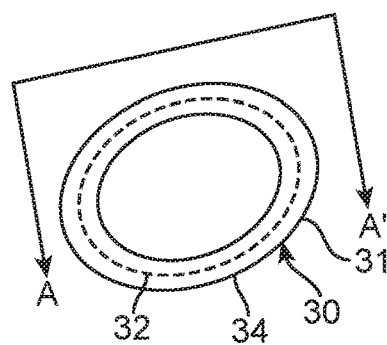
Figures 1, 2, 3, 4, 5, 6, 7:
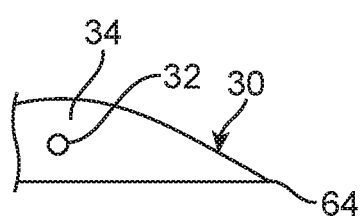
Figures 1, 2, 3, 4, 5, 6, 7:
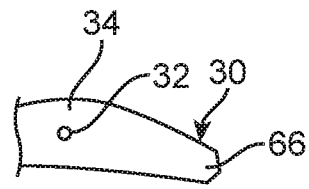
Figures 1, 2, 3, 4, 5, 6, 7:
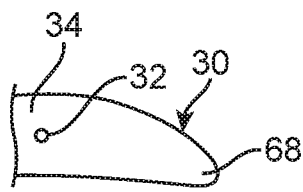
Figures 1, 2, 3, 4, 5, 6, 7, 8:
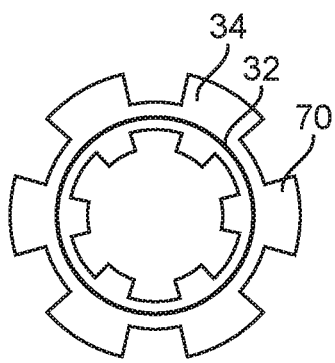
Figures 1, 2, 3, 4, 5, 6, 7, 8, 9:
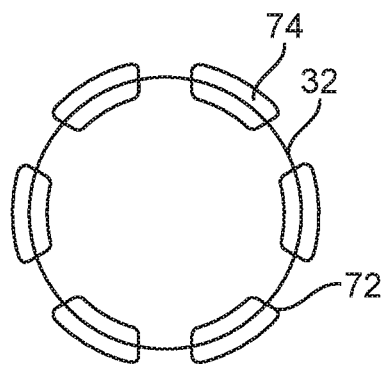
Figure 8A:
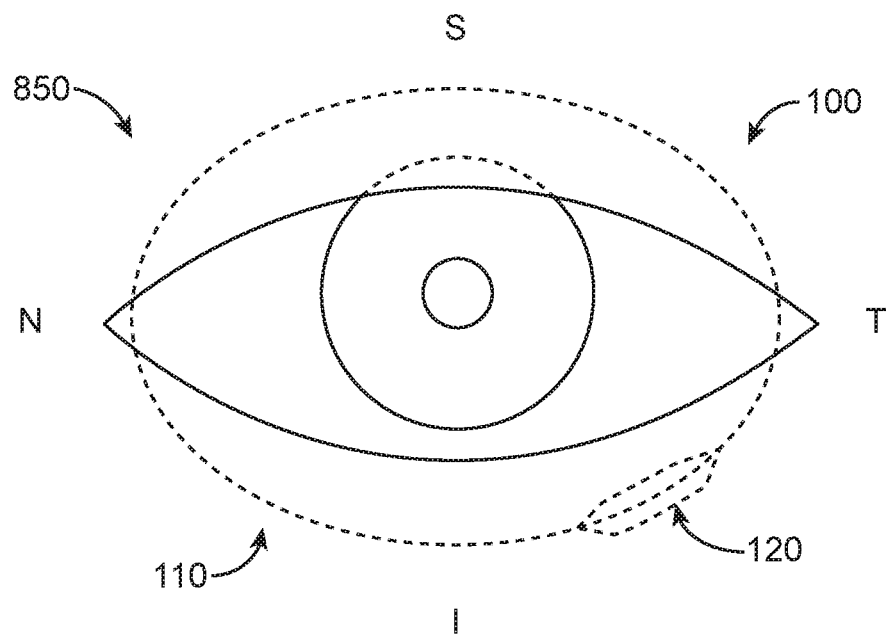
FIG. 8A shows treatment of a retention structure of an insert to increase a resistance to deflection of the retention structure, in accordance with an embodiment.
Figure 8B:
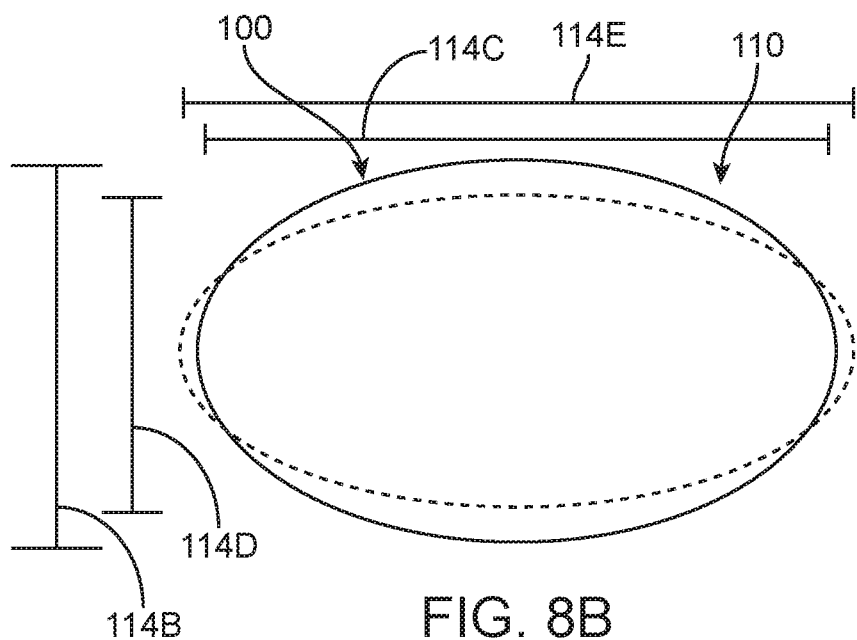
Figure 8C:
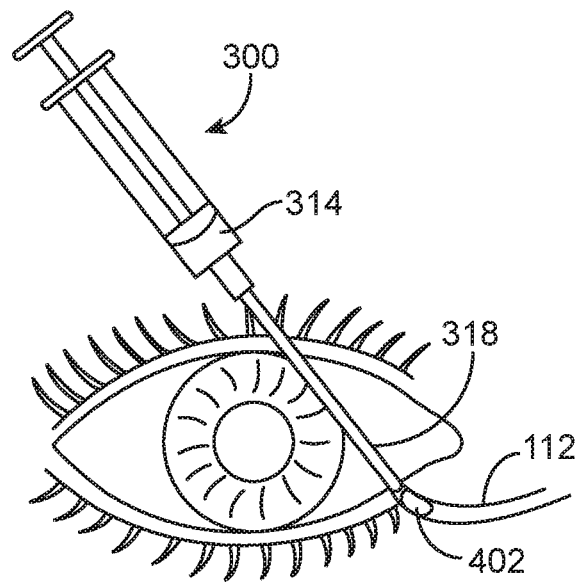
Figure 8D:
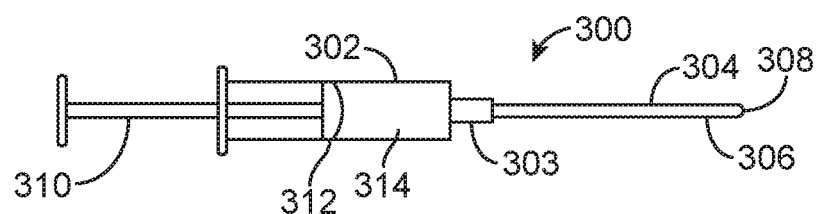
Figure 8E:
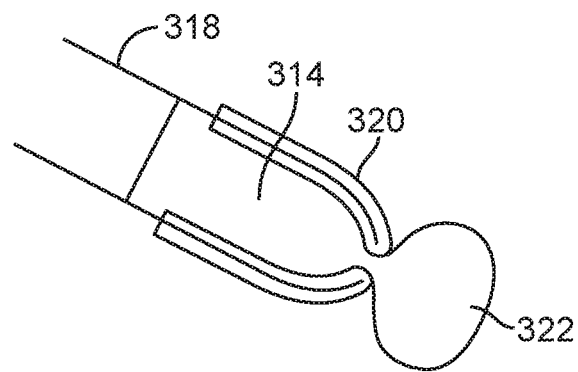
Figure 9:
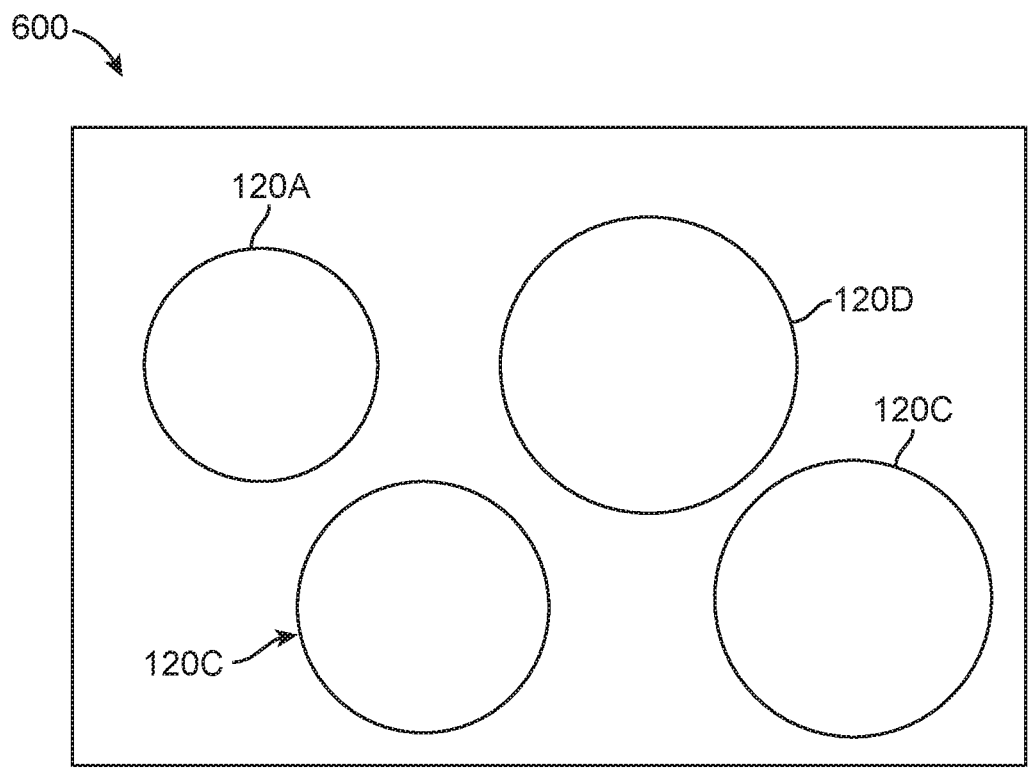
Figure 10:
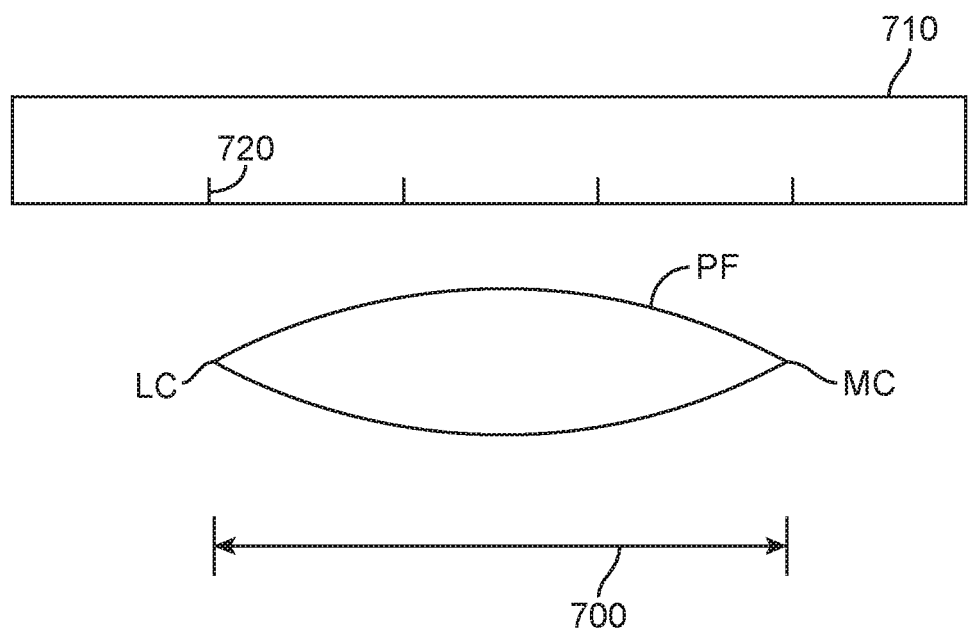
Figure 10A:
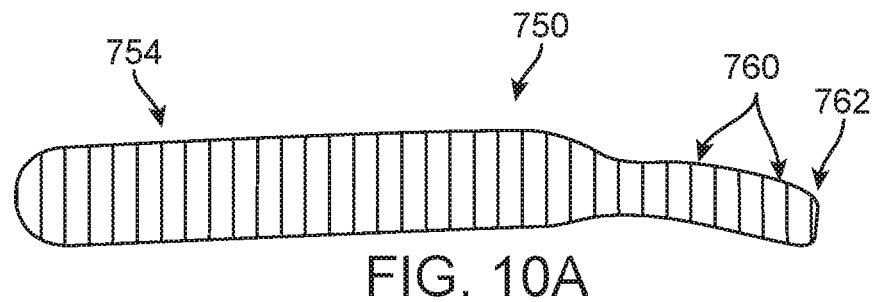
Figure 11A:
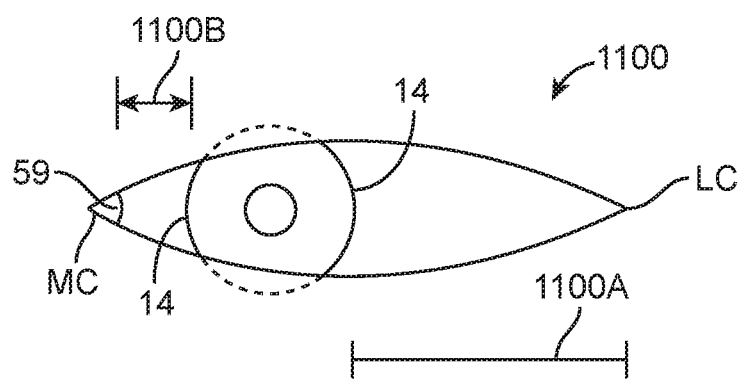
Figure 11B:
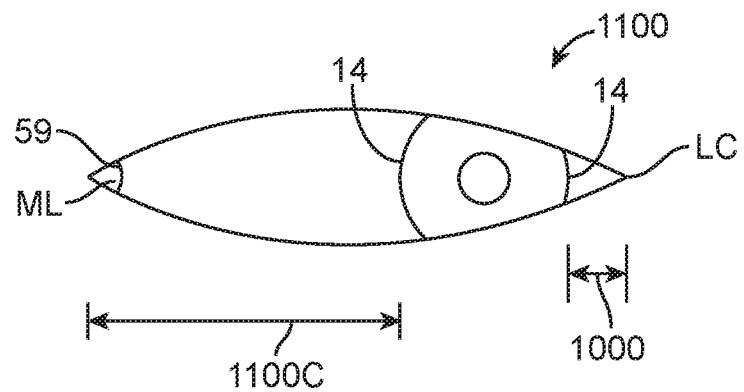
Figure 15:
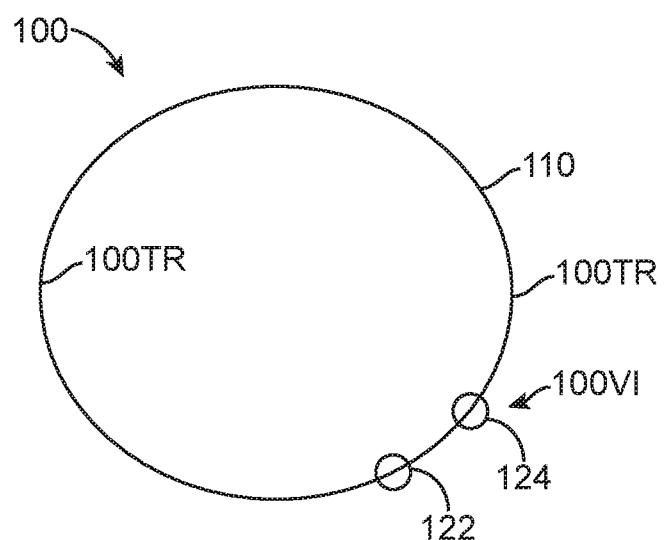
Figure 16A:
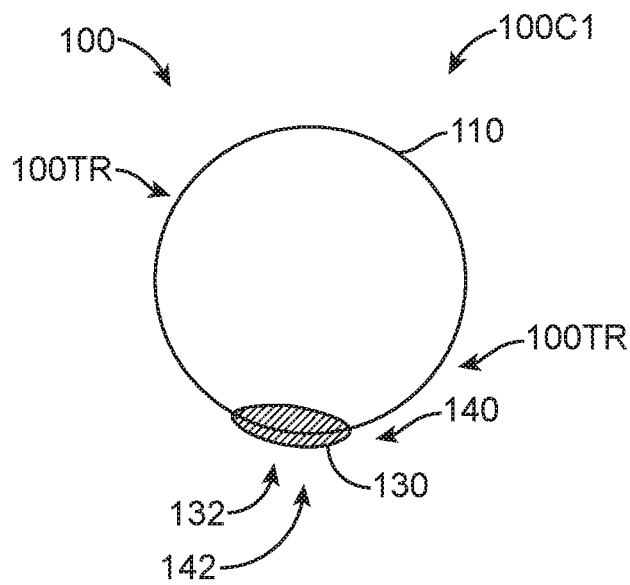
Figure 16B:
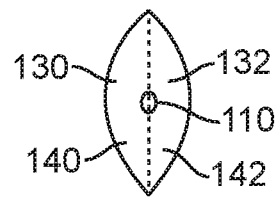
Figure 16C:
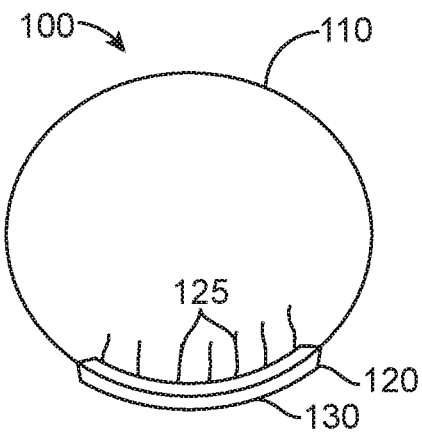
Figure 16D:
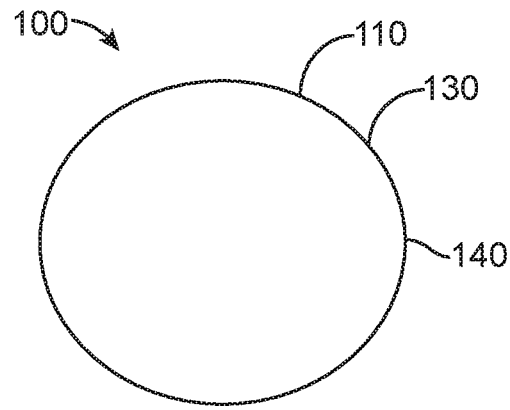
Figure 16E:
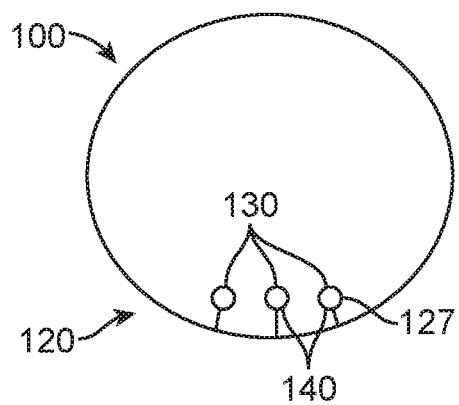
Figure 16F:
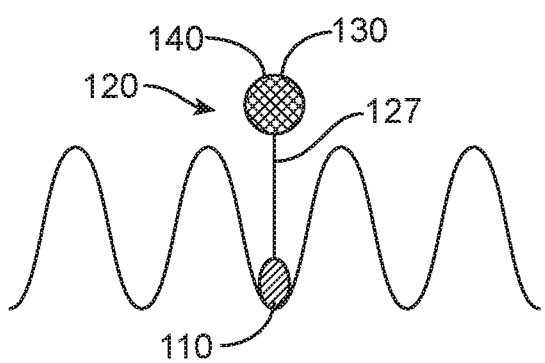
Figure 16G:
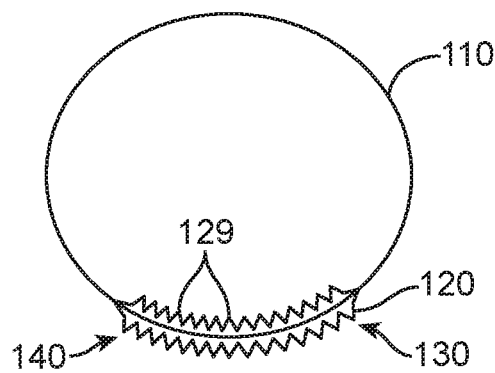
Figure 17A:
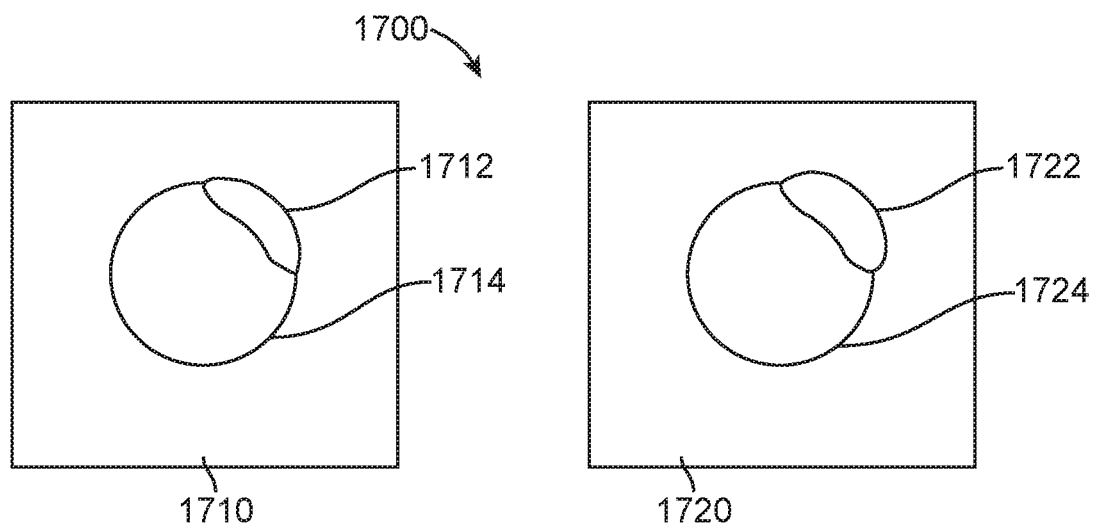
Figure 17B:
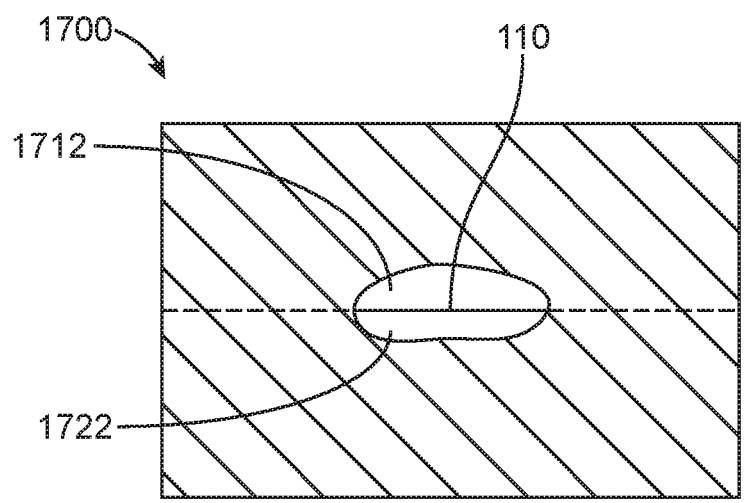
Figure 17C:
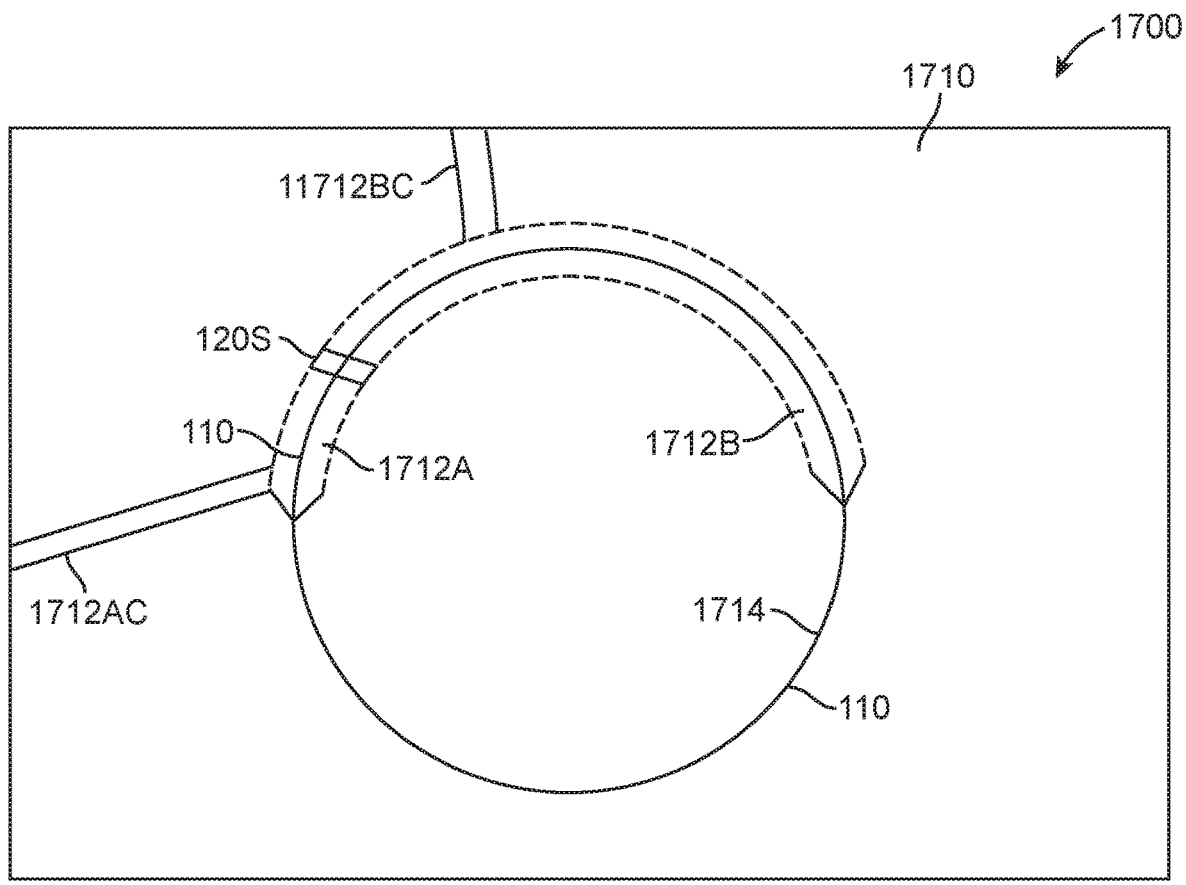
Figure 17D:
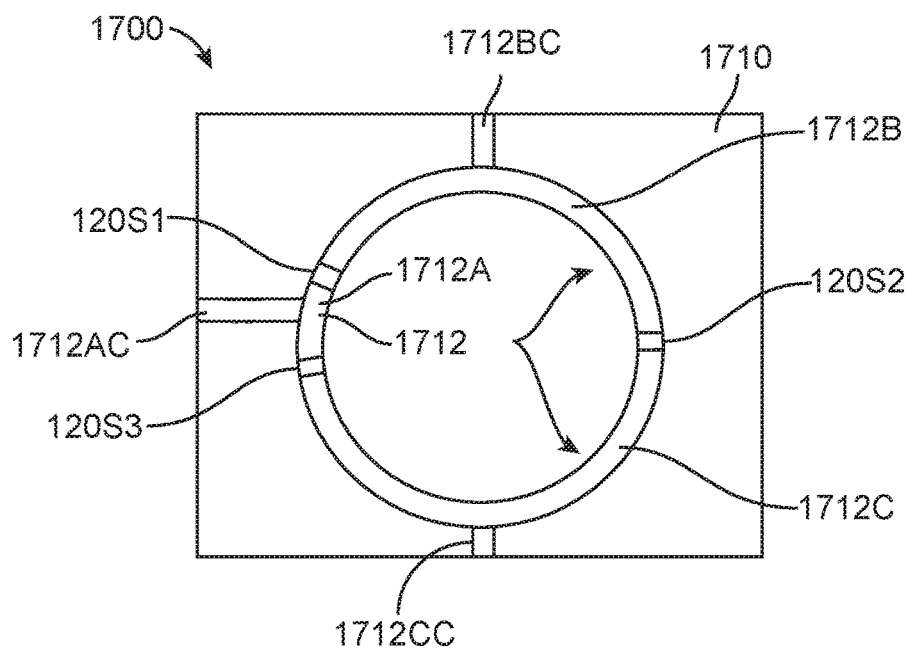
Figure 17E:
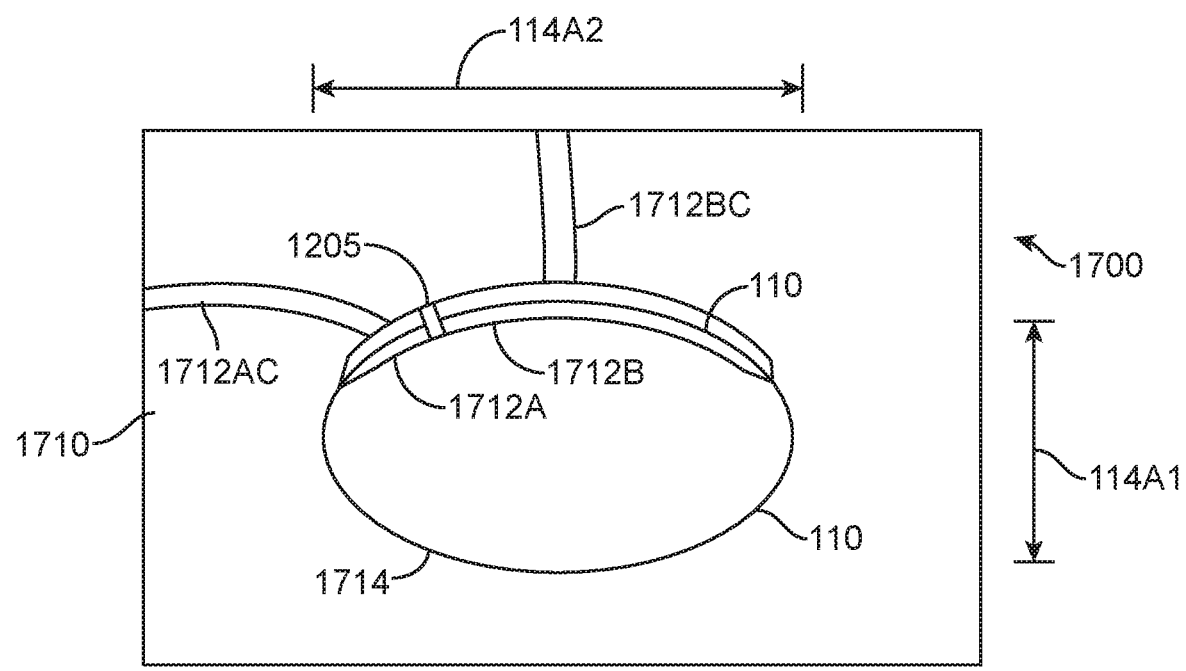
Figure 17F:
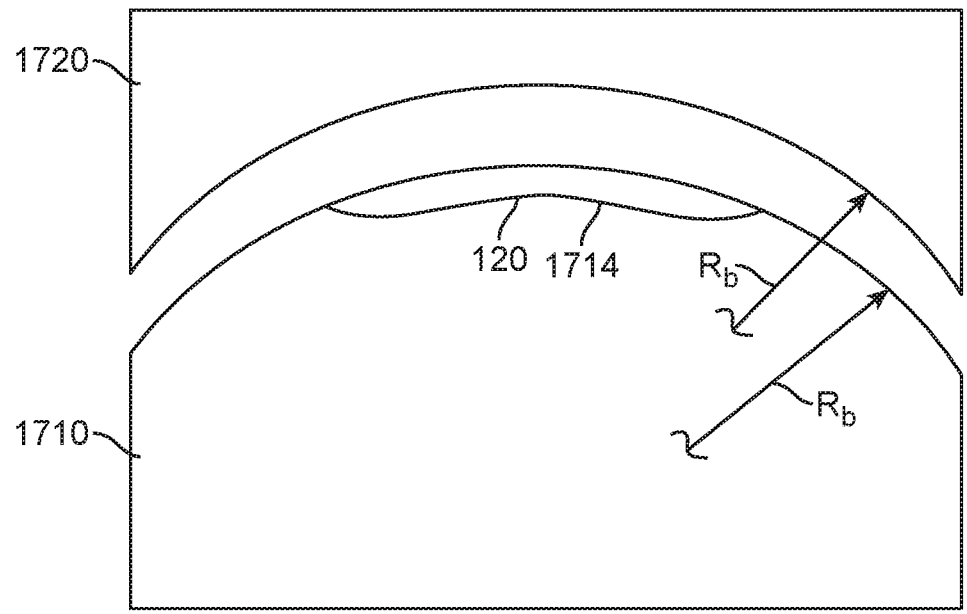
Figure 17G:
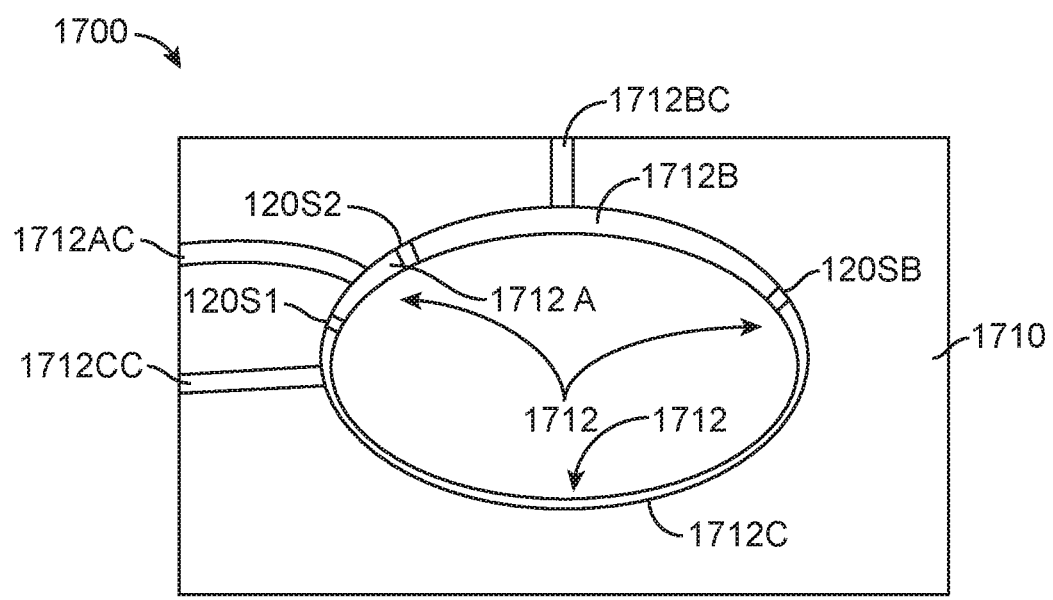
Figure 18:
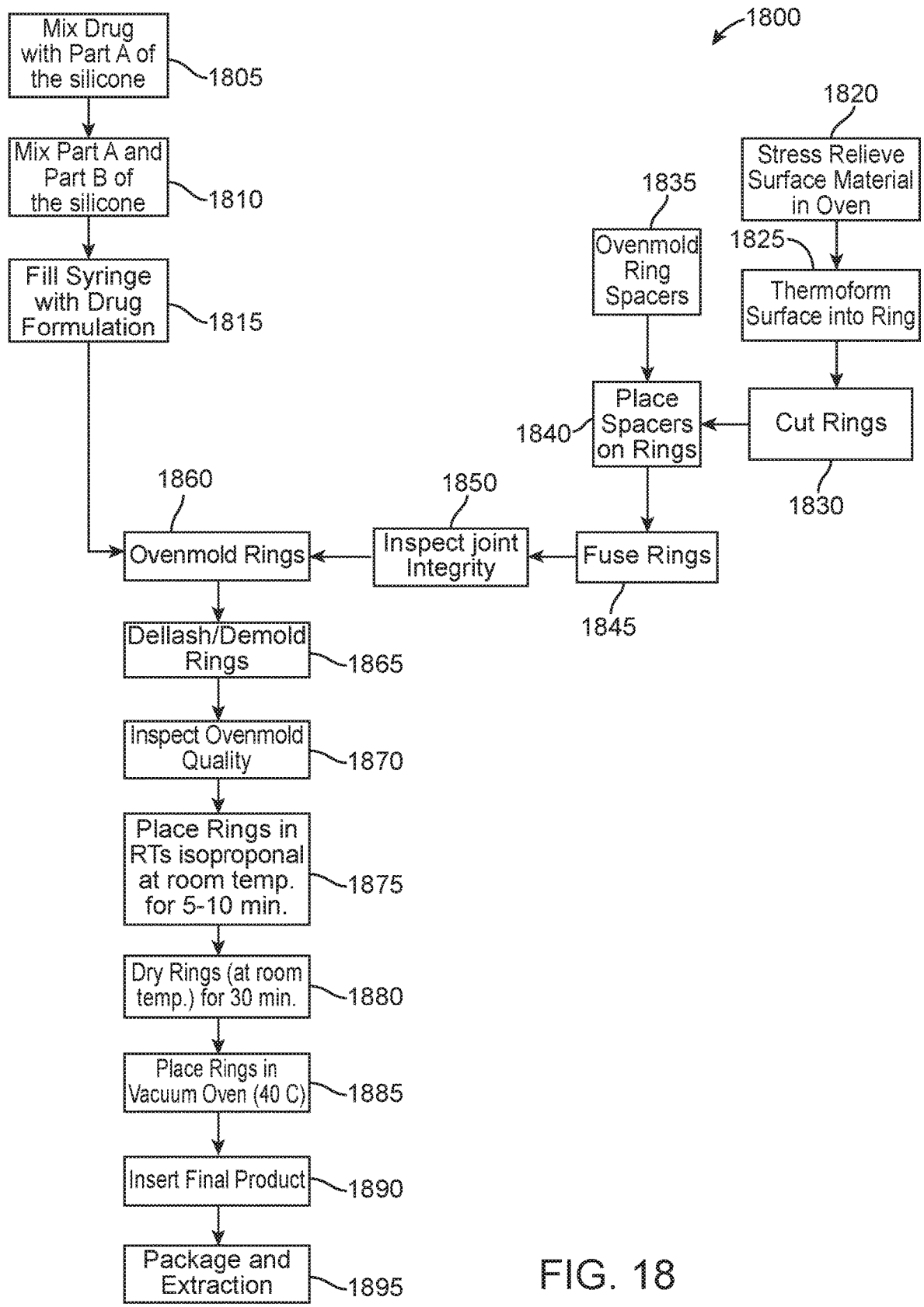
Figure 18A:
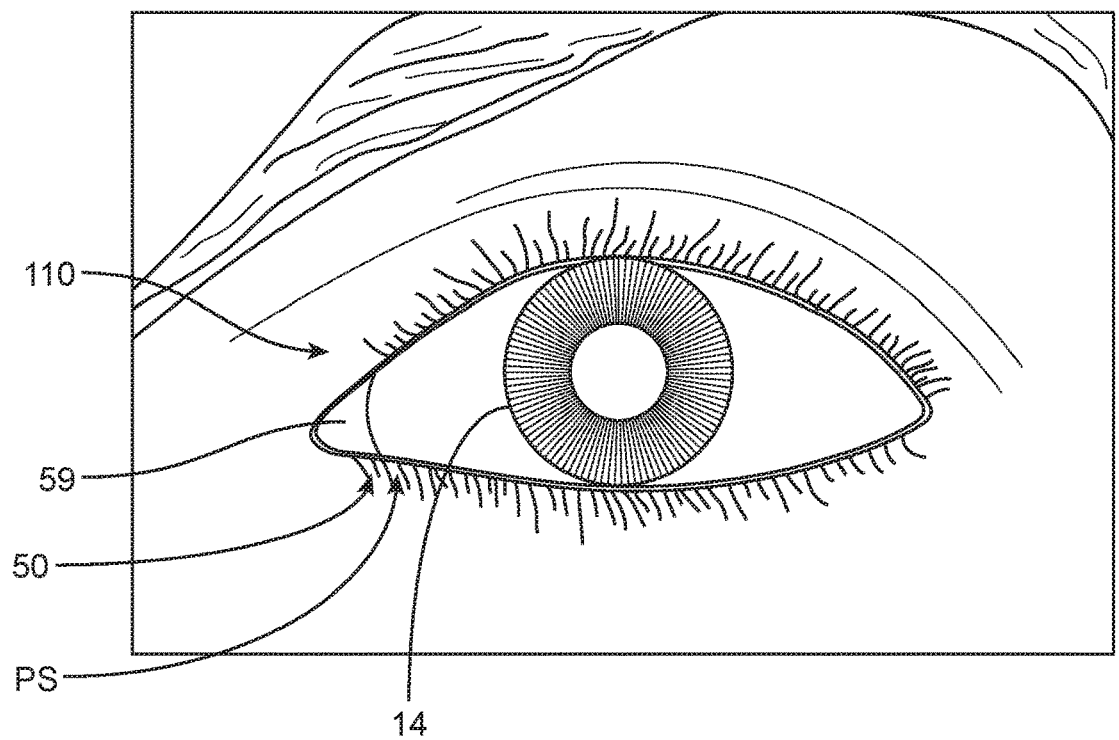
Figure 18B:
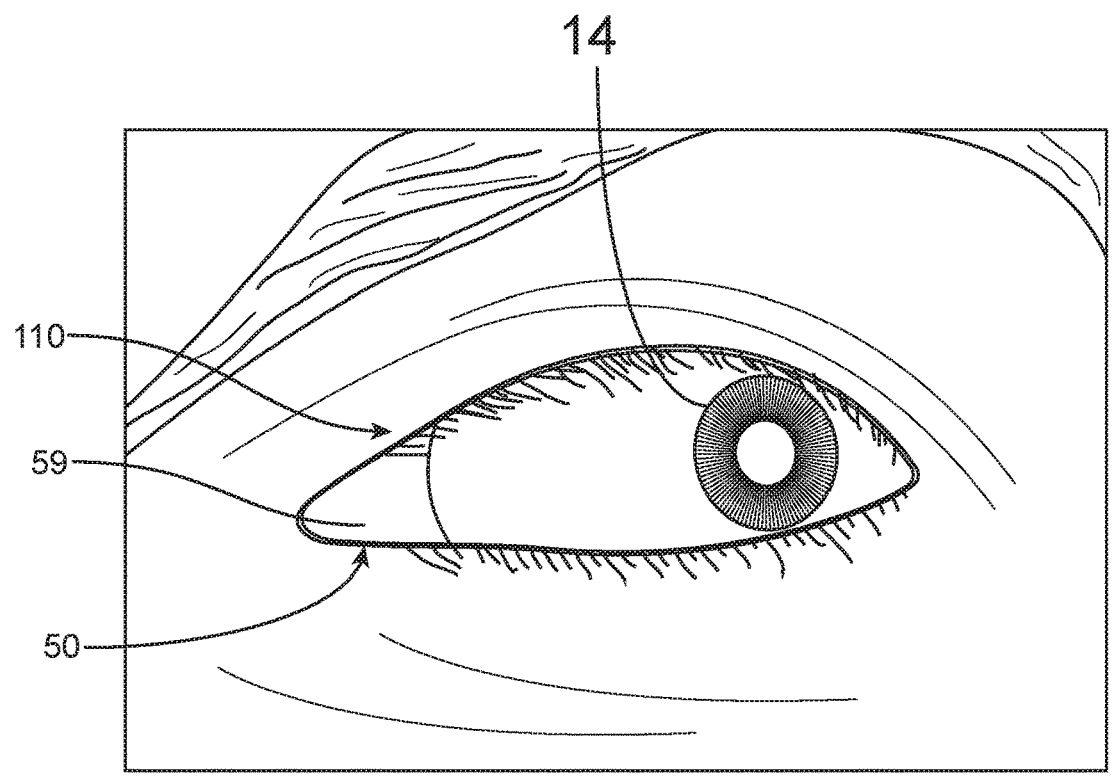
Figure 18C:
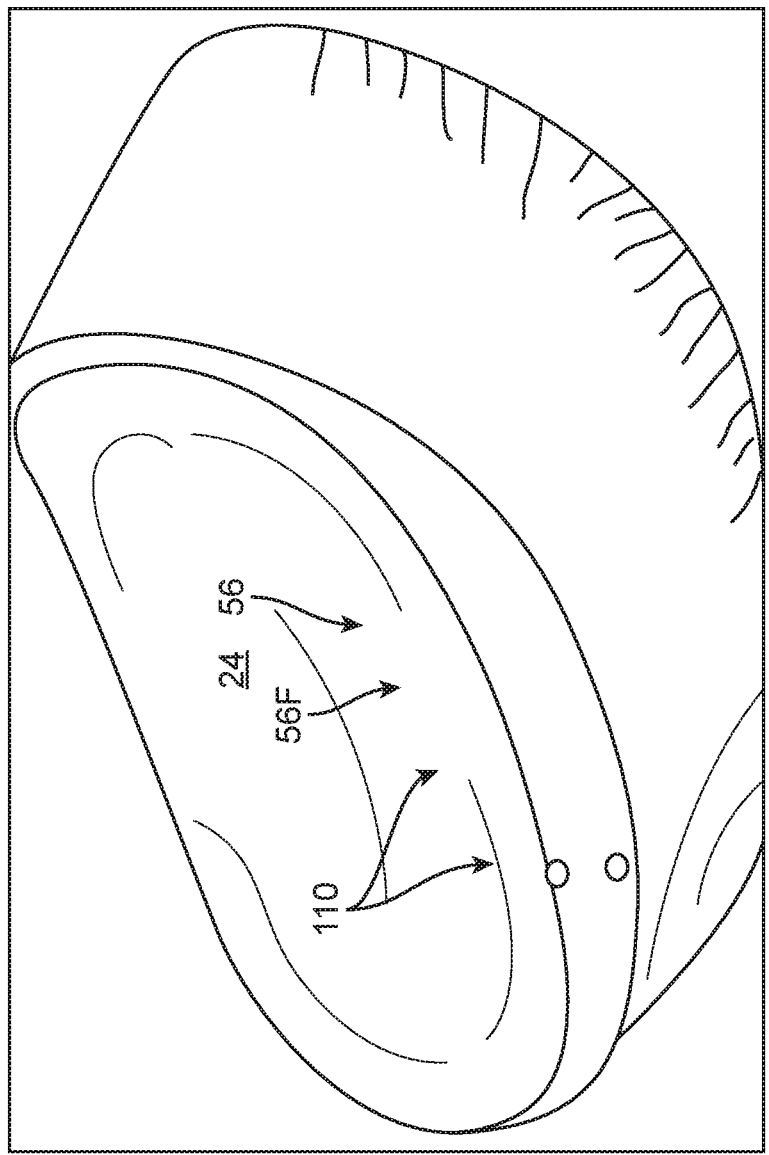
Figure 20A:
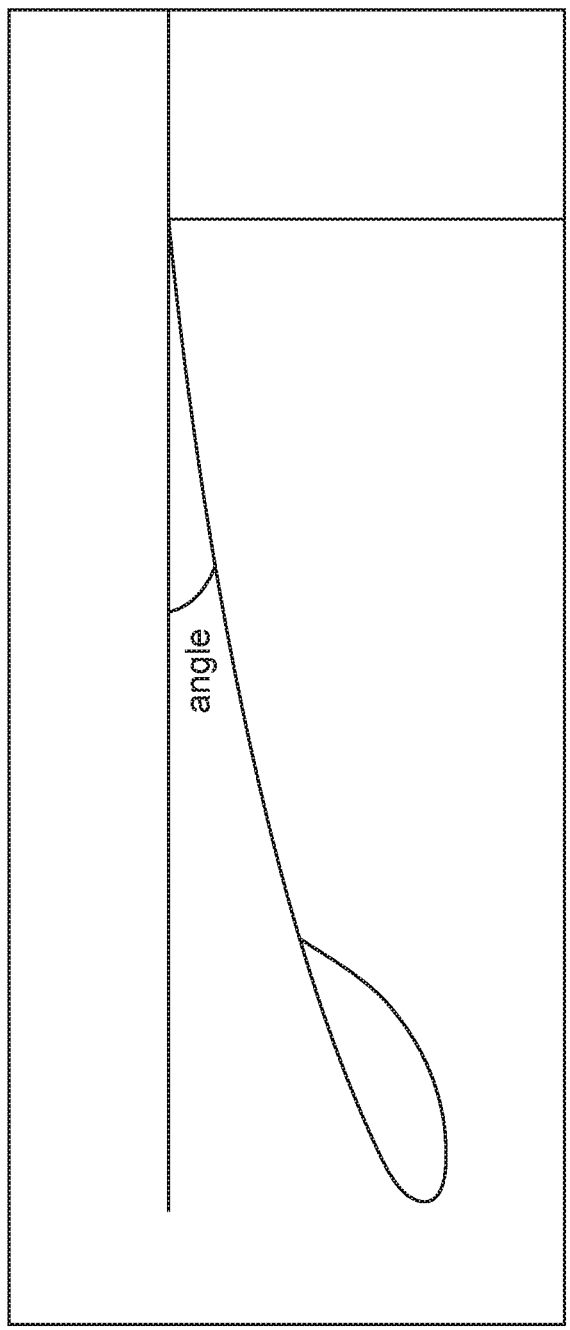
Figure 21:
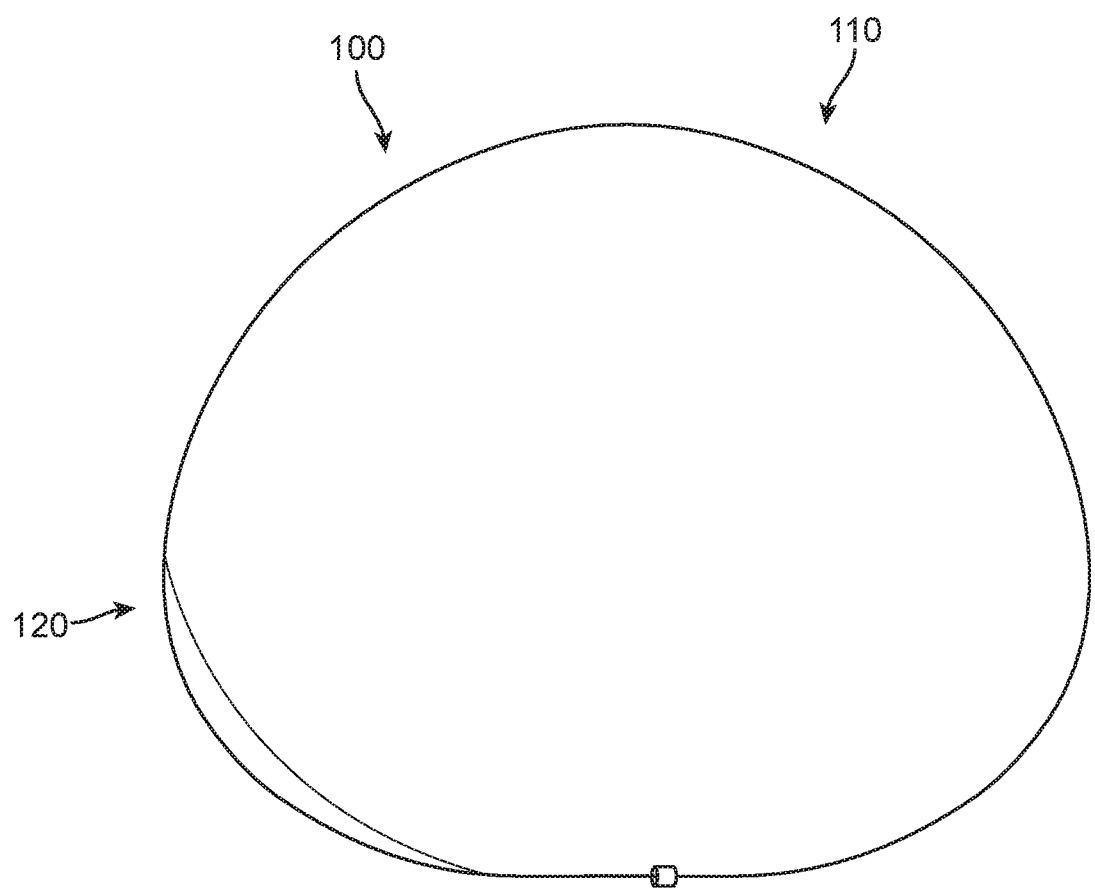
Figure 22:
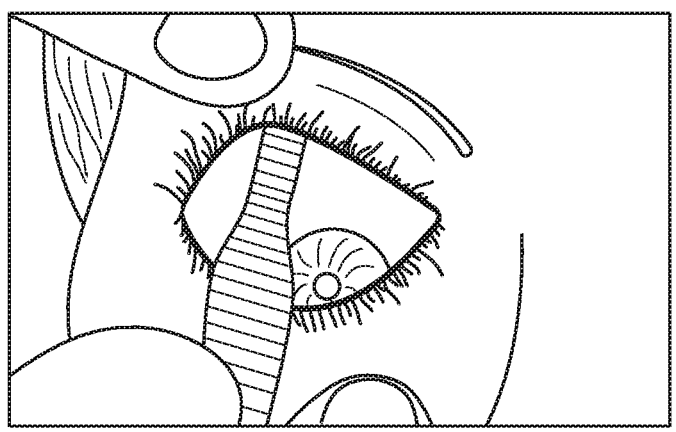
Figure 23:
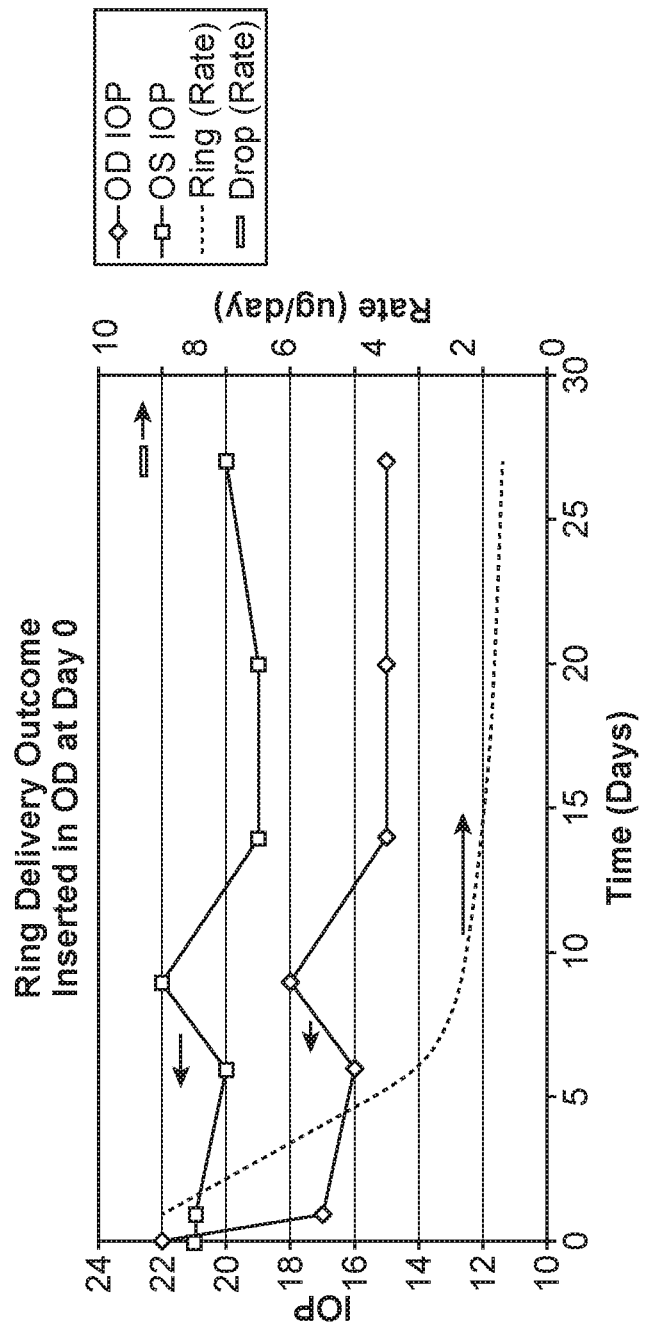
Figure 24:
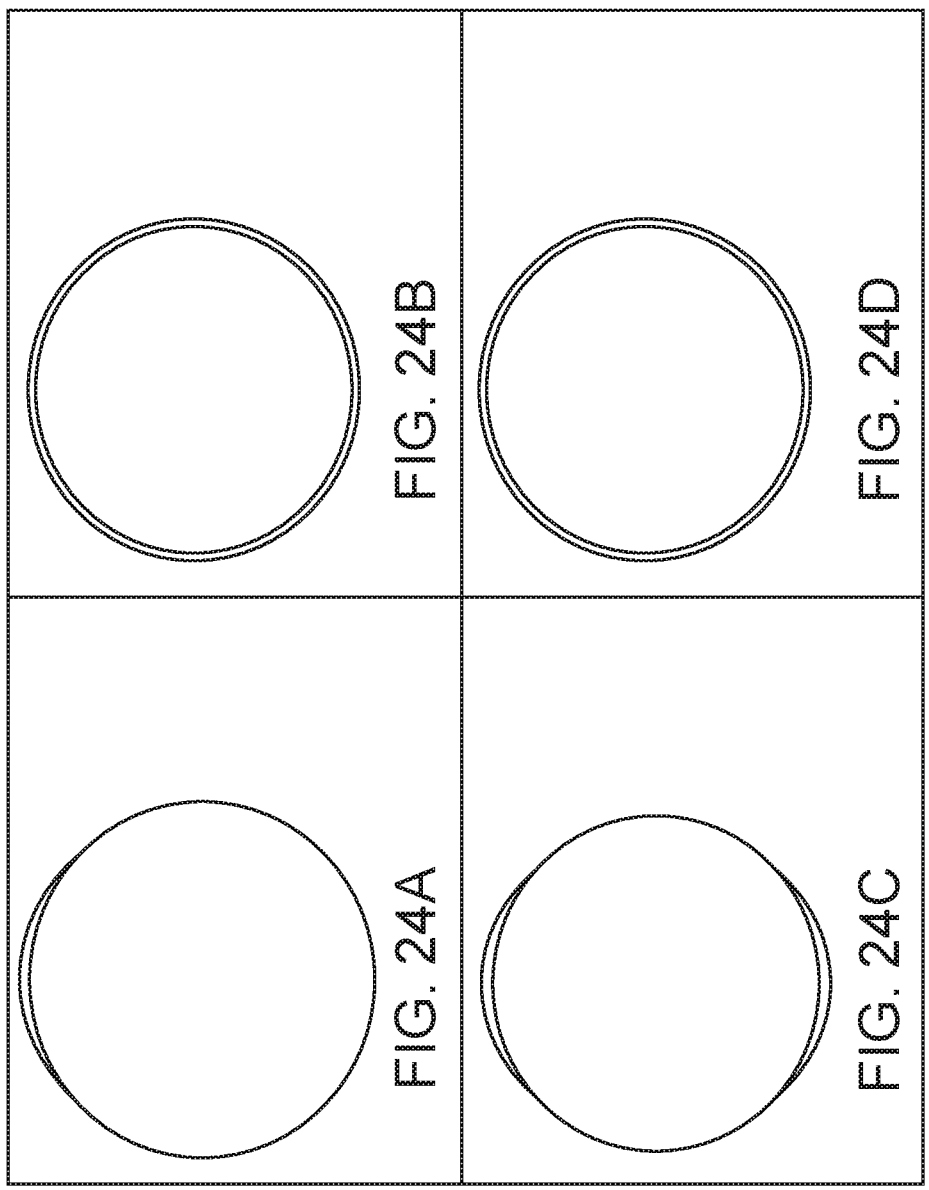
Figure 26A:
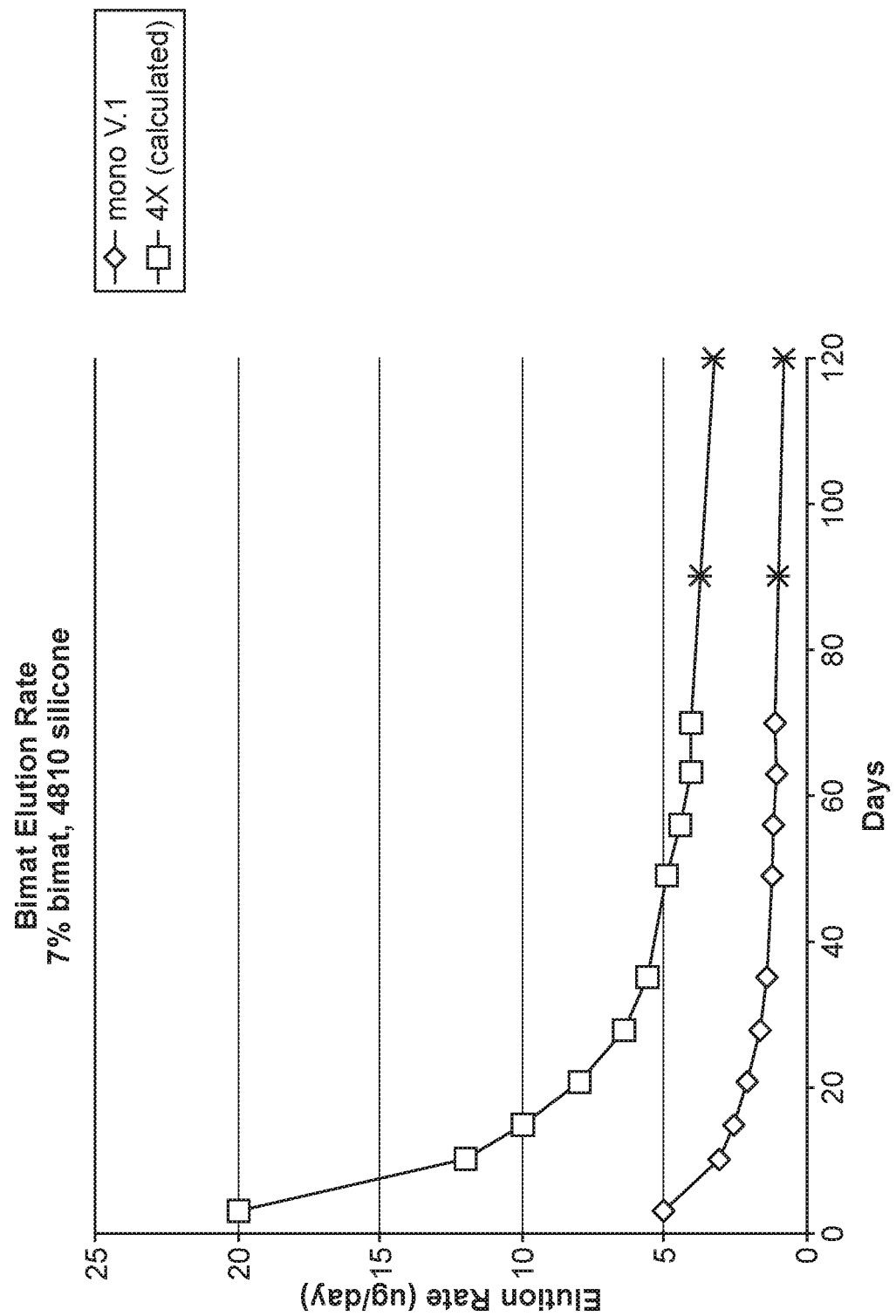
Figure 26B:
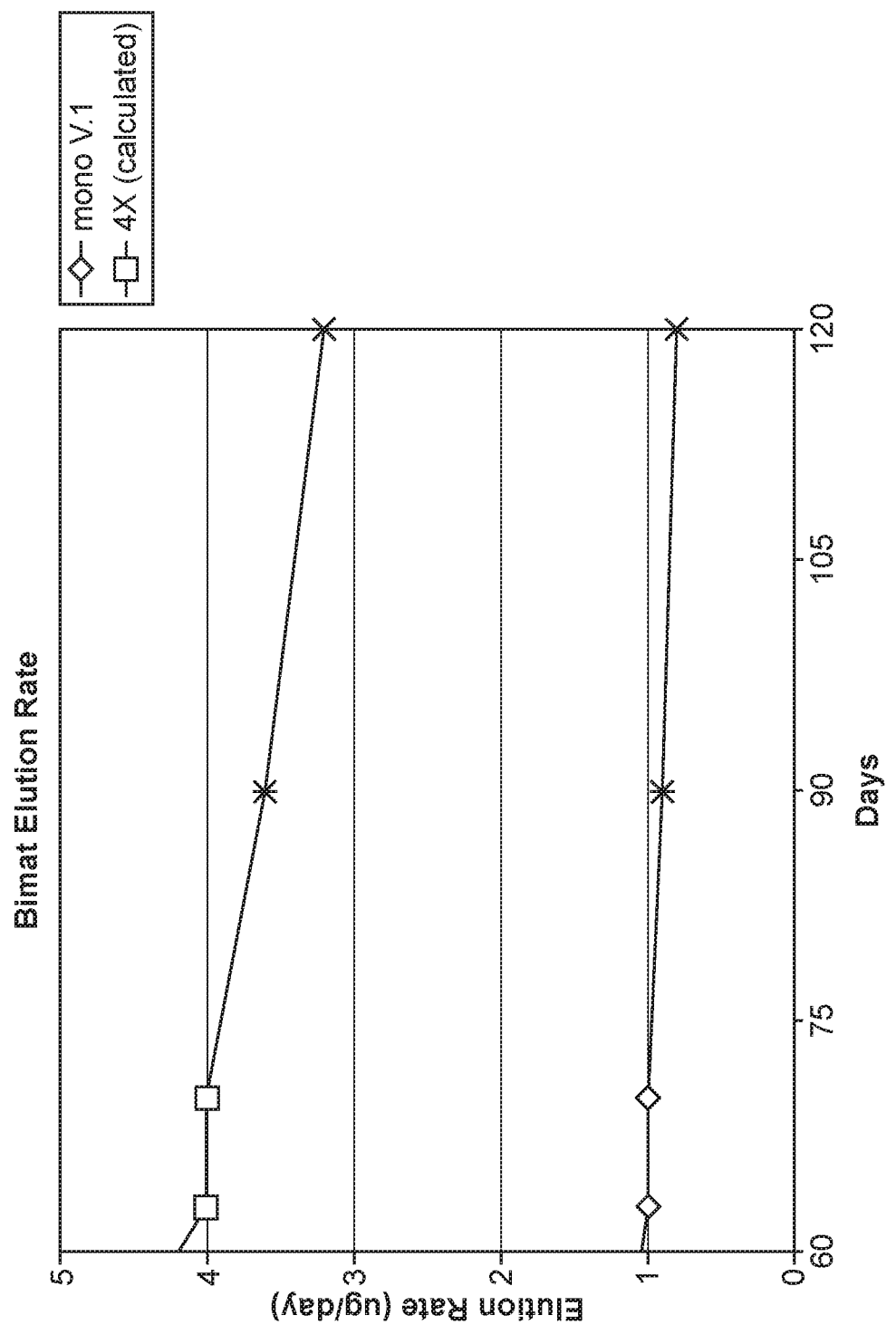
Figure 27:
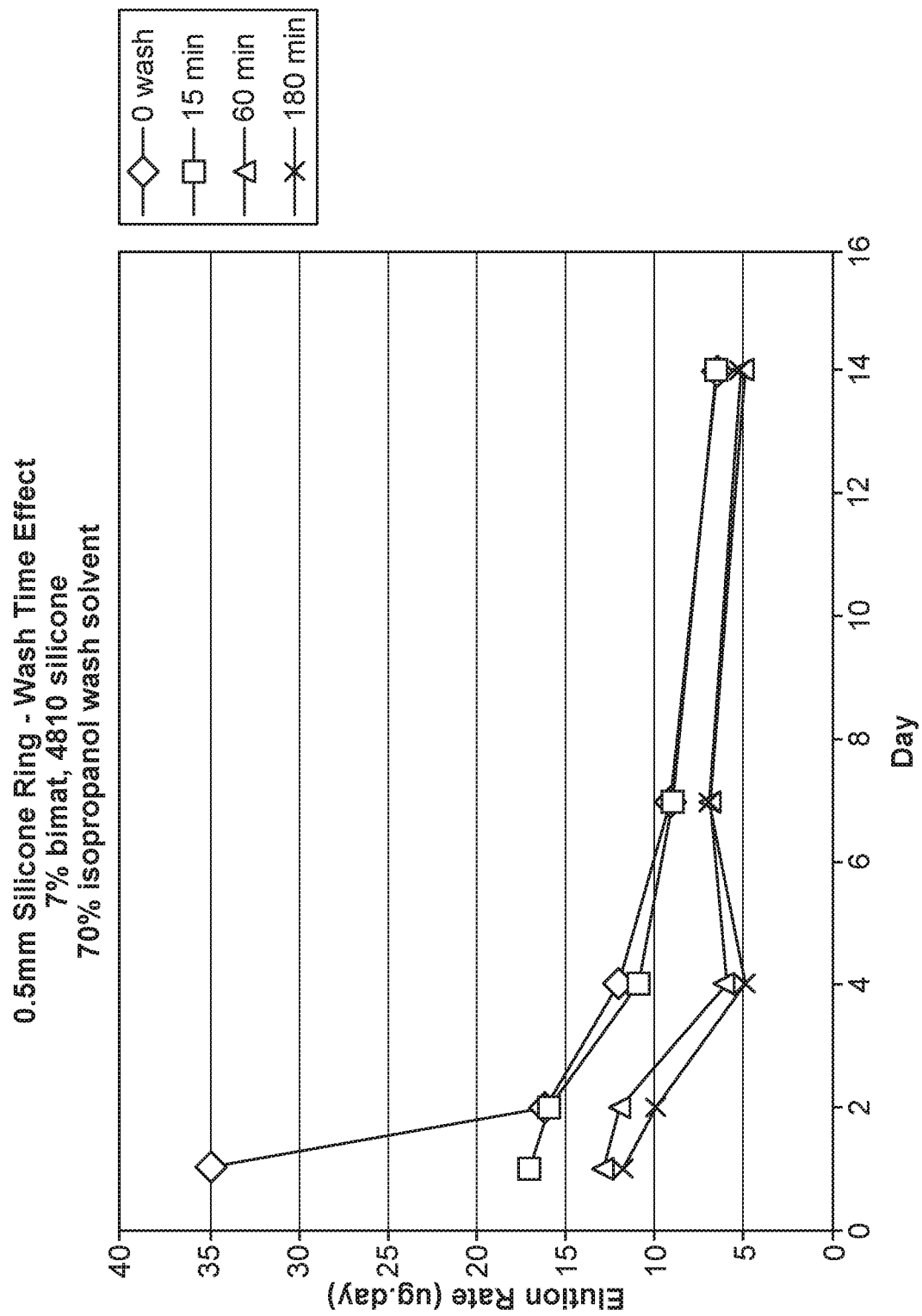
Figure 28:
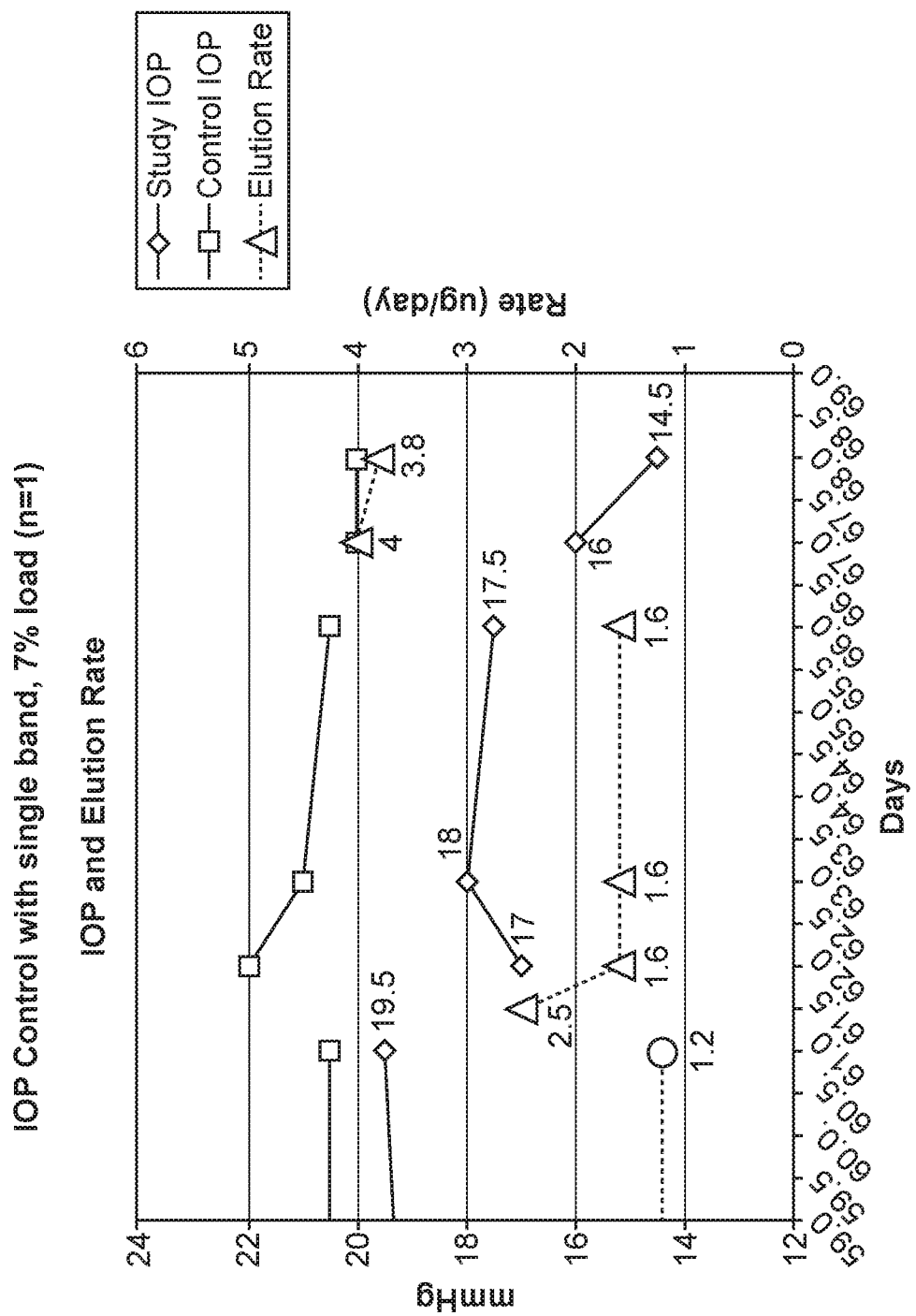

FIG. 8D depicts syringe system 300 with barrel 302, needle hilt 303, needle 304 with rounded tip 306 having outlet 308 and plunger 310 with pusher 312, in accordance with an embodiment;

FIG. 8E shows a syringe system being used to introduce hydrogel precursors into the cul-de-sac, for example into the fornix, with the precursors left in on or more of the cul-de-sac or the fornix, in accordance with an embodiment;

FIG. 9 shows a kit comprising a plurality of retention structures having incrementally increasing sizes to determine a size of the retention structure to fit the patient, in accordance with an embodiment;

FIG. 10 shows a measurement apparatus to measure a dimension of structure of the patient to determine a corresponding size of the retention structure to fit the patient, in accordance with an embodiment;

FIG. 10A shows a measurement apparatus to measure a depth of the conjunctival sac of the patient to determine a corresponding size of the retention structure to fit the patient, in accordance with an embodiment;

FIGS. 11A and 11B show a patient looking to a first side and a second side, respectively, to determine a dimension of the eye, in accordance with an embodiment;

FIGS. 12A1 and 12A2 show plan and side views, respectively, of the insert having a therapeutic agent and at least one optically transmissive portion and at least one visible portion, in accordance with an embodiment;

FIGS. 12B1 and 12B2 show insert 100 comprising second configuration 100C2, in accordance with an embodiment;

FIGS. 13A1 and 13A2 show a support structure configured to resist movement away from the inferior temporal portion of the conjunctival sac, in accordance with an embodiment;

FIGS. 13B1 and 13B2 show insert 100 comprising second configuration 100C2, in accordance with an embodiment;

FIGS. 14A1 and 14A2 show plane and side views, respectively, of structure comprising a first structure and a second structure spaced apart with distance to maintain the first structure and the second structure in the inferior temporal location of the conjunctival sac, in accordance with an embodiment;

FIGS. 14B1 and 14B2 show the insert 100 placed along at least a portion of the conjunctival sac of an eye, in accordance with an embodiment;

FIG. 15 shows insert comprising a C-shaped configuration with retention structure comprising a first end and a second end, in accordance with an embodiment;

FIG. 16A shows an insert comprising a therapeutic agent of matrix and a second therapeutic agent of a second matrix, in accordance with an embodiment;

FIG. 16B shows a cross sectional view of an insert as in FIG. 16A, in accordance with an embodiment;

FIG. 16C shows an insert comprising extensions to release a therapeutic agent, in accordance with an embodiment;

FIG. 16D shows a retention structure comprising a matrix containing a therapeutic agent, in accordance with an embodiment;

FIG. 16E shows an insert comprising a support structure having extensions to release therapeutic agent away from the retention structure, in accordance with an embodiment;

FIG. 16F shows a side cross sectional view of an insert comprising a support structure having extensions to release therapeutic agent away from the retention structure as in FIG. 16E, in accordance with an embodiment;

FIG. 16G shows a support structure comprising a plurality of outward extensions to increase a surface area of the matrix to release the therapeutic agent, in accordance with embodiments;

FIG. 17A shows a mold to make the insert comprising a first component and a second component, in accordance with an embodiment;

FIG. 17B shows the mold as in FIG. 17A having a preformed retention structure placed in the mold configured for injection of a flowable material, in accordance with an embodiment;

FIG. 17C shows a mold to make the insert comprising a first component and a second component, in which the mold comprises a first channel to inject a first flowable material comprising a first therapeutic agent and a second channel to inject a second flowable material comprising a second therapeutic agent, in accordance with an embodiment;

FIG. 17D shows a mold to make the insert comprising a first component and a second component, in which the mold comprises a first channel to inject a first flowable material comprising a first therapeutic agent and a second channel to inject a second flowable material comprising a second therapeutic agent and a third channel to inject a third flowable material substantially without therapeutic agent, in accordance with an embodiment;

FIGS. 17E and 17F show a spherical mold having an oval shaped channel to make the insert in which the mold comprises a first lower component comprising a convex spherical surface and a second upper component comprising a concave spherical surface to nest with the convex spherical surface, in accordance with an embodiment;

FIG. 17G shows a spherical mold having an oval shaped channel to make the insert in which the mold comprises a first channel to inject a first flowable material comprising a first therapeutic agent, a second channel to inject a second flowable material comprising a second therapeutic agent and a third channel to inject a flowable material without substantial therapeutic agent, in accordance with an embodiment;

FIG. 18 shows a manufacturing process, in accordance with an embodiment;

FIG. 18A shows an image of the insert placed on an eye with the retention structure under a fold of conjunctiva, in accordance with an embodiment;

FIG. 18B shows an image of the insert placed on the eye as in FIG. 18A with the eye looking temporally so as to expose the insert from under the fold of conjunctiva and such that the retention structure slides along the bulbar conjunctiva, in accordance with an embodiment;

FIG. 18C shows an image of the insert placed on an eye with the retention structure extending under a fold of conjunctiva, in accordance with an embodiment;

FIGS. 19A to 19F show placement locations of the support structure comprising silicone elastomer coupled to the retention structure as described herein, in accordance with embodiments;

FIG. 20A shows self-loading deflection of an insert, in accordance with an embodiment;

FIG. 21 shows an in situ formed retention structure subsequent to removal from an eye, in accordance with an embodiment;

FIG. 22 shows a digital image of a human eye measured with a measurement apparatus as described herein, in accordance with an embodiment;

FIG. 23 shows a graph of TOP over time for a patient having an insert placed on one eye and a control eye for at least about 1 month, in accordance with an embodiment;

FIG. 24A shows a tested insert comprising a suture and a single 75 degree silicone band, in accordance with an embodiment;

FIG. 24B shows a tested insert comprising silicone without a supporting suture, in accordance with an embodiment;

FIG. 24C shows a tested insert comprising a suture and two opposing 75 degree silicone bands, in accordance with an embodiment;

FIG. 24D shows an insert suitable for testing comprising an inner suture covered with an outer silicone layer along a 360 degree circumference, in accordance with an embodiment;

FIG. 25 shows deformation and curvature of an insert subsequent to placement in an eye with the insert curved so as to correspond to the curvature of the lid along the cul-de-sac, in accordance with an embodiment;

FIGS. 26A and 26B show rates of release of a prostaglandin comprising bimatoprost from a silicone matrix, in which the estimated rate of release for a matrix having 7% a prostaglandin comprising bimatoprost loaded on an insert as described herein is above 3 ug per day for at least about 120 days, in accordance with an embodiment;

FIG. 27 shows wash time and rates of release of therapeutic agent from matrices having varying amounts of wash, in accordance with an embodiment;

FIG. 28 shows TOP and rates of therapeutic agent release, in accordance with an embodiment.

DETAILED DESCRIPTION

Embodiments as described herein can be combined in many ways to provide inserts for placement in the eye for an extended time. The extended time can depend on the use of the insert and can be at least about one week, for example one month or more. In many embodiments, the insert can be easily placed in the eye and retained comfortably and continuously for an extended time of at least about two months, for example three months, and in many embodiments six months or more. The insert can be configured and formed in many ways and may comprise a therapeutic agent for drug delivery.

The embodiments as described herein can be used in many ways to release a combination of therapeutic agents simultaneously for an extending time. For example, a first therapeutic agent such as a prostaglandin can be combined with a second therapeutic agent such as a beta blocker. Each therapeutic agent may be provided on a segment of the insert. The prostaglandin may comprise an amount less than the beta blocker, and the size of the insert segments may correspond to the amount of therapeutic agent. For example, the amount of beta blocker can be from about five times the amount of prostaglandin to about fifty times the amount of prostaglandin. The beta blocker may be released at a rate substantially greater than the rate of the prostaglandin, for example at least about five times the rate of release of the prostaglandin. In many embodiments, the prostaglandin may comprise one or more of bimatoprost, latanoprost, or travoprost, and the beta blocker may comprise timolol, for example.

The insert can be sized and shaped to fit on the eye in many ways, such that when used on a patient population the insert can be easily inserted and provide comfort and retention for at least about 80% of the patients for at least about one month, for example comfortably retained for at least about 3 months for 80% of the patients. In many embodiments, the insert can be easily inserted and comfortably retained for at least about 90% of the patients for at least about one month. In many embodiments, the insert can be readily inserted by the patient, such that the insert can be replaced by the patient, for example replaced monthly to treat the patient for an extended time of at least about three months. The insert may comprise a unitary shape having a substantially constant cross-sectional diameter, or a shape having a varying cross sectional diameter, for example.

The therapeutic agent may be placed on the insert at a location corresponding to the treatment when placed. For example, when treating lacrimal gland disease the therapeutic agent can be placed on the insert at a location corresponding to placement near lacrimal gland when inserted. Alternatively, for glaucoma, the therapeutic agent may be located on an insert at a location that can provide improved retention, for example a location corresponding to one or more of the upper lid or the lower lid when placed.

The insert can be configured in many ways and can be configured to move when placed on the eye so as to provide improved comfort for the patient. The insert can be in situ formable or may comprise a shape memory material. In many embodiments, the insert and retention structure may comprise a material that will retain a shape provided prior to insertion, for example with molding, such that the insert will return substantially to the pre insertion shape when removed from the eye, for example one month after insertion. In many embodiments, one or more of the insert or the retention structure may comprise a resistance to deflection such that gravity may slightly alter the shape of the retention structure or support when self supporting, such that the retention structure may distort slightly and cannot completely overcome the distortional force of gravity. In many embodiments the insert may not comprise enough spring force to overcome friction completely, such that the shape may change slightly when placed.

In many embodiments, the insert is configured to move when placed in the eye. The eye can move, for example rotate within the eye socket, and the insert can move with the conjunctiva of the eye and may slide along the conjunctiva of the eye. In at least some embodiments, the insert can be configured to slide when placed in the eye, for example with a lubricous coating. Alternatively, a portion of the insert can be configured to adhere to the conjunctiva, for example with one or more of a sticky tacky surface, a dry hydrogel material or an adhesive.

As used herein the eye encompasses the eyeball and corresponding tissue structures such as the lids of the eye, the conjunctiva of the eye, and the lacrimal glands and tear ducts of the eye.

As used herein a conjunctival sac of the eye encompasses a sac of the eye formed with conjunctiva of one of the eyelids and corresponding bulbar conjunctiva.

As used herein like numerals and/or letters can denote like elements in the drawings as will be apparent to a person of ordinary skill in the art.

FIG. 1A shows an eye 10 suitable for incorporation with the insert apparatus. The eye has a light transmitting cornea 12 and a light transmitting lens 21 that form an image on the light sensing retina 26 so that the person can see. The eye comprises a light transmitting vitreous humor 27 between the lens 22 and retina 27. The eye 10 comprises an axis 10A extending between the cornea 12 and retina 26, and the axis 10A may comprise one or more known axes of the eye such as the visual axis, the line of sight, the optical axis, or other axis of the eye. The axis 10A extends an axial distance from cornea 12 to retina 26. The cornea 12 extends to a limbus 14 of the eye, and the limbus connects to a sclera 24 of the eye. The eye has an iris 18 that may expand and contract in response to light. The eye also comprises a choroid 28 disposed between the sclera 24 and the retina 26. The retina comprises the macula 25 for high acuity vision. The eye comprises a pars plana 20 located along the scleral portion of the eye near the limbus.

The eye comprises connective tissue structures to protect the eye and allow the eye to move. A pair of lids 40 open to allow the eye to see and close to protect the eye. An upper lid 42 extends across an upper portion of the eye and a lower lid 44 extends across a lower portion of the eye. The eyelids 40 define a palpebral fissure PF extending between the upper lid 42 and lower lid 44. Conjunctiva 50 comprises a loose tissue that protects the eye and allows the eye to move within the bony socket. The conjunctiva 50 comprises a lid portion comprising palpebral conjunctiva 58 and a globe portion comprising bulbar conjunctiva 56. The palpebral conjunctiva 58 lines the inner surface of the upper and lower eyelids that contact the cornea when the eyelids close. The conjunctiva extends from the palpebral conjunctiva 58 of each lid to the bulbar conjunctiva 56 located over the sclera 24 of the eyeball. The bulbar conjunctiva 56 connects to the eyeball near the limbus 14. The conjunctiva 50 extends from the palpebral conjunctiva 58 of each eyelid and reflects back to form a sac 52 comprising a cul-de-sac 53 and a fornix 54. The bulbar conjunctiva 56 is located over the sclera and translucent such that the white sclera can be readily seen.

FIG. 1B shows front view of the eye as in FIG. 1A. The pupil 16, iris 18 and sclera 24 can be readily seen with a front view of the eye. The medial canthus MC is located on a nasal end of the palpebral fissure PF, and the lateral canthus LC is located on a lateral end of the palpebral fissure. The human eye comprises a caruncle 59, which is located nasally near the medial canthus. A fold of the bulbar conjunctiva 56 comprising the plica semilunaris can be located near the caruncle 59. As the plica semilunaris PS can move with the eyeball, the plica semilunaris can move nasally under the caruncle when the patient looks nasal and can become increasingly visible when the patient looks temporally so as to rotate the plica semilunaris temporally. The eye may comprise additional folds of the bulbar and palpebral conjunctiva that extend circumferentially around the eye so as to allow the eye to rotate freely within the bony orbit.

FIG. 1C side sectional view of the conjunctiva of the upper lid 42 and lower lid 44 of the eye as in FIGS. 1A and 1B. The bulbar portion of the conjunctiva 56 comprises a plurality of folds 56F and the palpebral portion of the conjunctiva 50 comprises a plurality of folds 58F. The conjunctiva 50 reflects back between the bulbar conjunctiva 56 and the palpebral conjunctiva 58 at the fornix 54. The plurality of bulbar folds 56F and the plurality of palpebral folds 58F may each extend substantially circumferentially around at least a portion of the eye. The sac 52 comprises the cul-de-sac 53, and the cul-de-sac 53 comprises the fornix 54.

FIG. 1D shows a side sectional view of the upper lid of the eye as in FIGS. 1A to 1C and the folds of the conjunctiva. The bulbar conjunctiva 56 of the upper lid 42 has many folds 56F along the conjunctiva extending between the limbus and the fornix 54. The palpebral conjunctiva 58 of the upper lid comprises many folds 58F extending between the fornix and the lower margin of the upper eyelid 42. The bulbar conjunctiva 56 of the lower lid 44 has many folds 56F along the conjunctiva extending between the limbus and the fornix 54, and the palpebral conjunctiva 58 of the lower lid 44 comprises many folds 58F extending between the fornix and the upper margin of the lower eyelid 44.

The eye can move in many ways, for example with one or more of blinking, squeezing the eye shut, rotation, translation, cyclotorsion, or nystagmus, for example. For example, with rotation of the eye, the conjunctiva may move with the eye in some locations and slide along the eye in other locations. When the eye blinks, the upper lid and lower lids may slide a substantial distance along eye. In many patients, the eye may exhibit Bell's phenomenon, in which the eyeball may rotate upwards when an attempt is made to close the eyes.

FIG. 1E shows muscles of a pair of eyes that provide cyclotorsion of the eye suitable for combination in accordance with an embodiment as described herein. Cyclotorsion comprises one of many eye movements that may occur. The eye comprises many muscles that can be used to rotate the eyeball. Each eyeball is attached to a superior rectus muscle to rotate the eye superiorly and an inferior rectus muscle to rotate the eye inferiorly. The lateral rectus muscles rotate the eyeball laterally and the medial rectus muscles rotate the eye medially. Inferior and superior oblique muscles can cyclo rotate the eye about an axis extending substantially along the optical path of the eye.

Cyclotorsion of the eye can result from viewing of objects near and far to the patient. When the eyes adjust the viewing angle so as to focus on near or far objects, cyclovergence can occur. The type of the torsional vergence component can depend systematically on viewing angle elevation. When the eyes fixate on a nearby target, the eyes show in-torsion in up gaze, ex-torsion in down gaze, and no cyclotorsion at some intermediate elevation level. The embodiments described herein can allow sliding movement of the retention structure along the conjunctiva in response to torsional movement of the eye.

Embodiments similar to FIGS. 1-1-2 to 1-9-1 are shown in PCT App. No. PCT/US2010/037268, published as WO2010/141729 on Dec. 9, 2010, entitled "Anterior Segment Drug Delivery"; and U.S. patent application Ser. No. 13/151,001, filed on Jun. 1, 2010, entitled "Anterior Segment Drug Delivery", the full disclosures of which have been previously incorporated herein by reference and are suitable for combination in accordance with embodiments described herein.

FIG. 1-1-2 shows the lacrimal system 11 which is responsible for producing and draining the tear fluid. The lacrimal system consists of two general areas: first, the lacrimal gland 20, which secretes the tears, and its excretory ducts 22, which transport the fluid to the surface of the eye and, second, the lacrimal canaliculi 24, the lacrimal sac 26, and the nasolacrimal duct 28, which bring the tear fluid is conveyed into the nose cavity.

FIG. 1-2-1 shows an exemplary embodiment of a therapeutic system 30. The therapeutic system 30 comprises an ocular insert 31, and may also include an insertion device, a configuration altering material that dissolves (or swells, weakens, tightens, or effects some other activation mechanism) to reconfigure the implant from an insertion configuration to a deployed configuration, or the like. In alternative embodiments, activation of the insertion device (or some other tool) may also reconfigure the insert from the insertion configuration to the deployed configuration, or may simply releasably hold the insert in a manner so as to assist insertion. In still further embodiments, the ocular insert may not undergo significant changes in shape or other properties before, during, or after deployment. Regardless, the ocular insert is eventually positioned on a region outside an optical zone of an eye. The ocular insert comprises two structures: a first structure 32 and a second structure 34. FIG. 1-2-1 shows the exemplary therapeutic system 30 placed outside the optical zone of the eye.

First Structure

The first structure functions as a skeleton which largely holds the implant in place relative to the structures of the eye, thereby attaches the implant to the eye, and thus provides support for the second cushioning structure relative to the anterior portion of the eye. This first or skeletal structure preferably maintains the attachment of the therapeutic system to the anterior portion of the eye for at least thirty days. Should it become medically desirable or should a patient so desire, the therapeutic system may be removed sooner than the thirty days; however, from a physical standpoint, it is capable of maintaining the ocular insert of the anterior surface of the eye for at least thirty days. In some embodiments, the first structure may continue to help maintain the overall implant in the eye for sixty days or more, for ninety days or more, or even for 180 days or more, ideally with safe and effective delivery of therapeutic agents continuing throughout such implant periods. Alternative treatment devices and methods may benefit from shorter implant periods, optionally for periods of one or more days, at least a plurality of days, a week or more, two weeks or more, or the like.

Due to its role as skeleton for the insert 31 of therapeutic system 30, the first structure may determine the overall shape of the ocular insert. The first structure typically comprises a thin metal wire, a hard plastic such as nylon, PMMA, polycarbonate, polyethylene terepthalate, and/or another polymer, polypropylene or other synthetic suture material capable of providing the structural support to maintain the therapeutic system attached to the eye. The first structure may also comprise a coated plastic or metal such that the coating contains the therapeutic medication or provides easier attachment of the second, cushioning element to the skeletal member. The first structure may have a surface treatment such as plasma etching or the like to enable the second structure to be suitably attached to the skeletal member.

FIG. 1-2-2 shows a basic embodiment of the first structure. Here the first structure 32 is annular or ring-shaped and, has a diameter of at least 8 mm, and is sized to fit outside the optical zone of the cornea so as not to interfere with patient vision. The annulus of first structure 32 will preferably comprise a complete ring or toroid, but may have some gap along its circumference. The arc angle of the annulus in such embodiments will be over 180°. FIGS. 1-2-2 and 1-2-3 show a top view and cross-sectional view of the therapeutic system shown in FIG. 1-2-2. The therapeutic system can be sized much larger so that the edges of the structure will lie within the cul-de-sac of the eye. In the case where the therapeutic system is intended to be located within the cul-de-sac of the eye, the therapeutic system will desirably be produced in at least two sizes to accommodate varying sizes of eyes (e.g. pediatric versus adult, and optionally different adult eye sizes). Alternative shapes of the first structure may include those of the inserts shown and described in U.S. Pat. No. 3,995,635, the disclosure of which is incorporated herein by reference.

FIG. 1-2-4 shows an embodiment 36 of the therapeutic system 30 where the ring comprises two radially outwardly and/or anteriorly extending protrusions or bumps 38 on opposed portions of its surface. When the eye blinks, the lids "trap" the two bumps between the lids and push the ocular implant (which otherwise can freely glide on the surface of the eye) back into its therapeutically effective position outside the optical zone of the cornea.

FIG. 1-2-5 shows an alternative embodiment 30 of the ring-shaped therapeutic device system 30. In this embodiment, a crescent or banana-shaped reservoir 62 is attached to the inferior portion of the ocular insert.

FIGS. 1-3-1 to 1-3-3 show another embodiment of the therapeutic system 30 again including a ring-shaped structure with a diameter of at least 8 mm, sized to fit outside the optical zone of the cornea, and also having two or more haptics 66, each radiating from the ring-shaped structure across to the cul-de-sac of the eye, thus providing an additional support point for the therapeutic system. FIG. 1-3-1 shows the ring-shaped therapeutic system with haptics placed on the anterior structure of the eye. FIGS. 1-3-2 and 1-3-3 show a top- and a cross-sectional view, respectively, of ocular insert 64.

FIGS. 1-4-1 to 1-4-2 show an alternate embodiment 68 of the therapeutic system 30 in which two or more concentric ring-shaped structures 72 are held together by four or more haptics 50. The inner ring-shaped structure has a diameter of at least 8 mm and is sized to fit outside the optical zone of the cornea. The next (and subsequent) outer ring-shaped structures have progressively larger diameters, the outermost ring-shaped structure optionally having a diameter of at least 12 mm and being sized to fit on the sclera, fornix or cul-de-sac of the eye. FIG. 1-4-1 shows the embodiment 68 of the therapeutic system placed on the eye. FIG. 1-4-2 shows the embodiment 68 of the therapeutic system before insertion on the eye. The embodiment 68 has the advantage of providing a larger surface area for drug delivery, due to the presence of the two or more rings and four or more haptics. Additional insert shapes having enhanced surface areas may be seen in U.S. Pat. No. 4,540,417, the disclosure of which is incorporated by reference. FIG. 1-4-3 shows a related embodiment 69 that employs an eccentric design such that the one or more ring portions or arc segments 74 are present in the inferior area of the ring to target delivery to the area of the eye where tears may more readily pool, as in the cul-de-sac. This eccentric design may also stabilize the device in a more fixed position and be less likely to rotate out of position or move into the optical zone of the eye. In addition, targeting delivery to the cul-de-sac may enable more effective delivery of some medications to the nasolacrimal system in addition to the ocular surface, such as in the case of nasal allergy medications.

In the embodiments described above, the first structure typically remains of a constant size and shape, e.g. a ring-shape, or a ring with haptics that anchor/attach to the sclera, fornix or cul-de-sac of the eye.

In other embodiments, the first structure can expand or change shape so as to enhance its attachment to the anterior structure of the eye. FIGS. 1-5-1 through 1-5-3 show a serpentine embodiment 76 of therapeutic system 30 which shows an expandable ocular insert. FIG. 1-5-1 shows the embodiment 76 inserted on the surface of the eye; FIG. 1-5-2 shows the embodiment 76 before insertion, and FIG. 1-5-3 shows the embodiment in its expanded state. A variety of alternative serpentine configurations may be developed or modified so as to take advantage of the cushioning and/or configuration-changing techniques described herein, including those of U.S. Pat. No. 4,540,417, the disclosure of which is incorporated herein by reference.

With respect to the already described embodiments, the skeletal member can be shaped to conform to the radius of curvature of the eye.

The first structure can expand as it absorbs fluid from the tear fluid in the eye or can stretch through a spring action mechanism. Examples of materials that can swell upon insertion in the eye include PVPE, PVA and polyurethane gels. Examples of materials that may stretch through spring action include platinum alloys, titanium alloys, all stainless steel alloys & tempers, various clad metals and insulated wires. The first structure may comprise a shape-memory material, such as nitinol, which will allow it to change to a desired shape using thermal, magnetic or electromagnetic activation, from a martensitic to an austenitic state. Other examples of shape memory materials include shape memory polyurethanes, crosslinked trans-polyoctylene rubber, polynorbornene polymers, nitinol, polyethylene, PMMA, polyurethane, cross-linked polyethylene, cross-linked polyisoprene, polycycloocetene, polycaprolactone, copolymers of (oligo)caprolactone, PLLA, PL/DLA copolymers, PLLA PGA copolymers, thermoplastic polymers such as PEEK, crosslinked polyethylene terephthalate (PET) and polyethyleneoxide (PEO) block copolymers, block copolymers containing polystyrene and poly(1,4-butadiene), and other shape memory materials well-known to those of ordinary skill in the art.

Additional Configurations of the First Structure

FIGS. 1-6-1 and 1-6-2 show another embodiment 78 where the second cushioning structure comprises two hydrogel scleral contact lenses 80 attached to each other, so as to sandwich the first rigid structure between them. FIG. 1-6-1 shows the embodiment 78 placed on the surface of the eye; FIG. 1-6-2 shows the embodiment 78 before placement. In embodiment 78, the first structure 82 functions as a skeleton for the ocular insert and serves as a drug delivery material. As tear fluid penetrates the hydrogel lenses, it comes into contact with the first structure and causes the drug to elute into the tear fluid. Another embodiment (not shown) comprises an exoskeletal first structure comprising a drug delivery material attached to the anterior side of a contact lens. Another embodiment (also not shown) comprises a first structure comprising a drug delivery material placed on an eye and covered by a regular, non-drug delivery contact lens to provide a comfortable lid movement.

Second Structure

FIG. 1-7-1 shows a close-up of an exemplary ocular insert 31 of the therapeutic device system 30 in which the second structure 34 is disposed throughout the circumferential length of the first structure 32. The second structure 34 provides cushioning to facilitate extended implantation or wearing of the device, optionally inhibiting irritation to the eye sufficiently to encourage a patient to wear the therapeutic system for at least thirty days. The cushioning effect may be achieved at least in part by the material used in the second structure, as well as by the shape of the surfaces and/or edges of the second structure. In some embodiments, the second structure may comprise a coating.

The material of the second structure can be soft, biocompatible, and non-irritant. Examples of such material comprise polymers such as hydrogel or silicone.

Regardless of its overall shape and configuration, edges of the second structure are often shaped so as to inhibit friction between them and the inside portion of the eyelid. FIG. 1-7-2 shows a cross-section of a therapeutic device system comprising a second structure 34 with a tapered outer and/or inner edge 84. FIG. 1-7-3 shows a cross-section of a therapeutic device system comprising a second structure 34 with a beveled edge 86. FIG. 1-7-4 shows a cross-section of a therapeutic device system comprising a second structure 34 with a rounded edge 88. FIG. 1-8-1 shows a therapeutic device system 30 with a second structure 34 that may have an anterior and/or posterior surface 90 that can be shaped as well to the radius of curvature of the eye 70.

In some embodiments 92 the second, cushioning structure 94 is disposed only over certain discrete portions along the length of the first structure 32, desirably at locations where sharper edges or bends may provoke irritation to the eye. FIG. 1-9-1 shows the second, cushioning structure 94 disposed over discrete portions of the length of the first supporting structure 32.

In one embodiment, the first and second structure may comprise similar compositions or materials having differing durometers and/or other characteristics, particularly where the material can be processed so as to exhibit the desired properties for both the first and second structures.

Drug Delivery Matrix

The drug used in the therapeutic system will often be placed on, embedded, encapsulated or otherwise incorporated into a delivery matrix. The delivery matrix may be included in or on either the first skeletal structure or the second cushioning structure, or both. The delivery matrix, in turn, comprises either a biodegradable or a non-biodegradable material. The delivery matrix may include, although it is not limited to, a polymer. Examples of biodegradable polymers include protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid), and combinations thereof. Non-biodegradable polymers may comprise silicone, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.).

To prevent a potential allergic reaction to the ocular insert in a patient, the ocular insert, may comprise a hypoallergenic material. Either or both the first and/or second structure may comprise materials such as hydrogels, polyethylene glycol (PEG), or polyethylene oxide (PEO) that prevent adhesion of proteins and thus minimize the chance of developing an allergic reaction. Alternatively, the drug delivery matrix of the ocular insert may comprise an anti-allergenic and/or antihistaminic compound to prevent an allergic reaction to the ocular insert. In certain embodiments, the delivery matrix may also include other materials known in the art.

The embodiments of FIGS. 1-1-2 to 1-9-1 can be combined and modified in many ways in accordance with the embodiments and teachings as described herein so as to provide comfortable ocular inserts that can be worn for an extended time and provide therapeutic amounts of therapeutic agent for the extended time. The first structure as described above may comprise a retention structure as described herein having a resistance to inward deflection so as to inhibit expulsion and contact with the cornea. The resistance to inward deflection may comprise a hoop strength, or spring force, that inhibits contact with the cornea and can gently push the retention structure into the fornix of the eye so as to maintain placement of the insert within the eye, for example. The second structure as described above may comprise a support structure as described herein, and the support structure may contain a therapeutic agent. The support structure can be configured in many ways to contain the therapeutic agent and may comprise a soft cushioning matrix of the therapeutic agent supported with the retention structure, for example. The soft cushioning matrix can be configured to provide substantial amounts of therapeutic agent for an extended time, for example at least about 1 ug per day for at least about 1 month and in many embodiments at least about 3 ug per day for at least about 3 months.

The resistance to deflection to retain the insert may comprise a hoop strength or spring force, for example, and can be provided in many ways with many shapes of the first structure comprising the retention structure. For example, the insert may comprise a hoop, or ring shaped structure, and the resistance to deflection may comprise the hoop strength of the ring shaped structure. The ring shaped structure may comprise a gap in the ring, for example a "C" shaped ring, and the C-ring may provide a spring force sufficient to resist inward deflection of the insert toward the cornea and urge the arms of the insert toward the fornix. The insert may comprise a serpentine shaped first structure and second structure, for example as shown above, and the first structure can be configured to provide the resistance to deflection as described herein.

The second structure can be configured in many ways to provide cushioning to facilitate extended implantation or wearing of the device, and can inhibit irritation to the eye sufficiently to encourage a patient to wear the therapeutic system for at least thirty days. The cushioning second structure may comprise a soft support structure configured to contain a therapeutic agent, for example. The cushioning second structure may comprise a matrix containing a therapeutic agent, and the matrix may comprise a soft material to support inclusions of a therapeutic agent within the matrix.

The first structure can be pre-formed with a self supporting shape to fit the eye so as to extend away from a plane prior to placement, such that the insert comprises a curved shape prior to placement to fit the eye. The insert can be customized to the patient, and may be configured to the patient based on ethnicity of the patient. Work in relation to embodiments indicates that at least some ethnic populations may comprise a tighter lower lid than other ethnic populations, and that the insert may be one or more of identified or customized to fit the lower lid of the patient.

While the therapeutic agent can be loaded on the insert in many ways, in many embodiments the first skeletal structure may comprise the therapeutic agent. For example, the retention structure may comprise structures to contain the therapeutic agent such as openings, holes, a surface, or other structure to provide the therapeutic agent.

The insert may comprise at least portion configured to inhibit mucous formation, and the at least a portion can be configured for placement near the medial canthus where mucous can accumulate in the eye. The at least a portion may comprise one or more of a cross-sectional size of at least about one half of one mm, a lubricous coating, or combinations thereof, for example. The at least a portion may comprise the second cushioning structure, for example.

FIG. 2A shows an insert 100 for insertion into an eye. The insert 100 comprises a retention structure 110 and a support structure 120 to provide benefit to the wearer. The support structure 120 may comprise a first inclined surface of first tapered end portion 122 and a second inclined surface of second tapered end portion 124, so as to allow the support structure 120 to slide within the conjunctival sac of the eye. The first inclined surface of first tapered end portion 122 may comprise a curved surface 122C to couple the first inclined surface of first tapered end portion 122 to the generally elongate surface of the support structure that can be cylindrical. The first and second inclined surfaces can be configured in many ways and may comprise crescent, torpedo or other shapes so as to contact the conjunctiva within the sac and allow movement of the insert. The second inclined surface of second tapered end portion 124 may comprise a curved surface 124C to couple the second inclined surface of second tapered end portion 124 to the generally cylindrical surface of the support structure. The first inclined surface of first tapered end portion 122 and the second inclined surface of second tapered end portion 124 can decrease pressure to the conjunctiva when the support structure 120 is placed in the sac of the conjunctiva, and may encourage movement of the support structure 120 within the conjunctival sac, for example when the eye moves.

The retention structure can be sized to the eye in many ways and may comprise a dimension across 114A such as a diameter corresponding to a maximum diameter of the eye transverse to the optical path of the eye. The retention structure may comprise a diameter slightly larger than the maximum diameter of the eye transverse to the optical path, a diameter slightly smaller than the maximum diameter of the eye transverse to the optical path, or a diameter approximately equal to the maximum diameter of the eye transverse to the optical path. For example, the eye may comprise a maximum diameter of about 24 mm transverse to the axial length of the eye, and the dimension 114A of the retention structure can be slightly larger than the diameter of the eye, for example a diameter of about 25 mm. The dimension 114A of the retention structure can be determined based on a measurement of the patient such as a measurement of the eye as described herein, or based on fitting one or more of a plurality of retentions structure to the eye as described herein, or combinations thereof, for example.

The support structure 120 may comprise a container, for example. The container may comprise a drug reservoir containing a therapeutic agent 130 and release therapeutic amounts of the therapeutic agent for an extended time. Alternatively or in combination, the support structure 120 may comprise a matrix 140 supporting inclusions of a therapeutic agent 130 to release therapeutic amounts of the therapeutic agent for an extended time. The inclusions of the therapeutic agent may comprise one or more of particles, droplets, or crystals of the therapeutic agent.

In many embodiments support structure 120 comprises the matrix 130 having a surface area sized to release therapeutic amounts of the therapeutic agent for the extended time. The surface area of the matrix to release the therapeutic agent may comprise an exposed surface area, or a surface area at least partially covered with a non-matrix material, such as a lubricous coating, for example a hydrogel. The area of the matrix to release the therapeutic agent may correspond to a distance 126 of the support structure 120 and a cross sectional dimension 127 such as a diameter across the support structure 120. The rate of release of the therapeutic agent can be determined by one or more of a solubility of the therapeutic agent in the matrix material, the surface area of the matrix material, or the solubility of the therapeutic agent in the tear liquid of the eye. The therapeutic agent may comprise an amount of one or more of the therapeutic agents as described herein and the matrix material may comprise one or more of the matrix materials as described herein. For example, the matrix material may comprise silicone and the therapeutic agent may comprise inclusions of a prostaglandin such as bimatoprost crystals or latanoprost droplets.

The distance 126 can be sized such that the support structure 120 encompasses the whole of the retention structure 110, i.e., corresponds to 360 degrees around the retention structure, or may be less than 360 degrees, for example, it may encompass 270 degrees or 180 degrees. The distance 126 can be sized such that the support structure 120 can fit substantially within at least a portion of one or more of the conjunctival sacs as described herein. The distance 126 may correspond to no more than about 90 degrees around retention structure 110, for example. In many embodiments, the distance 126 corresponds to no more than about 80 degrees so as to fit within the inferior temporal portion of the conjunctival sac, for example no more than about 75 degrees. Alternatively or in combination, the distance 126 can be sized to fit within the inferior conjunctival sac of the eye, for example. The cross-sectional dimension 127 can be within a range from about 0.1 mm to about 3 mm across, for example within a range from about 0.5 to 2 mm across, for example.

The distance 126 and dimension 127 can be sized to have a volume corresponding to an appropriate amount of therapeutic agent. For example, the amount of therapeutic agent contained on support structure 120 can be within a range from about 1 ug to about 10,000 ug. For example, the support structure 120 can be approximately 10 mm long and have a cross sectional dimension of about 1 mm so as to comprise a volume of about 30 uL corresponding to a mass of about 30 mg. For a 30% loading of the therapeutic agent in the matrix, the corresponding amount of therapeutic agent is about 10,000 ug, and the amount of therapeutic agent can be increased or decreased based on the dimensions of support structure 120. For example, the amount of therapeutic agent can exceed 10,000 ug.

Table 1 shows examples of therapeutic agent 130 suitable for use with retention structure 110. The therapeutic agent 130 can be used in many ways, and may comprise one or more of many therapeutic agents delivered in one or more of many ways as described herein. The therapeutic agent 130 may comprise a component of retention structure 110, for example inclusions within a material of retention structure 110. Alternatively or in combination, retention structure 110 can be supported with support structure 120 such that support structure 120 contains the therapeutic agent 130 for release for an extended time as described herein.

TABLE 1

Examples of Indications and Therapeutic Agents

| Indication | Therapeutic Agent |
| --- | --- |
| Glaucoma (Prostaglandin) | Prostaglandin or analog (e.g. Bimatoprost or Latanoprost) |
| Glaucoma (Prostaglandin or analog + second drug, e.g. latanoprost or bimatoprost) | Bimatoprost + Carbonic Anhydrase Inhibitor (CAI) (dorzolamide) |
| Glaucoma (Canine) | Prostaglandin (e.g. Bimatoprost or Latanoprost) |
| Corneal Transplant, Prevention of Rejection | steroid |
| Bacterial Conjunctivitis | One or more newer antibiotics that have little resistance built up Therapeutic Agent Candidates |
| Dry Eye | Cyclosporine steroid (e.g.— Loteprednol, Fluoromethalone) Non-penetrating steroid (e.g. free acid of steroid) Doxycycline or azithromycin |

TABLE 1-continued

Examples of Indications and Therapeutic Agents

| Indication | |
| --- | --- |
| | Non-pharmacologic agent (e.g. lipid) Fatty alcohol (for example cetyl alcohol or stearyl alcohol) Fatty acid, for example long chain fatty acid Oil |
| Post-Cataract Surgery | Antibiotic + Steroid; (NSAID optional) |
| Post-Laser Surgery | Antibiotic + Steroid; (NSAID optional) |
| Allergy | Olopatadine |
| Trachoma | Doxycycline or other antibiotic |
| Blepharitis | Tetracycline, Doxycycline, Azithromycin, or other antibiotic Non-pharmacologic agent (e.g. lipid) Fatty alcohol (lipid cetyl alcohol) Fatty acid, for example long chain fatty acid Oil (e.g. silicone oil) |

Alternatively or in combination with the therapeutic agents in Table 2, the therapeutic agent 130 may comprise one or more of the following: anti-glaucoma medications, (e.g. adrenergic agonists, adrenergic antagonists (beta blockers), carbonic anhydrase inhibitors (CAIS, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic or the like. Examples of conditions that may be treated with the therapeutic agent(s) include but are not limited to glaucoma, pre and post surgical treatments, dry eye and allergies. In some embodiments, the therapeutic agent may comprise a lubricant or a surfactant, for example a lubricant to treat dry eye.

The therapeutic agent may comprise a prostaglandin analog suitable for treatment of glaucoma as described herein. The prostaglandin analog for the treatment of glaucoma may comprise one or more of latanoprost, bimatoprost, unoprostone or travoprost, for example.

The therapeutic agent 130 may comprise one or more of the following or their equivalents, derivatives or analogs: thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; anti-platelet agents; antimitotics; microtubule inhibitors; antisecretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Such anti inflammatory steroids contemplated for use in the methodology of the embodiments described here, include triamcinolone acetonide (generic name) and corticosteroids that include, for example, triamcinolone, dexamethasone, fluocinolone, cortisone, prednisolone, flumetholone, and derivatives thereof); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil 3; immunological drugs (such as vaccines and immune stimulants); hormonal agents (such as estrogens,—estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, anti-prostaglandins, prostaglandin precursors, including anti-glaucoma drugs including beta-blockers such as Timolol, betaxolol, levobunolol, atenolol, and prostaglandin analogues such as bimatoprost, travoprost, Latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

FIG. 2B shows a cross sectional view of retention structure 110. The retention structure 110 comprises a maximum dimension across 112 such as a diameter. The retention structure 110 can be shaped in many ways and may comprise an oval cross section or other non-circular cross sectional shape. The maximum dimension across retention structure 110 may generally comprise less than about 2 mm, for example 1 mm or less (e.g. 0.75 mm or less), such that the retention structure can fit within the one or more folds of the conjunctiva such as one or more folds of the bulbar conjunctiva extending between the limbus and the fornix, or the one or more folds of the palpebral conjunctiva extending between the eyelid margin and the fornix. Work in relation to embodiments as described herein suggests that a maximum cross sectional dimension of no more than about 1.0 mm can allow the retention structure to fit comfortably within the one or more folds of the conjunctiva away from the fornix, for example.

The retention structure 110 comprises a material and cross sectional size to fit within one or more folds of the conjunctiva and to allow deflection of the retention structure with at least some resistance to deflection so as to inhibit inward movement of the retention structure 110 to the cornea. Table 1A lists non-limiting examples of suture sizes and materials that can be used to provide retention structure 110. In many embodiments, the support structure 120 can be molded over the preformed retention structure 110 as described herein. Alternatively or in combination, the retention structure may comprise a molded structure, for example a molded material having hardness sufficient to provide the deflection with at least some resistance. For example, retention structure 110 may comprise a molded elastic material such as silicone or rubber having a hardness, so as to provide the resistance to deflection.

TABLE 1A

Suture Sizes and Structures Suitable for the Retention Structure.

| U.S.P. Designation | Collagen Diameter (mm) | Synthetic Absorbable Diameter (mm) | Non-Absorbable Diameter (mm) | American Wire Gauge | Polypropylene Self-Loading Deflection (degrees) | Nylon Self-Loading Deflection (degrees) | Resistance to Deflection (Polypropylene N per mm) |
| --- | --- | --- | --- | --- | --- | --- | --- |
| 6-0 | 0.1 | 0.070 | 0.070 | 38-40 | | | |
| 5-0 | 0.15 | 0.1 | 0.1 | 35-38 | 17 | 17 | |
| 4-0 | 0.2 | 0.15 | 0.15 | 32-34 | 12 | 12 | 0.1 |
| 3-0 | 0.3 | 0.2 | 0.2 | 29-32 | 12 | 8 | |
| 2-0 | 0.35 | 0.3 | 0.3 | 28 | | | |
| 0 | 0.4 | 0.35 | 0.35 | 26-27 | | | |
| 1 | 0.5 | 0.4 | 0.4 | 25-26 | | | |

The retention structure 110 may comprise an erodible material or a non-erodible material. Alternatively or in combination, the matrix material may comprise an erodible material. The material of the retention structure can be configured to erode such that the retention structure erodes at a rate corresponding to release of the therapeutic agent and no longer retains the support structure 120 comprising the therapeutic agent 130 when a dose of the therapeutic agent has been delivered for an extended time. This erosion of the retention structure can indicate to the patient that the therapeutic agent has been delivered and a new insert may be appropriate. Alternatively, the erosion of the retention structure can indicate completion of the treatment. For example, with post surgical placement of the insert, the retention structure of the insert can be configured to erode after several days, for example at about one week, so as to indicate completion of the prescribed treatment. Alternatively, the erodible matrix may erode at a rate faster than a rate of the erodible retention structure such the matrix is retained in the eye and erodes before the retention structure.

The insert 100 can be configured in many ways to indicate a condition of the insert to a patient or a treating physician, for example to indicate that one or more of removal or replacement of the insert may be appropriate. For example, the support structure can be configured to change color from a first color to a second color when the support structure has been placed in the eye for an amount of time. The support structure can be configured to change volume from a first amount to a second amount, in which a difference between the first amount and the second corresponds to an amount of time the support structure has been placed on the eye.

FIG. 2C shows an insert as in FIGS. 2A and 2B deflected in response to placement in an eye and corresponding force to urge the retention structure outward. Placement of the retention structure within the superior and inferior sacs of the conjunctiva of the eye can result in at least some deflection of the retention structure. For example, the retention structure can be deflected inwardly between the upper and lower lids so as to comprise a second configuration when placed in the eye comprising a first dimension across 114B and a second dimension across 114C corresponding to an oval or elliptical shape of the retention structure 110.

FIG. 2C1 shows a retention structure 110 self-loaded and deflected at an angle 110SLA. The retention structure may comprise a self-loading resistance to deflection, such that the retention structure 110 deflects to angle 110SLA when one end is supported and held in place and the weight of the intermediate portion 110I and opposite portion deflect the retention structure. The insert comprising retention structure 110 and support structure 120 can be measured similarly. Alternatively, the insert 100 can be measured without the retention structure 110 when the insert 100 does not comprise retention structure 110, for example. The retention structure may comprise an upper portion 110U comprising the supported end, and an intermediate portion 110I and a lower portion 110L supported with the end, for example.

FIG. 2C2 shows torsional force 110T of a retention structure 110 at a first location and resistance to twisting about an axis 110TA. The first location may comprise an upper portion 110U, for example, or a lower portion 110L, for example. The first location of the retention structure retention structure 110 may extend through a cross-section of the retention structure 110 comprising axis 110TA, for example. When the eye blinks, the force of the lid can engage a portion of the retention structure so as to provide torsional force 110T to the retention structure, and the retention structure can resist twisting of the retention structure. The resistance to self-loading deflection of the retention structure as described herein may correspond to the resistance to torsional deflection and the weight of the retention structure, for example.

The retention structure 110 can be deflectable and can be configured in many ways with a resistance to deflection, so as to inhibit deflection of the retention structure. The resistance to deflection may comprise a resistance to inward deflection, so as to inhibit inward deflection of the retention structure toward the cornea. The resistance to deflection may comprise a resistance to self-loading deflection, and the self-loading resistance to deflection may correspond to an angle of deflection when one end retention structure is held horizontally and the opposite end and intermediate portion of the retention structure deflect downward at an angle away from horizontal in response to gravity loading. The resistance to deflection may comprise a torsional resistance to deflection, for example, such that rotation of the retention structure about an axis extending through a cross-sectional diameter is inhibited, for example such that twisting of the retention structure along the portion is inhibited. The resistance to deflection may correspond to an inward pressure from the upper and lower fornices, and the resistance to deflection can be sufficient to inhibit contact with the cornea, for example when the eye blinks. Alternatively or in combination, the resistance to deflection may correspond to resistance to torsional rotation a portion of the retention structure under a lid such that the amount torsional rotation is inhibited. For example, when the upper lid blinks, the upper portion of the insert under the upper lid may resist rotation about an axis extending through a cross-section of the portion of retention structure under the upper lid. When the retention structure comprises a formed 3-D shape profile, the retention structure may comprise a resistance to deflection away from the formed 3-D shape profile toward a plane.

The resistance to deflection of the retention structure sufficient to inhibit contact with the cornea may correspond to a self-loading resistance to deflection, and the self-loading deflection angle can be within a range from about 0 degrees (i.e. rigid) to about 60 degrees, for example. In many embodiments, the retention structure can deflect at least about a degree so as to facilitate placement in the eye and allow the retention structure 110 to deflect when sliding and rotating along the conjunctival sacs about the axial length of the eye with cyclotorsion of the eye as described herein.

The resistance to inward deflection of the retention structure can be sufficient to inhibit contact with the cornea and can be within a range from about 0.01 N per mm to about 1 N per mm of inward deflection along dimension 114B, so as to allow the retention structure 110 to slide and rotate along the conjunctival sacs about the axial length of the eye with cyclotorsion of the eye and place the support structure 120 along the inferior temporal location of the conjunctival sac as described herein.

The retention structure 110 may comprise one or more of many materials, for example one or more materials of the first structure 32 as described herein. The material of retention structure 110 may comprise one or more of a metal, stainless steel, a wire, stainless steel wire, a shape memory material, a shape memory metal, Nitinol, a shape memory plastic, polypropylene, nylon, a thermoset polymer, a thermoset plastic or other preformed memory material for example. The retention structure 110 can be preformed with a shape as described herein corresponding to a shape of the eye. Alternatively or in combination, the retention structure 110 may comprise an in situ shape forming material that conforms to the shape of the conjunctiva of the eye and retains the formed shape corresponding to the conjunctiva, so as to provide a resistance to deflection away from the shape formed in situ. For example, the retention structure may comprise a circular shape prior to placement and form an oval shape when placed in the eye, and the retention structure may retain the oval shape when placed in the eye for a sufficient time such that the retention structure resists deflection away from the oval shape. The in situ shape forming material may comprise one or more of many materials such as polypropylene or nylon, for example.

The retention structure can be configured in many ways to provide the stiffness and resistance to deflection as described herein so as to provide comfort and retention of the insert. The resistance to deflection may comprise one or more of self-supporting resistance to deflection, an inward resistance to deflection, or a hoop strength of the retention structure, or combinations thereof, for example.

Table 1B shows examples of values of angles in degrees corresponding to the self-loading resistance to deflection that can be obtained in accordance with the teachings and embodiments described herein. The retention structure 110 may comprise a self-loading resistance to deflection so as to provide a self-loading deflection angle within a range from about 0 degrees to about 70 degrees, and one or more of many values within theses ranges for example. The self-loading deflection angle can be measured by holding one end of the insert horizontal and measuring deflection of the intermediate portion and opposing end relative to horizontal as described herein. Table 1B provides non-limiting examples, and the self-loading deflection angle can be lower, or greater, for example, and may vary with the cross sectional diameter of the retention structure so as to provide increased stiffness corresponding to increased surface area of the portion of the insert engaging the conjunctiva. The self-loading resistance to deflection of one of the examples of Table 1B can be combined with the self-loading resistance to deflection of another example of Table 1B so as to define the range. For example, the range can be from about 1 degree (Example 2 of Table 1B) to about 60 degrees (Example 21 of Table 1B). The retention structure may comprise one or more of a material, a dimension, or a shape so as to provide the self-loading resistance to deflection and corresponding deflection angle as described herein. Based on the teachings described herein, a person of ordinary skill in the art can conduct experiments so as to determine empirically the deflection angle and self-loading resistance to deflection of retention structure 110 so as to provide movement of the insert and retention structure on the conjunctiva and to inhibit contact with the cornea.

TABLE 1B

Self-Loading Deflection Angle of Retention Structure (degrees)

| Example | Angle (degrees) |
|---------|-----------------|
| 1 | 0 |
| 2 | 1 |
| 3 | 2 |
| 4 | 3 |
| 5 | 4 |
| 6 | 5 |
| 7 | 6 |
| 8 | 7 |
| 9 | 8 |
| 10 | 9 |
| 11 | 10 |
| 12 | 15 |
| 13 | 20 |
| 14 | 25 |
| 15 | 30 |
| 16 | 35 |
| 17 | 40 |
| 18 | 45 |
| 19 | 50 |
| 20 | 55 |
| 21 | 60 |
| 22 | 65 |
| 23 | 70 |

Table 1C shows examples of values of resistance to deflection in N per mm that can be obtained in accordance with the teachings and embodiments described herein. The retention structure 110 may comprise a resistance to deflection within a range from about 0.005 N/mm to about 10 N/mm, for example within a range from about 0.01 N per mm of deflection to about 1 N per mm of deflection, and one or more of many values within theses ranges for example. Table 1C provides non-limiting examples, and the resistance to deflection can be lower, or greater, for example, and may vary with the cross sectional diameter of the retention structure so as to provide increased stiffness corresponding to increased surface area of the portion of the insert engaging the conjunctiva. The resistance to deflection of one of the examples of Table 1C can be combined with the resistance to deflection of another example of Table 1C so as to define the range. For example, the range can be from about 0.05 N per mm (Example 5 of Table 1C) to about 0.5 N per mm (Example 14 of Table 1C). The retention structure may comprise one or more of a material or shape so as to provide the resistance to deflection as described herein. Based on the teachings described herein, a person of ordinary skill in the art can conduct experiments so as to determine empirically the resistance to deflection of retention structure 110 to provide movement of the insert and retention structure on the conjunctiva and to inhibit contact with the cornea.

TABLE 1C

Resistance to Deflection of Retention Structure (N/mm)

| Example | Resistance |
|---------|------------|
| 1 | 0.01 |
| 2 | 0.02 |
| 3 | 0.03 |
| 4 | 0.04 |
| 5 | 0.05 |
| 6 | 0.06 |
| 7 | 0.07 |
| 8 | 0.08 |
| 9 | 0.09 |
| 10 | 0.1 |
| 11 | 0.2 |
| 12 | 0.3 |
| 13 | 0.4 |
| 14 | 0.5 |
| 15 | 0.6 |
| 16 | 0.7 |
| 17 | 0.8 |
| 18 | 0.9 |
| 19 | 1 |
| 20 | 0.005 |
| 21 | 0.006 |
| 22 | 0.007 |
| 23 | 0.008 |
| 24 | 0.009 |
| 25 | 1.2 |
| 26 | 1.5 |
| 27 | 2 |
| 28 | 5 |
| 29 | 10 |

The retention structure can be configured in many ways to provide the resistance to deflection and to fit within one or more of the folds of conjunctiva as described herein. Table 1D list examples of maximum cross sectional dimensions, for example diameters, of retention structures in accordance with embodiments. The diameter of the retention structure can be within a range from about 0.05 mm to about 2 mm, for example, and one or more of many values within the range for example. The diameter of one of the examples of Table 1C can be combined with the diameter of another example of Table 1C so as to define the range. For example, the range can be from about 0.1 mm (Example 10) to about 0.5 mm (Example 14). Based on the teachings described herein, a person of ordinary skill in the art can conduct experiments so as to determine empirically the maximum dimension across retention structure 110 so as to fit the retention structure 110 within the one or more folds of conjunctiva as described herein and to provide movement of the insert and retention structure on the conjunctiva and so as to inhibit contact with the cornea.

TABLE 1D

Cross-sectional Diameters of retention structures (mm)

| Example | Diameter |
|---------|----------|
| 1 | 0.05 |
| 2 | 0.1 |
| 3 | 0.2 |
| 4 | 0.3 |
| 5 | 0.4 |
| 6 | 0.5 |
| 7 | 0.6 |
| 8 | 0.7 |
| 9 | 0.8 |
| 10 | 0.9 |
| 11 | 1 |
| 12 | 1.2 |
| 13 | 1.5 |
| 14 | 1.7 |
| 15 | 2 |

The examples of Table 1D can be combined in many ways with the examples of Tables 1A, 1B and 1C so as to provide the retention structure 110 having the resistance to deflection to inhibit contact with the cornea and cross sectional dimension to fit within one or more folds of the conjunctiva as described herein, and the ranges of Table 1C can be combined with the ranges of Table 1D, for example.

The retention structure may comprise a three dimensional profile corresponding to the eye of the patient, such that the retention structure extends away from a plane when free standing, for example when placed on a flat surface. The examples of Tables 1A, 1B, 1C, and 1D can be combined with the preformed shape to provide a resistance to deflection such that the retention structure extends away from a plane when placed on a flat surface and urges the portion of the retention structure placed under the lower lid toward the eyeball when the first portion of the retention structure is placed under the upper lid. Work in relation to embodiments also suggests that one or more of the resistance to deflection or the column strength can provide sufficient force so as to transmit circumferential torsional force from a first portion of the structure to a second portion of the structure, such that the first portion of the structure can urge the second portion of the structure. For example, the first portion comprising at least a portion of support structure 120 may urge a second portion comprising at least a portion retention structure 110 circumferentially around the pupil of the eye with cyclotorsion of the eye. The retention structure 110 may comprise a molded preformed retention structure, for example a molded silicone elastomer having the three dimensional oval shape corresponding to the bulbar conjunctiva of the eye of the patient, and the three dimensional molded shape may comprise a resistance to deflection toward a plane similar to the sutures of Table 1C. For example, work in relation to embodiments suggests that silicone elastomer having a cross-sectional diameter of within a range from about 0.5 mm to about 1.0 mm may have a resistance to deflection similar to a polypropylene suture having a cross-sectional diameter within a range from about 0.1 mm to about 0.2 mm.

Figure 2D:
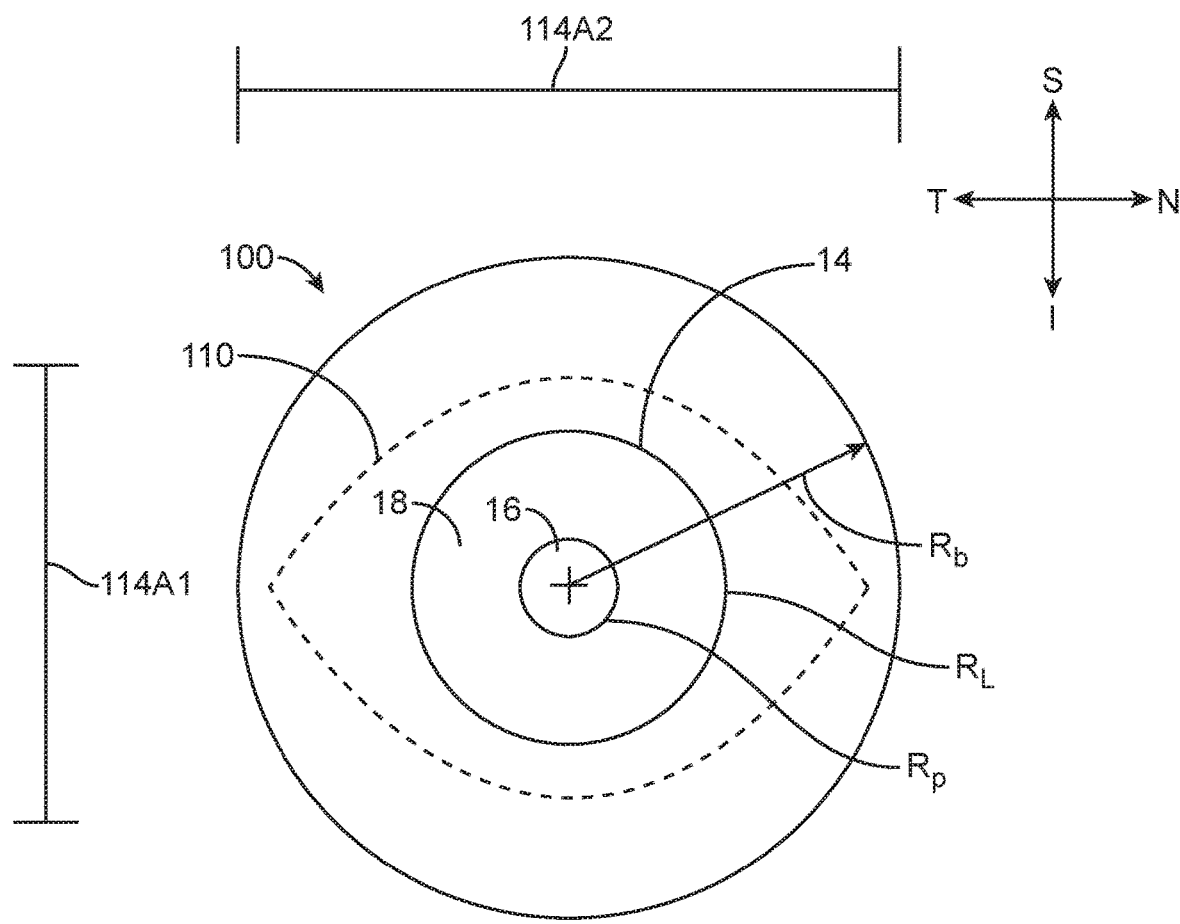
FIG. 2D shows an insert having a preformed oval shape extending along a convex spherical surface, such that the insert extends away from a plane and resists deflection toward the plane, in accordance with an embodiment.

FIG. 2D shows an insert having a preformed oval shape extending along a convex surface of an eye, such that the ring extends away from a plane and resists deflection toward a plane. The insert can be configured to deflect away from a plane in many ways and can be bent at one or more locations so as to extend away from the plane, or may comprise one or more curved portions extending away from the plane with curvature corresponding to the eye so as to fit the eye of the patient with the one or more curved portions, or combinations thereof. The plane may correspond to a plane of the limbus 14. The convex surface of the eye may comprise one or more of a spherical surface, a toric surface, an elliptical surface, a cylindrical surface, a conical surface, or combinations thereof, corresponding to one or more of the scleral surface or the bulbar conjunctival surface of the eye of patient. The insert 100 may comprise a three dimensional shape (hereinafter "3D") corresponding substantially to the shape of the insert when placed on the eye. The pre-formed shape of retention structure 110 prior to placement on the eye may comprise a substantially oval shape having an elevation profile corresponding to the oval shape placed on a spherical surface corresponding to the eyeball of the patient. The substantially oval preformed shape may comprise a first maximum dimension across 114A1 in a first direction corresponding to a superior-inferior direction along the eyeball of the patient and a second maximum dimension across 114A2 along a second direction corresponding to a nasal-temporal direction along the eyeball of the patient. The first maximum dimension across 114A1 may correspond to a minor axis of an ellipse and the second dimension across 114A2 may correspond to a major axis of an ellipse, although the generally oval shape may comprise one or more of many shapes such as lentoid, conic cross section, elliptical or other shape projected onto a spherical surface as described herein. The insert 100 may extend closer to the limbus 14 in along the superior and inferior portions than the nasal and temporal portions. As the eyeball may correspond to a substantially spherical surface, the eyeball may comprise a radius of curvature Rb corresponding to the spherical shape of the eyeball. Consequently, the nasal and temporal portions of the insert may extend away from a plane corresponding to the inferior and superior portions of the insert.

Figure 2E:
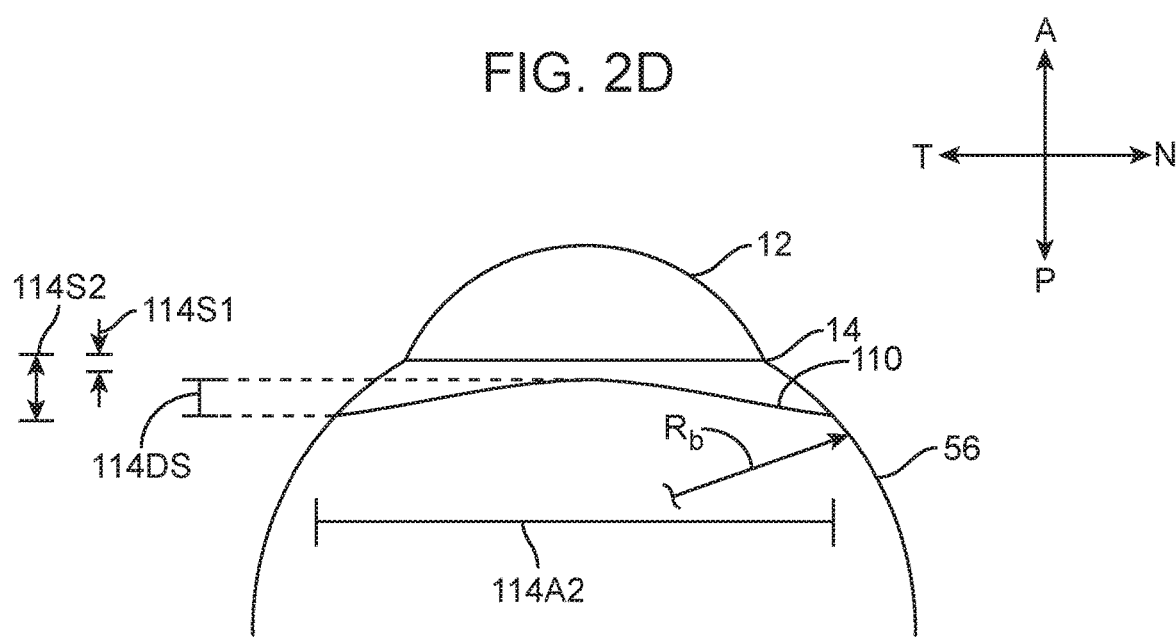
FIG. 2E shows a view of an insert as in FIG. 2D extending along nasal-temporal and anterior posterior directions, in accordance with an embodiment.

FIG. 2E shows a side view of an insert as in FIG. 2D extending along nasal-temporal and anterior posterior directions. The anterior direction A, the posterior direction P, the nasal direction N, and the temporal direction T are each shown. The insert may comprise a preformed 3D shape corresponding to the radius Rb and the first dimension across 114A1 and the second dimension across 114A2, such that the lower portion of the insert is urged posteriorly toward the bulbar conjunctiva when the upper lid covers at least a portion of the insert. Alternatively or in combination, the insert may comprise a preformed 3D shape corresponding to the radius Rb and the first dimension across 114A1 and the second dimension across 114A2, such that the lower portion of the insert resists deflection anteriorly away the bulbar conjunctiva when the upper lid covers at least a portion of the insert. This resistance to deflection can be provided with the insert preformed with the 3D profile corresponding to the radius Rb of the patient. The limbus 14 may correspond to a plane of the eye. The retention structure 110 may comprise a first preformed sag height 114S1 corresponding to an anterior-posterior elevation distance from the limbus to the inferior and superior portions of the insert. The retention structure 110 may comprise a second preformed sag height 114S2 corresponding to an anterior posterior elevation distance from the limbus to the nasal and temporal portions of the insert. The difference in the sag heights may comprise a differential sag height 114DS and the differential sag height 114DS may correspond to an amount the retention structure deflects from a plane when the insert is placed on a flat surface. The support structure 120 can be shaped similarly to the retention structure 110, such that the insert 100 comprises the three dimensional shape corresponding to the eye of the patient. The retention structure 110 may comprise one or more of many shapes as described herein, and the corresponding sag height profile extending around the insert can be determined based on the projection of the shape onto a spherical surface having radius Rb corresponding to the eye of the patient. The retention structure 110 and the support structure 120 comprising the three dimensional shape profiles may comprise the resistance to deflection as described herein.

The insert 100 comprising the retention structure having the 3D shape profile may comprise a surface to retain the insert. The surface may be configured in one or more of many ways to retain the insert. The surface may comprise a sticky, tacky surface to retain the insert within the one or more folds of the conjunctiva. The sticky, tacky surface may comprise a soft hydrophilic surface, such as the surface of a soft silicone elastomer. Alternatively or in combination, the surface may comprise a coating of hydrogel material as described herein, for example a substantially dry hydrogel material such that the dry hydrogel material may stick to the one or more folds when placed and moisture drawn from the tissue or mucus contacting the hydrogel. For example, the hydrogel coating may extend along a portion of the insert corresponding to the lacrimal gland. Alternatively, the insert may comprise a lubricous coating to encourage movement of the insert with the eye, such that the 3D shape profile can slide along the conjunctiva and resist deformation when the eye moves. For example, the lubricous coating can be placed over the insert at locations corresponding to one or more of the lacrimal gland or the caruncle. The insert 100 comprising the 3D shape profile as described herein may provide retention when substantially the entire surface of the insert 100 comprising the retention structure 110 and the support structure 120 are each coated with the lubricous coating as described herein, such that the insert 100 can slide along the sacs of the conjunctiva and seat the insert with movement of the insert along the conjunctiva. For example, the insert 100 may be dip-coated in a hydrogel, and the hydrogel can be moist so as to provide the lubricous coating and resist deflection of the insert away from the inferior bulbar conjunctiva with the 3D shape profile as described herein.

Figure 2F:
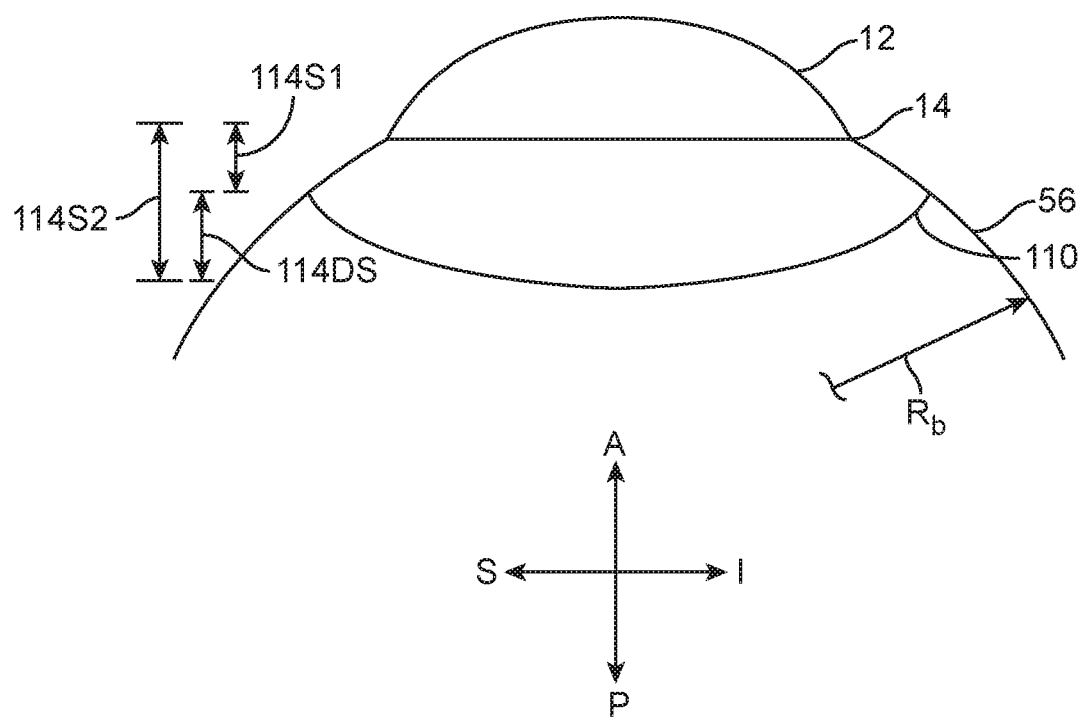
FIG. 2F shows a side view of an insert as in FIG. 2D extending along superior-inferior and anterior posterior directions, in accordance with an embodiment.

FIG. 2F shows a side view of an insert as in FIG. 2D extending along superior-inferior and anterior-posterior directions. The anterior direction A, the posterior direction P, the superior direction S, and the inferior direction I are each shown, along with the corresponding sag heights.

Figure 2G:
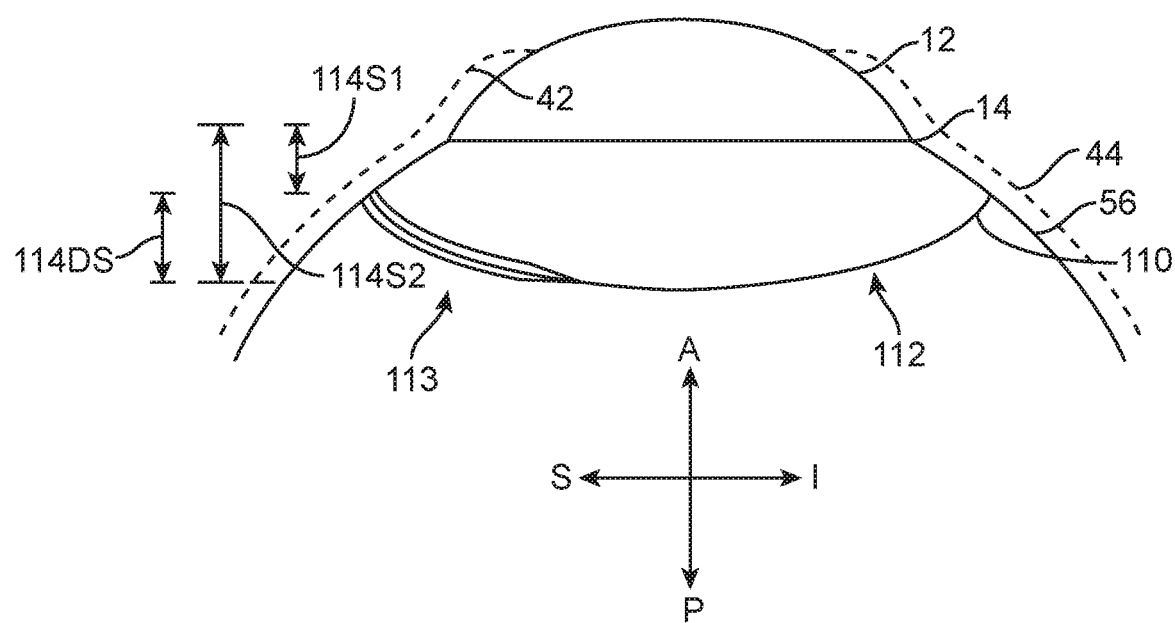
FIG. 2G shows an insert having a preformed oval shape extending along a convex spherical surface and in which the oval ring has a first portion corresponding to the upper conjunctival sac and a second portion corresponding to the lower conjunctival sac, in which the second portion corresponding to the lower conjunctival sac has a thinner cross section than the first portion corresponding to the upper conjunctival sac, such that the ring extends away from a plane and resists deflection toward the plane and places the second portion on the bulbar conjunctiva when the first portion is retained with the upper lid, in accordance with an embodiment.

FIG. 2G shows an insert having a preformed oval shape extending along a spherical surface and in which the oval ring has a first portion corresponding to the upper conjunctival sac and a second portion corresponding to the lower conjunctival sac and thinner than the second portion, such that the ring extends away from a plane and resists deflection toward a plane and urges the lower portion toward the inferior bulbar conjunctiva when the first portion is retained with the upper lid. The insert 100 may comprise a portion placed under the upper lid having a cross sectional size 113 greater than a portion of the insert placed under the lower lid having a cross sectional size 112. The thicker portion placed under the upper lid can be retained at least partially with the pressure of the lid, and the 3D shape profile of the insert can resist deflection of the lower portion away from the bulbar conjunctiva. The portion comprising the cross sectional size 113 may contain one or more therapeutic agents and matrices to contain the therapeutic agent such as a silicone matrix comprising inclusions of a therapeutic agent, and the portion comprising the cross sectional size 112 may comprise the retention structure 110 such as the suture or molded silicone ring segment as described herein.

Figure 2H:
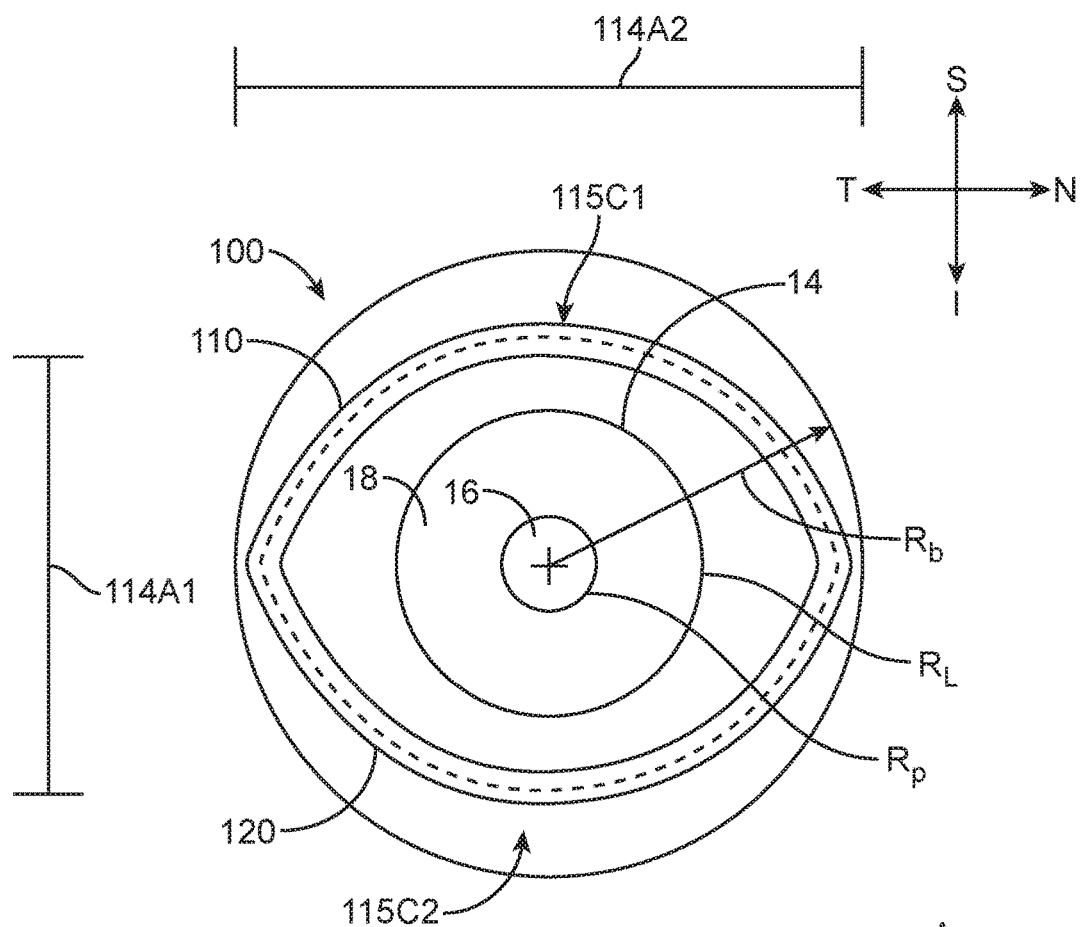
FIG. 2H shows an insert comprising a support structure and a retention structure having a preformed oval shape extending along a convex spherical surface, such that the insert extends away from a plane and resists deflection toward the plane, in accordance with an embodiment.

FIG. 2H shows an insert 100 comprising a support structure 120 and a retention structure 110 having a preformed oval shape extending along a convex spherical surface, such that the insert extends away from a plane and resists deflection toward the plane. The insert is shown as seen from the front of the patient so as to extend along nasal/temporal and anterior/posterior directions.

Figure 2I:
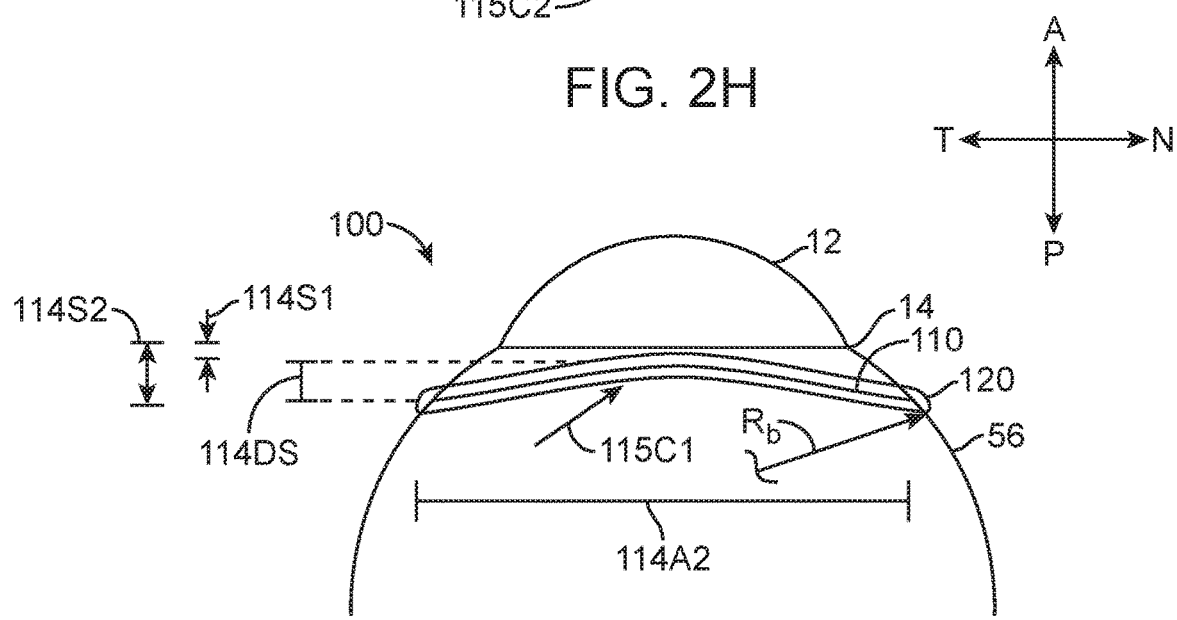
FIG. 2I shows a top view of an insert as in FIG. 2H extending along nasal-temporal and anterior posterior directions, in accordance with an embodiment.

FIG. 2I shows a top view of the insert 100 as in FIG. 2H extending along nasal-temporal and anterior posterior directions. The shape of the pre-formed insert 100 corresponds to the shape of inserts that have been in situ formed within the eye as described herein.

In many embodiments, the pre-formed shape of the insert 100 is determined substantially by the retention structure 110 that is covered with the support structure 120 comprising matrix 140 containing therapeutic agent 130 as described herein. Alternatively, the support structure 120 as described herein can be configured with sufficient stiffness so as to provide the preformed three-dimensional shape provide such that the insert can be provided without the retention structure. The upper (superior) portion of the insert 100 comprises a curvature 115C1 so that the insert bends posteriorly and toward the eye. The lower (inferior) portion of the insert 100 comprises a curvature 115C2 so that the insert bends posteriorly and toward the eye. The intermediate nasal portion of the insert 100 comprises a curvature 115C3 so that the insert bends anteriorly and away from the eye. The intermediate nasal portion of the insert 100 comprises a curvature 115C4 so that the insert bends anteriorly and away from the eye.

Figure 2J:
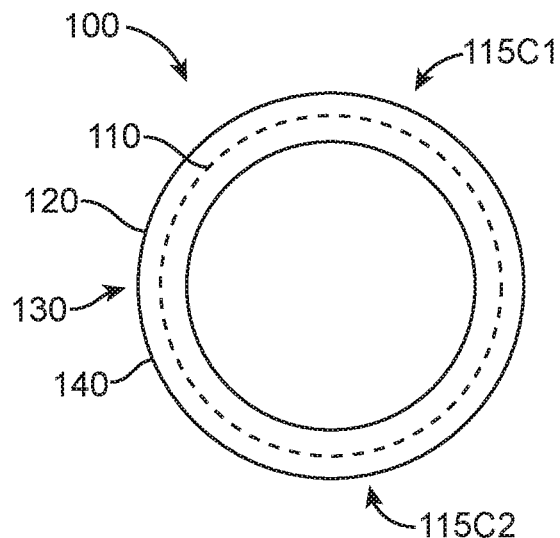
FIG. 2J shows an insert comprising a support structure and a retention structure having a preformed curved annular shape corresponding to the eyelid, such that the insert extends away from a plane and resists deflection toward the plane, in accordance with an embodiment.

FIG. 2J shows an insert 100 comprising a retention structure 110 having a preformed curved annular shape corresponding to the eyelid, such that the insert extends away from a plane and resists deflection toward the plane. In many embodiments, the pre-formed shape of the insert 100 is determined substantially by the retention structure 110 that is covered with the support structure 120 comprising matrix 140 containing therapeutic agent 130 as described herein. Alternatively, the support structure 120 as described herein can be configured with sufficient stiffness so as to provide the preformed three-dimensional shape provide such that the insert can be provided without the retention structure. The insert 100 comprises a support structure 120, as described herein such as a matrix 140 to contain and therapeutic agent 130. The upper portion comprises a curvature 115C1 corresponding to the upper lid of the patient and the lower portion 115C2 corresponding to the curvature of the lower lid of the patient.

Figure 2K:
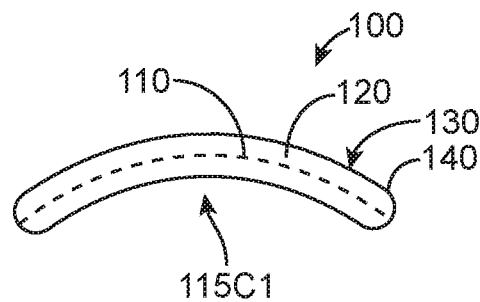
FIG. 2K shows a top view of an insert as in FIG. 2J extending along nasal-temporal and anterior posterior directions and having the preformed curved surface corresponding to the eyelid along the nasal temporal direction to fit the eye, in accordance with an embodiment.

FIG. 2K shows a top view of an insert as in FIG. 2J extending along nasal-temporal and anterior posterior directions and having the preformed curved surface corresponding to the eyelids along the nasal temporal direction to fit the eye.

Figure 2L:
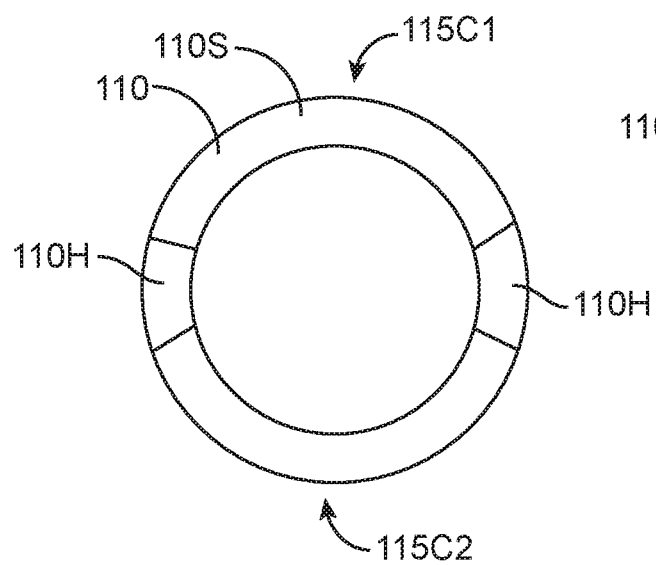
FIG. 2L shows an insert comprising a retention structure comprising hinge portion and a stiff portion having a preformed curved annular shape corresponding to the eyelid, such that the insert extends away from a plane and resists deflection toward the plane, in accordance with an embodiment.

FIG. 2L shows an insert 100 comprising a retention structure 110 comprising hinge portions 110H and a stiff portions 110S having a preformed curved annular shape corresponding to the eyelid, such that the insert extends away from a plane and resists deflection toward the plane. The upper portion and lower portions comprise curvatures 115C1, 115C2, respectively, corresponding to the eyelids. The hinge portions 110H allow the insert to bend and fit the eye. The stiff portions allow the upper and lower portions to extend into the upper and lower fornices of the eye. In many embodiments, the pre-formed shape of the insert 100 is determined substantially by the retention structure 110 that is covered with the support structure 120 comprising matrix 140 containing therapeutic agent 130 as described herein. Alternatively, the support structure 120 as described herein can be configured with sufficient stiffness so as to provide the preformed three-dimensional shape provide such that the insert can be provided without the retention structure.

Figure 2M:
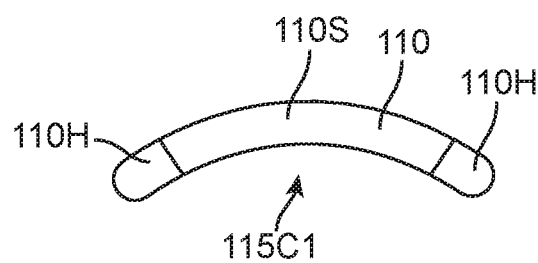
FIG. 2M shows a top view of an insert as in FIG. 2L extending along nasal-temporal and anterior posterior directions and having the stiff preformed curved surface corresponding to the eyelid along the nasal temporal direction to fit the eye, in accordance with an embodiment.

FIG. 2M shows a top view of an insert as in FIG. 2L extending along nasal-temporal and anterior posterior directions and having the stiff preformed curved surface corresponding to the eyelid along the nasal temporal direction to fit the eye.

Figure 2N:
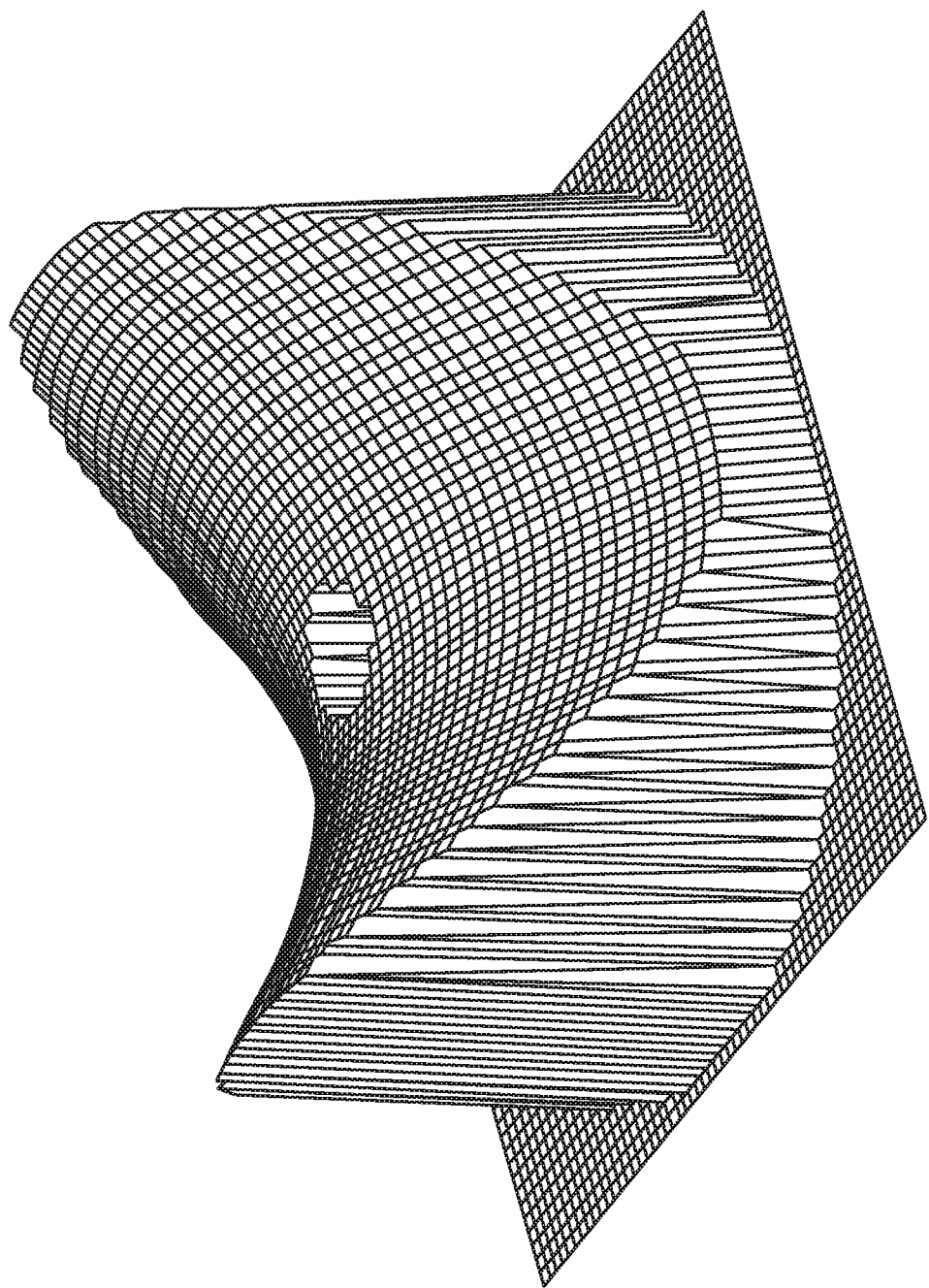
FIG. 2N shows an isometric view of an insert having a 3-D shape profile corresponding to a saddle having positive curvature along the nasal and temporal portions and opposing negative curvature along the inferior and superior portions, such that the nasal and temporal portions are posterior to the inferior and superior portions when placed, in accordance with an embodiment.

FIG. 2N shows an isometric view of an insert 100 having a 3-D shape profile corresponding to a saddle shape 100S (such as a hyperbolic paraboloid) having positive curvature away from the eye along the nasal and temporal portions and opposing negative curvature toward the eye along the inferior and superior portions, such that the nasal and temporal portions are posterior to the inferior and superior portions when placed. The saddle 100S may comprise shape and curvature corresponding to a mathematically defined saddle such as the saddle of astigmatism. Based on the teachings described herein, a person of ordinary skill in the art can determine the saddle shape to fit an eye of a patient. The insert 100 may comprise the retention structure 110 as described herein. This saddle shape corresponds to the shape of in situ formed inserts as described herein. The superior portion of the insert comprises a curvature 115C1 extending toward the eye of the patient, and the curvature 115C1 is configured to correspond to the eyelid of the patient. The inferior portion of the insert comprises a curvature 115C2 extending toward the eye of the patient, and the curvature 115C2 is configured to correspond to the eyelid of the patient. The temporal portion of the insert comprises a curvature 115C4 extending away from the eye. The nasal portion of the insert comprises a curvature 115C3 extending away from the eye. A contour is defined by the hyperbolic paraboloid surface and that contour may correspond to the contour of an outer edge of an embodiment of the device.

The saddle shaped insert provides upper and lower curved portions corresponding to curvature of the upper and lower lids of the eye.

In many embodiments, the pre-formed shape of the insert 100 is determined substantially by the retention structure 110 that is covered with the support structure 120 comprising matrix 140 containing therapeutic agent 130 as described herein. Alternatively, the support structure 120 as described herein can be configured with sufficient stiffness so as to provide the preformed three-dimensional shape provide such that the insert can be provided without the retention structure.

Figure 2O:
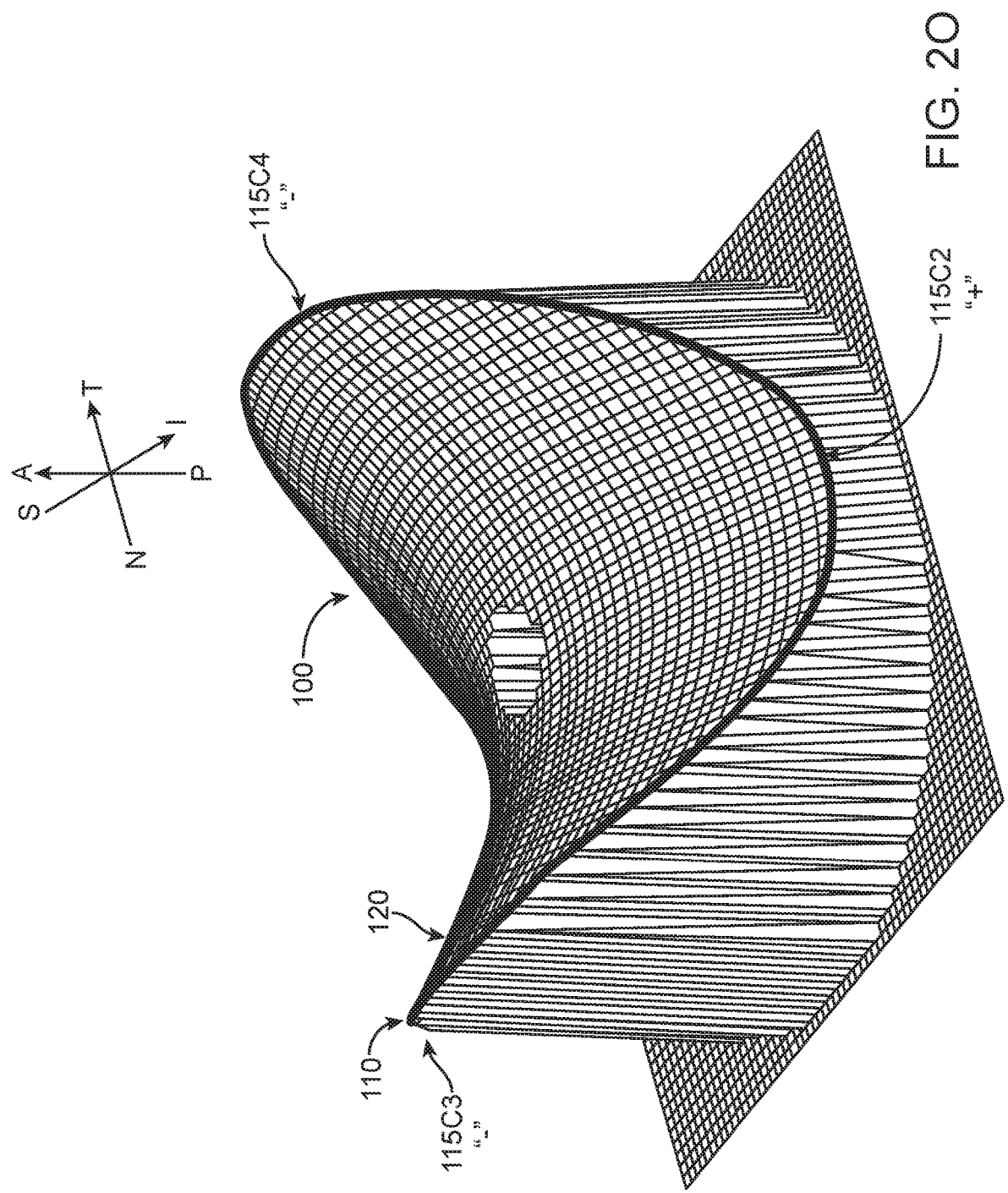
FIG. 2O shows an isometric view of an insert having a 3-D shape profile corresponding to a saddle having negative curvature along the nasal and temporal portions and opposing positive curvature along the inferior and superior portions, such that the nasal and temporal portions are anterior to the inferior and superior portions when placed, in accordance with an embodiment.

FIG. 2O shows an isometric view of an insert having a 3-D shape profile corresponding to a saddle having negative curvature along the nasal and temporal portions and opposing positive curvature along the inferior and superior portions, such that the nasal and temporal portions are anterior to the inferior and superior portions when placed. The superior portion comprises a curvature 115C1 away from the eye, and the inferior portion comprises a curvature 115C2 extending away from the eye. The nasal portion comprises a curvature 115C3 extending toward the eye, and the temporal portion comprises a curvature 115C4 extending toward the eye. The nasal and temporal portions are located anterior to the superior and inferior portions so as to urge the superior and inferior portions of the insert toward the upper and lower fornices of the eye.

This insert can be similar to the insert of FIG. 2N and may comprise many of the components and configurations of the insert of FIG. 2N, which can be rotated by 90 degrees so as to provide the placement as shown in FIG. 2O.

In many of the embodiments as described herein, and in particular with reference to the embodiments of FIGS. 2P1 to 2Z7, the pre-formed shape of the insert 100 is determined substantially by the retention structure 110 that is covered with the support structure 120 comprising matrix 140 containing therapeutic agent 130 as described herein. Alternatively, the support structure 120 comprising matrix 140 as described herein can be configured with sufficient stiffness so as to provide the preformed three-dimensional shape provide such that the insert can be provided without the retention structure. In either configuration, the insert may provide a resilient resistance to deflection, for example a hoop strength, so as to retain the insert, and the upper, lower and intermediate portions of the insert may each have a separate resistance to deflection so as to retain the insert.

FIG. 2P1 shows an insert 100 comprising a retention structure 110 having an upper portion 110U comprising a first durometer 110D1 and a second lower portion 110L comprising a second durometer 110D2. The insert can be configured in many ways. The second durometer can be lower than the first durometer, for example, such that the lower portion can be more flexible. The upper portion can slide into the upper fornix, and the hoop strength of the lower portion can urge the lower portion outward against the lid. By providing the lower portion with the lower durometer and lower hoop strength, the lower portion can be more easily retained by the lower lid when the upper lid draws the retention structure upward.

FIG. 2P2 shows an insert 100 comprising a retention structure 110 having an upper portion 110U and a lower portion 110L, in which the lower portion is curved inward toward the eye, for example with a lower bend. The lower portion 110L may comprise bent portions 110B1, 110B2 such that the upper portion is urged posteriorly toward the upper fornix when the insert is placed in the eye.

FIG. 2P3 shows an insert 100 comprising a retention structure 110 having a hinges 110H1, 110H2, to couple an upper portion 110U to a lower portion 110L and allow the upper portion to swing toward the lower portion. The hinges can be formed in many ways and may comprise one or more of a break in material, a low durometer material such as a silicone material, a scored suture, flattened material, or combinations thereof.

FIG. 2P4 shows an insert 100 comprising a retention structure 110 having an upper portion 110U and a lower portion 110L with bias curve such that the upper and lower portions extend posteriorly to the nasal and temporal portions prior to placement. The insert comprise a curvature 115C3 on the nasal side and a curvature 115C4 on the temporal side such that the upper and lower portions are located posterior to the nasal and temporal portions, so as to bias the inferior and superior portions posteriorly when the upper and lower portions are placed under the eyelids. The upper portion 110U may have a curvature 115C1 corresponding to the eyelid and the lower portion 110L may have a curvature 115C2 corresponding to the lower eyelid, as described herein for example.

FIG. 2P5 shows an insert 100 comprising a retention structure 110 having an upper portion 110U and a lower portion 110L with a biasing curve such that the upper and lower portions extend anterior to the nasal and temporal portions and away from the eye prior to placement. The insert comprise a curvature 115C3 on the nasal side and a curvature 115C4 on the temporal side such that the upper and lower portions are located anterior to the nasal and temporal portions, so as to bias the nasal and temporal portions posteriorly when the upper and lower portions are placed under the eyelids. The upper portion 110U may have a curvature 115C1 corresponding to the eyelid and the lower portion 110L may have a curvature 115C2 corresponding to the lower eyelid, as described herein for example.

FIG. 2P6 shows an insert 100 comprising a retention structure 110 having an oblong shape and having first upper portion 110U and a second lower portion 110L in which the upper portion comprises an elongate oval shape portion so as to extend into the upper fornix and the lower portion comprises a shorter wider oval shape so as to extend into the lower fornix. The retention structure may comprise a first maximum dimension across 114A1 in the vertical direction and a second maximum dimension across 114A2 in the horizontal direction. The elongate upper portion can be urged into the upper fornix. The insert 100 may comprise combinations of durometer. For example, the upper portion may comprise a more rigid durometer than the lower portion. Alternatively, the lower portion may comprise a more rigid durometer than the upper portion.

FIG. 2P7 shows an insert 100 comprising a retention structure 110 comprising an upper portion and a lower portion coupled with hinges 110H1, 110H2, so as to define an elliptical shape. The upper portion 110U and the lower portion 110L can swing toward each other. The hinges 110H1, 110H2 can be formed in one or more of many ways as described herein. The upper portion 110U and the lower portion 110L may comprise a stiff material, for example a rigid material.

FIG. 2P8 shows an insert 100 comprising a flexible redundant retention structure 110 to seat the retention structure in the eye. The flexible redundant retention structure may comprise at least some hoop strength and at least some chord length of the retention structure so as to fit the eye.

FIG. 2P9 shows an insert comprising an upper anchor 110AN. The upper anchor may comprise an upper or lower lattice section. The upper anchor may comprise additional amounts of therapeutic agent.

FIG. 2P10 shows an insert 100 comprising a lower anchor 110AN to resist pull of the round structure. The lower anchor may comprise a cushioning shock absorbing structure sized to fit within the lower fornix of the eye, for example. The lower anchor can resist pulling of the upper round portion of the retention structure. The lower anchor may comprise additional amounts of therapeutic agent.

Figure 2Q:
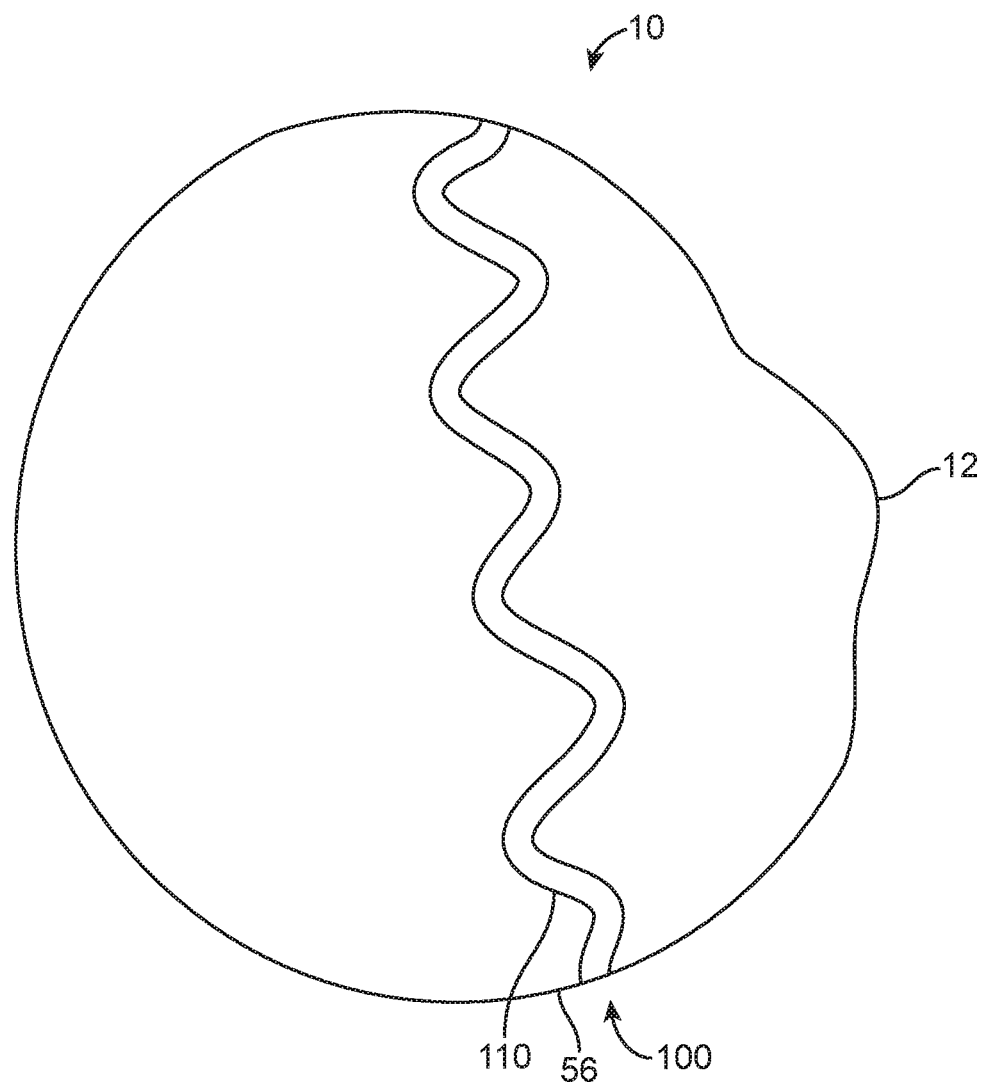
FIG. 2Q shows an insert comprising a retention structure configured to exert at least some pressure on the conjunctiva to retain the insert, in accordance with an embodiment.

FIG. 2Q shows an insert 100 comprising a retention structure 110 configured to exert at least some pressure on the conjunctiva to retain the insert. The retention structure 110 may comprise a lower surface having structures to engage the conjunctiva and inhibit slipping, for example ridges, notches, grooves.

Figure 2R:
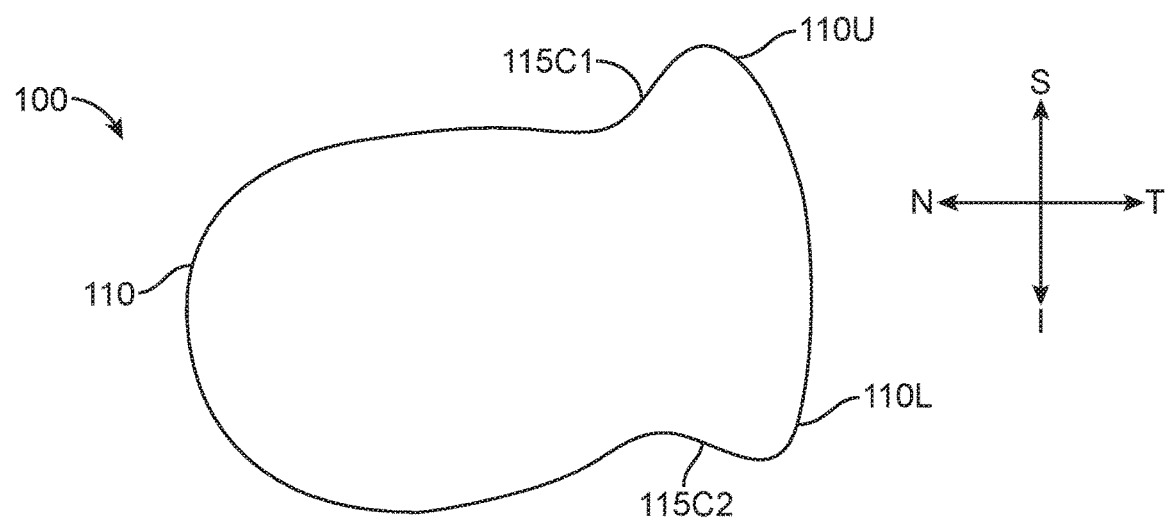
FIG. 2R shows an insert comprising a retention structure having a curved portion to extend laterally to the temporal fornix of the eye, in accordance with an embodiment.

FIG. 2R shows an insert 100 comprising a retention structure 110 having an outer curved portion to extend laterally to the temporal fornix of the eye. The outer temporal portion comprises an upper portion 110U having a curvature 115C1 and a lower portion having a curvature 115C2, such that the outer temporal portion curves posteriorly to fit the temporal fornix.

Figure 2S:
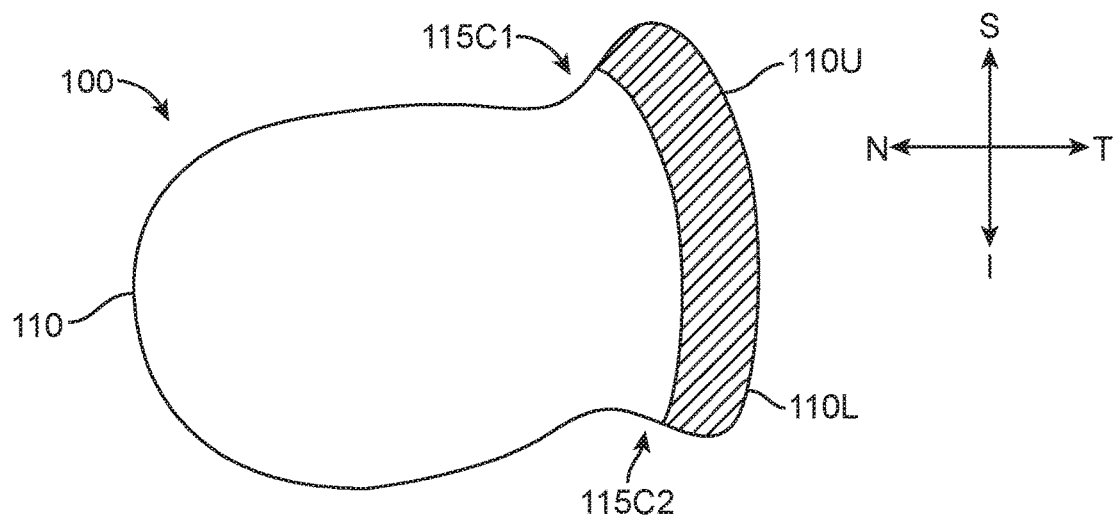
FIG. 2S shows an insert comprising a retention structure having an outer curved portion to extend laterally to the temporal fornix of the eye, in accordance with an embodiment.

FIG. 2S shows an insert 100 comprising a retention structure 110 having an outer curved portion to extend laterally to the temporal fornix of the eye. The outer curved portion comprises a solid material. The outer temporal portion comprises an upper portion 110U having a curvature 115C1 and a lower portion having a curvature 115C2, such that the outer temporal portion curves posteriorly to fit the temporal fornix.

Figure 2T:
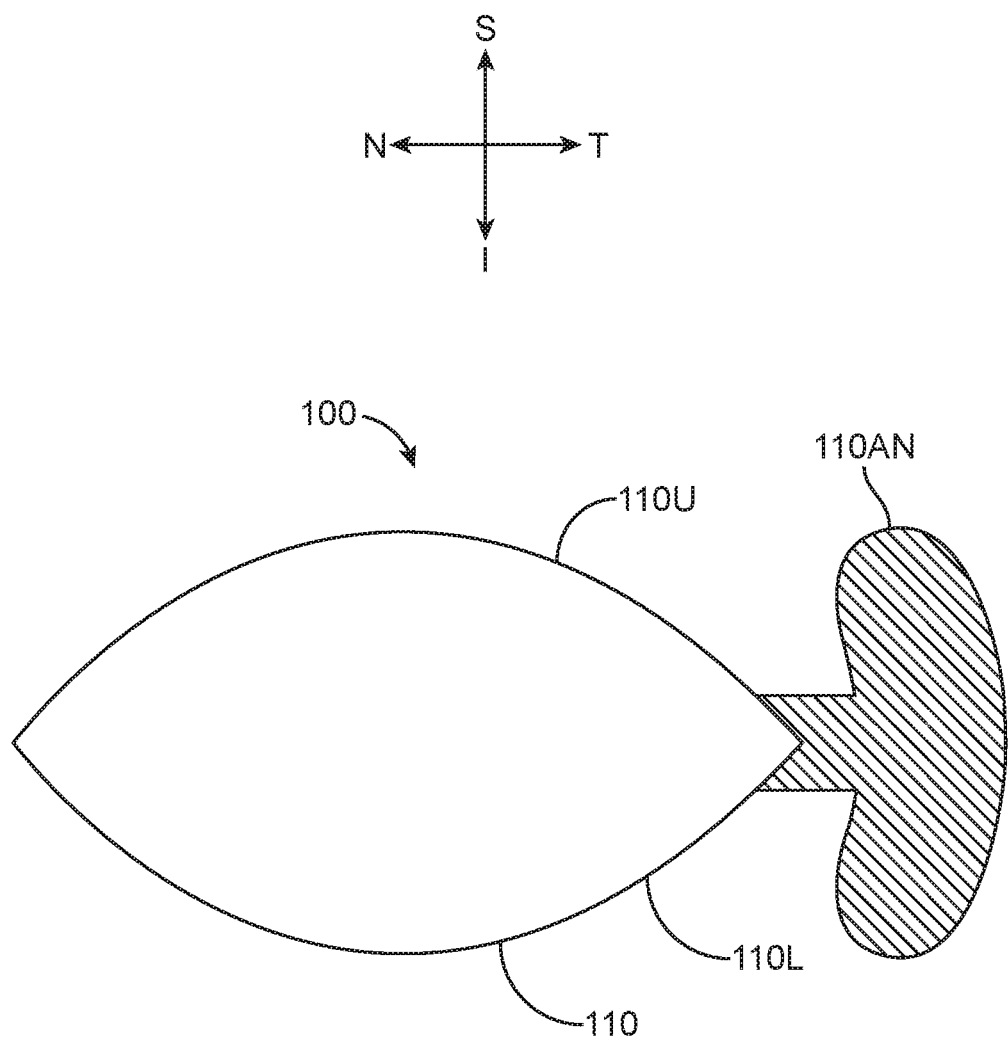
FIG. 2T shows an insert comprising a retention structure having an outer anchor portion to extend laterally to the temporal fornix of the eye, in accordance with an embodiment.

FIG. 2T shows an insert 100 comprising a retention structure 110 having an outer anchor portion 110AN to extend laterally to the temporal fornix of the eye. The retention structure 110 comprises an upper portion 110U and a lower portion 110L.

Figure 2U:
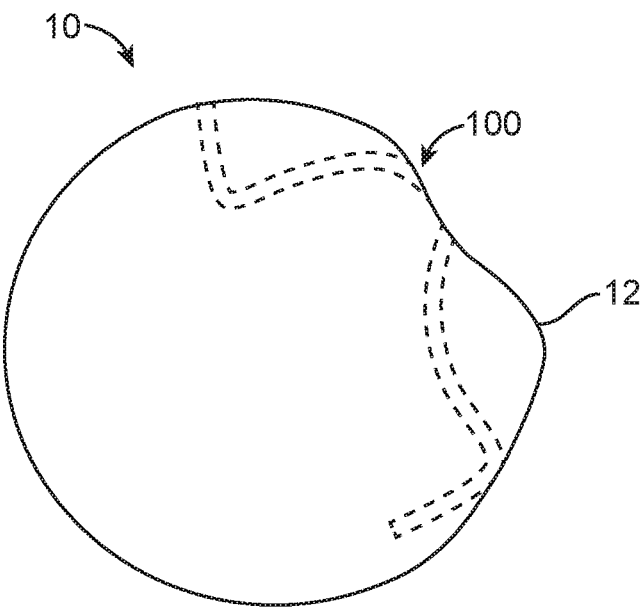
FIGS. 2U and 2V show an insert comprising a retention structure having an upper portion sized to extend into the upper fornix and a lower portion sized to extend into a lower fornix with an intermediate portion between the upper and lower portions and wherein the upper and lower portions curve posteriorly from the intermediate portion to fit the upper and lower fornices, respectively, in accordance with an embodiment.
Figure 2V:
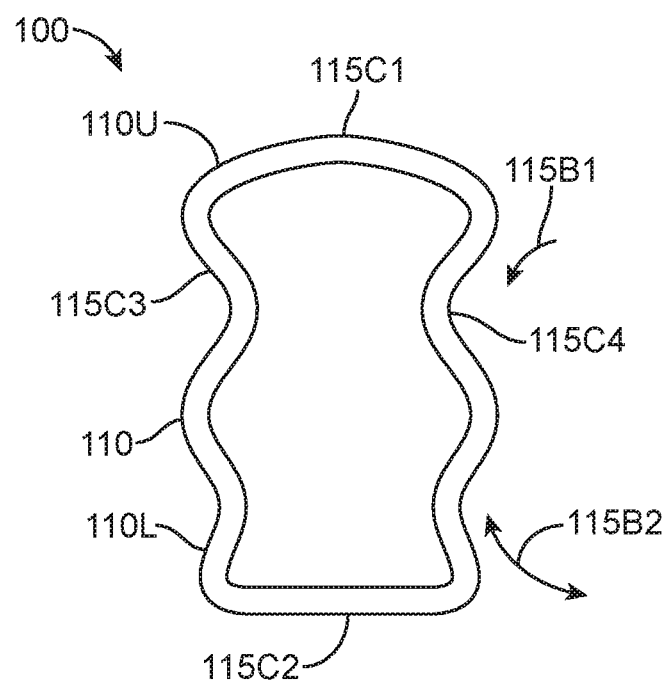

FIGS. 2U and 2V show an insert 100 comprising a retention structure 110 having an upper portion 110U sized to extend into the upper fornix and a lower portion 110L sized to extend into a lower fornix with an intermediate portion extending between the upper and lower portions. The upper portion 110U and the lower portions 110L may each curve posteriorly from the intermediate portion so as to fit within the upper and lower fornices, respectively. The upper portion 110U can be sized to extend deep into the upper fornix and substantially toward the upper end of the fornix so as to anchor the upper portion 110U within the eye. The lower portion 110L can be sized to extend substantially toward the lower end of the lower fornix. The intermediate portion can be sized to extend near the lateral canthus and medial canthus and receive the cornea therebetween with sufficient space so as to inhibit contact with the cornea. When placed on the eye 10, the upper portion 110U can extend a greater distance from the pupil than the lower portion 110L.

The portions of the retention structure can be shaped to fit the cornea. The upper portion 110U and the lower portion 110L can each be curved posteriorly, for example bent with a biasing curve, so as to engage the upper and lower fornix respectively, and urge the intermediate portion posteriorly toward the eye. For example, the upper portion can be curved posteriorly with a third curvature 115C3 and a fourth curvature 110C4 as described herein. The upper portion may comprise a curvature 115C1 corresponding the eyelid as described herein. The curved upper and lower portions may comprise the resistance to deflection to inhibit contact with the cornea as described herein.

FIG. 2W shows an insert 100 comprising a retention structure 110 having an upper portion 110U comprising a hydrophilic surface 110HL and a lower portion 110L comprising a hydrophobic surface 110HB. The hydrophobic surface may comprise a sticky tacky surface to improve retention of the insert and the hydrophilic surface may comprise a lubricous coating. The therapeutic agent may be provided with a support structure 120 coupled to the insert 100 as described herein.

FIGS. 2X1 and 2X2 show front and side views, respectively, of an insert 100 comprising an upper portion 110U and a lower portion 110L and a stiff portions 110S to angularly bias the upper portion and the lower portion, for example toward each other. The stiff portion 110S can be coupled to the upper 110U and the lower portion 110L in one or more of many ways, so as to allow deflection of one or more of the upper portion 110U or the lower 110L. The upper portion 110U and the lower portion 110L may each comprise a resilient resistance to deflection, for example a hoop strength as described herein. The upper end of the upper portion and the lower end of the lower portion may be inclined toward each other at an angle, such that the upper portion and the lower portion are each placed in the corresponding fornix of the eye and the stiff portion 110S is placed anteriorly to the upper portion 110U and the lower portion 110L.

Figure 2Y:
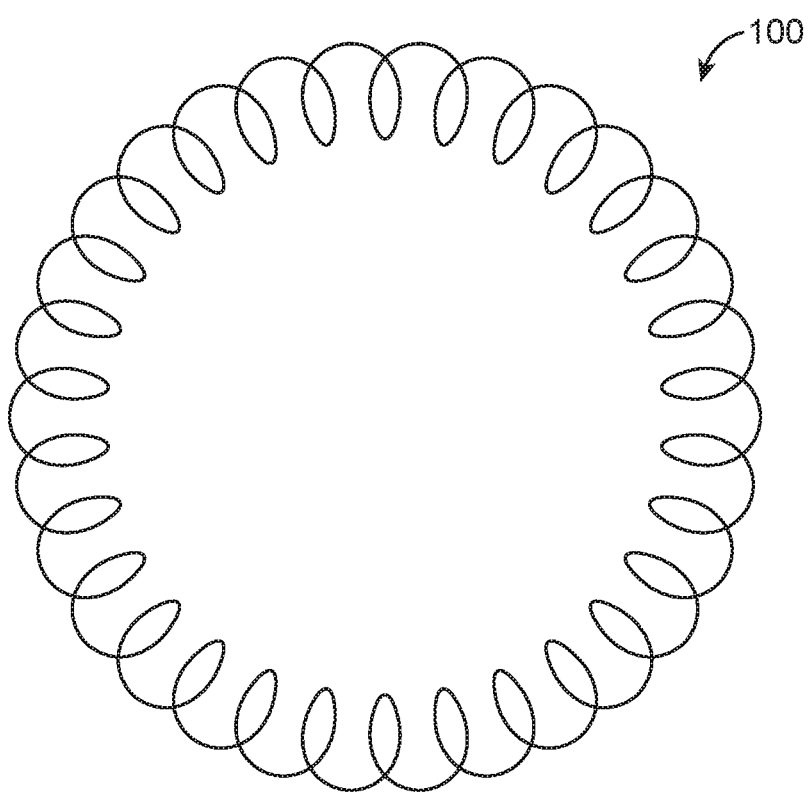
FIG. 2Y shows an insert comprising an expandable retention structure to allow the insert to be stretched to fit the eye, in accordance with an embodiment.

FIG. 2Y shows an insert 100 comprising an expandable retention structure 110 to allow the insert to be stretched to fit the eye. The insert may comprise a stretchable member such as a one or more of coil, a helical coil, or a serpentine structure, so as to adjust the longest dimension across insert 100.

FIG. 2Z1 shows an insert 100 comprising a retention structure 110 having an upper portion 110U and a lower portion 110L coupled with a variable joint 110J to as to vary a size of the retention structure and insert. The joint 110J can be adjusted in many ways so as to vary a size of the insert.

FIG. 2Z2 shows a telescopic joint of an insert as in FIG. 2Z1. The telescopic joint 110J can be configured to allow the size of the insert 100 to be adjusted, for example based on a measurement of the patient. The telescopic joint can be adjusted to fit the patient, and then locked into position, for example by crimping the joint or applying an adhesive, for example.

FIG. 2Z3 shows a shock absorbing spring joint 110J of an insert 100 as in FIG. 2Z1. The shock absorbing joint may comprise a spring mechanism to absorb force transmitted from the lower portion 110L to the upper portion 110U, and vice versa, for example when the eye blinks or moves quickly.

FIG. 2Z4 shows a ratcheting joint 110J of an insert as in FIG. 2Z1. The ratcheting joint 110J may comprise a sliding mechanism to receive the upper portion 110U of the insert and the upper portion can be advanced in to the ratcheting joint 110J so as to decrease a size of the insert, for example based on a measurement of the eye as described herein. The ratcheting mechanism may comprise one or more known ratcheting mechanisms and may comprise at least one tooth and a plurality of grooves so as to adjust the circumferential length of the insert.

FIGS. 2Z5 and 2Z6 show front and side views, respectively, of an insert 100 comprising an elongate shape having upper and lower portions sized to extend into upper and lower fornices, respectively, so as to provide substantially greater amounts of therapeutic agent 130 than the intermediate portions locatable near the lateral and medial canthus. The insert 100 may comprise a retention structure 110 comprising an upper portion 110U and a lower portion 110U. The upper portion 110U can extend into the upper portion of the insert so as to support and provide stiffness to the upper portion of the insert. The lower portion 110L can extend along the lower portion of the insert so as to provide support and stiffness to the lower portion of the insert. The upper portion of the insert and the lower portion of the insert may comprise a thickness greater than the intermediate portion of the insert, so as to contain substantial amounts of therapeutic agent with the each of the upper and lower portions of the insert.

FIGS. 2Z7 and 2Z8 show front and side views, respectively, of a rigid insert 100 having a curved shape sized to fit the eye of the patient such that the insert can be worn comfortably for an extended time. The rigid insert 100 may comprise one or more materials as described herein, for example polyacrylate, polycarbonate, metal, or other material. The rigid insert may comprise a rigid matrix 140 comprising a therapeutic agent 130. The rigid insert can be sized such that contact of the inner portion with the cornea is inhibited, and such that the outer portion extends to the fornix of the eye when placed. The insert can be adhered to a portion of the eye, for example with an adhesive or other material or structure as described herein.

The embodiments of 2A to 2Z7 are provided as non-limiting examples and can be combined and modified in many ways. In many embodiments, the insert is provided with a drug delivery matrix material having a one or more of a stiffness or spring bias corresponding to the above described retention structures, such that the insert can be provided without a skeletal structure and provide the function of the skeletal structure. For example, the drug delivery matrix may comprise materials having a durometer and cross-sectional dimensions so as to provide the function of the retention structure. Alternatively or in combination, a support structure as described herein such as the drug delivery matrix can be provided over the retention structure as described herein, for example.

FIG. 3A1 shows an insert placed between folds of conjunctiva. The insert can be placed between the bulbar conjunctiva and lid of the eye such that the insert is placed between one or more folds 56F of the bulbar conjunctiva and one or more folds 58F of the palpebral conjunctiva, for example. The insert 100 comprising the resistance to deflection can interact with the conjunctiva in many ways and can one or more of stretch the conjunctiva, form a fold of conjunctiva, deform the conjunctiva, deform the conjunctiva to form a fold, deform the conjunctiva to form a flap of conjunctiva, embed within folds of conjunctiva, or fit between the folds of conjunctiva, as described herein, so as to be retained comfortably on the eye for an extended time. The insert 100 comprising the resistance to deflection can stretch or compress, the conjunctiva in many ways and so as to receive the insert. For example, the insert can be placed between the bulbar and palpebral conjunctiva so as to one or more of stretch or compress the bulbar conjunctiva 56 and the palpebral conjunctiva 58 so as to comfortably retain the insert therebetween. The one or more of stretching or compression of the bulbar conjunctiva can form a fold of conjunctiva, or reshape the conjunctiva so as to retain the insert 100.

FIG. 3A2 shows a fold of conjunctiva receiving the insert 100. The insert 100 may be received with a naturally occurring fold of conjunctiva, or a fold created with the insert 100. The insert 100 may displace the conjunctiva so as to shape the conjunctiva. For example, the conjunctiva can be molded with the insert 100. The insert 100 comprising the resistance to deflection as described herein can urge and displace the conjunctiva to receive the insert. For example, the insert 100 comprising the resistance to deflection can urge of conjunctiva such that the conjunctiva can be deformed and insert received with the deformed conjunctiva, for example in a fold of deformed conjunctiva. In many embodiments, the folds of conjunctiva can be urged with the insert having the resistance to deflection such that a fold is formed in the conjunctiva and shaped to receive the insert. The insert 100 having the resistance to deflection may form a pocket within the conjunctiva to receive the insert within the pocket, for example. The insert 100 can be configured with the resistance to deflection in many ways to shape and/or deform the conjunctiva as described herein, for example with retention structure 110 or alternatively without retention structure 110.

FIG. 3A3 shows an insert sized to fit between folds of conjunctiva. The insert may comprise a size corresponding to the one or more folds of conjunctiva, such that the insert can fit one or more folds of conjunctiva. The insert 100 may comprise sufficient resistance to deflection so as to shape the conjunctiva and to receive the insert, for example with a fold or pocket.

FIG. 3A4 shows a retention structure of an insert as in FIGS. 2A to 2C placed on an eye such that the retention structure fits into one or more of a plurality of folds 56F of the bulbar conjunctiva 56 located away from fornix 54. The retention structure 110 can be received in one or more of the several folds 56F of conjunctiva located between the fornix 54 and cornea 12. In many embodiments, each of the plurality of folds of the bulbar conjunctiva comprises an invagination corresponding to an invagination depth, and the cross-sectional dimension of the retention structure corresponds to the invagination depth such that the elongate retention structure fits within and extends along the invagination. The retention structure 110 can be received in one or more of the folds 58F of palpebral conjunctiva 58F located between the fornix 54 and lid margin, for example when the retention structure 110 moves with the eye. The retention structure 110 may comprise the resistance to deflection so as to urge the retention structure 110 to fit within the fold, for example.

FIG. 3B shows a retention structure under a fold 56F of bulbar conjunctiva. The fold 56F of bulbar conjunctiva can extend circumferentially around the eye about axis 10A of the eye. The retention structure 110 can be deflectable along the fold 56F such that the retention structure 110 can be retained in the fold. Alternatively or in combination, the retention structure 110 may comprise sufficient resistance to deflection so as to deform the conjunctiva such that the fold of conjunctiva extends over the retention structure. The retention structure 110 may comprise the resistance to deflection as described herein such that the movement of retention structure 110 toward the cornea can be inhibited substantially when the retention structure 110 is received within the fold 56F. The retention structure 110 can be similarly received and deflect along folds 58F of the palpebral conjunctiva away from fornix 54. Alternatively, the matrix material insert 100 may comprise the resistance to deflection without retention structure 110, such that the insert 100 can fit under the folds of bulbar conjunctiva.

FIGS. 3C1 to 3C3 show a retention structure 110 under a fold 56F of bulbar conjunctiva 56 moving with rotation of the eye 10. The retention structure can be retained within the sac away from fornix 54 at an initial location of the fold 56F as shown in FIG. 3C1. The eyeball can rotate such that the fold 56F moves with the eyeball toward a margin 40M of the lid 40 as shown in FIG. 3C2. The lid margin 40M can be moved away from the fold 56F such that the retention structure 110 can be seen under the flap 56F of conjunctiva.

Figure 3D:
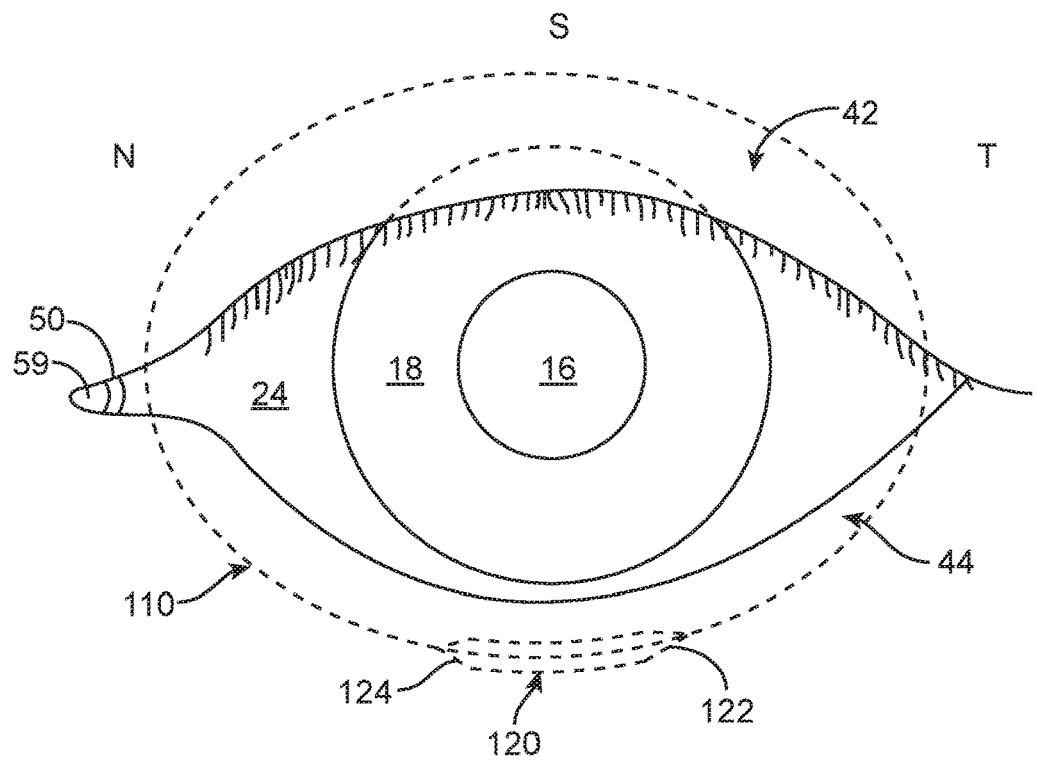
FIG. 3D shows an initial inferior placement of an insert comprising a retention structure, in accordance with an embodiment.

FIG. 3D shows an initial inferior placement of support structure 120 of insert 100 in an eye such as a left eye of a patient. The retention structure 110 and support structure 120 are configured to allow rotation of the insert 100 around the axis 10A of the eye, for example in response to cyclo torsional movement of eye 10 about axis 10A. The retention structure 110 comprises the resistance to deflection as described herein, and the support structure 120 comprises the first inclined surface of first tapered end portion 122 and the second inclined surface of second tapered end portion 124 to allow sliding of the support structure 120 and retention structure 110 along the conjunctival sacs.

Figure 3E:
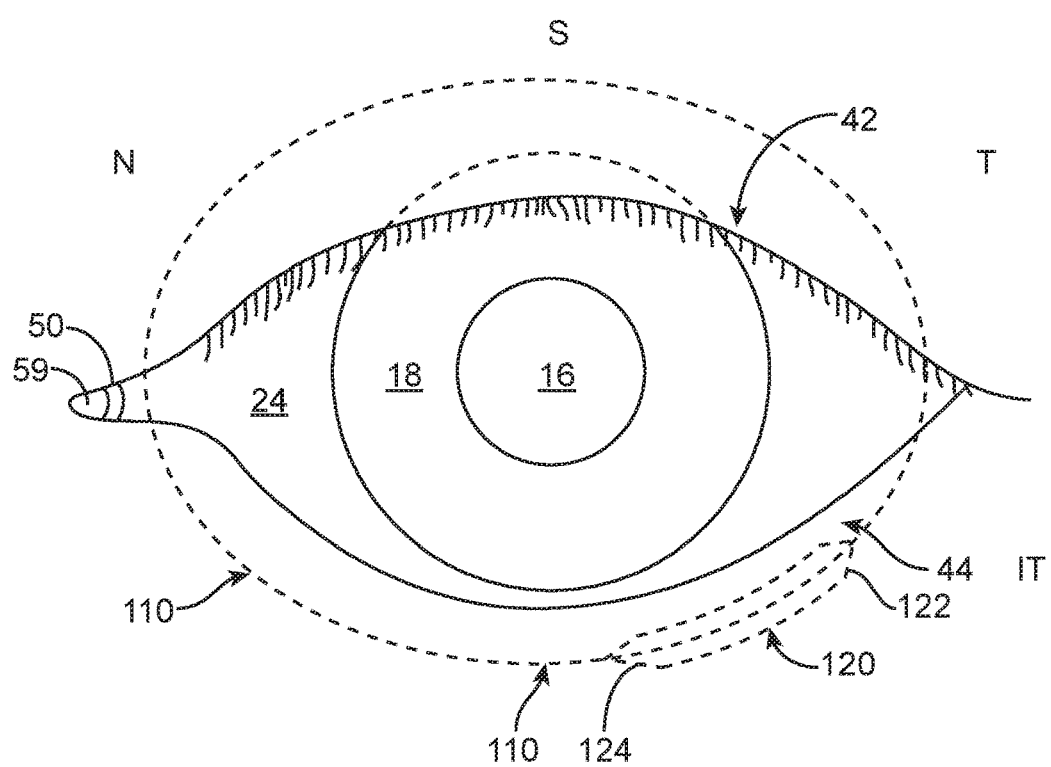
FIG. 3E show an insert initially placed as in FIG. 3D which has moved rotationally along the conjunctiva about an axis of rotation extending through a pupil of the eye, in accordance with an embodiment.

FIG. 3E shows insert 100 initially placed as in FIG. 3D which has moved rotationally along the conjunctiva about an axis of rotation extending through pupil 16 of the eye 10. The insert is shown in an inferior temporal location of the sac, and this self-seating migration of the insert can provide improved comfort for the patient. The resistance to deflection of the retention structure 110 can be configured so as to allow the retention structure 110 to bend within the sac and permit movement such as rotation of the retention structure and support structure 120. The inclined surfaces of the support structure 120 can allow movement of the support structure along one or more locations of the conjunctiva. For example, the inclined surfaces may urge the insert toward the inferior temporal location in response to one or more of movement of the eye, cyclo torsional movement of the eye, or increased clearance for the insert away from the skull within the sac. Work in relation to embodiments described herein suggests that cyclo torsion of the eye can be related to rotational movement of the insert 100. In at least some patients, the orbit of the eye has an elongate horizontal (i.e. nasal-temporal) dimension near the rim so as to provide increased clearance for the insert compared with the inferior location shown in FIG. 3D.

Figure 3F:
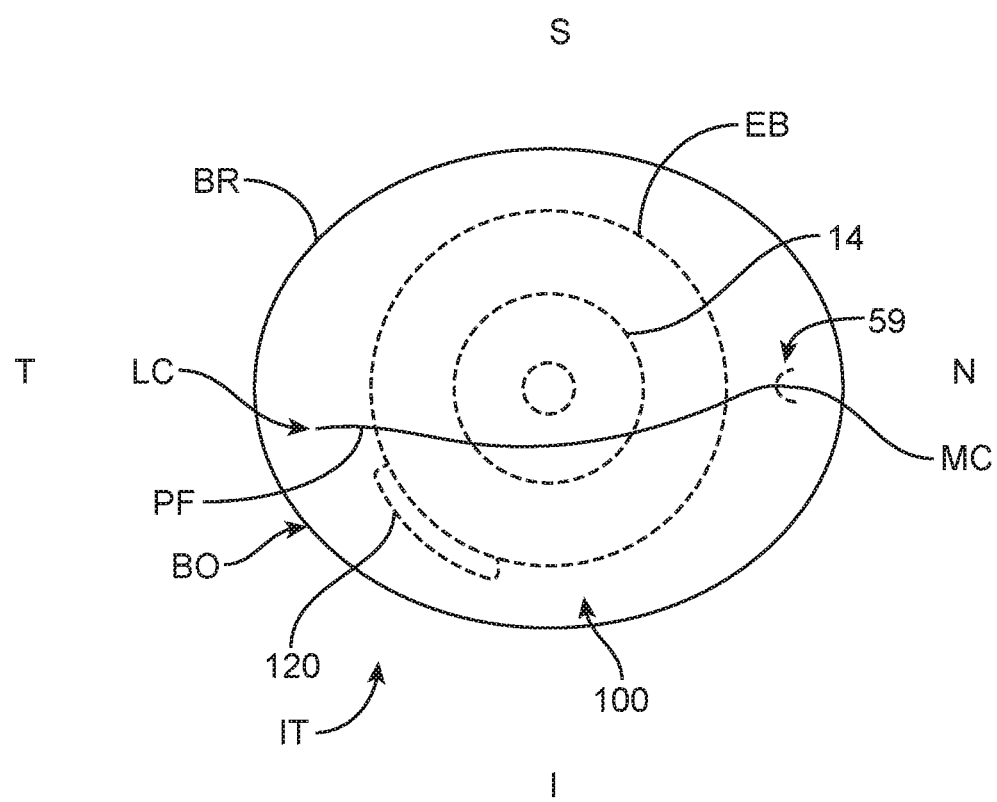
FIG. 3F shows the an insert located at an inferior temporal location of the conjunctiva of the eye and the orbit, in accordance with an embodiment.

FIG. 3F shows an insert located at an inferior temporal location of the lower conjunctival sac of the eye and the orbit, such as an orbit of a right eye of the patient. The bony orbit BO of the skull of the patient is defined at least in part by a bony rim BR extending around the eye socket. The bony orbit comprises a first nasal temporal maximum dimension across substantially aligned with the palpebral fissure PF and a second superior inferior maximum dimension across transverse to the palpebral fissure PF. The outer dimension of the sclera 24 of fits within the bony orbit BO. In many embodiments, the retention structure 110 of insert 100 is sized in proportion to the maximum diameter of the sclera transverse to the optical axis of the eye, for example to within about two millimeters of the maximum diameter of the sclera transverse to the optical axis of the eye. In many embodiments, the retention structure 110 deflects when placed in the eye as described herein.

The bony orbit comprises dimensions to receive the insert in the conjunctival sac and allow movement of the insert within the conjunctival sac and retain the insert. The maximum dimension across the adult human eye transverse to the axial length is about 24 mm, and the dimension of palpebral fissure is about 30 mm. The first nasal temporal maximum dimension across the bony orbit is greater than the second superior inferior dimension across. In the adult human, dimensions of bony orbit are about 40 mm long and about 30 mm vertically. The anterior entrance of the orbit can form a rough rectangle measuring approximately 43 mm (within a range from about 36-47 mm) wide by 34 mm (within a range from about 26-42 mm) high, as described in the Atlas of Clinical and Surgical Orbital Anatomy, published on the world wide web (expertconsultant.com). The orbit may attain a widest dimension at about 15 mm behind the bony rim, such that the rim may constrain rotational movement of the retention structure 110 and support structure 120 of insert 100, for example with cyclo torsion of the eye.

In some patients, the superior-inferior dimension across the bony rim BR of the bony orbit BO increases temporally away from the middle of the bony orbit, so as to define an inferior temporal location of the bony orbit corresponding to a location of the inferior conjunctival sac having an increased size to accommodate the support structure 120 of insert 100. The support structure 120 can be sized to fit comfortably within the inferior temporal location and allow rotation of insert 100 with cyclotorsion or other movement of the eye 10, for example. Work in relation to embodiments suggest that the first inclined surface of first tapered end portion 122 and the second inclined surface of second tapered end portion 124 can be subjected to different pressures of the conjunctiva within the sac such that the support structure 120 may be urged toward the inferior temporal location of the lower conjunctival sac.

Figure 3G:
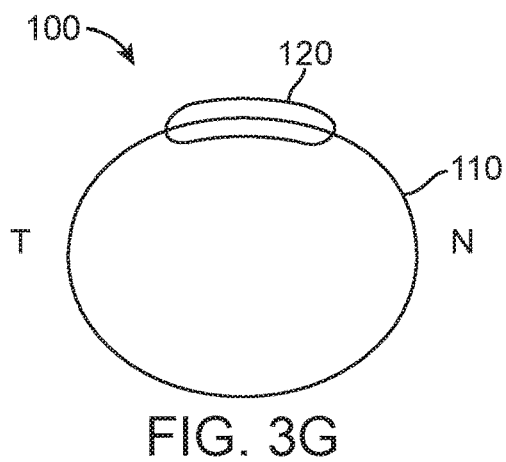
FIG. 3G shows the support structure placed superiorly, in accordance with an embodiment.

FIG. 3G shows the support structure 120 and retention structure 110 as described herein placed superiorly. The superior placement can be used with patients who may have a droopy lower eyelid, for example. The upper lid can retain the support structure 120 comprising the therapeutic agent 130 contained within matrix 140, for example. The retention structure 110 can be sized to fit within one or more of the plurality of folds of the inferior conjunctiva, for example the inferior bulbar conjunctiva as described herein.

FIG. 3G-1 shows the support structure placed superiorly at an initial location of the superior conjunctival sac 52. The superior conjunctival sac 52 comprising upper lid 42 can receive the support structure 120 comprising therapeutic agent 130 contained within matrix 140, and the pressure of the upper lid can urge the support structure upward toward the cul-de-sac and fornix.

FIG. 3G-2 shows the support structure 120 seated in the cul-de-sac 53 comprising fornix 54 of the superior conjunctival sac 52 following placement as in FIG. 3G-1. The retention structure 110 can extend along the lower sac and fit within the one or more folds of the lower sac, for example bulbar folds, as described herein.

Figure 3H:
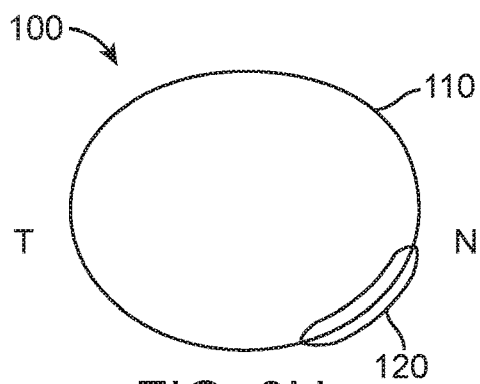
FIG. 3H shows the support structure located at an inferior nasal location of the eye so as to extend near the caruncle, in accordance with an embodiment.

FIG. 3H shows the support structure 120 located at an inferior nasal location of the eye so as to extend near the caruncle. The support structure 120 may comprise a low resistance to deflection, for example less than the retention structure 110, such that the support structure and retention structure can deflect together on the eye. This low resistance to deflection can permit placement of the support structure 120 at many locations as described herein.

Figure 3I:
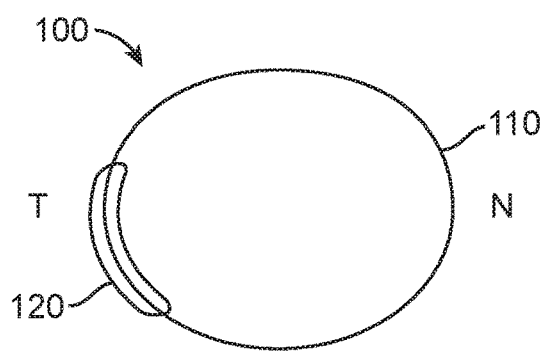
FIG. 3I shows the support structure placed at a temporal location of the eye, in accordance with an embodiment.

FIG. 3I shows the support structure 120 placed at a temporal location of the eye.

Figure 3J:
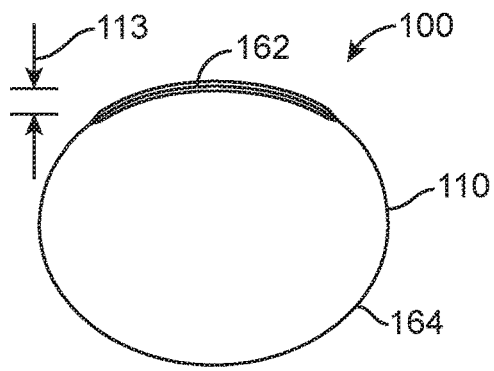
FIG. 3J shows retention structure comprising a first portion having a first resistance to deflection and a second portion having a second resistance to deflection less than the first portion, in accordance with an embodiment.
Figures 1, 3J:
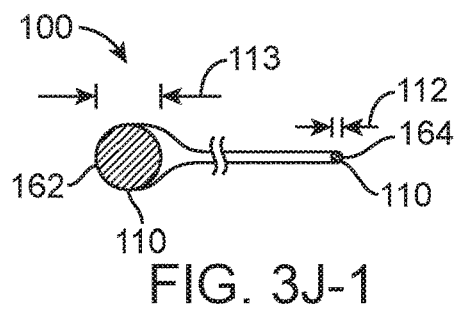

FIG. 3J shows retention structure 110 comprising a first portion 162 having a first resistance to deflection and a second portion 164 having a second resistance to deflection less than the first portion. The first resistance to deflection less than the second resistance to deflection may comprise one or more of a varying thickness of retention structure 110, a varying material of retention structure 110 or a plurality of materials of retention structure 110. The first portion 162 may comprise a greater cross sectional dimension; e.g., diameter, than the second portion, so as to increase the resistance to deflection of the first portion relative to the second portion, for example. This increased resistance to deflection can permit the first portion 162 of the retention structure to be placed under the superior (upper) lid so as to inhibit movement of the first portion 162 toward the cornea. The sizing of the first portion 162 can urge the first portion toward the fornix 54. The relatively smaller cross-sectional size of the second portion 164 can permit the second portion to fit within the one or more folds of the inferior (lower) sac of the eye as described herein.

FIG. 3J-1 shows a side cross sectional view of the retention structure 110 as in FIG. 3J. The retention structure 110 may comprise a cross sectional dimension 112 of the elongate second portion of the retention structure, and a cross sectional dimension 113 of the first portion 162 of the retention structure. The first portion 162 and the second portion 164 may comprise substantially the same material such that the thinner second portion has the resistance to deflection lower than the thicker second portion as described herein.

Figure 3K:
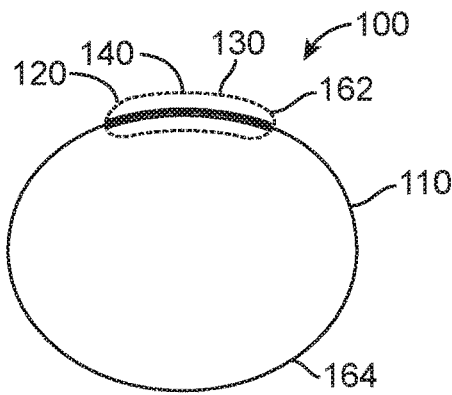
FIG. 3K shows an insert comprising a support structure comprising a matrix of therapeutic agent on the retention structure as in FIG. 3J, in accordance with an embodiment.

FIG. 3K shows an insert 100 comprising a support structure 120 comprising a matrix 140 of therapeutic agent 130 on the retention structure 110 as in FIG. 3J. The support structure 120 can be located on retention structure 110 so as to correspond to one or more support structure locations as described herein, such as nasal placement, temporal placement, inferior placement, superior placement, or inferior temporal placement, when the wider first portion 162 is placed superiorly, for example. For example, the support structure 120 comprising the matrix 140 and the wider first portion 162 can be placed superiorly, for example. Alternatively or in combination, the support structure 120 comprising matrix 140 of therapeutic agent 130 can be placed at one or more of many locations on the retention structure 110 corresponding to one or more locations of the eye when the first portion is placed superiorly. For example, the support structure 120 comprising matrix 140 containing therapeutic agent 130 can be located on retention structure 110 for placement inferiorly when the wider first portion 162 is placed superiorly, for example.

Figure 3L:
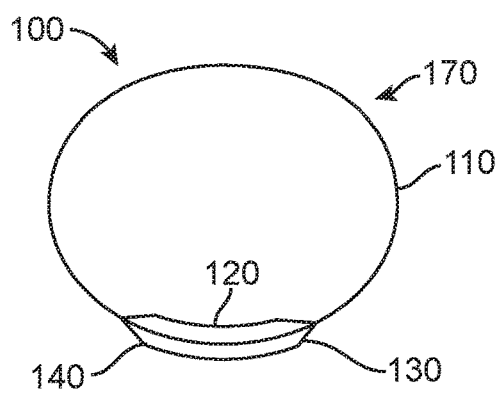
FIG. 3L shows an insert comprising a lubricous coating, in accordance with an embodiment.
Figures 1, 3L:
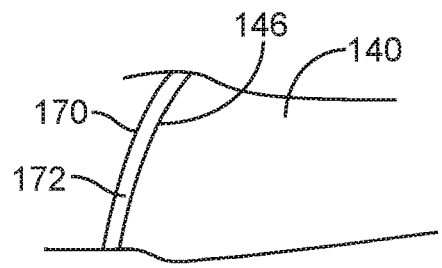

FIG. 3L shows an insert comprising a lubricous coating. The lubricous 170 coating can allow the insert to move along the conjunctiva of the eye and can cover one or more of the retention structure 110 or the support structure 120. For example, the lubricous coating may cover the support structure 120 comprising matrix 140 containing therapeutic agent 130, and the therapeutic agent 130 can be released through the surface of the matrix 140 as described herein. Alternatively or in combination, the lubricous coating may cover at least a portion of the retention structure. For example the lubricous coating 170 may cover a portion of the retention structure corresponding to locations near the lacrimal gland. Alternatively, the lubricous coating 170 may cover the support structure and the retention structure, for example with dip coating of insert 100.

FIG. 3L-1 shows a layer 172 of the lubricous coating 170 on a surface 172 of the matrix 140 as in FIG. 3L. The layer 172 may extend over the surface the matrix 140 that releases the therapeutic agent as described herein. The therapeutic agent 130 can be released through the layer 172, and the rate of release can be determined substantially by surface area of the matrix 140 and the solubility of the therapeutic agent in the tear of the eye.

The lubricous coating may comprise one or more of an oil, a surfactant, a hydrogel, polyvinyl alcohol (PVA), hydroxyethyl methacrylate (HEMA), sodium polyacrylate, acrylate polymers and copolymers having hydrophilic groups, N-vinylpyrrolidone (NVP), agarose, methylcellulose, ethylene oxide (ETO), polyethylene oxide (PTO) or hyaluronan, for example.

Figure 4A:
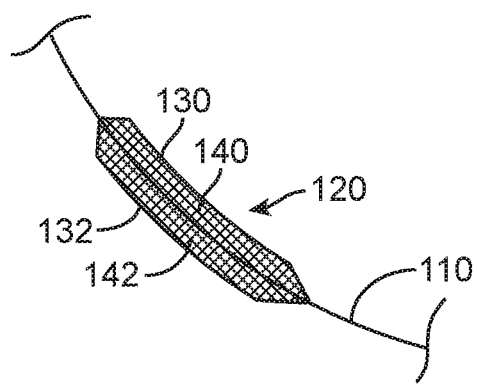
FIG. 4A shows an insert comprising a plurality of therapeutic agents loaded on a first portion of the support structure and a second portion of the support structure, in accordance with an embodiment.

FIG. 4A shows an insert comprising a plurality of therapeutic agents loaded on a first portion of the support structure 120 and a second portion of the support structure 120. The support structure 120 can be configured to reside in the inferior temporal location of the conjunctival sac or other location as described herein. The plurality of therapeutic agents may comprise therapeutic agent 130 contained within matrix 140 and a second therapeutic agent 132 contained within a second matrix 142, for example. The first matrix 140 and second matrix 142 may comprise similar materials, for example silicone elastomer comprising siloxane. While many matrix materials can be used, work in relation to embodiments suggests that known commercially available silicone elastomer from NuSil can be used as the matrix material.

Figure 4B:
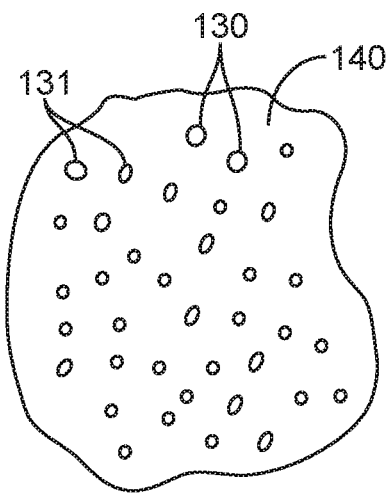
FIG. 4B shows a matrix comprising inclusions of a therapeutic agent, in accordance with an embodiment.

FIG. 4B shows a matrix comprising inclusions 131 of a therapeutic agent 130 in matrix 140. The inclusions 131 may comprise particles of the therapeutic agent such as one or more of solid particles, liquid particles, crystals or droplets of the therapeutic agent within the matrix 140. The solid particles can provide release of therapeutic amounts of the therapeutic agent for an extended time, and the release rate connects can be one of more of zero order release, first order release, or intermediate release rates, or combinations thereof. For example, the release rate can be substantially zero order when the inclusions 131 remain in the matrix and transition to substantially first order when the inclusions have substantially dissolved.

Figure 4C:
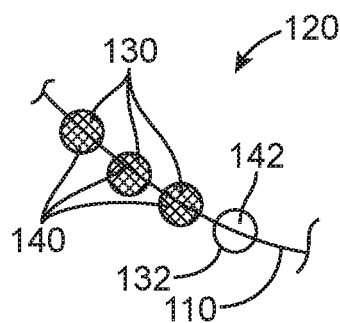
FIG. 4C shows a plurality of support structures comprising a plurality of therapeutic agents placed together on a retention structure at a location corresponding to placement along an inferior temporal portion of the conjunctiva of the eye, in accordance with an embodiment.

FIG. 4C shows support structure 120 comprising a plurality of support structures, in which the plurality of support structures comprise a plurality of therapeutic agents placed together on a retention structure at a location corresponding to placement along an inferior temporal portion of the conjunctiva of the eye. The plurality of support structures can be spaced apart so as to extend a distance 126 on retention structure 120 suitable for placement along the inferior temporal portion of the conjunctival sac as described herein. The plurality of structures may comprise therapeutic agent 130 within matrix 140 to release the therapeutic agent and second therapeutic agent 132 within second matrix 142 to release the second therapeutic agent.

Figure 4D:
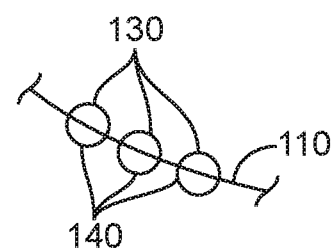
FIG. 4D shows a plurality of support structures along a retention structure, in accordance with an embodiment.

FIG. 4D shows a support structure 120 comprising a plurality of support structures located along retention structure 110 to release the therapeutic agent 130. The plurality of support structures can be shaped in many ways, and may comprise round objects such as spherical balls, or cylinders, for example. The plurality of support structures can extend a distance along retention structure 110 for placement in the inferior temporal location of the conjunctival sac. The plurality of objects may increase the surface area of the matrix to increase the rate of release of the therapeutic agent with the increased surface area, for example.

Figure 4E:
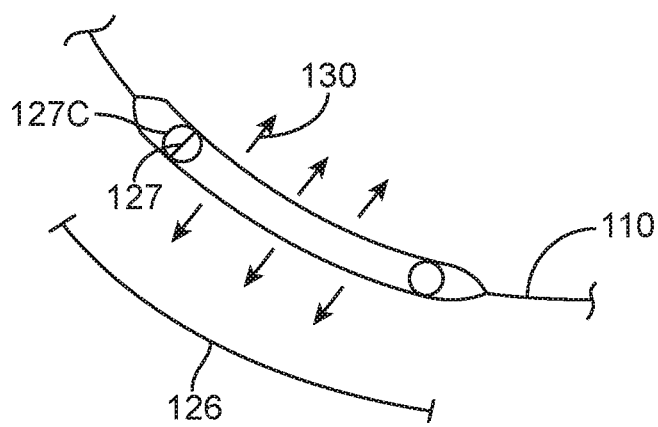
FIG. 4E shows release of a therapeutic agent from a matrix having a surface area sized to treat the patient for an extended time, in accordance with an embodiment.

FIG. 4E shows release of a therapeutic agent from a matrix 140 having a surface area sized to treat the patient for an extended time. The matrix 140 comprises a surface area defined substantially by distance 126 and cross sectional dimension 127, such as a diameter. The cross-sectional dimension may correspond to a distance around the structure 120 such as a circumference 127C. The area of the matrix 140 may correspond substantially to the circumference 127C multiplied by the distance 126.

Figure 4F:
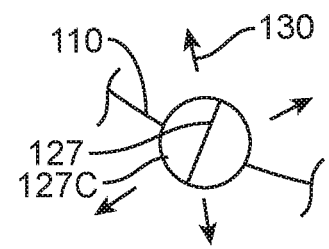
FIG. 4F shows release of a therapeutic agent from a spherical surface of a spherical matrix structure located on a retention structure, in which the spherical surface has an area to release therapeutic amounts of the therapeutic agent for the extended time, in accordance with an embodiment.

FIG. 4F shows release of a therapeutic agent from a spherical surface of a support structure 120 comprising matrix located on a retention structure 110. The spherical surface has an area to release therapeutic amounts of the therapeutic agent for the extended time. The structure 120 comprises dimension across 127, which may comprise a diameter across the spherical structure. The surface area of the matrix can be readily determined in many ways by one of ordinary skill in the art, for example by the relationship: Surface Area=PI*(Diameter)^2.

Figure 4G:
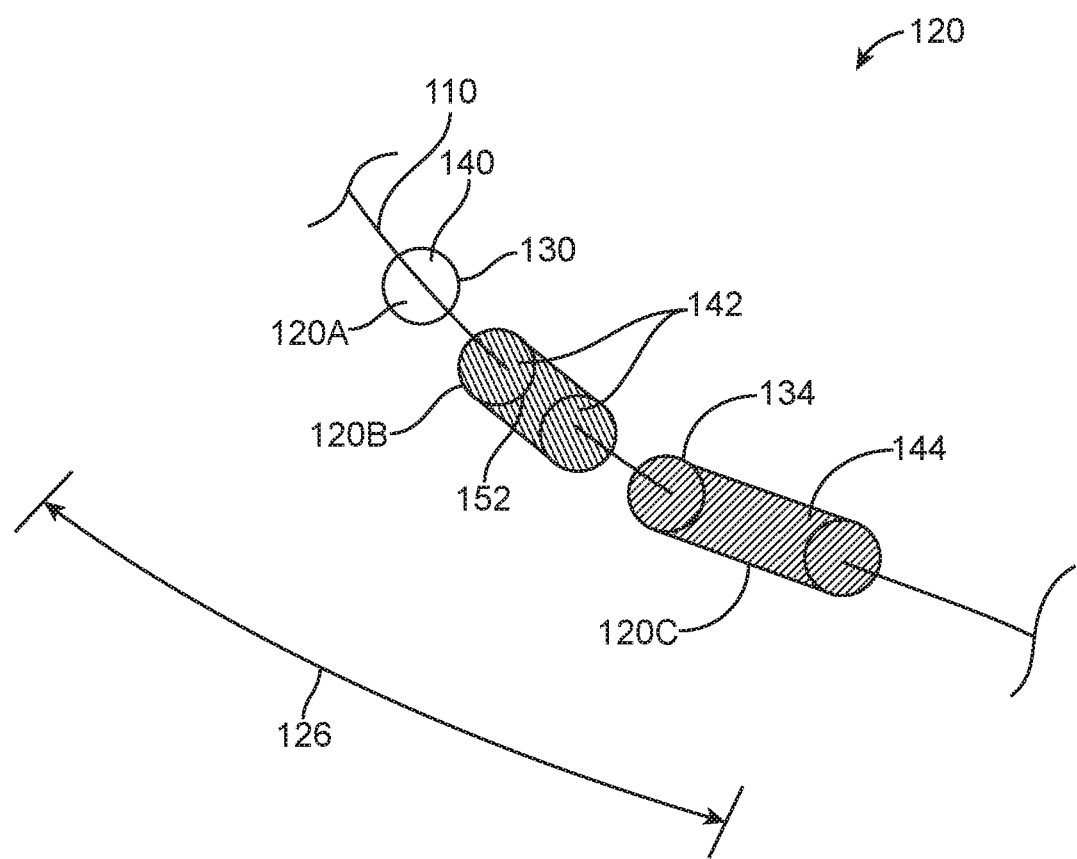
FIG. 4G shows a plurality of at least three support structures along a retention structure comprising a plurality of at least three therapeutic agents, in accordance with an embodiment.

FIG. 4G shows support structure 120 comprising a plurality of at least three support structures along a retention structure comprising a plurality of at least three therapeutic agents. The structure comprising the at least three therapeutic agents can extend a distance 126 for placement in the conjunctival sac, for example within an inferior temporal portion of the sac as described herein. The at least three support structures may comprise a first support structure 120A comprising a first therapeutic agent 130, a second support structure 120B comprising a second therapeutic agent 132 and a third support structure comprising a third therapeutic agent 134. The first therapeutic agent 130 can be contained within first matrix 140, the second therapeutic agent 132 contained within second matrix 142 and the third therapeutic agent 134 contained within third matrix 144. Each of the therapeutic agents may be contained on one or more matrices of one or more support structures.

FIG. 4G-1 shows a plurality of support structures comprising a first therapeutic agent contained within a first matrix and a second therapeutic agent contained within a second matrix. The insert 100 may comprise a support structure 120 comprising a plurality of segments in which each segment comprises a matrix to contain a therapeutic agent. The first segment 120ASA may comprise the first therapeutic agent 130 contained in the first matrix 140 as described herein. The second segment 120BSA may comprise the second therapeutic agent 132 contained in a second matrix 142. The first segment can be separated from the second segment with a separator 120S. The first segment, the second segment, and the separator may comprise similar materials, for example silicone elastomer, such that the first segment and the second segment can bond to the separator. Each of the segments may comprise segments of a ring and be sized to slide along the conjunctival sacs with torsion as described herein. The retention structure 110 may extend through each of the segments and the separator.

The surface area and loading of the therapeutic agent of each segment may correspond to the rate of release of each therapeutic agent. For example, different regions of the insert, for example different segments may have different drugs and surface areas of the matrix for different release rates. The first therapeutic agent may comprise a prostaglandin such as one or more of bimatoprost, latanoprost, or travoprost, and the second therapeutic agent may comprise a beta blocker such as timolol. The beta blocker can be released at a rate that is faster than the prostaglandin, for example within a range from about 5 to 20 times the rate of release of the prostaglandin, for example 10×. The portion of support structure 120 comprising the beta blocker may comprise a proportionally greater surface area to provide the rate of release, for example a surface area that is at least about twice the surface area of the prostaglandin, for example a surface area within a range from about 5 to 20 times the surface area of the prostaglandin. The prostaglandin and the beta blocker may each comprise inclusions within the first or second matrix, respectively.

Each segment comprising the surface area and therapeutic agent may be coated. The coating may comprise a material that readily passes the therapeutic agent, such as a hydrogel. Alternatively, the coating may comprise a material that inhibits release of the therapeutic agent, and a size and number of the holes for each segment configured to release the therapeutic agent at therapeutic rates for an extended time. For example, the size and number of holes of the segment comprising the beta blocker can provide at least about 2 twice the surface area to release the beta blocker, for example at least about 5 to 20 times the surface area to release the beta blocker relative to the prostaglandin. In many embodiments, one or more of the support structure 120 and the retention structure 110 comprise a pre-insertion three dimensional shape profile as described herein, for example to resist deflection away from the inferior bulbar conjunctiva.

FIG. 4G-2 shows a retention structure comprising a ring, in which the ring comprises a plurality of ring segments. The retention structure 110 may comprise the support structure 120 to contain the therapeutic agent 130. The ring segments may comprise different drugs at different rates on single ring. The insert 100 comprising the ring structure may comprise a substantially constant cross-sectional diameter, or a varying cross-sectional diameter as described herein. The insert 100 comprises a first support portion 120A comprising a first therapeutic agent 130, a second support portion 120B comprising a second therapeutic agent 132 and a third portion substantially without therapeutic agent and comprising a retention structure 110. The first portion 120A can be separated from the third portion with a first separator 120S1. The first portion 120A can be separated from the second portion 120B with a second separator 120S2. The second portion can be separated from the third portion with a third separator 120S3. Each of the first portion 120A, the second portion 120B, the third portion, the first separator, the second separator and the third separator may comprise a similar material, for example silicone. The portions can contact the separators so as to bond to the separators when the portions are cured, such that the insert may comprise a plurality of segment portions bonded together with the separators.

FIG. 4G-3 shows an annular insert comprising a retention structure comprising 100 an annular ring and an annular support 120 comprising a matrix 140 of therapeutic agent 130 covering the retention structure. The annular support structure 120 comprises a cross-sectional dimension 127 sized to provide therapeutic amounts of the therapeutic agent for the extended time. The matrix may comprise one or more of many materials as described herein, for example silicon and therapeutic agent.

FIG. 4G-4 shows a cross-sectional view of the retention structure and support structure of FIG. 4G-3. The cross-sectional dimension 117D across the retention structure 110 is sized to provide the resistance to deflection so as to retain the insert within the eye, for example with the hoop strength. The retention structure 110 may comprise one or more of many materials as described herein, such as a silicone having a durometer of at least about 60 A, for example a durometer of 80 A. In many embodiments, the retention structure 110 comprises a durometer less than the durometer of matrix 140.

An insert comprising unitary structure can be utilized with the drug eluting structure and resistance to deflection, as described herein. The unitary insert can be configured so as to provide deflection and drug release as described herein. The insert may comprise inclusions of a therapeutic agent contained in a matrix as described herein. The matrix containing the therapeutic agent may comprise strength and resistance to deflection similar to the insert comprising the skeleton as described herein. The matrix 140 may comprise a support 120 comprising a support material of the matrix. The matrix 140 may comprise a support material having a hardness so as to provide the resistance to deflection as described herein, such that the function of the retention structure can be provided by the matrix 140 without the retention structure, for example. The support material may comprise one or more of a silicone, a poly acrylate, or a polycarbonate for example, having a harness sufficient to provide the resistance to deflection.

The cross-sectional dimension across a portion of the insert can be sized to provide the resistance to deflection so as to retain the insert within the eye, for example with the resistance to self-loading deflection as described herein. The material may comprise a durometer of 50A or more, for example 80 A or more, so as to provide the resistance to deflection. In many embodiments, the unitary insert comprises a silicone material having a durometer of about 80 A or more, and inclusions of the therapeutic agent.

The unitary insert comprising one or more of the resistance to deflection, the resistance to self-loading deflection, the self-loading deflection angle, the torsional resistance twisting, or the hoop strength, or combinations thereof as described herein, can be combined with any one or more shapes or structures as described herein. For example, the unitary insert may comprise the one or more of self-loading resistance to deflection, the self-loading deflection angle, the hinges, the 3D shape profile, the bias, the curved bias, or the dual durometer upper and lower portions, for example, with reference to Tables 1A to 1D and FIGS. 2A to 2Z7, for example.

FIG. 4H shows an insert 100 comprising a support structure 120 comprising an at least partially erodible structure 170 comprising an erodible material 176 to release a therapeutic agent 130 for an extended time. The erodible structure 170 can be coupled to the retention structure 110 as described herein.

FIG. 4I shows a transverse cross sectional view of the at least partially erodible structure 170 comprising the erodible material 176 as in FIG. 4H. A barrier material 174 is shaped to define a chamber 172 of the support structure 120. A channel 173 extends from chamber 172 to an opening to release the therapeutic agent. The channel 176 can be blocked with an erodible material to inhibit release of the therapeutic agent 130 contained in the chamber. When material 176 erodes, the channel 173 opens to release the therapeutic agent.

FIG. 4J shows a side cross sectional view of the structure 170 comprising the erodible material 176 as in FIGS. 4H and 4I. A plurality of chambers may contain therapeutic agent 130, and the plurality of chambers may comprise a first chamber 172 and a second chamber 174. The erodible material may be located on a substantially non-erodible support, such as a substrate 178, and the erodible material occupy a channel defined with a substantially non-erodible material, such that the material erodes along an exposed surface of the material. The substrate 178 can be positioned on a first side of the erodible material and the plurality of chambers on a second side of the erodible material so as to define an erosion path 179. The erosion path may comprise a linear path, and the containers may comprise openings arranged along the linear path to release the therapeutic agent from each container in sequence. The erosion path can be linear, for example straight, or curved. The erosion path can be arranged to sequentially release the therapeutic agent from each of the plurality of chambers, for example from the first chamber first and the second chamber second. Alternatively, the order can be reversed. The rate of erosion and spacing of the chambers can be arranged so as to release an amount of the therapeutic agent at substantially regular intervals, for example daily. The plurality of chambers and erodible material can be arranged in many ways to release the therapeutic agent at regular intervals for an extended time of at least one week, for example one month or more such as an extended time of two or more months. For example, the plurality of chambers may comprise 90 chambers to release a therapeutic amount each day for at least about three months. The plurality of chambers may comprise 180 or more chambers to provide the extended release for at least about 6 months, for example. The sizing of the chambers and spacing can be manufactured in many ways, for example with nano-technology and etching to form the chambers and deposition to form the erodible material.

FIG. 4K shows a reservoir chamber having channel 173 occluded with erodible material 176 as in FIGS. 4H to 4J.

FIG. 4L shows the container as in FIG. 4K having the material 176 eroded away from the channel to release the therapeutic agent 130 from the reservoir chamber.

FIG. 4M shows a pump 180 to release a therapeutic agent 130 with pulsatile flow. The pump 180 may comprise one or more of many pumps such as an osmotic pump 182, and active pump such as a micro-electro-mechanical (hereinafter "MEMS") pump. The pump can be configured to provide pulsatile flow at regular intervals so as to release the therapeutic agent 130 at regular intervals.

The pump 180 may comprise an osmotic pump 182 coupled to a valve 186 configured to open at regular intervals. The pump 180 can be coupled to a chamber 183 enclosed with an elastically expandable barrier material such as an elastic membrane 184 so as to contain therapeutic agent 130. The chamber 183 can swell in volume in response to increased pressure so as to elastically stretch the membrane 184. The valve 186 can open in response to increased pressure of the chamber 183 so as to release a pulsatile amount of therapeutic agent 130 from the chamber 183 into the eye.

FIG. 4N shows a release profile of therapeutic agent 130 of the pump 180 as in FIG. 4M. The release profile corresponds to an amount of therapeutic agent released over a time. The pulsatile release profile may comprise a bolus of therapeutic agent released at substantially regular intervals, for example approximately twice per day. The bolus of therapeutic agent 130 can be released at the substantially regular intervals for at least about one month, for example at least about two or more months. In many embodiments, the therapeutic amounts of the therapeutic agent can be released with pulsatile flow at substantially regular intervals for at least about 3 months (90 days), for example 4 months, or 6 months or more.

FIG. 4O shows a pressure profile of a chamber of the pump as in FIGS. 4M and 4N. When the pressure in the chamber reaches a threshold amount, the valve 186 can open substantially so as to release a therapeutic amount of the therapeutic agent 130 with pulsatile flow as shown with one of the peaks of the profile of FIG. 4N.

Figure 4P:
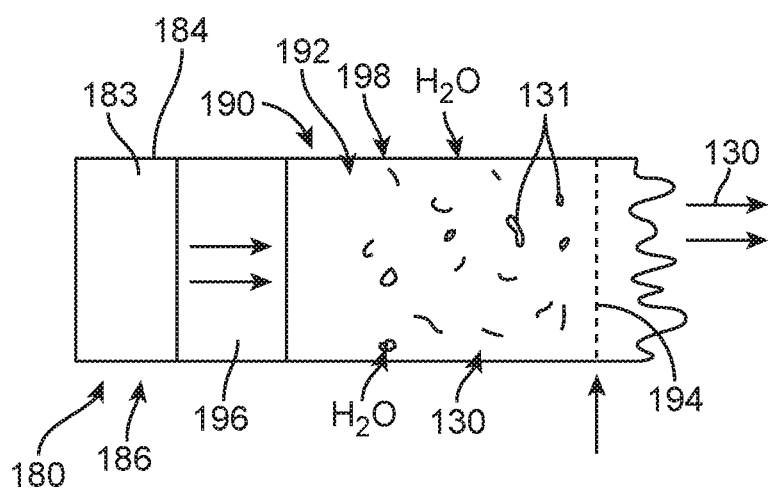
FIG. 4P shows reservoir chamber comprising inclusions of a therapeutic agent coupled to an osmotic pump with a piston so as to release therapeutic agent with pulsatile flow, in accordance with an embodiment.

FIG. 4P shows a container 190 comprising inclusions 131 of a therapeutic agent coupled to an osmotic pump 180 with a movable or deflectable component 196 such as one or more of a piston or a diaphragm, so as to release therapeutic agent with pulsatile flow. The container may comprise a material 198 to inhibit release of the therapeutic agent. The material 198 may extend substantially around the container 190 so as to define a chamber 192. The chamber 192 may have a reservoir of therapeutic agent contained therein. The pump 180 may comprise the osmotic pump 182 coupled to a valve 186 such that the valve 186 can open to advance the movable or deflectable component 196 with pressure. The movable or deflectable component 196 may comprise a piston that can be advanced toward chamber 192 with deflection so as to decrease a volume of the chamber and release therapeutic agent 130 from the chamber 192 with pulsatile flow, for example. The movable or deflectable component 196 may comprise a diaphragm that can be advanced toward chamber 192 with deflection so as to decrease a volume of the chamber and release therapeutic agent 130 from the chamber 192 with pulsatile flow, for example.

The container 190 can be configured in many ways to release the therapeutic amounts of the therapeutic agent 130 with pulsatile flow. The container 190 may contain inclusions 131 of therapeutic agent 130 that is nearly insoluble in water, for example a prostaglandin such as latanoprost or bimatoprost. The pulsatile flow of the pump can increase the pressure to the container 190 with coupling of the movable or deflectable component 196. The pressure pulse can decrease the volume of the chamber such that the therapeutic agent is released from the container with pulsatile flow. The chamber 192 can be substantially defined with a material 198 such that the volume of the chamber 192 decreases when the movable or deflectable component 196 such as a piston advances toward chamber 192. In many embodiments, at least a portion of the chamber comprises a porous structure having pores sized to release molecules of the therapeutic agent and substantially inhibit release of the inclusions of the therapeutic agent, such that molecules of the therapeutic agent can be released with the pulse and release of the inclusions substantially inhibited.

Figure 4Q:
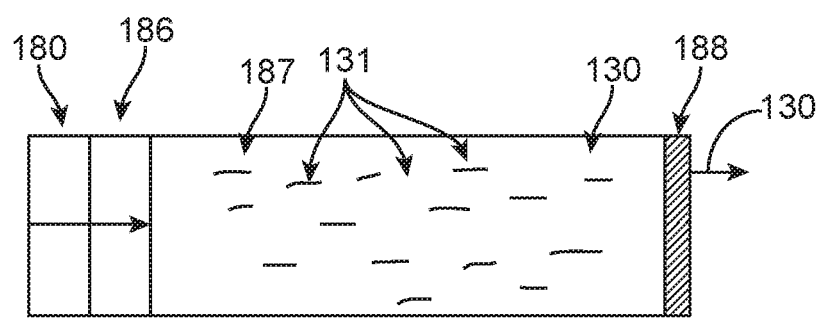
FIG. 4Q shows reservoir chamber comprising inclusions of a therapeutic agent coupled to valve of an osmotic pump so as to release therapeutic agent with pulsatile flow, in accordance with an embodiment.

FIG. 4Q shows reservoir chamber comprising inclusions of a therapeutic agent coupled to valve of an osmotic pump so as to release therapeutic agent with pulsatile flow.

An insert can comprise a retention structure and a support structure comprising a reservoir chamber to contain a therapeutic agent and a passive diffusion release mechanism to release the therapeutic agent 13. The retention structure may comprise one or more of the retention structure components as described herein, for example a wire. The support structure may comprise one or more support structures as described herein, for example a container comprising a chamber to contain therapeutic agent. The support structure may comprise one or more mechanisms to release the therapeutic agent with controlled diffusion, for example one or more holes in the container extending to the chamber. The support structure may comprise metal, for example, and the retention structure may comprise metal that can be fastened to the metallic support structure in one or more of many ways, for example with welding. The retention structure may comprise the resistance to deflection as described herein to retain the insert within the eye, for example.

An insert can comprise a retention structure and a support structure comprising a reservoir chamber to contain a therapeutic agent and a mechanism to release the therapeutic agent in response to blinking of the eye. The reservoir chamber may comprise a wall that can be one or more of folded, rolled or compressed, such that pressure exerted when the eye blinks can be transmitted to the reservoir chamber so as to release the therapeutic agent. The mechanism to release the therapeutic agent 130 may comprise one or more mechanisms capable of releasing the therapeutic agent in response to pressure, such as a plurality of openings, a valve, or a membrane, for example. The mechanism can be coupled to the wall of the reservoir chamber so as to release therapeutic agent in response to blinking of the eye.

The insert configured to release therapeutic agent in response to blinking can have the benefit of providing additional therapeutic agent as needed. For a patient having dry eye, the patient is more likely to blink when the eye has less hydration and less likely to blink when the eye has more liquid. By providing a therapeutic agent released in response to blinking, the patient can receive a greater amount of therapeutic agent when the eye is dry and more therapeutic agent is appropriate, and the eye can receive less therapeutic agent when the eye is hydrated and additional therapeutic agent of lesser benefit. The therapeutic agent may comprise one or more of many therapeutic agents suitable for treating the eye as described herein, and in many embodiments suitable for treating dry eye such as one or more of a lipid, a phospholipid, an oil, or a silicone oil, for example.

The insert configured to release therapeutic agent in response to blinking can be configured to release therapeutic agent in response to the patient pressing on the insert, for example, such that the patient can administer additional therapeutic agent as appropriate.

Figure 5A:
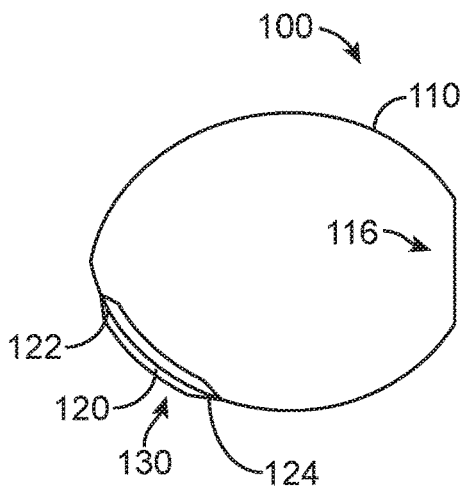
FIG. 5A shows an insert comprising a lentoid retention structure having an end portion shaped to inhibit contact with the caruncle of the eye when the support structure comprising the therapeutic agent is placed on the inferior temporal location of the eye, in accordance with an embodiment.

FIG. 5A shows an insert comprising a lentoid retention structure 110 having an end portion 116 shaped to inhibit contact with the caruncle of the eye when placed on the eye when the support structure 120 comprising the therapeutic agent 130 is placed on the inferior temporal location of the eye. The end portion 116 can be shaped in many ways to inhibit contact with the caruncle and may comprise an indent, for example. The support structure 120 may comprise a crescent profile comprising first inclined surface of first tapered end portion 122 and second inclined surface of second tapered end portion 124 as described herein. The lentoid structure may comprise an upper curved portion for placement under the upper lid and a lower curved portion curved for placement under the lower lid, and the radius of curvature of each of the upper curved surface and the lower curved surface can be dimensioned to correspond with dimensions of the upper fornix and lower fornix, respectively.

Figure 5B:
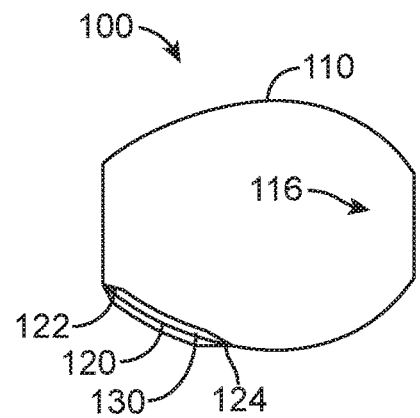
FIG. 5B shows an insert comprising a lentoid retention structure having decreased width to inhibit contact with the caruncle of the eye when the support structure comprising the therapeutic agent is placed on the inferior temporal location of the eye, in accordance with an embodiment.

FIG. 5B shows an insert 100 comprising a lentoid retention structure 110 having end portion 116 and decreased width to inhibit contact with the caruncle of the eye when placed on the eye when the support structure 120 comprising the therapeutic agent 130 is placed on the inferior temporal location of the eye.

Figure 5C:
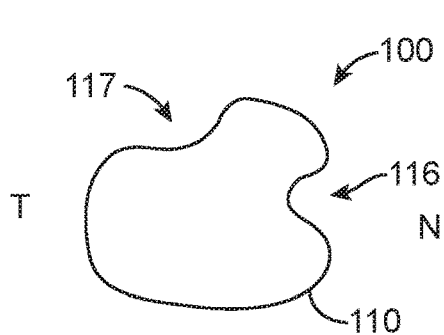
FIG. 5C shows an insert comprising a retention structure shaped with an inward extension to inhibit irritation of the lacrimal gland and an inward extension to inhibit contact with the caruncle of the eye, in accordance with an embodiment.

FIG. 5C shows insert 100 comprising a retention structure 110 shaped with an inward extension 117 to inhibit irritation of the lacrimal gland and an inward extension 116 to inhibit contact with the caruncle of the eye. The extension 117 can extend a distance so as to inhibit contact and engagement of the conjunctival tissue over the lacrimal gland, and the distance may correspond to about 90 degrees around the pupil of the eye, for example. The extension 117 can deflect inward, or outward, from the retention structure, for example. The extension 116 can extend a distance so as to inhibit contact and engagement of the retention structure 110 with the caruncle, and the distance may correspond to about 90 degrees around the pupil of the eye, for example. The extension 116 can deflect inward, or outward, from the retention structure, for example.

Figure 5D:
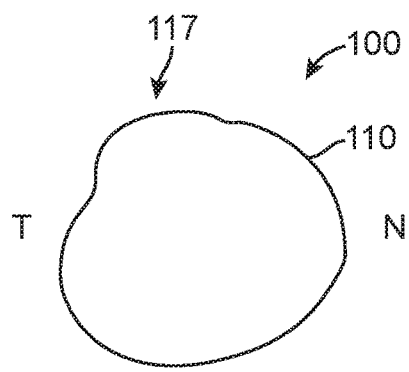
FIG. 5D shows an insert comprising a retention structure shaped with an outward extension to inhibit irritation of the lacrimal gland of the eye, in accordance with an embodiment.

FIG. 5D shows an insert 100 comprising a retention structure 110 shaped with an outward extension 117 to inhibit irritation of the lacrimal gland of the eye.

Figure 5E:
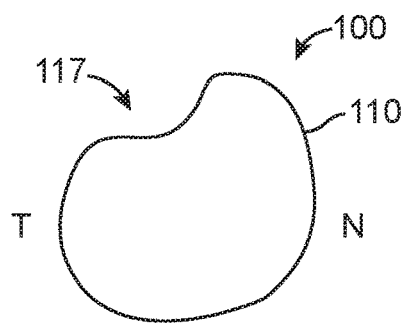
FIG. 5E shows an insert comprising a retention structure shaped with an inward extension to inhibit irritation of the lacrimal gland of the eye, in accordance with an embodiment.

FIG. 5E shows an insert 100 comprising a retention structure 110 shaped with an inward extension 117 to inhibit irritation of the lacrimal gland of the eye.

Figure 5F:
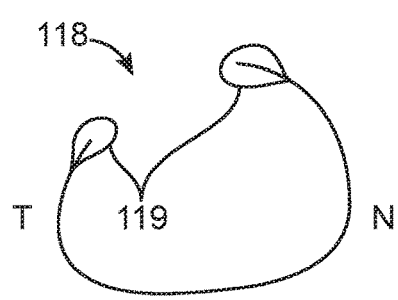
FIG. 5F shows an insert comprising a retention structure having an open end portion to inhibit irritation of the lacrimal gland of the eye, in accordance with an embodiment.

FIG. 5F shows an insert 100 comprising a retention structure 110 having an open end portion 118 to inhibit irritation of the lacrimal gland of the eye. The open end portion 118 comprises a first end 119 and a second end 119 having a gap extending there between to inhibit contact of the tissue near the lacrimal gland. The gap may correspond to about ninety degrees of arc around the globe so as to inhibit contact with the tissue near the lacrimal gland. The first end 119 and the second end 119 may comprise an increase cross sectional size in relation to the elongate portion of the retention structure to inhibit penetration of the epithelium, for example.

Figure 5G:
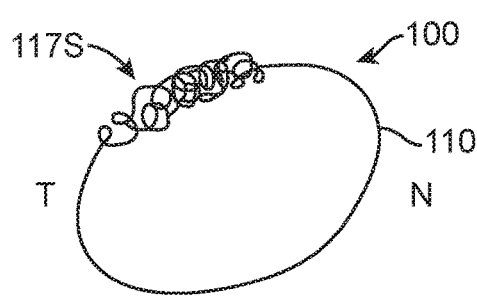
FIG. 5G shows an insert comprising a retention structure having a soft material to inhibit irritation of the lacrimal gland and the caruncle of the eye, in accordance with an embodiment.

FIG. 5G shows an insert 100 comprising a retention structure having a soft material 117S to inhibit irritation of the lacrimal gland and the caruncle of the eye. The soft material 117S may comprise a hydrogel or other soft material, for example. The soft material 117S may extend over an elongate portion of the retention structure 110, or the retention structure 110 may comprise a first end and a second end as described herein having the soft material extending between the first end and the second end.

Figure 5H:
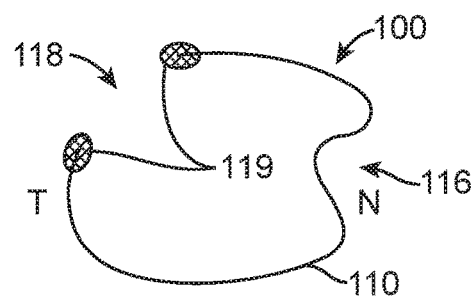
FIG. 5H shows a retention structure comprising an open end portion to inhibit irritation of the lacrimal gland and an inward extension portion to inhibit contact with the caruncle of the eye, in accordance with an embodiment.

FIG. 5H shows a retention structure 100 comprising an open end portion 118 to inhibit irritation of the lacrimal gland and an inward extension 116 to inhibit contact with the caruncle of the eye.

Figure 5I:
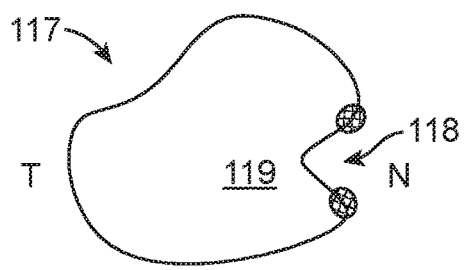
FIG. 5I shows a retention structure comprising an inward extension portion to inhibit contact irritation of lacrimal gland and an open end portion to inhibit contact with the caruncle of the eye, in accordance with an embodiment.

FIG. 5I shows a retention structure 100 comprising an inward extension 117 to inhibit contact irritation of lacrimal gland and an open end portion 118 to inhibit contact with the caruncle of the eye.

The retention structure 110 as described herein can be combined with one or more of the support structure 120, the therapeutic agent 130 and the matrix 140 in many ways. When the retention structure 110 having the one or more portions to inhibit irritation of one or more of the caruncle or the lacrimal gland is placed, the support structure 120 can be located at one or more of a superior location under the upper lid, an inferior location under the lower lid, an inferior temporal location under the lower lid, an inferior nasal location under the lower lid, a temporal location under one or more of the upper lid or the lower lid, and combinations thereof.

Figure 5J:
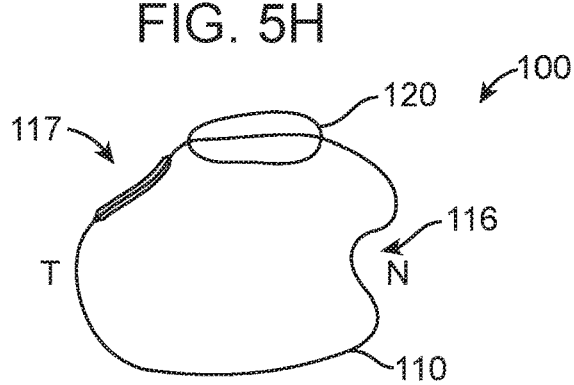
FIG. 5J shows an insert comprising a retention structure shaped with an inward extension to inhibit irritation of the lacrimal gland and an inward extension to inhibit contact with the caruncle of the eye, in which the support structure is located on the retention structure so as to correspond with a superior placement under the superior eyelid, in accordance with an embodiment.

FIG. 5J shows an insert 100 comprising a retention structure 110 shaped with an inward extension 117 to inhibit irritation of the lacrimal gland and an inward extension 116 to inhibit contact with the caruncle of the eye, in which the support structure 120 is located on the retention structure 110 so as to correspond with a superior placement under the superior eyelid.

The retention structures as described herein, for example with reference to FIGS. 5A to 5J, may comprise a 3D shape elevational profile prior to placement corresponding to the retention structure placed on a spherical surface having a radius of curvature corresponding to the eye of the patient, and the retention structure can be configured to retain substantially the pre placement shape and resist deflection away from the pre placement shape.

Figure 6A:
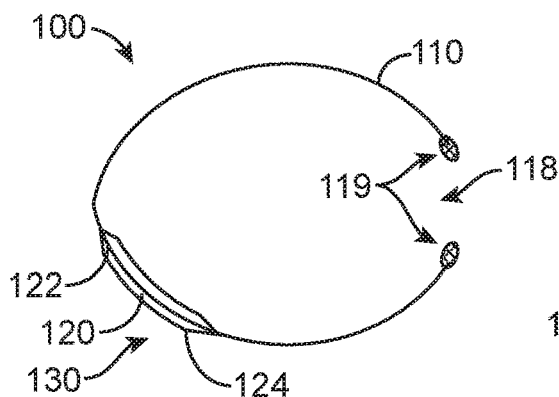
FIG. 6A shows an insert comprising a lentoid retention structure having an open end portion to inhibit contact with the caruncle of the eye when placed on the eye with the support structure comprising the therapeutic agent placed on the inferior temporal location, in accordance with an embodiment.

FIG. 6A shows an insert 100 comprising a lentoid retention structure 110 having an open end portion 118 to inhibit contact with the caruncle of the eye when placed on the eye with the support structure 120 comprising the therapeutic agent 130 placed on the inferior temporal location as described herein. The open end portion 118 can fit many sizes of eyes with one retention structure and may facilitate sizing and placement of insert 100. The open end portion 118 can be sized to inhibit contact with one or more of the lacrimal gland or the caruncle, for example.

Figure 6B:
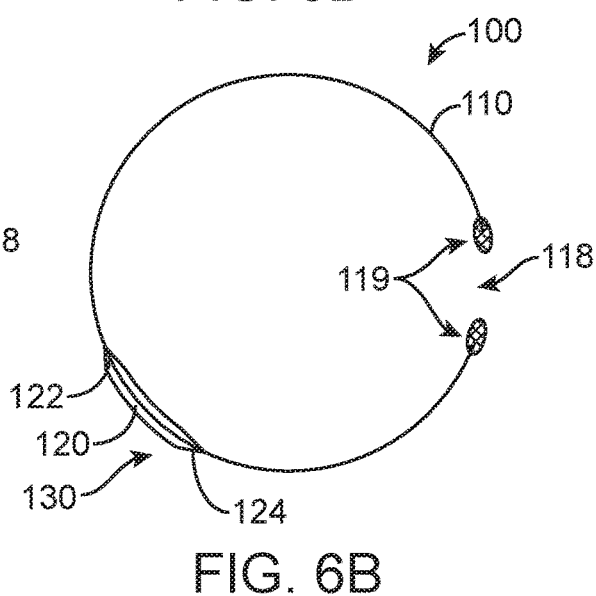
FIG. 6B shows an insert comprising a circular retention structure having an open portion to inhibit contact with the caruncle of the eye when placed on the eye with the support structure comprising the therapeutic agent placed on the inferior temporal location of the eye, in accordance with an embodiment.

FIG. 6B shows an insert 100 comprising a circular retention structure 110 having an open portion to inhibit contact with the caruncle of the eye when placed on the eye with the support structure 120 comprising the therapeutic agent 130 placed on the inferior temporal location of the eye as described herein. The open end portion 118 can fit may sizes of eyes with one retention structure and may facilitate sizing and placement of insert 100. The open end portion 118 can be sized to inhibit contact with one or more of the lacrimal gland or the caruncle, for example.

Figure 6C:
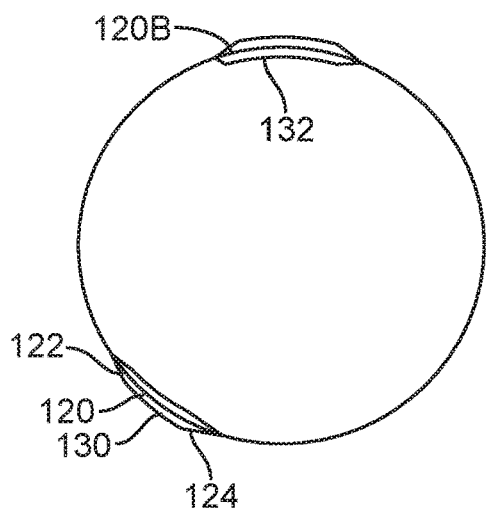
FIG. 6C shows an insert comprising a round retention structure having first support structure comprising a first therapeutic agent at a first location corresponding to an inferior temporal location of the eye and a second support structure comprising a second therapeutic agent at a second location corresponding to a superior location of the eye, in accordance with an embodiment.

FIG. 6C shows an insert 100 comprising a round retention structure having first support structure 120 comprising a first therapeutic agent 130 at a first location corresponding to an inferior temporal location of the eye and a second support structure 120B comprising a second therapeutic agent 132 at a second location corresponding to a superior location of the eye.

Figure 6D:
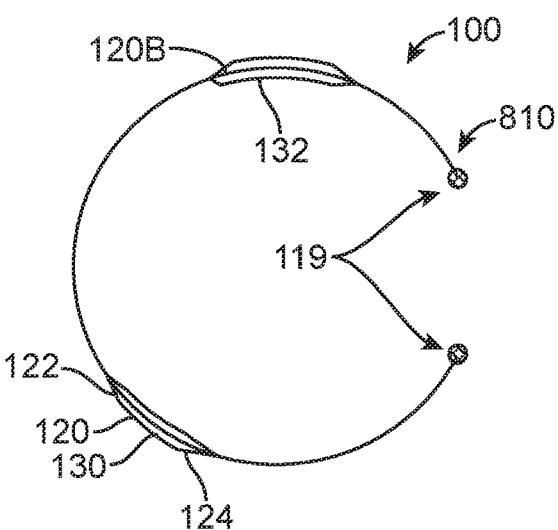
FIG. 6D shows an insert comprising a round retention structure having an open end and a first support structure comprising a first therapeutic agent at a first location corresponding to an inferior temporal location of the eye and a second support structure comprising a second therapeutic agent at a second location corresponding to a superior location of the eye, in accordance with an embodiment.

FIG. 6D shows an insert comprising a round retention structure having an open end and a first support structure 120 comprising a first therapeutic agent 130 at a first location corresponding to an inferior temporal location of the eye and a second support structure 120B comprising a second therapeutic agent 132 at a second location corresponding to a superior location of the eye. The retention structure may comprise end portions 119, and the end portions 119 may have a cross sectional dimension greater than the elongate portion of retention structure 110 so as to inhibit penetration of the epithelium and into the conjunctival tissue of the eye, for example. Alternatively, the end portions 119 may comprise a cross sectional size similar to the elongate portions retention structure 110, for example when the cross sectional dimension 112 of the elongate portion of retention structure 110 comprises at least about 0.5 mm, for example.

The embodiments as described herein and in particular with reference to FIGS. 5A to 6D can be configured in many ways, and may comprise a 75 degree, a 180 degree or a 360 degree drug release element, for example. The inserts can be fully coated or may comprise a 360 degree or greater drug release element as described herein, for example. In many embodiments, the insert can be coated with a cushioning material, for example a soft silicone or hydrogel.

Work in relation to embodiments suggests that it can be helpful to fit the retention structure 110 to the patient, or identify an insert 100 having an appropriately sized retention structure. The retention structure 110 of insert 100 can be identified based on measurement of one or more of a circumference of the head of the patient, a dimension between eyes of the patient, a depth of the upper fornix, a depth of the lower fornix, a distance extending between a lateral canthus and a medial canthus of the eye, a distance extending between a cul-de-sac of the eye and a limbus of the eye, a dimension of the orbit, or a fornix depth measured with a fornicometer. For example, a dimension of a physical characteristic of a population of patients can be measured, and one or more inserts placed in each member of the population to determine empirically the size of the insert corresponding to the measured dimension such that a patient can be fit with the measured insert. A fornicometer to measure fornix depth and area is described in "Measurement of fornix depth and area: a novel method of determining the severity of fornix shortening", Kawakita et al., Eye (2009) 23, 1115-1119. While non-limiting examples are shown in accordance with embodiments as described herein, a person of ordinary skill in the art can determine many suitable patient measurements to fit retention structure 110 of insert 100 to an eye of the patient based on the teachings described herein.

The retention structures as described herein, for example with reference to FIGS. 6 to 8, may comprise a 3D shape elevational profile prior to placement corresponding to the retention structure placed on a spherical surface having a radius of curvature corresponding to the eye of the patient, and the retention structure can be configured to retain substantially the preplacement shape and resist deflection away from the preplacement shape.

FIGS. 7A and 7B show plan and side cross-sectional views, respectively, of an insert 100 comprising an outer retention structure 110 having a resistance to deflection to remain within the eye for an extended time. The insert 100 may comprise inclusions 131 of therapeutic agent 130 contained within a matrix 140 as described herein. The matrix 140 may comprise a soft material, for example a soft silicone, liquid, or other material contained within the retention structure 110. The retention structure 110 may comprise a material having a higher durometer than the matrix material, for example. The retention structure 110 may comprise a material to inhibit release of the therapeutic agent, and a plurality of holes 110H may extend through the retention structure to release the therapeutic agent.

In many embodiments, the matrix 140 comprises a soft material, and the retention structure 110 comprises a coating placed on the soft matrix material comprising the inclusions 131 of the therapeutic agent. The coating can be placed on the matrix in many ways and may comprise one or more of a dip coating or a vapor coating. The coating may comprise one or more of luminous vapor deposition of silicone in layers, or hydrogel dip coating, for example. A soft cushioning coating or other coating as described herein can be provided over the surface of the retention structure.

The retention structure 110 can be configured to provide a resistance to deflection so as to maintain placement of the insert in the eye, for example one or more of a deflection resistance or a hoop strength as described herein. The thickness of and diameter of the retention structure can be dimensioned so as to provide the resistance to deflection.

FIGS. 7C and 7D show plan and side cross-sectional views, respectively, of an arcuate C-shaped insert comprising an outer retention structure having a resistance to deflection to remain within the eye for an extended time. The C-shaped insert may comprise many components of the insert described above with reference to FIGS. 7A and 7B. The C-shaped insert may comprise a resistance to inward deflection, for example a spring force, such that the insert can resist being urged inward by the eyelids so as to inhibit movement of the insert toward the cornea when the eye blinks. The C-shaped insert can be sized and provided with spring force so as to urge outward against the upper and lower fornices of the eye to retain the insert. Alternatively, the insert can be placed substantially in the upper fornix or the lower fornix and have its forces directed at temporal and nasal directions, for example. The insert may comprise a gap distance extending between ends of the insert, and the gap distance can decrease slightly in response to inward force of the eyelids and increase so as to urge the upper and lower fornices apart slightly.

The embodiments as described herein and in particular with reference to FIGS. 7A to 7D can be configured in many ways, and may comprise portions configured with the drug release and may comprise a 75 degree, a 180 degree or a 360 degree drug release element for example. The inserts can be fully coated or may comprise a 360 degree or greater drug release element, for example. In many embodiments, the insert can be coated with a cushioning material, for example a soft silicone or hydrogel.

FIG. 8A shows treatment 850 of a retention structure 110 of an insert 100 to increase a resistance to deflection of the retention structure. The insert 100 can be placed in the eye 10 with the retention structure 110 comprising a compliant configuration. The retention structure 110 comprises a shape corresponding to the shape of the eye, and the retention structure 110 is treated. The shape of the compliant retention structure may correspond to the shape of the conjunctival sac and the one or more folds as described herein, for example. The retention structure 110 can be treated in many ways, for example with energy or water of the eye to increase the resistance to deflection.

FIG. 8B shows in situ forming of a retention structure of an insert comprising an in situ formable material. The insert may comprise a first configuration having dimension 114A in an unloaded configuration prior to placement such as a diameter across as described above, and a second configuration comprising a shorter dimension 114B and a longer dimension 114C when placed in the eye as described above. When the insert comprises the second configuration, the insert can initially exert a force in response to deflection such that the retention structure exerts an outward force toward the fornices of the conjunctiva. When the insert has been left in the eye for an amount of time, the insert may be formed so as to comprise an in situ formed third configuration such that the insert comprises shorter dimension 114D and longer dimension 114E. When the insert is removed the insert may retain substantially the shape of the third configuration, for example. When the insert comprises the formed third configuration, the insert may resist deflection away from shorter dimension 114D and longer dimension 114E. The in situ formed configuration may comprise one or more of many shapes such as an oval, an ellipse, a saddle, or combinations thereof, for example. The in situ formed configuration may comprise at least a portion of retention structure 110 extending away from a plane corresponding to other portions of the retention structure, for example when the in situ formed retention structure is placed on a planar surface with at least a portion extending away from the surface as described herein.

The in situ formable material may comprise one or more of polypropylene or a known in situ formable material.

FIG. 8C shows a flowable material 140F placed on the eye to form at least a portion of the insert 100.

The in situ formable insert can be formed in many ways. The in situ formable insert can be formed by placing a liquid or flowable material 140F on the conjunctiva 50 of the eye 10 at a location corresponding to the intended location of the insert, for example away from the cornea 12 along the cul-de-sac. The flowable material can be placed in many ways on the conjunctiva, for example along a portion of the cul-de-sac, along a substantially arcuate path along a majority of the cul-de-sac, along at least a portion of both cul-de-sacs, or in a C-shaped oval or other shape as described herein. The amount of flowable material placed may comprise a predetermined amount, and the concentration of therapeutic agent in the flowable material 140F may comprise a predetermined concentration, such that the amount of flowable material placed on the eye comprises a predetermined amount of material and a predetermined amount of therapeutic agent so as to release therapeutic amounts for an extended time as described herein. The liquid or flowable material 140F may comprise a therapeutic agent 130 and a support material that can cure to form a matrix, for example. The liquid or flowable material can solidify so as to form the insert having one or more of the retention structure or the matrix as described herein. For example, the insert may comprise the unitary insert comprising the matrix material having the self-loading resistance to deflection as described herein. The flowable material can be injected into the cul-de-sac of the eye and allowed to solidify, for example.

Examples of flowable materials capable of solidifying on the eye are published in U.S. patent application Ser. No. 12/704,692, entitled "Drug Delivery Through Hydrogel Plugs", Published as US2010/0209478A1, the entire disclosure of which is incorporated herein by reference and suitable for combination in accordance with at least some embodiments described herein. The amount of flowable matrix material 140F placed on the eye can be sufficient so as to provide an amount of therapeutic agent in accordance with embodiments as described herein, for example. Alternatively or in combination, the flowable matrix material 140F can be shaped so as to provide the surface area of the matrix comprising solidified flowable material for sustained release for the extended time as described herein. The flowable matrix material can be combined with a retention structure as described herein, for example combined with the retention structure before placement or after placement on the eye. The flowable matrix material can be coated or provided in a retention structure or on a retention structure as described herein, for example.

FIG. 8D depicts syringe system 300 with barrel 302, needle hilt 303, needle 304 with rounded tip 306 having outlet 308 and plunger 310 with pusher 312. The amount of therapeutic agent placed can be sufficient so as to provide therapeutic amounts for an extended time as described herein, for example with a substantial amount extra amount of therapeutic agent removed from the eye upon completion of treatment as described herein. A solution of hydrogel precursors 314 and therapeutic agent may be placed in barrel 302 and dispensed through needle 304 and out outlet 308. One embodiment of syringe system includes alternative needle with a hydrophobic coating that produces a high contact angle between the needle and precursor solution to assist forming drop and/or assist in leaving the solution after it is placed in the patient by virtue of the resistance of the needle to spreading of solution. The amount of therapeutic precursor material placed may comprise a predetermined volume of flowable material so as to provide a predetermined amount of therapeutic agent.

FIG. 8E depicts syringe system 300 being used to introduce hydrogel precursors 314 into the cul-de-sac 53, for example into the fornix 54, with the precursors being left in on or more of the cul-de-sac or the fornix, for example. The precursors form covalent bonds with each other to create a crosslinked hydrogel insert 100 as described herein. The insert 100 can swells as fluids are imbibed from its surroundings. The introduction of hydrogel precursors in a fluid state with subsequent formation of the hydrogel is referred to as in situ formation of the hydrogel because the hydrogel is created at the site of its intended use.

The hydrogel may contain linkage which gradually hydrolyze in the presence of water at a predetermined rate, gradually sloughing off in the patients tears. The hydrogel is composed substantially of water and polyethylene glycol (PEG), widely considered an inert and biocompatible material. Additional description of hydrogel materials and therapeutic agent delivery are available on the world wide web at the website of Ocular Therapeutix (ocutx.com).

The amount of therapeutic agent that be placed on the eye can be much larger than a punctual plug device, for example. In many embodiments, the flowable material 140F comprising the formulation is non-absorbable.

FIG. 9 shows a kit 600 comprising a plurality of retention structures having incrementally increasing sizes to determine a size of the retention structure to fit the patient. The kit may comprise a first insert having a first retention structure 110A having a first maximum dimension across such as a first diameter, a second retention structure 110B having a second maximum dimension across such as a second diameter, a third retention structure 110C having a third maximum dimension across such as a third diameter, and a fourth retention structure 110D comprising a fourth maximum dimension across such as a fourth diameter, for example. The retention structures can be sized in many ways and comprise a plurality of diameters, for example of 22 mm, 23 mm, 24 mm, 25 mm, 26 mm, 27 mm, 28 mm, 29 mm, and 30 mm. When a retention structure 110 among the plurality has been appropriately fit to the eye, an insert 100 can be identified from among a plurality of inserts and placed in the eye. When the insert 100 comprises support structure 120 the kit 600 can be configured such that the first retention structure 110A comprises first support structure 120A similar to support structure 120, the second retention structure 110B comprises second support structure 120B similar to support structure 120, the third retention structure 110C comprises third support structure 120C similar to support structure 120, and the fourth retention structure 110D comprises fourth support structure 120D similar to support structure 120 of insert 100, for example.

The ring structures of FIG. 9 may comprise a 3D shape elevational profile prior to placement corresponding to the retention structure placed on a spherical surface having a radius of curvature corresponding to the scleral portion of the eyeball of the patient, and the retention structure of the kit may comprise 3D shape profiles corresponding to a plurality of radii Rb of the eyeball of the patient, for example radius Rb corresponding to 20 mm, 21 mm, 22 mm, 23 mm, 24 mm, 25 mm, 26 mm, 27 mm, 28 mm, 29 mm and 30 mm.

FIG. 10 shows a measurement apparatus 710 having markings 720 to measure a dimension of structure of the patient to determine a corresponding size of the retention structure to fit the patient. The patient can be measured in many ways, and one or more measurements of the patient may correspond to the size of the retention structure that fits the patient. For example, a size of the palpebral fissure PF extending between the lateral canthus and medial canthus can be measured and may correspond substantially to the size of the retention structure to fit the patient. The dimension of the palpebral fissure can be measured with a ruler, for example, and the size of the retention structure can be determined based on the dimensions of the palpebral fissure. A nomogram can receive as input the dimensions of the palpebral fissure and provide as output an identification of the insert, such that retention structure for placement on the patient can be identified based on the measured patient dimension. Based on the teachings described herein, a person of ordinary skill in the art can determine empirically the correspondence between the measured dimension of the patient and the size of retention structure such that the nomogram can be provided to identify the size of the retention structure based on the measured dimension of the patient such as the palpebral fissure.

Alternatively, the measurement apparatus 710 may comprise a curved structure sized to extend from a lateral canthus of the eye and a medial canthus of the eye. The curved structure may comprise markings corresponding to widths of a palpebral fissure extending between the lateral canthus and the medial canthus, for example.

FIG. 10A shows a measurement apparatus 750 to measure a depth of the conjunctival sac of the patient to determine a corresponding size of the retention structure to fit the patient. The measurement apparatus 750 may comprise a plurality of indicia 760 to indicate a depth of the conjunctival sac. The plurality of indicia can be located at incremental distances from a distal end portion 752. The measurement apparatus 750 comprises a handle 754. The handle and the end portion having the markings can be transparent so that the user can easily visualize the tissue beneath the markings.

FIGS. 11A and 11B show a patient looking to a first side and a second side, respectively, to measure a plurality of dimensions 1100 of the eye to fit the retention structure 110 of insert 100 to the eye. The plurality of measured dimensions 1100 of the eye may comprise a distance 1100A from the limbus 14 to the lateral canthus when the patient looks nasally, for example. Alternatively or in combination, the plurality of dimensions 1100 may comprise a distance 1100B from the limbus 14 to the caruncle 59 when the patient looks nasally. The plurality of measured dimensions 1100 of the eye may comprise a distance 1100C from the limbus 14 to the lateral canthus LC when the patient looks temporally, for example. Alternatively or in combination, the plurality of dimensions 1100 may comprise a distance 1100D from the limbus 14 to the caruncle 59 when the patient looks temporally.

In many embodiments, the retention structure 110 and support structure 130 can be visible to permit the user to see the insert to confirm that the retention structure is well placed in the eye, for example. The folds of conjunctiva may cover the retention structure to decrease visibility. For example, the plica semilunaris may cover the retention structure near the caruncle and medial canthus so as to decrease visibility of the portion of the retention structure extending across the medial portion the palpebral fissure. However, in many embodiments it can be beneficial to have at least a portion of the retention structure or the support structure less visible.

FIGS. 12A1 and 12A2 show plan and side views, respectively, of the insert 100 having a therapeutic agent and at least one optically transmissive portion 100TR and at least one visible portion 100VI. The optically transmissive portion 100TR may comprise an optically transmissive material such as silicone, nylon, or suture material. The visible portion may comprise an optically visible material such as a dark material, a colored material, a light colored material, a fluorescent material, a light colored material, or combinations thereof for the patient to see the insert when the lid is moved. The color of the insert may indicate the formulation or therapeutic agent, or formulation of therapeutic agent, for example.

The optically visible portion can be configured for placement under the lid. The optically transparent material can be configured to extend between the lids when placed on the eye.

The insert 100 comprises a first configuration 100C1 prior to placement and a second configuration 100C2 when placed in the eye, such that the insert can deflect along the conjunctival sac.

FIGS. 12B1 and 12B2 show insert 100 comprising a second configuration 100C2. The second configuration 100C2 comprises a superior inferior dimension across 100SI and a nasal temporal dimension across 100NT. The nasal temporal dimension across 100NT can be greater than the inferior-superior dimension across 100SI. The second configuration 100C2 comprises an anterior-posterior deflection 100AP corresponding to anterior-posterior deflection of the deflection of the insert 100 and retention structure 110 when placed in the eye.

The insert 100 and retention structure 110 can comprise many configurations. The insert 100 and retention structure 110 may comprise a substantially uniform thickness extending substantially around a circumference of insert 100 in the first configuration 100C1.

FIGS. 13A1 and 13A2 show a support structure 120 configured to resist movement away from the inferior temporal IT portion of the conjunctival sac. The support structure 120 comprises a distance 126 sized to fit the IT portion of the conjunctival sac, and a first inclined surface of first tapered end portion 122 and a second inclined surface of second tapered end portion 124 opposite the first inclined surface. The first inclined surface urges the structure toward the second inclined surface in response to pressure of the lids and the second inclined surface of second tapered end portion 124 urges structure 120 toward the first inclined surface of first tapered end portion 122, such that movement away from the IT portion of the conjunctival sac is inhibited in response to increased pressure of the lid at one or more of the temporal location of the lid or the inferior location of the lid.

FIGS. 13B1 and 13B2 show insert 100 comprising second configuration 100C2.

The second configuration 100C2 comprises superior inferior dimension across 100SI and nasal temporal dimension across 100NT. The nasal temporal dimension across 100NT can be greater than the inferior-superior dimension across 100SI. The second configuration 100C2 comprises an anterior-posterior deflection 100AP corresponding to anterior-posterior deflection of the deflection of the insert 100 and retention structure 110 when placed in the eye. The support structure 120 and retention structure 110 can rotate, such that the retention structure 110 and support structure 120 comprise a rotated configuration 100C2R.

The support structure 120, the optically transmissive portion 100TR and optically visible portion 100VI can be arranged on the insert 100 such that the optically transmissive portion 100TR is located near the nasal canthus or the medial canthus and the optically visible portion 100VI is covered by the upper lid or the lower lid. This allows the insert to be seen by the user to confirm the insert is placed on the eye and also to decrease visibility of the insert during normal gaze.

FIGS. 14A1 and 14A2 show plan and side views, respectively, of structure 120 comprising a first structure 120S1 and a second structure 120S2 spaced apart with distance 126 to maintain the first structure and the second structure in the inferior temporal location of the conjunctival sac. The first structure 120S1 may comprise the first inclined surface of first tapered end portion 122 and the second structure 120S2 may comprise the second inclined surface of second tapered end portion 124. The distance 126 can be sized to limit movement of the insert 100, and in accordance with dimension of transmissive portion 100TR and visible portion 100V, such that the transmissive portion 100TR remains substantially in the canthus.

FIGS. 14B1 and 14B2 show the insert 100 placed along at least a portion of the conjunctival sac of an eye.

In many embodiments, structure 120 may comprise one or more structures to retain the insert 100 with an intended orientation of the transmissive portion 100TR and the optically visible portion 100VI.

FIG. 15 shows insert 100 comprising a C-shaped configuration with retention structure 110 comprising a first end and a second end.

FIG. 16A shows insert 100 comprising a therapeutic agent 130 of matrix 140 and a second therapeutic agent 132 of a second matrix 142. FIG. 16B shows a cross sectional view of an insert as in FIG. 16A. The matrix 140 may comprise a first component and the matrix 140 may comprise a second matrix 142. The first matrix and the second matrix can be coupled to the retention structure 110, such that the retention structure extends along the matrix 140 and the second matrix 142. The first matrix may comprise silicone and the second matrix may comprise silicone and the retention structure may extend between the first matrix and the second matrix with the first matrix attached to the second matrix. In alternate embodiments, the first matrix may not be attached directly to the second matrix, for example.

FIG. 16C shows an insert 100 comprising extensions 125 to release therapeutic agent 130 from support structure 120. The extensions 125 can extend inward toward the pupil of the eye to release the therapeutic agent into the tear of the eye, for example when support structure is received in one or more folds of the conjunctiva as described herein. The extensions 125 may comprise a material suitable to receive the therapeutic agent 130 from support structure 120 on a first end of the extension and release the therapeutic agent toward the pupil near a second end. The extension 125 may comprise one or more of many materials and may comprise silicone or hydrogel, for example. The support structure 120 may comprise matrix 140, and the matrix 140 may comprise silicone and the extensions may comprise silicone so as to release silicone to the tear toward the pupil, for example.

FIG. 16D shows insert 100 comprising a retention structure 110 comprising a matrix 140 containing a therapeutic agent 130. The retention structure 110 may comprise inclusions of therapeutic agent 130 as described herein and a matrix material to provide a resistance to deflection as described herein. For example, the matrix material may comprise silicone and an inclusions of a prostaglandin embedded within the matrix. The retention structure 110 comprising the matrix material can be sized so as to provide a resistance to deflection as described herein, and the therapeutic agent can be released from the surface of the retention structure 110.

FIG. 16E shows an insert 100 comprising a support structure 120 having extensions 129 sized to release therapeutic agent 130 away from the retention structure 120.

FIG. 16F shows a side cross sectional view of the insert comprising the support structure having extensions to release therapeutic agent away from the retention structure as in FIG. 16E. The therapeutic agent 130 may be contained in matrix 140 having a surface area and volume sized to release therapeutic amounts of the therapeutic agent for an extended time. The extensions 129 can extend between the retention structure 110 and matrix 140 so as to position matrix 140 toward the tear of the eye away from the fold receiving the retention structure 110, such that the therapeutic agent can be released to the tear from the surface of the retention structure 110 for the extended time.

FIG. 16G shows a support structure comprising a plurality of outward extensions to increase a surface area of the matrix to release the therapeutic agent. The therapeutic agent 130 may be contained in matrix 140 having a surface area and volume sized to release therapeutic amounts of the therapeutic agent for an extended time. The extensions 129 may comprise an extension of the matrix 140 and may extend away from the retention structure 110 to release the therapeutic agent to the tear from the surface of the retention structure 110 for the extended time. At least a portion of the extensions 129 can be directed inward toward the pupil of the eye.

FIG. 17A shows components of a mold 1700 to make the insert 100 comprising a first component 1710 and a second component 1720. The first component 1710 may comprise a first channel 1712 sized to form a first portion of support structure 120 and a first channel 1714 sized to receive a first portion of preformed retention structure 110. The second component 1720 may comprise a second channel 1722 sized to form a second portion of support structure 120 and a second channel 1724 sized to receive a second portion of preformed retention structure 110. The first component and the second component can be placed in contact with the first channels aligned with the second channels. In many embodiments, the preformed retention structure may be threaded through a spacer, for example a small silicone bead, sized to place the retention structure 110 near a central portion of the channel defined by first channel 1712 and second channel 1722. This placement of the preformed retention structure away from the surface of the first channel 1712 and the surface of the second channel 1722 can increase smoothness of the support structure 120 formed with the first channel and the second channel.

FIG. 17B shows the mold as in FIG. 17A having a preformed retention structure placed in the mold configured for injection of a flowable material. The flowable material can be injected into the mold 1700 and cured to form insert 100. The flowable material may comprise the therapeutic agent, such that the support structure 120 comprises the therapeutic agent. Alternatively, the matrix comprising the therapeutic agent may comprise a solid matrix that can be placed in the channels sized to form the support structure 120, and the flowable material injected around the preformed solid matrix. For example, the matrix may comprise a preformed silicone matrix containing the therapeutic agent placed in the mold and the flowable silicone material injected around the silicone matrix.

In many embodiments, the inclusions of the therapeutic agent are formed in a matrix with a method of manufacturing the therapeutic device. The method comprises dissolving particles of a therapeutic agent in one or more of a first component comprising vinyl or a second component comprising a catalyst and a hydride. The one or more of the first component or the second component comprises a solvent to dissolve the matrix. The first component and the second component are combined to form a curable material comprising the therapeutic agent dissolved in the solvent. The solvent is removed from the curable material to form inclusions of the therapeutic agent in a matrix comprising the first component cured with the second component.

The matrix comprising the inclusions of the therapeutic agent can be coupled to the retention structure in many ways. For example, the curable material comprising the therapeutic agent dissolved in the solvent can be placed in the mold 1700 and cured around the retention structure 110 to form the matrix comprising the first component cured with the second component. Alternatively, the matrix comprising the first component cured with the second component can be formed, placed in the mold and a flowable material injected around the matrix.

FIG. 17C shows a mold 1700 to make the insert comprising a first component 1710 and a second component 1720, in which the mold comprises a first channel 1712AC to inject a first flowable material comprising a first therapeutic agent 130 and a second channel 1712BC to inject a second flowable material comprising a second therapeutic agent 132. The first channel 1712AC extends to a channel 1712 comprising a portion 1712A having a size and shape corresponding to the area and volume of the first matrix 140 comprising the first therapeutic agent. The second channel 1712BC extends to channel 1712 comprising a portion 1712B having a size and shape corresponding to the area and volume of the second matrix 142 comprising the second therapeutic agent 132. A separator 120S can be placed in the mold prior to injection of the one or more flowable materials comprising the therapeutic agent so as to separate the portions. The separator 120S can hold the retention structure 110, for example a suture, away from a surface of the mold such that the retention structure can be embedded away from a surface of the matrix.

FIG. 17D shows a mold to make the insert comprising a first component 1710 and a second component 1720, in which the mold comprises a first channel 1712AC to inject a first flowable material comprising a first therapeutic agent 130 and a second channel 1712BC to inject a second flowable material comprising a second therapeutic agent 132 and a third channel 1712CC to inject a third flowable material substantially without therapeutic agent. The first channel 1712AC extends to a channel 1712 comprising a portion 1712A having a size and shape corresponding to the area and volume of the first matrix 140 comprising the first therapeutic agent. The second channel 1712BC extends to first channel 1712 comprising a portion 1712B having a size and shape corresponding to the area and volume of the second matrix 142 comprising the second therapeutic agent 132. The third channel 1712CC extends to first channel 1712 comprising a portion 1712C having a size and shape corresponding to the retention structure 110. The separator 120S can be placed in the mold prior to injection of the one or more flowable materials comprising the therapeutic agent so as to separate the portions. For example, the first separator 120S1 can separate the first portion from the second portion; the second separator 120S2 can separate the second portion from the third portion; and the third separator 120S3 can separate the third portion from the first portion. The separators may comprise materials similar to the portions similar to a cured form of the flowable material, such that the portions can bond to the separators when cured. For example, each of the portions and each of the separators may comprise silicone elastomer.

FIGS. 17E and 17F show a spherical mold 1700 having an oval shaped channel to make the insert in which the mold comprises a first lower component 1710 comprising a convex spherical surface and a second upper component 1720 comprising a concave spherical surface to nest with the convex spherical surface. Although a convex spherical surface is shown, the convex surface may comprise one or more of a toric surface, a conic surface, a spherical surface, a cylindrical surface, or a spherical surface. The concave surface may comprise a surface profile so as to correspond and nest with the convex surface and may comprise one or more of a toric surface, a conic surface, a spherical surface, a cylindrical surface, or a spherical surface. The convex surface may comprise the lower surface and the concave surface may comprise the upper surface of the mold. Each of the convex spherical surfaces may correspond to the radius of curvature of the eyeball comprising the sclera. Many components and channels of the mold are similar to FIGS. 17C and 17D. The channels of the mold can be formed on the spherical surface of the mold so as to provide the 3D shape profile of the insert. The mold may comprise one or more channels corresponding to first dimension 114A1 and second dimension 114A2 of the insert, and the oval dimensions can be placed on the convex spherical surface and the concave spherical surface, so as to form the insert having 3D shape profile comprising the first sag height and the second sag height and resistance to deflection toward a plane as described herein.

FIG. 17G shows a spherical mold 1700 having an oval shaped channel on the spherical surface to make the insert in which the mold comprises a first channel to inject a first flowable material comprising a first therapeutic agent, a second channel to inject a second therapeutic agent and a third channel to inject a flowable material without substantial therapeutic agent as described herein.

FIG. 18 shows a manufacturing process 1800 in accordance with embodiments. At a step 1820 the suture material is stress relieved in the oven. At a step 1825 the suture is thermoformed into a ring. The suture can be formed into a ring by wrapping the suture around a mandrel with a diameter of approximately 25 mm and heated to about 150° C. for one hour to heat-set the ring shape. At a step 1830 the ring is cut. The suture is trimmed to the correct length and the ends thermally welded together to form the suture ring.

At a step 1805 the drug is mixed with part A of the silicone. For example, a prostaglandin comprising bimatoprost can be mixed into the medical grade silicone. At a step 1810 part A and part B of the silicone are mixed. At a step 1815 a syringe is filled with the drug formulation.

A step 1835 ring spacers are overmolded. At step 1840 spacers are placed on rings. At a step 1845 rings are fused. At a step 1850 joint integrity is inspected.

At a step 1860 rings are overmolded. The formed suture can be overmolded with medical grade silicone and cured at elevated temperature to form the silicone segments. At a step 1865 the rings are deflashed/demolded. At a step 1870 the overmold quality is inspected. At a step 1875 rings are placed in 70% isopropanol at room temperature for 5-60 minutes. At a step 1880 the rings are dried at room temperature for at least about 30 minutes. At a step 1885 the rings are placed in a vacuum oven at 40 degrees Centigrade. At a step 1890 the insert undergoes final inspection. At a step 1895, the insert is packaged and subsequently sterilized by e-beam radiation prior to arrival at the medical facility.

The method 1800 provides a non-limiting example of a method of manufacturing a therapeutic insert in accordance with at least some embodiments as described herein. A person of ordinary skill in the art will recognize many variations and adaptations based on the teachings described herein. For example, the steps of the method can be performed in any order, and the steps can be deleted, or added, and may comprise multiple steps or sub-steps based on the teachings described herein. Further the method can be modified so as to provide any insert as described herein and so as to provide one or more of the functions any one or more of the inserts as described herein.

Verification Processes and Release Testing

Machinery used during the manufacturing process that can influence the performance of the device can be tested to verify that it meets appropriate specifications and tolerances. Machinery included in this testing may include the refrigerator in which the prostaglandin comprising bimatoprost is stored, the mixer in which the prostaglandin comprising bimatoprost is mixed with the silicone, and the packaging sealer machine. Additionally, appropriate equipment such as ovens and balance can be kept within calibration.

Prior to release of clinical product, all lots will be tested by appropriate statistical sampling for mechanical integrity, sterility, drug content uniformity, drug purity, elution profile, and residual chemicals to ensure that the clinical lots are consistent with the product specification.

Drug Loading and Dosing

The therapeutic agent can be provided in many ways as described herein. In many embodiments, an amount of the therapeutic agent is provided with a matrix comprising a support material and the therapeutic agent. The amount of therapeutic agent contained in the matrix may comprise from about 0.1% to about 50% of the matrix. Table 3 lists amounts of drug that can be loaded on the insert in accordance with embodiments, and the amount can be higher, or lower than the values shown in Table 3.

The inserts as described herein can be combined with the matrix as described herein in many ways. The insert may comprise one or more eluting elements. For example one eluting element having an arc length of 75 degrees, two eluting elements of 75 degrees each, or a single eluting elements extending substantially 360 degrees around the ring. The largest cross sectional dimension of the eluting element can be a diameter within a range from about 0.5 to 1 mm, for example. The surface area of the eluting structures can be compared, for example with a ratio, and the volume of the eluting structures available to store therapeutic agent can be compared.

The amount of therapeutic agent may comprise about 4.4 mg (4,400 ug), for example with 7% therapeutic agent loaded onto a silicone matrix. With 50% loading, the amount of therapeutic agent can be about 7× greater, for example about 30 mg.

The amount of therapeutic agent loaded on insert 100 can be substantially greater than needed to treat the patient for an extended time. For example, with 4.4 mg of prostaglandin comprising bimatoprost on an insert, the amount released for 6 months of treatment can be about 0.4 mg so as to provide at least about 3 ug per day, such that about 90% of the therapeutic agent may remain on insert when the insert is removed upon completion of treatment. The insert comprising excess storage of the therapeutic agent can provide for release of therapeutic agent within a therapeutic window above the minimum effective release rate and below a rate of release corresponding to potential side effects. The amount of excess therapeutic agent can vary and may comprise one or more of at least about twice the amount to be released to the eye over the extended time, at least about three times the amount to be released to the eye, at least about four times the amount to be released to the eye, or at least about five times the amount to be release to the eye, for example.

The drug release structure as described herein can be configured in many ways to release the therapeutic agent, for example with one or more of a matrix, a matrix surface area, a reservoir, a reservoir chamber, a pump, an osmotic pump, or a diffusion mechanism, and combinations thereof. Examples of amounts of therapeutic agent as described herein that can be release from the insert placed on the eye include at least about 3 ug per day of therapeutic agent released for an extended time of at least about 60 days. The therapeutic agent may comprise a prostaglandin such as bimatoprost, and at least about 3 ug of prostaglandin such as bimatoprost can be released each day for at least about 60 days. The therapeutic agent may comprise a prostaglandin such as bimatoprost, and at least about 4 ug of the prostaglandin such as bimatoprost can be released each day for at least about 60 days, for example. The therapeutic agent may comprise a prostaglandin such as bimatoprost, and the amount of therapeutic agent released each day can be within a range from about 5 ug to about 9 ug for at least about 60 days. The therapeutic agent may comprise a prostaglandin such as bimatoprost, and the amount of therapeutic agent released each day for an extended time can be within a range from about 5 ug to about 9 ug. The extended time is within a range from about 120 days to 180 days, for example.

TABLE 3

Therapeutic Agent Loading and Surface Area

| Design Variable | Mono v. 1.0 | Mono v. 2.0 | Duo v. 1.0 | Duo v. 2.0 | Silicone— Suture #1 | Silicone— Suture #2 | Silicone— Suture #3 |
|---|---|---|---|---|---|---|---|
| # eluting segments | 1 | 1 | 2 | 2 | 1 | 1 | 1 |
| Largest diameter of eluting structure | 1 mm | 1 mm | 1 mm | 1 mm | 0.5 mm | 0.75 mm | 1 mm |
| Ratio of surface areas | 1.0 (47.9 mm$^2$) | 1.5 (72.9 mm$^2$) | 2.0 (95.7 mm$^2$) | 3.0 (145.8 mm$^2$) | 2.7 (128.3 mm$^2$) | 4.0 (192.5 mm$^2$) | 5.3 (256.6 mm$^2$) |
| Ratio of volume | 1.0 (10.4 mm$^3$) | 1.6 (16.6 mm$^3$) | 2.0 (20.9 mm$^3$) | 3.2 (33.2 mm$^3$) | 1.5 (16.0 mm$^3$) | 3.5 (36.1 mm$^3$) | 6.1 (64.2 mm$^3$) |

TABLE 3-continued

Therapeutic Agent Loading and Surface Area

| Design Variable | Mono v. 1.0 | Mono v. 2.0 | Duo v. 1.0 | Duo v. 2.0 | Silicone— Suture #1 | Silicone— Suture #2 | Silicone— Suture #3 |
|---|---|---|---|---|---|---|---|
| Geometry of eluting structure | Arc (75°) | Arc (110°) | Double Arc (75° × 2) | Double Arc (110° × 2) | Circular (360°) | Circular (360°) | Circular (360°) |
| Drug loading (bimatoprost) | 7% (~700 µg) | 7% (~1162 µg) | 7% (~1463 µg) | 7% (~2324 µg) | 7% (~1120 µg) | 7% (~2527 µg) | 7% (~4494 µg) |
| Silicone durometer | 10A | 10A | 10A | 10A | 10A | 10A | 10A |

Mechanism of Action—Exemplary Prostaglandin-Bimatoprost

While many therapeutic agents can be used, many embodiments comprise a prostaglandin such as bimatoprost as the therapeutic agent. The insert can provide controlled drug delivery to the eye, while ensuring that the amount of drug delivered to the eye is safe. Bimatoprost itself is a prostamide, a synthetic structural analog of prostaglandin with ocular hypotensive activity. This prostamide is believed to lower intraocular pressure (IOP) in humans by increasing outflow of aqueous humor through both the trabecular meshwork and uveoscleral routes. The insert can be placed on the surface of the eye, with silicone eluting an amount of medication per day. When used clinically, the efficacy of the insert can extend to 180 days or more, after which the insert be replaced by a new insert containing an additional dose of bimatoprost.

Instructions for Use

The insert can be provided as a component of a kit, in which the kit comprises the insert and instructions for use. For example, the kit 600 may comprise the plurality of retention structures, an insert, and the instructions for use. The instructions for use may include the instructions listed below, for example.

The insert should be maintained at room temperature in an area free of environmental extremes. The storage location at the clinical site must have restricted access available only to study personnel.

Procedure: The eyelids will be pulled back by the doctor's gloved fingers and, using forceps, a surgical spear (e.g. Weck-cel) and/or the doctor's gloved fingers, the Insert will be placed in the upper and lower fornices. Once the Insert is in place, given its ring-shaped skeleton it is anticipated that the eyelids will keep the Insert in place.

The ocular insert is first placed by the doctor in the upper fornix using forceps, a surgical spear (e.g. Weck-cel) and/or the doctor's gloved fingers.

The ocular insert is next placed by the doctor in the lower fornix using forceps, a surgical spear (e.g. Weck-cel) and/or the doctor's gloved fingers.

The physician examines the placement of the insert. The blue suture can be seen in the nasal corner of the eye.

The instructions for use may be used with a clinical study, and instructions appropriate to the study provided.

The Investigator, or designee, may be responsible for keeping current and accurate records of the Inserts dispensed and implanted. The study inserts can be stored in a secure area in order to prevent unauthorized distribution. The investigational insert may be inserted only in volunteers entered into the study, in accordance with the conditions specified in the Protocol.

The Insert is supplied sterile to the clinical site.

When the study is completed or terminated by the Sponsor, all unused study inserts may be returned to the Sponsor (or its authorized representative), or destroyed under the direction of the same. The Sponsor, or designee, will verify study Insert accountability and complete the Product Return Shipment Form. All product accounting procedures can be completed before the study is considered completed. The inserts can be intended for one-time use only.

EXPERIMENTAL

Initial studies have been conducted to determine dimensions and materials suitable for use with insert 100 comprising retention structure 110 and support structure 120. The following non-limiting examples show insertable devices and methods in accordance with embodiments as described herein.

Example 1. Initial Experiments with Test Devices

Inserts have been constructed in accordance with the teachings described herein. The inserts 100 comprised a ring shaped retention structure 110 composed of a 4-0 nylon suture and a silicone support structure 120. Initial studies suggested that the first inclined surface of the first tapered end portion 122 and the second inclined surface of the second tapered end portion 124 can provide improved comfort. Additional inserts having the inclined surfaces were constructed, and the test inserts were placed in the eyes of one human subject for approximately 29 days and well tolerated.

FIG. 18A shows an image of the insert 100 placed on an eye with the retention structure 110 under a fold of bulbar conjunctiva comprising the plica semilunaris PS adjacent the caruncle 59 as described herein. The eye and retention structure are shown with the patient looking forward and a first separation distance extending between the limbus 14 and the retention structure 110.

FIG. 18B shows an image of the insert placed on the eye as in FIG. 18A with the eye looking temporally so as to expose the insert from under the fold 56F of bulbar conjunctiva 56 comprising the plica semilunaris and such that the retention structure slides along the bulbar conjunctiva so as to provide a second separation distance between the visible portion of retention structure 110 and the limbus. The second separation distance corresponds to at least about twice the first separation distance. The separation distance from the limbus 14 of the eye to the visible portion of the retention structure 110 has increased substantially as compared with the patient looking forward.

FIG. 18C shows an image of the insert placed on an eye with the retention structure extending under a fold 56F of bulbar conjunctiva 56. The retention structure 110 fits under fold 56F.

Example 2. Experiments with a Population of Test Subjects

Additional experiments were conducted with additional volunteers having inserts placed in their eyes. These studies indicated varying results and that the sizing of the ring shaped structure to the size of the eye can be helpful.

FIGS. 19A to 19F show placement locations of the support structure comprising silicone elastomer coupled to the ring shaped retention structure as described herein. The inserts were placed on human eyes and comfortably retained on the eyes for several days at the locations shown. The silicone elastomer support structure comprised a maximum cross-sectional diameter of about 1.5 mm and a length of about 12 mm. The retention structure comprised a 4-0 polypropylene suture sized to fit the wearer as described herein. The subjects were fit to a 24, 26 or 28 mm retention structure as described herein, and the support structure comprising silicone was placed substantially as shown in the figures, although in some instances the insert rotated at least partially around the pupil of the eye subsequent to placement.

Figure 19A:
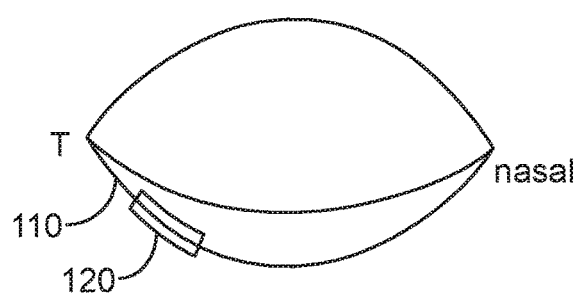

FIG. 19A shows an insert placed in the right eye (hereinafter "OD") and the support structure 120 worn at an inferior temporal location with the retention structure 110 sized to fit within conjunctival folds as described herein.

Figure 19E:
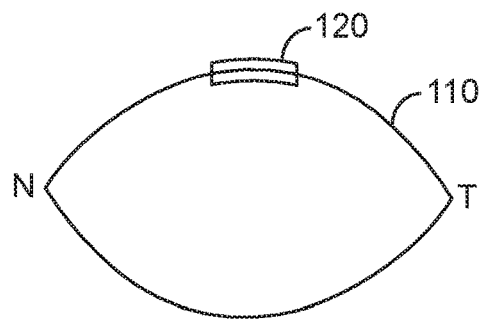
Figure 19B:
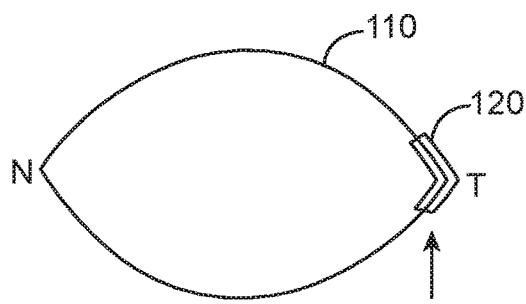

FIG. 19B shows an insert placed in the left eye (hereinafter "OS") and the support structure 120 worn at a temporal location with the retention structure 110 sized to fit within conjunctival folds as described herein.

Figure 19F:
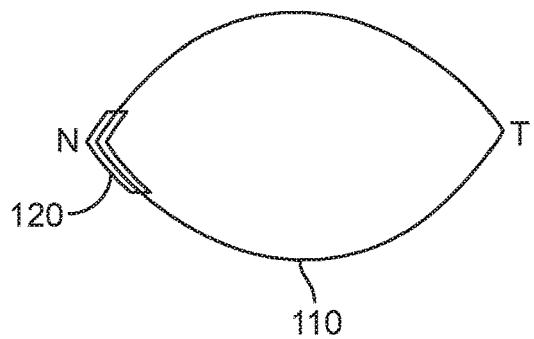
Figure 19C:
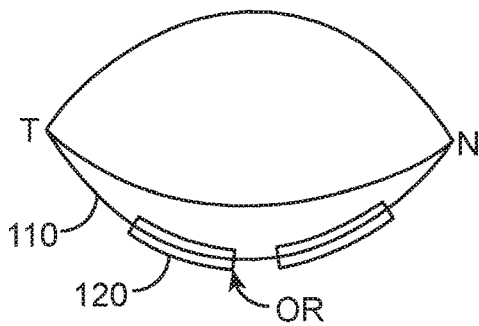

FIG. 19C shows an insert placed in the right eye OD and the support structure 120 worn at an inferior location with the retention structure 110 sized to fit within conjunctival folds as described herein.

Figure 19D:
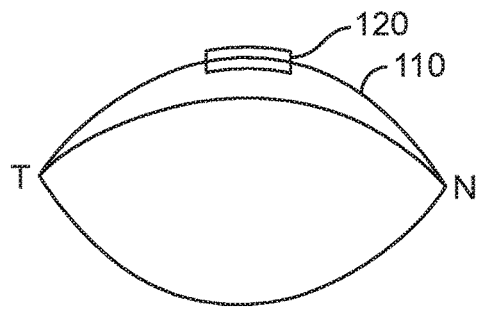

FIG. 19D shows an insert placed in the right eye OD and the support structure 120 worn at a superior location with the retention structure 110 sized to fit within conjunctival folds as described herein.

FIG. 19E shows an insert placed in the left eye OS and the support structure 120 worn at an superior location with the retention structure 110 sized to fit within conjunctival folds as described herein. This subject started with the support structure placed within the inferior sac of the eye and retention with the lower lid was less than ideal, possibly related to a loose lower lid of the subject. The insert was subsequently placed along the superior sac and well retained with the support structure under the upper lid.

FIG. 19F shows an insert placed in the left eye OS and the support structure 120 worn at nasal location near the caruncle with the retention structure 110 sized to fit within conjunctival folds as described herein.

Experiment 3—Measurements of Resistance to Deflection

While the resistance to deflection of the insert can be measured in many ways, the resistance to deflection based on self-loading deflection of the insert can be performed readily with simple test equipment. The insert can be held horizontally on one end and the angle of deflection of the insert away from horizontal based on gravity can be measured.

FIG. 20A shows measurement self-loading deflection of a retention structure of an insert. The insert can be held horizontally on one end and the angle away from horizontal measured so as to determine the self-loading resistance to deflection.

The self-loading resistance to deflection of several ring structures was measured. Each ring structure had a 26 mm diameter. Rings made of 3-0 Prolene, 4-0 Prolene, 5-0 Prolene, 3-0 Nylon, 4-0 Nylon, 5-0 Nylon, durometer 30 A silicone and durometer 50 A silicone were measured. An image of each ring was taken and software (ImageJ, NIH freeware for image processing/measurements) was used to measure the angle of deflection for each ring. Three ring samples were measured for each material and the self-loading angle of deflection averaged for each of the measurements. The results of the measurements are shown in Table 4.

TABLE 4

Self-Loading Angle of Deflection

| Description of Ring | Angle 1 | Angle 2 | Angle 3 | Ave Angle Deflection |
|---|---|---|---|---|
| 3-0 Prolene | 13 | 12 | 12 | 12 |
| 4-0 Prolene | 12 | 14 | 12 | 12 |
| 5-0 Prolene | 11 | 25 | 15 | 17 |
| 3-0 Nylon | 12 | 8 | 6 | 8 |
| 4-0 Nylon | 18 | 18 | 0 | 12 |
| 5-0 Nylon | 21 | 14 | 15 | 17 |
| 30A silicone | 83 | 82 | 90 | 85 |
| 50A silicone | 67 | 52 | 60 | 60 |

The Prolene and Nylon sutures provided greater resistance to deflection that silicone based on the measured self-loading deflection. The nylon sutures had average angles of deflection of 8 degrees, 12 degrees and 17 degrees for the 3-0, 4-0 and 5-0 sutures, respectively. The Prolene sutures had average angles of deflection of 12 degrees, 12 degrees and 17 degrees for the 3-0, 4-0 and 5-0 sutures, respectively. The durometer 30 A silicone has a self-loading deflection angle of about 85 degrees and the harder 50 A silicone has a self-loading deflection angle of about 60 degrees.

This self-loading deflection data can be combined with retention of the inserts as described herein to determine the resistance to deflection so as to retain the insert in the eye. This data indicates that a self-loading deflection of less than about 60 degrees can provide sufficient resistance to deflection so as to retain the insert in the eye. The measurable self-loading deflection also indicates that the retention structure can move and deflect so as to change shape and provide comfort to the patient.

Experiment 4—In Situ Forming of the Retention Structure

FIG. 21 shows an insert as described herein removed from an eye. The insert initially comprised a circular retention structure comprising a polypropylene suture and was placed in an eye for a plurality of days so as to in situ form the retention structure. The in situ formed configuration comprised a non-planar oval shape when placed on a flat surface. The in situ formed configuration comprises at least a portion of retention structure extending away from a plane corresponding to other portions of the retention structure. The in situ formed retention structure is shown placed on a planar surface with at least a portion extending away from the surface.

Experiment 5—Measurement of Eyes to Determine Sizes of the Retention Structure

FIG. 22 shows a digital image of a human eye measured with a measurement apparatus as described herein. The patient can be asked to look down, and the instrument inserted at least partially into the conjunctival sac to measure a distance from the fornix of the eye to the limbus of the eye with the patient looking down. The measured distance can be used to determine a size of the retention structure to be placed in the eye, for example and initial size identified from among a plurality of sizes.

Additional experiments are contemplated to determine appropriate sizing of the retention structure based on measurements of the patient, for example as described herein.

Experiment 6—Test Devices Loaded with Therapeutic Agent

Test devices comprising a ring shaped retention structure comprising a nylon suture and a support structure 120 having inclined surfaces were placed in an eye of a subject. The support structure comprised a therapeutic agent contained in a silicone matrix. The silicone matrix comprised inclusions of the therapeutic agent as described herein, and the therapeutic agent comprised a prostaglandin. The silicone matrix comprised NuSil Med 4810 and the amount prostaglandin comprised about 2% bimatoprost. The cross-sectional diameter of the support comprising the matrix was about 1 mm and extended about 90 degrees around the ring shaped suture with the suture extending there through. The amount of therapeutic agent within the matrix can be increased with additional studies and embodiments, for example to within a range from about 5-10% prostaglandin such as bimatoprost.

FIG. 23 shows a graph of TOP over time for a patient having an insert placed on one eye and a control eye for at least about 1 month. The ring was inserted in the right eye (OD) and the TOP decreased from about 22 mm Hg to within a range from about 15 to 18 mm Hg to about 28 days post-op. The TOP of the untreated left eye (OS) remained substantially constant and within a range from about 19 mm Hg to about 22 mm Hg. The therapeutic agent comprised a prostaglandin, bimatoprost, and the estimated amount released per day started at approximately 22 ug/day and decreased to approximately 1 ug/day. The corresponding amount per day for drops to the eye of the therapeutic agent is approximately 9 ug/day.

Experiment 7—Evaluation of Patient Response to Insert Devices

FIG. 24A shows a tested insert comprising a suture ring and a single 75 degree silicone band on the suture ring. The suture was made of polypropylene (prolene 4-0), having a nominal cross-section 0.150 mm. The silicone band was composed of medical grade silicone having a durometer of 10A (Shore A) and a cross-sectional diameter 1.0 mm and extended over the suture.

FIG. 24B shows a tested insert comprising a silicone ring without a supporting suture. The silicone ring was composed of medical grade silicone having durometer 10 A. The silicone ring comprised a cross-sectional diameter of 0.5 mm.

FIG. 24C shows a tested insert comprising a suture ring and two opposing 75 degree silicone bands on the suture ring. The suture material and silicone material were the same as the insert in FIG. 24A.

FIG. 24D shows an insert suitable for testing comprising an inner suture ring covered with soft silicone around a 360 degree circumference. The suture may comprise a prolene (4-0) or a nylon (4-0) suture, each having cross-sectional diameter of 0.150 mm. The silicone can be medical grade silicone having a durometer within a range from about 10 A to about 50 A, for example. The cross sectional dimension of the silicone can be within a range from about 0.25 mm to about 1.5 mm, for example within a range from about 0.5 mm and 1.0 mm.

Clinical testing of the insert shown in FIGS. 24A to 24C has shown that the deflection resistance provided by the suture material, which may correspond to hoop strength of the suture, can substantially increase retention in human subjects. Testing of the insert comprising the suture shown in FIG. 24A showed that seven of ten subjects could retain the ring comfortably for four weeks. However, for the insert comprising durometer 10 A silicone without the suture as shown in FIG. 24B, only two of ten test subjects were able to retain the ring for 10 days. The durometer 10 A silicone comprises a much softer material having a much lower resistance to deflection, which may correspond to hoop strength, than the durometer 30 A silicone. For the insert having two silicon bands as shown in FIG. 24C, five of seven subjects were able to retain the ring comfortably at three weeks and the study was ongoing at week three.

Experimental testing of the insert shown in FIGS. 24A to 24C has shown that a mucus can form around the exposed suture material of the embodiments of FIGS. 24A and 24C having a diameter of about 0.15 mm, and that relatively little mucus may form around the larger silicone portion of these inserts having a diameter within a range from about 0.5 to 1.0 mm, for example. The cushioning provided by the soft silicone material over the stiff suture material may also decrease mucus formation. The accumulation of mucus on the retention structure may decrease clearance of mucus from the eye. As the decreased accumulation of mucus may be related to increased biocompatibility of a plurality of inserts worn successively for several years, the larger diameter of the soft silicone portion over the suture may provide improved biocompatibility.

The insert may comprise at least portion configured to inhibit mucous formation, and the at least a portion can be configured for placement near the medial canthus where mucous can accumulate in the eye. The at least a portion may comprise one or more of a cross-sectional size of at least about one half of one mm, a lubricous coating, a soft material, or combinations thereof, for example.

Additional clinical studies have been conducted with silicone inserts similar to FIG. 24B having a Shore A durometer of 10 or a Shore A durometer of 50. For the inserts comprising a Shore A durometer of 10, four eyes were tested and only one retained the insert which was removed after about one week. For the inserts comprising a Shore A durometer of 50, six eyes were tested and only two retained the insert which was removed after about one week. These data indicate that the retention structure as described herein, for example with reference to FIGS. 24A and 24C provides improved retention of the insert. Alternatively or in combination, a material more rigid than durometer 50 A can be used to form a unitary insert such that the more rigid material provides the resistance to deflection and the drug delivery matrix as described herein. For example, a unitary ring as described herein with reference to FIG. 24B can be manufactured with a durometer 80 A silicone loaded with therapeutic agent, such that the silicone drug delivery matrix provides the resistance to deflection and release of therapeutic agent as described herein.

Experiment 8—Clinical Study to Determine Safety, Comfort and Retention of Ocular Insert without Bimatoprost (Placebo Device) in Humans An open-label, single arm exploratory study to assess the comfort and retention of the ocular insert as described herein in healthy volunteers took place. During the study, an ocular insert without drug was placed in the eyes of 10 volunteers for up to 28 days. The results of the study showed the insert to be safe, comfortable and well-retained over an extended period of time. Following is a detailed summary of the study and its results:

Objectives:
1. To determine the safety profile of the ocular insert.
2. To determine comfort of the ocular insert.
3. To determine whether the ocular insert can be retained in the fornices over an extended period of time.

Study Design:

Up to 20 healthy volunteers, between the ages of 21-65 (mean 45.1 years) could be enrolled in the study and monitored for up to 28 days while wearing the insert in one eye. Safety, comfort and retention, as well as follow-up on any adverse events were tracked and recorded on follow-up visits on days 0, 1, 3, 7, 14, 21 and 28. A second enrollment period took place for a small subset of subjects who participated in the first enrollment period of the study. In the second enrollment period the insert was placed for up to 7 days in order to determine comfort and retention while placing the insert at a different orientation from the one used in the first enrollment period. Follow-up visits were on days 0, 1, 3, and 7.

Description of Insert:

The ocular insert was a ring-shaped structure made of polypropylene, a commercially available non-absorbable suture material available under the trade name Prolene™, manufactured by Johnson & Johnson Ethicon. The structure was coated in sections with medical grade silicone provided by NuSil Silicone Technology, and has a diameter of 20 to 28 mm (several sizes of the insert are available) and the cross-sectional diameter of the ring varied from about 0.05 mm (7-0 suture) to about 0.20 mm (3-0 suture). In this study, no drug was put into the ocular insert.

Criteria for Evaluation:
1. Safety: Biomicroscopy, slit-lamp photography and visual acuity examinations took place, as well as follow-up on any adverse events at baseline and during all follow-up visits.
2. Retention: On all follow-up visits, subjects were examined to determine the presence of the Insert in the eye.
3. Comfort: On all follow-up visits, subjects were also asked to fill out a comfort questionnaire, in which they were requested to mention in detail any physical or emotional discomfort felt while wearing the ocular insert.

Results:

For 10 subjects enrolled in the study since safety, comfort and retention outcomes were deemed to be sufficient to guide the research and development. Subjects were aged 23-63 (mean 45.1 years) and included 4 males and 6 females.

Eight out of 10 subjects completed the study and 28 day follow-up period. In two of the subjects the Insert was not retained for more than 4 days.

Safety Conclusions: The results of the study show that the ocular insert is safe. Safety related events were as follows:

No Serious Adverse Events occurred in the study.

One adverse event occurred in subject HSG 003. In this subject, conjunctival redness went from none to moderate between baseline and day 1. Although redness begun to resolve over the following week it was still noticeable at day 7 and therefore the Insert was removed and replaced with a smaller diameter Insert, which was well retained and comfortable for the duration of the study without any adverse events.

The majority of participants had mild conjunctival redness and/or mucus collection which did not qualify as adverse events (2 grades of change from baseline). All instances were intermittent in nature, did not cause discomfort to the subjects and did not require any treatment.

Retention Conclusions: In 8 out of 10 subjects the insert was retained for the entire duration of the study. In 2 (RS 008 and TZA 007) of these 8 subjects the Insert was repositioned between day 2 and day 3 so the silicone band was placed in the upper fornix.

Comfort Conclusions: Data from the comfort questionnaires, comparing overall comfort of study eye (SE), in which the ring was inserted, and control eye (CE) in which there was no Insert during study visits.

Discomfort values were at their highest immediately after insertion, and gradually declined until stabilizing on a value reasonably close to the level of discomfort reported in the control eye.

The second, 7-day enrollment period demonstrated that for most patients, the optimal orientation for maximal retention and comfort was given when placing the silicone part of the ring in the upper fornix of the eye.

Overall Conclusions:

The study, designed to determine safety, retention and comfort of the ocular insert without drug for up to 28 days, showed that the Insert was safe, well retained and comfortable. These conclusions are based on monitoring of adverse events, the high percentage of retention and reports by patients of a high level of comfort, which increased over time.

The Protocol and Informed Consent Form (ICF) were reviewed and approved by an Institutional Review Board (IRB), who was also kept informed of any serious adverse events and any amendments to the protocol.

The study was performed in accordance with the recommendations guiding physicians in biomedical research involving human subjects adopted by the 18th World Medical Assembly, Helsinki, Finland, 1964 and later amendments.

Experiment 9—Evaluation of Inserts Shaped In Situ

FIG. 25 shows in situ deformation and curvature of an insert subsequent to placement in an eye with the insert curved so as to correspond to at least the curvature of the lid along the cul-de-sac. The insert was initially flat and comprised a polypropylene suture retention structure 110 and silicone support structure 120. The insert was oriented as shown and such that the upper silicone portion was placed over the lacrimal gland toward the superior temporal portion of the eye. The model eye is shown to indicate alignment of the insert to the eye and the corresponding in situ formed curvature of the insert to the eye.

The insert was removed after being worn for a few days. The upper portion of the insert corresponding to the upper lid comprised a curvature 115C1 that curved posteriorly toward the patient so as to follow the upper lid of the eye along the fornix. The lower portion of the insert corresponding to the lower lid comprised a curvature 115C2 that curved posteriorly toward the patient so as to follow the lower lid of the eye along the fornix. The intermediate portions of the insert located between the upper and lower portions of the insert comprised a curvature 115C3 and a curvature 115C4 at locations corresponding to the lateral canthus and medial canthus. The intermediate portions comprising the curvature 115C3 and the curvature 115C4 are curved away from the patient so as to curve anteriorly.

Several inserts removed from eyes have shown a saddle shape similar to the insert shown in FIG. 25 and as described herein. This saddle shape and curvatures corresponds to the saddle of astigmatism known in the field of optics, for example. The in situ forming of the shape of the may provide decreased pressure and irritation to the eye and may provide improved biocompatibility.

The in situ formed shapes can be used to determine a pre-insertion and pre-formed shape of the insert prior to placement on the eye. The pre-formed insert may comprise an in situ formable material such as polypropylene, for example, or a non-in situ formable material such as a metal wire or robust shape memory material, for example. The pre-formed insert may comprise upper and lower portions curved toward the patient and intermediate nasal and temporal portions curved away from the patient, for example.

FIGS. 26A and 26B show rates of release of prostaglandin comprising bimatoprost from an insert comprising a silicone matrix. The estimated rate of release for a matrix having 7% prostaglandin comprising bimatoprost loaded on the insert is above 3.5 ug per day for at least about 90 days. The rate of release of prostaglandin comprising bimatoprost was measured from a matrix comprising medical grade silicone having an approximate durometer of 10 A. The configuration of the insert and matrix is described in Table 3 with reverence to mono v.1 which comprises a 1 mm diameter silicone matrix extending along a 75 degree arc length. The surface area was 47.9 mm$^2$ and the volume 10.4 mm$^3$. For the 7% loading the amount of drug loaded on the device was about 700 μg. The rate of release of about 0.9 ug/day for 90 days was measured and the rate of release for 120 days was estimated.

The therapeutic agent was released for 70 days above 1 ug per day. Based on Table 3, the matrix can be configured to release additional amounts therapeutic agent. For example, the rate of release can be increased by more than 4× by extending the matrix 360 degrees around the suture.

FIG. 27 shows wash time and rates of release of therapeutic agent from matrices having varying amounts of wash in a 70% isopropanol bath. The experiments were conducted with silicone rings having 7% prostaglandin comprising bimatoprost and medical grade silicone having a rated durometer of Shore A 10 without drug. The elution rate for the unwashed matrix ("0 wash") was about 35 ug per day and decreased substantially. The elution rate for the matrix washed for 15 minutes was about 17 ug per day, after about 2 days, the matrix washed for 15 minutes released therapeutic agent at a rate similar to the unwashed matrix, indicating that the 15 minute removed therapeutic agent from the surface and did not remove detectable amounts of therapeutic agent from deeper portions of the matrix. The 60 minute and 180 minute was matrices showed similar results and an initial rate of release of about 13 ug per day which decreased to about 5 ug per day at 15 days. By day 14 the rate of release was substantially the same for each of the unwashed matrix, the matrix washed for 15 minutes, matrix washed for 60 minutes, and the matrix washed for 180 minutes. This data indicates that washing the matrix in a solvent can decrease variability of the rate of release of the therapeutic agent.

FIG. 28 shows examples TOP and rates of therapeutic agent release in accordance with embodiments. The graph shows TOP for days 59 to 69 of a test subject. The initial studies on the test subject appear to indicate it may be helpful to provide greater amounts of therapeutic agent than would be provided based on eye drop estimates. The TOP was measured and amounts of therapeutic agent estimated. The amount of therapeutic agent released was estimated by using paired devices such that the insert placed in the eye had a corresponding "twin" insert. The twin insert was placed in a solution when the patient insert was placed in the eye. The measured rate of release of the twin placed in solution was used to determine the rate of release of the insert placed in the eye.

The data of this small study indicate that in at least some instances for some patients, the target threshold amount of therapeutic agent released continuously from an insert placed in the eye may be greater than the amount provided to tissue by drops. It was observed that providing amounts of therapeutic agent greater than the estimated amount provided by drops may provide an improved result. It was observed that after about sixty days the TOP had increased to about 19.5 mm Hg was close to the control eye, and the determined rate of release was about 1.2 ug of prostaglandin comprising bimatoprost per day. The insert was replaced with a second insert providing a rate of release of about 1.6 to 2.5 ug per day based on twin measurements, and the TOP decreased to within a range from about 17 to 18 mm Hg. The second insert was replaced with a third insert providing over 3.8 to 4 ug per day based on twin measurements, and the TOP decreased further to within a range from 14.5 to 16 mm Hg.

These preliminary data indicate that at least about 3 ug per day of prostaglandin such as bimatoprost may provide an improved decrease in TOP as compared with less than 3 ug per day, for example.

Based on the teachings described herein, a person of ordinary skill in the art can determine empirically the amount of therapeutic agent to be provided for an extended time, for example the amount of prostaglandin such as bimatoprost eluted for six months so as to provide therapeutic relief from a disease condition of the eye such as glaucoma.

The embodiments as described herein are provided as non-limiting examples and can be combined and modified in many ways. In many embodiments, the insert is provided with a drug delivery matrix material having a one or more of a stiffness or spring bias corresponding to the above described retention structures, such that the insert can be provided without a skeletal structure and provide the function of the skeletal structure. For example, the drug delivery matrix may comprise materials having a durometer and cross-sectional dimensions so as to provide the function of the retention structure. Alternatively or in combination, a support structure as described herein such as the drug delivery matrix can be provided over the retention structure as described herein, for example.

The embodiments as described herein can be configured in many ways, and may comprise portions coated with the drug release matrix, and may comprise a 75 degree, a 180 degree or a 360 degree drug release matrix for example. In many embodiments, the insert can be coated with a cushioning material, for example a soft silicone.

Each of the above-described embodiments can be combined with the other embodiments in accordance with the teachings described herein, and a person of ordinary skill in the art will readily recognize many such combinations. For example, one or more elements of one or more embodiments described in any one figure can be combined with any one or more elements of another figure, such that the inventors have described and reserve the right to claim any combination of elements, structures, functions, and steps as described herein.

While the exemplary embodiments have been described in some detail, by way of example and for clarity of understanding, those of ordinary skill in the art will recognize that a variety of modifications, adaptations, and changes may be employed. Hence, the scope of the present disclosure shall be limited solely by the appended claims.

What is claimed is:

1. A method of treating an eye of a patient, the method comprising:
   placing a ring-shaped drug delivery device onto an anterior surface of the eye underneath the upper and lower eyelids, the drug delivery device comprising:
      an inner skeletal structure forming an annulus;
      an outer matrix structure encapsulating a length of the annulus such that the length of the inner skeletal structure is contained within the outer matrix structure; and
      a therapeutic agent configured to be released from the device for an extended time,
      wherein an inner diameter of the ring-shaped drug delivery device is at least as large as an outer diameter of the eye's cornea, and wherein the drug delivery device has a pre-insertion contour prior to being placed on the eye that is generally planar;
   conforming in situ the pre-insertion contour of the drug delivery device to a post-insertion contour that is generally non-planar; and
   releasing the therapeutic agent from the device for the extended time,
   wherein the drug delivery device is configured to retain the post-insertion contour for a period of time after removal from the eye.

2. The method of claim 1, wherein placing the device onto the anterior surface comprises placing the device at least partially within the conjunctival sacs.

3. The method of claim 1, wherein placing the device onto the anterior surface comprises placing the device on the conjunctiva, wherein the device is received in one or more of a plurality of folds of the conjunctiva.

4. The method of claim 3, wherein the one or more of the plurality of folds comprises a plurality of bulbar folds of the conjunctiva.

5. The method of claim 4, wherein the device is movable along the bulbar conjunctiva when the eye moves to retain the device on the conjunctiva.

6. The method of claim 3, wherein the one or more of the plurality of folds comprises a plurality of palpebral folds of the conjunctiva.

7. The method of claim 1, further comprising:
   measuring a dimension of the patient to obtain a measured dimension; and
   identifying, based on the measured dimension, the drug delivery device among a plurality of drug delivery devices having different inner diameters.

8. The method of claim 7, wherein the measured dimension comprises one or more of a circumference of the head of the patient, a dimension between eyes of the patient, a depth of the upper fornix, a depth of the lower fornix, a distance extending between a lateral canthus and a medial canthus of the eye, a distance extending between a cul-de-sac of the eye and a limbus of the eye, a dimension of the orbit, or a fornix depth measured with a fornicometer.

9. The method of claim 1, further comprising:
   placing a second ring-shaped drug delivery device on a second eye of the patient, the second drug delivery device comprising:
      an inner skeletal structure forming an annulus;
      an outer matrix structure encapsulating a length of the annulus such that the length of the inner skeletal structure is contained within the outer matrix structure; and
      a therapeutic agent configured to be released from the device; and
   releasing the therapeutic agent from the second drug delivery device.

10. The method of claim 1, wherein the extended time the therapeutic agent is released is at least about one week up to about six months.

11. The method of claim 1, further comprising removing the drug delivery device from the eye.

12. The method of claim 1, wherein the therapeutic agent comprises bimatoprost and wherein releasing the therapeutic agent from the device for the extended time comprises releasing between 1 ug bimatoprost per day up to about 22 ug bimatoprost per day for at least about 30 days, at least about 60 days, at least about 120 days, up to about 180 days.

13. The method of claim 1, wherein the outer matrix structure comprises a silicone material and the inner skeletal structure comprises polypropylene, wherein the therapeutic agent is contained within the outer matrix structure.

14. The method of claim 1, wherein the therapeutic agent is contained within only the outer matrix structure, or wherein the therapeutic agent is contained within only the inner skeletal structure, or wherein the therapeutic agent is contained within both the inner skeletal structure and the outer matrix structure.

15. The method of claim 1, wherein the therapeutic agent comprises a prostaglandin analogue selected from the group consisting of bimatoprost, latanoprost, and travoprost.

16. The method of claim 1, wherein the therapeutic agent is configured to treat one or more conditions selected from the group consisting of dry eye, glaucoma, one or more allergy symptoms, bacterial conjunctivitis, trachoma, blepharitis, infection, and inflammation.

17. The method of claim 1, wherein the therapeutic agent is selected from the group consisting of a non-pharmacologic agent, a lipid, a phospholipid, a fatty alcohol, a fatty acid, an oil, and a silicone oil.

18. The method of claim 1, wherein the therapeutic agent comprises a first therapeutic agent that is a prostaglandin and a second therapeutic agent that is a beta blocker.

19. The method of claim 18, wherein the prostaglandin is selected from the group consisting of one or more of bimatoprost, latanoprost, and travoprost.

20. The method of claim 18, wherein the beta blocker is selected from the group consisting of timolol, betaxolol, levobunolol, and atenolol.

21. The method of claim 18, wherein the prostaglandin comprises an amount less than an amount of the beta blocker.

22. The method of claim 21, wherein the amount of the beta blocker is between about five and fifty times the amount of the prostaglandin.

23. The method of claim 18, wherein the beta blocker is released at a rate substantially greater than a rate of the prostaglandin is released.

24. The method of claim 23, wherein the rate the beta blocker is released is at least about five times the rate the prostaglandin is released.

25. The method of claim 1, wherein the therapeutic agent is selected from the group consisting of a steroid; a non-steroidal anti-inflammatory (NSAID); an antibiotic; a glaucoma treatment medication; an antihistamine and mast cell stabilizer; an anti-allergenic product; a dry eye medication; and an anesthetic.

26. The method of claim 25, wherein the steroid is selected from the group consisting of at least one of glucocorticoids, aprogestins, amineralocorticoids, corticosteroids, cortisone, hydrocortisone, prednisone, prednisolone, methylprednisone, triamcinolone, fluoromethalone, dexamethasone, medrysone, betamethasone, loteprednol, fluocinolone, flumethasone, rimexolone mometasone, androgens, testosterone, methyltestosterone, and danazol; the non-steroidal anti-inflammatory (NSAID) is selected from the group consisting of at least one of piroxicam, aspirin, salsalate, diflunisal, ibuprofen, ketoprofen, nabumetone, piroxicam, naproxen, diclofenac, indomethacin, sulindac, tolmetin, etodolac, ketorolac, oxaprozin, and celecoxib; the antibiotic is selected from the group consisting of at least one of amoxicillin, penicillin, sulfa drugs, erythromycin, streptomycin, tetracycline, clarithromycin, terconazole, azithromycin, bacitracin, ciprofloxacin, evofloxacin, ofloxacin, levofloxacin, moxifloxacin, gatifloxacin, aminoglycosides, tobramycin, gentamicin, polymyxin B combinations, wherein the polymyxin B combinations are selected from the group consisting of polymyxin B/trimethoprim, polymyxin B/bacitracin, and polymyxin B/neomycin/gramicidin; the glaucoma treatment medication is selected from the group consisting of at least one of beta-blockers, mitotics, carbonic anhydrase inhibitors, prostaglandins, prostaglandin analogs, seretonergics, muscarinics, dopaminergic agonists, and adrenergic agonists; the anti-allergenic product is selected from the group consisting of at least one of loteprednol, olopatadine hydrochloride, sodium chromoglycate, antazoline, methapyriline, chlorpheniramine, cetrizine, pyrilamine, and prophenpyridamine; and wherein the dry eye medication is cyclosporine.

27. The method of claim 25, wherein the glaucoma treatment medication is one or more of timolol, betaxolol, levobunolol, atenolol, pilocarpine, brinzolamide, dorzolamide, travoprost, bimatoprost, or latanoprost.

28. The method of claim 1, further comprising a lubricous coating selected from the group consisting of an oil, a surfactant, a hydrogel, polyvinyl alcohol (PVA), hydroxyethyl methacrylate (HEMA), sodium polyacrylate, acrylate polymers and copolymers having hydrophilic groups, N-vinylpyrrolidone (NVP), agarose, methylcellulose, ethylene oxide (ETO), polyethylene oxide (PTO) and hyaluronan.

29. The method of claim 1, wherein the therapeutic agent forms inclusions in the outer matrix structure, the inclusions of therapeutic agent comprising one or more of particles, droplets, or crystals of the therapeutic agent.

30. The method of claim 1, wherein the outer matrix structure encapsulates 360 degrees around the annulus of the inner skeletal structure.

31. The method of claim 1, wherein the outer matrix structure encapsulates less than 360 degrees around the annulus of the inner skeletal structure.

32. The method of claim 1, wherein the outer matrix structure is formed into a plurality of structures, each of the plurality of structures encapsulates less than 360 degrees of the annulus.

33. The method of claim 1, wherein the outer matrix structure is formed of a silicone material, polyurethane material, or a hydrogel material.

34. The method of claim 1, wherein the inner skeletal structure is formed of a material selected from the group consisting of polypropylene, nylon, PMMA, polycarbonate, polyethylene terepthalate, polyethylenes, and polyether ether ketone (PEEK).

35. The method of claim 1, wherein the inner skeletal structure has a cross-sectional diameter of between about 0.05 mm and about 0.5 mm and the outer matrix structure has a cross-sectional diameter of about 0.25 mm to about 1.5 mm.

36. The method of claim 1, wherein the inner skeletal structure is comprised of polypropylene and has a cross-sectional diameter of between about 0.05 mm and about 0.5 mm and the second material is comprised of silicone and has a cross-sectional diameter of about 0.25 mm to about 1.5 mm.

37. The method of claim 36, wherein the silicone has a durometer of at least about Shore A 10 to at least about Shore A 80.

38. The method of claim 1, wherein the inner skeletal structure is formed to have a self-loading resistance to deflection within a range from about 0.005 N/mm to about 10 N/mm.

39. The method of claim 1, wherein the inner skeletal structure is formed to have a first self-loading resistance to deflection between about 1 degree and about 60 degrees, wherein the first self-loading resistance to deflection comprises a deflection angle between a first portion of the inner skeletal structure and a second portion of the inner skeletal structure when the first portion is supported and held in place and the weight of the second portion deflects the inner skeletal structure.

40. The method of claim 1, wherein the outer matrix structure is of a durometer that is lower than a durometer of the inner skeletal structure.

41. The method of claim 1, wherein the inner skeletal structure determines the pre-insertion contour and the post-insertion contour of the device.

42. The method of claim 1, wherein the post-insertion contour has a shape of at least a portion of the anterior surface of the eye.

43. The method of claim 1, wherein the post-insertion contour has a shape of at least a portion of the anterior surface of the eye outside of the cornea.

44. The method of claim 1, wherein the post-insertion contour has a shape of at least a region of a fornix of the eye.

45. The method of claim 1, wherein the post-insertion contour has a shape of at least a portion of the bony orbit of the eye.

46. The method of claim 1, wherein the device resists deflection away from the post-insertion contour.

\* \* \* \* \*